United States Patent
Shultz et al.

(10) Patent No.: US 6,730,479 B2
(45) Date of Patent: May 4, 2004

(54) DETECTION OF NUCLEIC ACID HYBRIDS

(75) Inventors: John William Shultz, Verona, WI (US); Martin K. Lewis, Madison, WI (US); Donna Leippe, Madison, WI (US); Michelle Mandrekar, Oregon, WI (US); Daniel Kephart, Cottage Grove, WI (US); Richard Byron Rhodes, Madison, WI (US); Christine Ann Andrews, Cottage Grove, WI (US); James Robert Hartnett, Madison, WI (US); Trent Gu, Madison, WI (US); Ryan J. Olson, Madison, WI (US); Keith V. Wood, Madison, WI (US); Roy Welch, Palo Alto, CA (US)

(73) Assignee: Promega Corporation, Madison, WI (US)

( * ) Notice: Subject to any disclaimer, the term of this patent is extended or adjusted under 35 U.S.C. 154(b) by 197 days.

(21) Appl. No.: 09/790,417

(22) Filed: Feb. 22, 2001

(65) Prior Publication Data

US 2001/0031470 A1 Oct. 18, 2001

Related U.S. Application Data

(63) Continuation of application No. 09/358,972, filed on Jul. 21, 1999, which is a continuation-in-part of application No. 09/252,436, filed on Feb. 18, 1999, now Pat. No. 6,159,693, which is a continuation-in-part of application No. 09/042,287, filed on Mar. 13, 1998.

(51) Int. Cl.$^7$ .......... C12Q 1/68; C12N 15/00; C12N 15/63; C12N 1/20; C07H 21/04
(52) U.S. Cl. .......... 435/6; 435/320.1; 435/252.8; 435/174; 435/183; 536/23.7; 530/350; 935/10; 935/24; 935/72
(58) Field of Search .......... 435/6, 320.1, 252.8, 435/174, 183; 536/23.7; 530/350; 935/10, 24, 72

(56) References Cited

U.S. PATENT DOCUMENTS

| | | | |
|---|---|---|---|
| 4,303,752 A | 12/1981 | Kolehmainen et al. | 435/8 |
| 4,331,762 A | 5/1982 | Nakajima et al. | 435/190 |
| 4,338,395 A | 7/1982 | Leon et al. | 435/17 |
| 4,352,881 A | 10/1982 | Inagawa et al. | 435/17 |
| 4,357,420 A | 11/1982 | Bostick et al. | 435/8 |
| 4,368,261 A | 1/1983 | Klose et al. | 435/15 |
| 4,371,611 A | 2/1983 | Fusee | 435/14 |
| 4,394,445 A | 7/1983 | Nix et al. | 435/19 |
| 4,415,655 A | 11/1983 | De Castro et al. | 435/17 |
| 4,438,124 A | 3/1984 | Meister et al. | 424/270 |
| 4,443,594 A | 4/1984 | Buckmann | 536/27 |
| 4,446,231 A | 5/1984 | Self | 435/7 |
| 4,460,684 A | 7/1984 | Bauer | 435/14 |
| 4,485,177 A | 11/1984 | Siedel et al. | 436/547 |
| 4,595,655 A | 6/1986 | Self | 435/7 |
| 4,683,195 A | 7/1987 | Mullis et al. | 435/6 |
| 4,683,202 A | 7/1987 | Mullis et al. | 435/91 |
| 4,735,897 A * | 4/1988 | Vary et al. | 435/6 |
| 4,743,561 A | 5/1988 | Shaffar | 436/501 |
| 4,755,458 A | 7/1988 | Rabbani et al. | 435/5 |
| 4,800,159 A | 1/1989 | Mullis et al. | 435/172.3 |
| 5,356,776 A | 10/1994 | Kambara et al. | 435/6 |
| 5,389,512 A | 2/1995 | Sninsky et al. | 435/5 |
| 5,391,480 A | 2/1995 | Davis et al. | 435/6 |
| 5,399,491 A | 3/1995 | Kacian et al. | 435/6 |
| 5,403,711 A | 4/1995 | Walder et al. | 435/6 |
| 5,445,933 A | 8/1995 | Eadie et al. | 435/6 |
| 5,494,810 A | 2/1996 | Barany et al. | 435/91.52 |
| 5,498,523 A | 3/1996 | Tabor et al. | 435/6 |
| 5,512,439 A | 4/1996 | Hornes et al. | 435/6 |
| 5,516,663 A | 5/1996 | Backman et al. | 435/91.2 |
| 5,530,192 A | 6/1996 | Murase et al. | 800/205 |
| 5,541,311 A * | 7/1996 | Dahlberg et al. | 536/23.7 |
| 5,561,044 A | 10/1996 | Walker et al. | 435/6 |
| 5,573,906 A | 11/1996 | Bannwarth et al. | 435/6 |
| 5,622,824 A | 4/1997 | Koster et al. | 435/6 |
| 5,648,232 A | 7/1997 | Squirrell | 435/34 |

(List continued on next page.)

FOREIGN PATENT DOCUMENTS

| | | | |
|---|---|---|---|
| EP | 0 229 601 A | 11/1986 | |
| EP | 639 647 A | 7/1994 | |
| EP | 0 663 447 A | 12/1994 | |
| EP | 0 894 867 A | 11/1997 | |
| GB | 2055200 | 12/1981 | .......... G01N/21/76 |
| WO | WO 90/05530 | 5/1990 | |
| WO | WO 91/17264 | 11/1991 | |
| WO | WO 92/13963 | 8/1992 | |
| WO | WO 94/25619 | 11/1994 | .......... C12Q/1/00 |
| WO | WO 95/21938 | 8/1995 | |

(List continued on next page.)

OTHER PUBLICATIONS

Mizrahi et al., "Mecahanism of DNA polymerase I: exonuclease/polymerase activity switch and DNA sequence dependence of pyrophosphorolysis and misincorporation reactions", Proc. Natl. Acad. sci. USA, (1986), vol. 83, pp. 5769–5773.*

(List continued on next page.)

Primary Examiner—Kenneth R. Horlick
(74) Attorney, Agent, or Firm—Welsh & Katz, Ltd.

(57) ABSTRACT

Processes are disclosed using the depolymerization of a nucleic acid hybrid to qualitatively and quantitatively analyze for the presence of a predetermined nucleic acid. Applications of those processes include the detection of single nucleotide polymorphisms, identification of single base changes, speciation, determination of viral load, genotyping, medical marker diagnostics, and the like.

8 Claims, 2 Drawing Sheets

U.S. PATENT DOCUMENTS

| | | | |
|---|---|---|---|
| 5,660,988 A | 8/1997 | Duck et al. | 435/6 |
| 5,667,964 A | 9/1997 | Ho | 435/5 |
| 5,683,877 A | 11/1997 | Lu-Chang et al. | 435/6 |
| 5,691,146 A | 11/1997 | Mayrand | 435/6 |
| 5,723,591 A | 3/1998 | Livak et al. | 536/22.1 |
| 5,731,146 A | 3/1998 | Duck et al. | 435/6 |
| 5,736,365 A | 4/1998 | Walker et al. | 435/91.2 |
| 5,741,635 A | 4/1998 | Boss et al. | 435/4 |
| 5,759,820 A | 6/1998 | Hornes et al. | 435/91.1 |
| 5,763,181 A | 6/1998 | Han et al. | 435/6 |
| 5,766,849 A | 6/1998 | McDonough et al. | 435/6 |
| 5,786,139 A | 7/1998 | Burke et al. | 435/6 |
| 5,786,183 A | 7/1998 | Ryder et al. | 435/91.2 |
| 5,814,491 A | 9/1998 | Vijg et al. | |
| 5,824,517 A | 10/1998 | Cleuziat et al. | 435/91.2 |
| 5,834,202 A | 11/1998 | Auerbach | 435/6 |
| 5,840,873 A | 11/1998 | Nelson et al. | 536/24.3 |
| 5,843,660 A | 12/1998 | Schumm et al. | 435/6 |
| 5,849,547 A | 12/1998 | Cleuziat et al. | 435/91.21 |
| 5,853,981 A | 12/1998 | Kondo et al. | 435/5 |
| 5,854,033 A | 12/1998 | Lizardi | 435/91.2 |
| 5,861,242 A | 1/1999 | Chee et al. | 435/5 |
| 5,863,736 A | 1/1999 | Haaland | 435/6 |
| 5,866,337 A | 2/1999 | Schon | 435/6 |
| 5,869,252 A | 2/1999 | Bouma et al. | 435/6 |
| 5,871,902 A | 2/1999 | Weininger et al. | 435/5 |
| 5,876,924 A | 3/1999 | Zhang et al. | 435/5 |
| 5,876,930 A | 3/1999 | Livak et al. | 435/6 |
| 5,876,978 A | 3/1999 | Willey et al. | 435/91.2 |
| 5,880,473 A | 3/1999 | Ginestet | 250/458.1 |
| 5,882,856 A | 3/1999 | Shuber | 435/6 |
| 5,885,775 A | 3/1999 | Haff et al. | 435/6 |
| 5,888,819 A | 3/1999 | Goelet et al. | 435/5 |
| 5,902,722 A | 5/1999 | Di Cesare et al. | 435/4 |
| 5,945,312 A * | 8/1999 | Goodman et al. | 435/91.1 |
| 6,007,987 A | 12/1999 | Cantor et al. | 435/6 |
| 6,066,483 A | 5/2000 | Riggs et al. | 435/194 |

FOREIGN PATENT DOCUMENTS

| | | | |
|---|---|---|---|
| WO | WO 96/41014 | 12/1996 | |
| WO | WO 97/41256 | 11/1997 | |
| WO | WO 98/13523 | 4/1998 | C12Q/1/68 |
| WO | WO 98/54362 | 4/1998 | |
| WO | WO 98/28440 | 7/1998 | C12Q/1/68 |

OTHER PUBLICATIONS

A.E. Sippel, "Purification and Characterization of Adenosine Triphosphate: Ribonucleic Acid Adenyltransferase from *Escherichia coli*" *Eur. J. Biochem.* 37:31–40 (1973).

K. Chowdhury, N. Kaushik, V.N. Pandey and M.J. Modak, "Elucidiation of the Role of Arg 110 of Murine Leukemia Virus Reverse Transcriptase in the Catalytic Mechanism: Biochemical Characterization of Its Mutant Enzymes," *Biochemistry*, 35:16610–16620 (1996).

S. Karamohamed, M. Ronaghi and P. Nyren, "Biolumino-metric Method for Real–Time Detection of Reverse Transcriptase Activity", *Biotechniques*, 24:302–306 (Feb., 1998).

B. Hove–Jensen, K.W. Harlow, C.J. King, R.L. Switzer, "Phosphoribosylpyrophosphate Synthetase of *Escherichia coli*", *J. Biol. Chem.*, 261(15):6765–6771 (1986).

P. Nyren, S. Karamoharred and M. Ronaghi, "Detection of Single–Base Changes Using a Bioluminometric Primer Extension Assay", *Anal. Biochem.*, 244:367–373 (Jan. 15, 1997).

M. Ronaghi, S. Karamohamed, B. Pettersson, M. Uhlen and P. Nyren, "Real–Time DNA Sequencing Using Detection of Pyrophosphate Release," *Anal. Biochem.*, 242:84–89 (1996).

T.A. Rozovskaya, V.O. Rechinsky, R.S. Bibilashvili, M.Y. Karpeisky, N.B. Tarusova, R.M. Khomutov, H.B.F. Dixon, "The Mechanism of Pyrophosphorolysis of RNA by RNA Polymerase", *Biochem. J.*, 224: 645–650 (1989).

M.P. Deutscher and A. Kornberg, "Enzymatic Synthesis of Deoxyribonucleic Acid", *J. Biol. Chem.*, 244(11):3019–28 (1969).

J.D. Moyer and J.F. Henderson, "Nucleoside Triphosphate Specificity of Firefly Luciferase", *Anal. Biochem.*, 131:187–189 (1983).

C. Blondin, L. Serina, L. Weismuller, A. Gilles and O. Barzu, "Improved Spectrophotometric Assay of Nucleoside Monophosphate Kinase Activity Using the Pyruvate Kinase/Lactate Dehydrogenase Coupling System", *Anal. Biochem.*, 220:219–21 (1994).

S. Tabor and C.C. Richardson, "DNA Sequence Analysis With a Modified Bacteriophage T7 DNA Polymerase", *J. Biol. Chem.*, 265(14):8322–8328 (1990).

R.S. Chittock, J.–M. Hawronsky, J. Holah and C.W. Wharton, "Kinetic Aspects of ATP Amplification Reactions", *Anal. Biochem.*, 255:120–126 (Jan. 1, 1998).

Kung, et al., "Picogram Quantitation ofTotal DNA–Binding Proteins in a Silicon Sensor–Based System", *Anal. Biochem.*, 187:220–227 (1990).

Srivastavan & Modak., *J. Biol. Chem.*, 255(5):2000–2004 (1980).

Sano & Feix, *Eur. J. Biochem.*, 71:577–583 (1976).

Sabina, et al., *Science*, 223:1193–1195 (1984).

Parks & Agarwal in *The Enzymes*, vol. 9:307–333, P. Boyer Ed. (1973).

Shimofuruya & Suzuki, *Biochem. Intl.*, 26(5):853–861 (1992).

Nyren, et al., "Detection of Single–Base Changes Using a Bioluminometric Primer Extension Assay", *Anal. Biochem.*, 244:367–373 (1997).

P. Bernard et al., *Am. J. Pathol.*, 153:1055–1061 (1998).

G. Garinis et al., *J. Clin. Lab. Anal.*, 13:122–125 (1999).

Holguin, et al., *Eur. J. Clin. Microbiol. Infect. Dis.*, 18:256–259 (1999).

Boriskin, et al., *Arch. Dis. Child.*, 80:132–136 (1999).

de Vega, et al., "Primer Terminus Stabilizing at the 3'–5'exonuclease active site of_29 DNA polymerase. Involvement of two amino acid residues highly conserved in proofreading DNA polymerases", *EMBO J.*, 15(5):1182–1192 (1996).

S. Patel et al., *Biochemistry*, 30:511–525 (1991).

I. Wong et al., *Biochemistry*, 30:526–537 (1991).

S. Zinnen et al., *J. Biological Chemistry*, 269(39):24195–24202 (1994).

J. Lindquist, Dept. of Bacteriology, University of Wisconsin–Madison,http://www.bact.wisc.edu/bact102/102dil3.html.

J. Lindquist, Dept. of Bacteriology, University of Wisconsin–Madison, http://www.bact.wisc.edu/bact102/102dil3a.html.

Most Probable Number (MPN), WQA Glossary of Terms, 3rd Ed., Water Quality Association.

P. Nyren, B. Pettersson, and M. Uhlen. "Solid Phase DNA Minisequencing by an Enzymatic Luminometric Inorganic Pyrophosphate Detection Assay," *Anal. Biochem.*, 208:171–175 (1993).

M. Ronaghi, S. Karamohamed, B. Pettersson, M. Uhlen, and P. Nyren, "Real–Time DNA Sequencing Using Detection of Pyrophosphate Release," *Anal. Biochem.*, 242:84–89 (1996).

J. Schultz, D. Leippe, K. Lewis, R. Lyke, M. Nelson, and C. Reynolds., "Detection of Low Levels of Nucleic Acids by Enzymatic Conversion to Substrates for Luciferase", Poster presented Jul. 25–29, 1998 at a Protein Society meeting in San Diego, California.

Heid, et al., "Real Time Quantitative PCR", *Genome Research*, 6:986–994 (1996).

Nagano, et al., "Detection of Verotoxin–Producing *Escherichia coli* O157:H7 by Multiplex Polymerase Chain Reaction", *Microbiol. Immunol.*, 42(5), 372–376 (1998).

Sherlock, et al., "Assessment of diagnostic quantitative fluorescent multiplex polymerase chain reaction assays performed on single cells", *Ann. Hum. Genet.* 62:9–23 (1998).

Axton, et al., "A Single–Tube Multiplex System for the Simultaneous Detection of 10Common Cystic Fibrosis Mutations", *Human Mutation*, 5:260–262 (1995).

Poyser et al., "Multiplex genotyping for cystic fibrosis from filter paper blood spots", *Ann. Clin. Biochem.*, 35:611–615 (1998).

Caudai, et al., "Detection of HCV and GBV–C/HGV injection by multiplex PCR in plasma samples of transfused subjects", *J. Virol Meth.*, 70: 79–83 (1998).

Songsivilai, et al., "Improved Amplification System for Detection of Hepatitis C virus Genome that Simultaneously Differentiates Viral Genotype", *Southeast Asian J. Trop. Med. Public Health*, 27(2): 237–243 (1996).

Oyofo, et al., "Detection of Enterotoxigenic *Escherichia coli*, Shigella and Campylobacter spp. by Multiplex PCR Assay", *J. Diarrhoeal Dis. Res.*, 14(3): 207–210 (1996).

L. Ripoll, et al., "Multiplex PCR–mediated Site–directed Mutagenesis for One–step Determination of Factor V Leiden and G20210A Transition of the Prothrombin Gene", pp. 960–961 (1997).

L. Ripoll, et al., "Multiplex ASA PCR for a Simultaneous Determination of Factor V Leiden Gene, G—A 20210 Prothrombin Gene and C—T 677 MTHFR Gene Mutations", *Thromb Haemost*, 79:1054–1055 (1998).

X. Xu et al., "Two Multiplex PCR–Based DNA Assays for the Thrombosis Risk Factors Prothrombin G20210A and Coagulation Factor V G1691A Polymorphisms", *Thrombosis Research* 93:265–269 (1999).

E. Gomez, et al., "Rapid Simultaneous Screening of Factor V Leiden and G20210A Prothrombin Variant by Multiplex Polymerase Chain Reaction on Whole Blood", *Blood* 91(6): 2208–2211 (1998).

D. Linfert, et al., "Rapid Multiplex Analysis for the Factor V Leiden and Prothrombin G20210A Mutations Associated with Hereditary Thrombophilia", *Connecticut Medicine* 62(9):519–525 (1998).

P. Nyren, et al., *Anal. Biochem.*, 244:367–373 (1997).

S. Borman, "Developers of Novel DNA Sequences Claim Major Performance Advances", *C&EN*, pp. 37–40 (Jul. 24, 1995).

P. Belgrader, et al., "PCR Detection of Bacteria in Seven Minutes", *Science Magazine* 284:449–450 (1999).

K. Hayashi *Genetic Analysis: Techniques and Applications* 9:73–79 (1992).

Newton et al., *Nucl. Acids Res.*, 17:2503–2516 (1989).

Wu et al., *Proc. Natl. Acad. Sci., USA*, 86:2757–2760 (1989).

T. Nikiforov, et al., *Nucl. Acids Res.*, 22:4167–4175 (1994).

C. Wittwer, et al., *Biotechniques*, 22:130–138 (1997).

P. Holland, et al., *Proc. Natl. Acad. Sci., USA*, 88:7276–7280 (1991).

R. Kramer, et al., *Nat. Biotechnol.*, 14:303–308 (1996).

J. Schultz, D. Leippe, K. Lewis and M. Nelson, "Non–radioactive Measurement of DNA Using Coupled Enzymatic Reactions", Presentation Mar. 16–20, 1998 at a Parenteral Drug Association meeting in San Francisco, California.

Seq ID No. 1, "Blast Archaeal Gemone Sequences at Center of Marine Biotechnology" Online, May 21, 1999, Retrieved on Aug. 7, 200 @ http://Combdna.umbi.umd.edu/bags.html.

http://Comb5–156.umbi.umd.edu/cgi–bin/PfurGene.Pl?GeneID=894645&Dataset=Nayb&Geneidtxt–994645, Online! XP002144446, Retrieved from the internet on Aug. 7, 2000.

Giartosio, et al., "Thermal stability of hexameric and tetrameric nucleoside diphosphate kinases: Effect of subunit interaction", *J. Biol. Chem.*, 271(30):17845–17851 (1996).

Bi, W., et al., "Detection of known mutation by proof–reading PCR", *Nucleic Acid Research*, GB, 26(12):3073–3075 (1998).

Kawarabayashi, et al., "Complete Sequence and Gene Organization of the Genome of hyper–thermophilic Archaebacterium, *Pyrococcus horikoshii* OT3", *DNA Research*, 5:55–76 (1998).

\* cited by examiner

Fig. 1

A Wild Type Template

3' CTGAGCAGTACAGAGTCGAAATC 5' 10866(SEQ ID NO:197)
TCTGACTCGTCATGTCTCAGCTTTAGTTTAATACGACTCACTATAG 10865(SEQ ID NO:196)
                           T   A                                 G
GTCTCTTTCTGTTATATCAAG 5'  3' TCCACCTTAGTGTGACTC 10865(SEQ ID NO:196)
5' TTGCAGAGAAAGACAATATAGTTCTTGGAGAAGTGGAATCACACTGAGTGGA 10870(SEQ ID NO:194)
                                                    G
3' CCACTTCCACCTTAGTGTGACTC 5' 10869(SEQ ID NO:198)

B Mutant Template

3' CTGAGCAGTACAGAGTCGAAATC 5' 10866(SEQ ID NO:197)
TCTGACTCGTCATGTCTCAGCTTTAGTTTAATACGACTCACTATAG
                           T   A                                 G
GTCTCTTTCTGTTATATCAAG 5'  3' TCCACCTTAGTGTGACTC 10865(SEQ ID NO:196)
5' TTGCAGAGAAAGACAATATAGTTCTTTGAGAAGGTGGAATCACACTGAGTGGA 10994(SEQ ID NO:195)
                                                    G
3' ACACTTCCACCTTAGTGTGACTC 5' 10989(SEQ ID NO:199)

Fig. 2

A.
5' ...CCCGGAGAGACCTCCTTAAGGGCCATATTATTCGTCGATTCCAGTGTTGGCCAAACGG  T...3'
                                                                 A
3' AGCTAAGGTCACAACCGGTTGCCGCTTTATTATACCGGGG 5'
SEQ ID NO:286
SEQ ID NO:287

B.
5' ...CCCGGAGAGACCTCCTTAAGGGCCATATTATTCGTCGATTCCAGTGTTGGCCAAACGG  T...3'
                                                                  A
3' GGGCCTCTCTGGAGGAATTCCCGGTATAATAAAGCAGCTAAGGTCACAACCGGTTTGCCGCTTTATTATACCGGGG 5'
SEQ ID NO:286
SEQ ID NO:288

C.
5' CCCGGAGAGACCTCCT 3'
3' GGGCCTCTCTGGAGGAATTCCCGGTATAATAAAGCAGCTAAGGTCACAACCGGTTTGCCGCTTTATTATACCGGGG 5'
SEQ ID NO:289
SEQ ID NO:288

D.
5' CCCGGAGAGACCTCCTTAAGGGCCATATTATTCGTCGATTCCAGTGTTGGCCAAACGGCGAAATAATATGGCCCC 3'
3' GGGCCTCTCTGGAGGAATTCCCGGTATAATAAAGCAGCTAAGGTCACAACCGGTTTGCCGCTTTATTATACCGGGG 5'
SEQ ID NO:290
SEQ ID NO:288

E.
3' CCCGGTATAATAAAGC─────────────────────┐
5' CCCGGAGAGACCTCCTTAAGGGCCATATTATTCGTCGATTCCAGTGTTGGCC─┘
SEQ ID NO:290

SEQUENCE LISTING

```
<160> NUMBER OF SEQ ID NOS: 290

<210> SEQ ID NO 1
<211> LENGTH: 22
<212> TYPE: DNA
<213> ORGANISM: Homo sapiens
<220> FEATURE:
<223> OTHER INFORMATION: probe for human prohibitin gene

<400> SEQUENCE: 1
ctgaacatgc ctgccaaaga cg                                              22

<210> SEQ ID NO 2
<211> LENGTH: 22
<212> TYPE: DNA
<213> ORGANISM: Homo sapiens
<220> FEATURE:
<223> OTHER INFORMATION: probe for human prohibitin gene

<400> SEQUENCE: 2
ctgaacatgc ctgccaaaga tg                                              22

<210> SEQ ID NO 3
<211> LENGTH: 22
<212> TYPE: DNA
<213> ORGANISM: Homo sapiens
<220> FEATURE:
<223> OTHER INFORMATION: probe for human prohibitin gene

<400> SEQUENCE: 3
caggaacgta ggtcggacac at                                              22

<210> SEQ ID NO 4
<211> LENGTH: 63
<212> TYPE: DNA
<213> ORGANISM: Homo sapiens
<220> FEATURE:
<223> OTHER INFORMATION: target for "C" allele of prohibitin gene

<400> SEQUENCE: 4 ctgctgggc tgaacatgcc tgccaaagac gtgtccgacc tacgttcctg gcccctcga      60
```

```
gct                                                              63

<210> SEQ ID NO 5
<211> LENGTH: 63
<212> TYPE: DNA
<213> ORGANISM: Homo sapiens
<220> FEATURE:
<223> OTHER INFORMATION: Target for "C" allele of  prohibitin gene

<400> SEQUENCE: 5
cgagggggcc aggaacgtag gtcggacacg tctttggcag gcatgttcag ccccagcaga    60
gct                                                              63

<210> SEQ ID NO 6
<211> LENGTH: 63
<212> TYPE: DNA
<213> ORGANISM: Homo sapiens
<220> FEATURE:
<223> OTHER INFORMATION: Target for "T" allele of human prohibitin gene

<400> SEQUENCE: 6
ctgctggggc tgaacatgcc tgccaaagat gtgtccgacc tacgttcctg gccccctcga    60
gct                                                              63

<210> SEQ ID NO 7
<211> LENGTH: 63
<212> TYPE: DNA
<213> ORGANISM: Homo sapiens
<220> FEATURE:
<223> OTHER INFORMATION: Target for "T" allele of human prohibitin gene

<400> SEQUENCE: 7
cgagggggcc aggaacgtag gtcggacaca tctttggcag gcatgttcag ccccagcaga    60
gct                                                              63

<210> SEQ ID NO 8
<211> LENGTH: 74
<212> TYPE: DNA
<213> ORGANISM: Cytomegalovirus

<400> SEQUENCE: 8
cgcttctacc acgaatgctc gcagaccatg ctgcacgaat acgtcagaaa gaacgtggag    60
cgtctgttgg agct                                                  74

<210> SEQ ID NO 9
<211> LENGTH: 74
<212> TYPE: DNA
<213> ORGANISM: cytomegalovirus

<400> SEQUENCE: 9
ccaacagacg ctccacgttc tttctgacgt attcgtgcag catggtctgc gagcattcgt    60
ggtagaagcg agct                                                  74

<210> SEQ ID NO 10
<211> LENGTH: 74
<212> TYPE: DNA
<213> ORGANISM: mutant Cytomegalovirus

<400> SEQUENCE: 10
cgcttctacc acgaatgctc gcagatcatg ctgcacgaat acgtcagaaa gaacgtggag    60
cgtctgttgg agct                                                  74
```

<210> SEQ ID NO 11
<211> LENGTH: 74
<212> TYPE: DNA
<213> ORGANISM: mutant Cytomegalovirus

<400> SEQUENCE: 11
ccaacagacg ctccacgttc tttctgacgt attcgtgcag catgatctgc gagcattcgt    60
ggtagaagcg agct                                                     74

<210> SEQ ID NO 12
<211> LENGTH: 21
<212> TYPE: DNA
<213> ORGANISM: Cytomegalovirus
<220> FEATURE:
<223> OTHER INFORMATION: probe for Cytomegalovirus

<400> SEQUENCE: 12
ctaccacgaa tgctcgcaga c                                             21

<210> SEQ ID NO 13
<211> LENGTH: 21
<212> TYPE: DNA
<213> ORGANISM: Cytomegalovirus
<220> FEATURE:
<223> OTHER INFORMATION: probe for mutant cytomegalovirus

<400> SEQUENCE: 13
ctaccacgaa tgctcgcaga t                                             21

<210> SEQ ID NO 14
<211> LENGTH: 21
<212> TYPE: DNA
<213> ORGANISM: Cytomegalovirus
<220> FEATURE:
<223> OTHER INFORMATION: probe for cytomegalovirus

<400> SEQUENCE: 14
tgacgtattc gtgcagcatg g                                             21

<210> SEQ ID NO 15
<211> LENGTH: 21
<212> TYPE: DNA
<213> ORGANISM: Cytomegalovirus
<220> FEATURE:
<223> OTHER INFORMATION: target for cytomegalovirus

<400> SEQUENCE: 15
tgacgtattc gtgcagcatg a                                             21

<210> SEQ ID NO 16
<211> LENGTH: 56
<212> TYPE: DNA
<213> ORGANISM: Cytomegalovirus
<220> FEATURE:
<223> OTHER INFORMATION: target for cytomegalovirus

<400> SEQUENCE: 16
ctctttaagc acgccggcgc ggcctgccgc gcgttggaga acggcaagct cacgca       56

<210> SEQ ID NO 17
<211> LENGTH: 56
<212> TYPE: DNA
<213> ORGANISM: Cytomegalovirus
<220> FEATURE:

-continued

<223> OTHER INFORMATION: target for mutant cytomegalovirus

<400> SEQUENCE: 17
cagcagtgcg tgagcttgcc gttctccaac gcgcggcagg ccgcgccggc gtgctt 56

<210> SEQ ID NO 18
<211> LENGTH: 56
<212> TYPE: DNA
<213> ORGANISM: Cytomegalovirus
<220> FEATURE:
<223> OTHER INFORMATION: target for mutant cytomegalovirus

<400> SEQUENCE: 18
ctctttaagc acgccggcgc ggcctgccgc gcgtcggaga acggcaagct cacgca 56

<210> SEQ ID NO 19
<211> LENGTH: 55
<212> TYPE: DNA
<213> ORGANISM: Cytomegalovirus
<220> FEATURE:
<223> OTHER INFORMATION: target for mutant cytomegalovirus

<400> SEQUENCE: 19
cagcagtgcg tgagcttgcc gttctccgcg cgcggcaggc cgcgccggcg tgctt 55

<210> SEQ ID NO 20
<211> LENGTH: 56
<212> TYPE: DNA
<213> ORGANISM: Cytomegalovirus
<220> FEATURE:
<223> OTHER INFORMATION: target for mutant cytomegalovirus

<400> SEQUENCE: 20
ctctttaagc acgccggcgc ggcctgccgc gcgtttgaga acggcaagct cacgca 56

<210> SEQ ID NO 21
<211> LENGTH: 56
<212> TYPE: DNA
<213> ORGANISM: Artificial Sequence
<220> FEATURE:
<223> OTHER INFORMATION: target for mutant cytomegalovirus

<400> SEQUENCE: 21
cagcagtgcg tgagcttgcc gttctcaaac gcgcggcagg ccgcgccggc gtgctt 56

<210> SEQ ID NO 22
<211> LENGTH: 21
<212> TYPE: DNA
<213> ORGANISM: Cytomegalovirus
<220> FEATURE:
<223> OTHER INFORMATION: probe for cytomegalovirus

<400> SEQUENCE: 22
ggcgcggcct gccgcgcgtt g 21

<210> SEQ ID NO 23
<211> LENGTH: 21
<212> TYPE: DNA
<213> ORGANISM: Cytomegalovirus
<220> FEATURE:
<223> OTHER INFORMATION: probe for cytomegalovirus

<400> SEQUENCE: 23
ggcgcggcct gccgcgcgtc g 21

<210> SEQ ID NO 24
<211> LENGTH: 21
<212> TYPE: DNA
<213> ORGANISM: Cytomegalovirus
<220> FEATURE:
<223> OTHER INFORMATION: probe for cytomegalovirus

<400> SEQUENCE: 24
gcgtgagctt gccgttctcc g                                          21

<210> SEQ ID NO 25
<211> LENGTH: 65
<212> TYPE: DNA
<213> ORGANISM: Homo sapiens
<220> FEATURE:
<223> OTHER INFORMATION: target for human Factor V gene

<400> SEQUENCE: 25
ctaatctgta agagcagatc cctggacagg cgaggaatac agagggcagc agacatcgaa    60
gagct                                                               65

<210> SEQ ID NO 26
<211> LENGTH: 69
<212> TYPE: DNA
<213> ORGANISM: Homo sapiens
<220> FEATURE:
<223> OTHER INFORMATION: target for human Factor V gene

<400> SEQUENCE: 26
agctcttcga tgtctgctgc cctctgtatt cctcgcctgt ccaggatct gctcttacag    60 attagagct                                                           69

<210> SEQ ID NO 27
<211> LENGTH: 65
<212> TYPE: DNA
<213> ORGANISM: Homo sapiens
<220> FEATURE:
<223> OTHER INFORMATION: target for human Factor V Leiden gene

<400> SEQUENCE: 27
ctaatctgta agagcagatc cctggacagg caaggaatac agagggcagc agacatcgaa    60
gagct                                                               65

<210> SEQ ID NO 28
<211> LENGTH: 69
<212> TYPE: DNA
<213> ORGANISM: Homo sapiens
<220> FEATURE:
<223> OTHER INFORMATION: target for human Factor V Leiden gene

<400> SEQUENCE: 28
agctcttcga tgtctgctgc cctctgtatt ccttgcctgt ccaggatct gctcttacag    60 attagagct                                                           69

<210> SEQ ID NO 29
<211> LENGTH: 22
<212> TYPE: DNA
<213> ORGANISM: Homo sapiens
<220> FEATURE:
<223> OTHER INFORMATION: probe for human Factor V gene

<400> SEQUENCE: 29
ctgctgccct ctgtattcct cg                                         22

```
<210> SEQ ID NO 30
<211> LENGTH: 22
<212> TYPE: DNA
<213> ORGANISM: Homo sapiens
<220> FEATURE:
<223> OTHER INFORMATION: probe for human Factor V  gene

<400> SEQUENCE: 30
ctgctgccct ctgtattcct tg                                              22

<210> SEQ ID NO 31
<211> LENGTH: 65
<212> TYPE: DNA
<213> ORGANISM: Cytomegalovirus
<220> FEATURE:
<223> OTHER INFORMATION: wt CMV target

<400> SEQUENCE: 31
cgtgtatgcc actttgatat tacacccatg aacgtgctca tcgacgtcaa cccgcacaac      60
gagct                                                                 65

<210> SEQ ID NO 32
<211> LENGTH: 65
<212> TYPE: DNA
<213> ORGANISM: Cytomegalovirus
<220> FEATURE:
<223> OTHER INFORMATION: wt CMV target

<400> SEQUENCE: 32
cgttgtgcgg gttcacgtcg atgagcacgt tcatgggtgt aatatcaaag tggcatacac      60
gagct                                                                 65

<210> SEQ ID NO 33
<211> LENGTH: 65
<212> TYPE: DNA
<213> ORGANISM: Cytomegalovirus
<220> FEATURE:
<223> OTHER INFORMATION: mutant CMV target

<400> SEQUENCE: 33
cgtgtatgcc actttgatat tacacccgtg aacgtgctca tcgacgtcaa cccgcacaac      60
gagct                                                                 65

<210> SEQ ID NO 34
<211> LENGTH: 65
<212> TYPE: DNA
<213> ORGANISM: Cytomegalovirus
<220> FEATURE:
<223> OTHER INFORMATION: mutant CMV target

<400> SEQUENCE: 34
cgttgtgcgg gttcacgtcg atgagcacgt tcacgggtgt aatatcaaag tggcatacac      60
gagct                                                                 65

<210> SEQ ID NO 35
<211> LENGTH: 21
<212> TYPE: DNA
<213> ORGANISM: Cytomegalovirus
<220> FEATURE:
<223> OTHER INFORMATION: probe for cytomegalovirus

<400> SEQUENCE: 35
cactttgata ttacacccgt g                                               21
```

```
<210> SEQ ID NO 36
<211> LENGTH: 70
<212> TYPE: DNA
<213> ORGANISM: Listeria
<220> FEATURE:
<223> OTHER INFORMATION: Description of Unknown Organism:Lysteria iap
<223> OTHER INFORMATION: Listeria iap gene

<400> SEQUENCE: 36
gaagtaaaac aaactacaca agcaactaca cctgcgccta aagtagcaga aacgaaagaa      60
actccagtag                                                             70

<210> SEQ ID NO 37
<211> LENGTH: 70
<212> TYPE: DNA
<213> ORGANISM: Listeria
<220> FEATURE:
<223> OTHER INFORMATION: Listeria iap gene

<400> SEQUENCE: 37
ctactggagt ttctttcgtt tctgctactt taggcgcagg tgtagttgct tgtgtagttt      60
gttttacttc                                                             70

<210> SEQ ID NO 38
<211> LENGTH: 30
<212> TYPE: DNA
<213> ORGANISM: Listeria
<220> FEATURE:
<223> OTHER INFORMATION: probe for Listeria iap (LM2)

<400> SEQUENCE: 38
gcaactacac ctgcgcctaa agtagcagaa                                       30

<210> SEQ ID NO 39
<211> LENGTH: 30
<212> TYPE: DNA
<213> ORGANISM: Listeria
<220> FEATURE:
<223> OTHER INFORMATION: probe for Listeria iap (LM1)

<400> SEQUENCE: 39
ttctgctact ttaggcgcag gtgtagttcg                                       30

<210> SEQ ID NO 40
<211> LENGTH: 70
<212> TYPE: DNA
<213> ORGANISM: Listeria
<220> FEATURE:
<223> OTHER INFORMATION: Listeria hyl gene

<400> SEQUENCE: 40
catcgacggc aacctcggag acttacgaga tattttgaaa aaaggcgcta cttttaatcg      60
agaaacacca                                                             70

<210> SEQ ID NO 41
<211> LENGTH: 70
<212> TYPE: DNA
<213> ORGANISM: Listeria
<220> FEATURE:
<223> OTHER INFORMATION: probe for Listeria hyl

<400> SEQUENCE: 41
tggtgtttct cgattaaaag tagcgccttt tttcaaaata tctcgtaagt ctccgaggtt      60
```

```
gccgtcgatg                                                            70

<210> SEQ ID NO 42
<211> LENGTH: 30
<212> TYPE: DNA
<213> ORGANISM: Listeria
<220> FEATURE:
<223> OTHER INFORMATION: probe for Listeria hyl

<400> SEQUENCE: 42
ctcggagact tacgagatat tttgaaaaaa                                      30

<210> SEQ ID NO 43
<211> LENGTH: 30
<212> TYPE: DNA
<213> ORGANISM: Listeria
<220> FEATURE:
<223> OTHER INFORMATION: probe for Lysteria hyl

<400> SEQUENCE: 43 tttttcaaa atatctcgta agtctccgag                                       30

<210> SEQ ID NO 44
<211> LENGTH: 60
<212> TYPE: DNA
<213> ORGANISM: Salmonella
<220> FEATURE:
<223> OTHER INFORMATION: Salmonella target

<400> SEQUENCE: 44
tttaattccg gagcctgtgt aatgaaagaa atcaccgtca ctgaacctgc ctttgtcacc     60

<210> SEQ ID NO 45
<211> LENGTH: 60
<212> TYPE: DNA
<213> ORGANISM: Salmonella
<220> FEATURE:
<223> OTHER INFORMATION: Salmonella target

<400> SEQUENCE: 45
ggtgacaaag gcaggttcag tgacggtgat ttctttcatt acacaggctc cggaattaaa     60

<210> SEQ ID NO 46
<211> LENGTH: 30
<212> TYPE: DNA
<213> ORGANISM: Salmonella
<220> FEATURE:
<223> OTHER INFORMATION: probe for Salmonella

<400> SEQUENCE: 46
tgtgtaatga agaaatcac cgtcactgaa                                       30

<210> SEQ ID NO 47
<211> LENGTH: 30
<212> TYPE: DNA
<213> ORGANISM: Salmonella
<220> FEATURE:
<223> OTHER INFORMATION: probe for Salmonella

<400> SEQUENCE: 47
ttcagtgacg gtgatttctt tcattacaca                                      30

<210> SEQ ID NO 48
<211> LENGTH: 24
<212> TYPE: DNA
```

```
<213> ORGANISM: probe for kanamycin gene
<220> FEATURE:
<223> OTHER INFORMATION: probe for kanamycin  RNA

<400> SEQUENCE: 48
gcaacgctac ctttgccatg tttc                                          24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence:probe for
      kanamycin RNA, altered at 3' terminus

<400> SEQUENCE: 49
gcaacgctac ctttgccatg tttg                                          24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence:probe to
      kanamycin RNA, altered at 3' terminus

<400> SEQUENCE: 50
gcaacgctac ctttgccatg ttta                                          24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence:probe to
      kanamycin RNA, altered at 3' terminus

<400> SEQUENCE: 51
gcaacgctac ctttgccatg tttt                                          24

<210> SEQ ID NO 52
<211> LENGTH: 30
<212> TYPE: DNA
<213> ORGANISM: rabbit
<220> FEATURE:
<223> OTHER INFORMATION: probe to globin mRNA

<400> SEQUENCE: 52
atggtgcatc tgtccagtga ggagaagtct                                    30

<210> SEQ ID NO 53
<211> LENGTH: 30
<212> TYPE: DNA
<213> ORGANISM: rabbit
<220> FEATURE:
<223> OTHER INFORMATION: probe to globin mRNA

<400> SEQUENCE: 53
agacttctcc tcactggaca gatgcaccat                                    30

<210> SEQ ID NO 54
<211> LENGTH: 26
<212> TYPE: DNA
<213> ORGANISM: rabbit
<220> FEATURE:
<223> OTHER INFORMATION: probe to globin mRNA
```

```
<400> SEQUENCE: 54
gctgctggtt gtctacccat ggaccc                                              26

<210> SEQ ID NO 55
<211> LENGTH: 26
<212> TYPE: DNA
<213> ORGANISM: rabbit
<220> FEATURE:
<223> OTHER INFORMATION: probe to globin mRNA

<400> SEQUENCE: 55
gggtccatgg gtagacaacc agcagc                                              26

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence:probe to
      globin mRNA, modified at 3' terminus

<400> SEQUENCE: 56
agacttctcc tcactggaca gatgcaccaa                                          30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence:probe to
      globin mRNA, modified at 3' terminus

<400> SEQUENCE: 57
agacttctcc tcactggaca gatgcaccag                                          30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence:probe to
      globin mRNA, modified at 3' terminus

<400> SEQUENCE: 58
agacttctcc tcactggaca gatgcaccac                                          30

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence:probe to
      globin mRNA, modified at 3' terminus

<400> SEQUENCE: 59
gggtccatgg gtagacaacc agcaga                                              26

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence:probe to
      globin mRNA, modified at 3' terminus

<400> SEQUENCE: 60
```
gggtccatgg gtagacaacc agcagg                                        26

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence:probe to
      globin mRNA, modified at 3' terminus

<400> SEQUENCE: 61
gggtccatgg gtagacaacc agcagt                                        26

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence:probe to
      globin mRNA, modified penultimate to 3' end

<400> SEQUENCE: 62
agacttctcc tcactggaca gatgcacccc                                    30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence:probe to
      globin mRNA, modified penultimate to 3' end

<400> SEQUENCE: 63
agacttctcc tcactggaca gatgcaccgc                                    30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence:probe to
      globin mRNA, modified penultimate to 3' end

<400> SEQUENCE: 64
agacttctcc tcactggaca gatgcacctc                                    30

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence:probe to
      globin mRNA, modified penultimate to 3' terminus

<400> SEQUENCE: 65
gggtccatgg gtagacaacc agcacc                                        26

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence:probe to
      globin mRNA, modified penultimate to 3' terminus

<400> SEQUENCE: 66
gggtccatgg gtagacaacc agcatc                                        26

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence:probe to globin mRNA, modified penultimate to 3' terminus

<400> SEQUENCE: 67
gggtccatgg gtagacaacc agcaac 26

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence:probe to globin mRNA with mismatch 3 from 3' end

<400> SEQUENCE: 68
agacttctcc tcactggaca gatgcactat 30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence:probe to globin mRNA wtih mismatch 4 from 3' end

<400> SEQUENCE: 69
agacttctcc tcactggaca gatgcatcat 30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence:probe to globin mRNA with mismatch 5 from 3' end

<400> SEQUENCE: 70
agacttctcc tcactggaca gatgctccat 30

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence:probe to globin mRNA, modified at 3' terminus

<400> SEQUENCE: 71
agacttctcc tcactggaca gatgtaccat 30

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence:probe for globin mRNA with mismatch 3 from 3' terminus

<400> SEQUENCE: 72
gggtccatgg gtagacaacc agctgc 26

```
<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence:probe to
      globin mRNA with mismatch 4 from 3' terminus

<400> SEQUENCE: 73
gggtccatgg gtagacaacc agtagc                                          26

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence:probe for
      globin mRNA with mismatch 5 from 3' terminus

<400> SEQUENCE: 74
gggtccatgg gtagacaacc atcagc                                          26

<210> SEQ ID NO 75
<211> LENGTH: 30
<212> TYPE: DNA
<213> ORGANISM: Escherichia coli
<220> FEATURE:
<223> OTHER INFORMATION: probe to beta-galactosidase gene

<400> SEQUENCE: 75
cagtcacgac gttgtaaaac gacggccagt                                      30

<210> SEQ ID NO 76
<211> LENGTH: 30
<212> TYPE: DNA
<213> ORGANISM: Escherichia coli
<220> FEATURE:
<223> OTHER INFORMATION: probe to beta-galactosidase gene

<400> SEQUENCE: 76
actggccgtc gttttacaac gtcgtgactg                                      30

<210> SEQ ID NO 77
<211> LENGTH: 30
<212> TYPE: RNA
<213> ORGANISM: kanamycin RNA oligo
<220> FEATURE:
<223> OTHER INFORMATION: kanamycin RNA oligo

<400> SEQUENCE: 77
agagucuuga cggauccagg uaccaguaaa                                      30

<210> SEQ ID NO 78
<211> LENGTH: 24
<212> TYPE: DNA
<213> ORGANISM: Upstream probe for kanamycin

<400> SEQUENCE: 78
tgatcgtaag agtcttgacg gatc                                            24

<210> SEQ ID NO 79
<211> LENGTH: 24
<212> TYPE: DNA
<213> ORGANISM: Downstream kanamycin probe

<400> SEQUENCE: 79
```
tcattcgtga ttgcgcctga gcga                                                  24

<210> SEQ ID NO 80
<211> LENGTH: 24
<212> TYPE: DNA
<213> ORGANISM: internal probe for kanamycin
<220> FEATURE:
<223> OTHER INFORMATION: internal probe for kanamycin

<400> SEQUENCE: 80
gcaacgctac ctttgccatg tttc                                                  24

<210> SEQ ID NO 81
<211> LENGTH: 24
<212> TYPE: DNA
<213> ORGANISM: synthesis probe for kanamycin
<220> FEATURE:
<223> OTHER INFORMATION: synthesis probe for Kanamycin RNA

<400> SEQUENCE: 81
aaatcactcg catcaaccaa accg                                                  24

<210> SEQ ID NO 82
<211> LENGTH: 65
<212> TYPE: DNA
<213> ORGANISM: Cytomegalovirus
<220> FEATURE:
<223> OTHER INFORMATION: cymegalovirus target

<400> SEQUENCE: 82
cgtgtatgcc actttgatat tacacccatg aacgtgctca tcgacgtgaa cccgcacaac          60
gagct                                                                      65

<210> SEQ ID NO 83
<211> LENGTH: 65
<212> TYPE: DNA
<213> ORGANISM: Cytomegalovirus
<220> FEATURE:
<223> OTHER INFORMATION: cytomegalovirus target

<400> SEQUENCE: 83
cgttgtgcgg gttcacgtcg atgagcacgt tcatgggtgt aatatcaaag tggcatacac          60
gagct                                                                      65

<210> SEQ ID NO 84
<211> LENGTH: 65
<212> TYPE: DNA
<213> ORGANISM: Cytomegalovirus
<220> FEATURE:
<223> OTHER INFORMATION: mutated cytomegalovirus target

<400> SEQUENCE: 84
cgtgtatgcc actttgatat tacacccgtg aacgtgctca tcgacgtgaa cccgcacaac          60
gagct                                                                      65

<210> SEQ ID NO 85
<211> LENGTH: 65
<212> TYPE: DNA
<213> ORGANISM: Cytomegalovirus
<220> FEATURE:
<223> OTHER INFORMATION: mutated cytomegalovirus target

<400> SEQUENCE: 85

```
cgttgtgcgg gttcacgtcg atgagcacgt tcacgggtgt aatatcaaag tggcatacac      60
gagct                                                                 65

<210> SEQ ID NO 86
<211> LENGTH: 21
<212> TYPE: DNA
<213> ORGANISM: Cytomegalovirus
<220> FEATURE:
<223> OTHER INFORMATION: cytomegalovirus probe

<400> SEQUENCE: 86
cactttgata ttacacccat g                                               21

<210> SEQ ID NO 87
<211> LENGTH: 23
<212> TYPE: DNA
<213> ORGANISM: Artificial Sequence
<220> FEATURE:
<223> OTHER INFORMATION: n = AN INOSINE WHICH CAN HYBRIDIZE TO ANY BASE
<223> OTHER INFORMATION: Description of Artificial Sequence: probe for
      NDPK from Pyrococcus furiosis

<400> SEQUENCE: 87
atnatnaaag ccngatcggc ngt                                             23

<210> SEQ ID NO 88
<211> LENGTH: 25
<212> TYPE: DNA
<213> ORGANISM: Artificial Sequence
<220> FEATURE:
<223> OTHER INFORMATION: n = inosine which can hybridize to any base
<223> OTHER INFORMATION: Description of Artificial Sequence:probe for
      NDPK from Pyrococcus furiosis

<400> SEQUENCE: 88
aaagtcnccn ctgnatngtn ccngg                                           25

<210> SEQ ID NO 89
<211> LENGTH: 21
<212> TYPE: DNA
<213> ORGANISM: Pyrococcus furiosus
<220> FEATURE:
<223> OTHER INFORMATION: probe for NDPK from Pyrococcus furiosis

<400> SEQUENCE: 89
gagaagcact atgaggagca c                                               21

<210> SEQ ID NO 90
<211> LENGTH: 486
<212> TYPE: DNA
<213> ORGANISM: Pyrococcus furiosus

<400> SEQUENCE: 90
atgaacgaag ttgaaagaac attggtaatc ataaagcccg acgcagtagt tagggtcta     60 ataggtgaaa ttataagcag gtttgagaag aaaggcctca agattgttgg aatgaagatg   120
atctggatag acagggagtt ggctgagaag cactatgagg agcacaaagg aaagcccttc   180
tttgaggctc tcatagatta cataacgaaa gctccagtag ttgttatggt ggttgaggga   240
aggtatgcag tagaagtagt tagaaagatg gctggagcta ctgatccaaa ggacgcagca   300
cctgggacaa ttaggggaga ttatggactt gacataggag atgcaatcta caacgtgatt   360
catgccagtg attcaaagga aagtgcggag agggaaataa gcctgtactt taaacctgaa   420
gaaatttatg aatactgcaa agctgcagat tggttttaca gggaaaagaa gcaggctaaa   480
``` tgctga 486

<210> SEQ ID NO 91
<211> LENGTH: 161
<212> TYPE: PRT
<213> ORGANISM: Pyrococcus furiosus
<220> FEATURE:
<223> OTHER INFORMATION: NDPK from Pyrococcus furiosis

<400> SEQUENCE: 91

Met Asn Glu Val Glu Arg Thr Leu Val Ile Ile Lys Pro Asp Ala Val
 1               5                  10                  15
Val Arg Gly Leu Ile Gly Glu Ile Ile Ser Arg Phe Glu Lys Lys Gly
            20                  25                  30
Leu Lys Ile Val Gly Met Lys Met Ile Trp Ile Asp Arg Glu Leu Ala
        35                  40                  45
Glu Lys His Tyr Glu Glu His Lys Gly Lys Pro Phe Phe Glu Ala Leu
    50                  55                  60
Ile Asp Tyr Ile Thr Lys Ala Pro Val Val Met Val Val Glu Gly
65                  70                  75                  80
Arg Tyr Ala Val Glu Val Val Arg Lys Met Ala Gly Ala Thr Asp Pro
                85                  90                  95
Lys Asp Ala Ala Pro Gly Thr Ile Arg Gly Asp Tyr Gly Leu Asp Ile
            100                 105                 110
Gly Asp Ala Ile Tyr Asn Val Ile His Ala Ser Asp Ser Lys Glu Ser
        115                 120                 125
Ala Glu Arg Glu Ile Ser Leu Tyr Phe Lys Pro Glu Glu Ile Tyr Glu
    130                 135                 140
Tyr Cys Lys Ala Ala Asp Trp Phe Tyr Arg Glu Lys Lys Gln Ala Lys
145                 150                 155                 160
Cys

<210> SEQ ID NO 92
<211> LENGTH: 25
<212> TYPE: DNA
<213> ORGANISM: Pyrococcus furiosus
<220> FEATURE:
<223> OTHER INFORMATION: primer for coding region of NDPK

<400> SEQUENCE: 92
gggtgctttt catgaacgaa gttga                                          25

<210> SEQ ID NO 93
<211> LENGTH: 27
<212> TYPE: DNA
<213> ORGANISM: Pyrococcus furiosus
<220> FEATURE:
<223> OTHER INFORMATION: primer for coding region of NDPK

<400> SEQUENCE: 93
aagggcaaaa attctagagt tcagcat                                        27

<210> SEQ ID NO 94
<211> LENGTH: 20
<212> TYPE: DNA
<213> ORGANISM: rabbit
<220> FEATURE:
<223> OTHER INFORMATION: probe for wild-type B-globin targets

<400> SEQUENCE: 94

```
cccttggacc cagaggttct                                              20

<210> SEQ ID NO 95
<211> LENGTH: 20
<212> TYPE: DNA
<213> ORGANISM: rabbit
<220> FEATURE:
<223> OTHER INFORMATION: probe for mutant B-globin targets

<400> SEQUENCE: 95
cccttggacc cagaggttga                                              20

<210> SEQ ID NO 96
<211> LENGTH: 20
<212> TYPE: DNA
<213> ORGANISM: rabbit
<220> FEATURE:
<223> OTHER INFORMATION: probe for wild-type B-globin PCR targets

<400> SEQUENCE: 96
cttcatccac gttcaccttg                                              20

<210> SEQ ID NO 97
<211> LENGTH: 20
<212> TYPE: DNA
<213> ORGANISM: rabbit
<220> FEATURE:
<223> OTHER INFORMATION: probe for mutant B-globin PCR targets

<400> SEQUENCE: 97
cttcatccac gttcacctag                                              20

<210> SEQ ID NO 98
<211> LENGTH: 26
<212> TYPE: DNA
<213> ORGANISM: rabbit
<220> FEATURE:
<223> OTHER INFORMATION: PCR target probe for Beta-globin

<400> SEQUENCE: 98
gtacggctgt catcacttag acctca                                       26

<210> SEQ ID NO 99
<211> LENGTH: 27
<212> TYPE: DNA
<213> ORGANISM: rabbit
<220> FEATURE:
<223> OTHER INFORMATION: PCR target probe for Beta-globin

<400> SEQUENCE: 99
tgcagcttgt cacaagtgca gctcact                                      27

<210> SEQ ID NO 100
<211> LENGTH: 75
<212> TYPE: DNA
<213> ORGANISM: Campylobacter jejuni
<220> FEATURE:
<223> OTHER INFORMATION: probe to Campylobacter jejuni

<400> SEQUENCE: 100
cttgaagcat agttcttgtt tttaaacttt gtccatcttg agccgcttga gttgagttgc  60
cttagtttta atagt                                                   75

<210> SEQ ID NO 101
<211> LENGTH: 70
```

```
<212> TYPE: DNA
<213> ORGANISM: Campylobacter jejuni
<220> FEATURE:
<223> OTHER INFORMATION: probe to Campylobacter jejuni

<400> SEQUENCE: 101
actattaaaa ctaaggcaac tcaagcggct caagatggac aaagtttaaa aacaagaact        60
atgcttcaag                                                              70

<210> SEQ ID NO 102
<211> LENGTH: 30
<212> TYPE: DNA
<213> ORGANISM: Campylobacter jejuni
<220> FEATURE:
<223> OTHER INFORMATION: probe to Campylobacter jejuni

<400> SEQUENCE: 102
agttcttgtt tttaaacttt gtccatcttg                                        30

<210> SEQ ID NO 103
<211> LENGTH: 30
<212> TYPE: DNA
<213> ORGANISM: Campylobacter jejuni
<220> FEATURE:
<223> OTHER INFORMATION: probe to Campylobacter jejuni

<400> SEQUENCE: 103
caagatggac aaagtttaaa aacaagaact                                        30

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence:probe to
      prothrombin pcr productm, with phosphorothioate
      linkages between the first five bases on the 5'
      end

<400> SEQUENCE: 104
atagcactgg gagcattgag gc                                                22

<210> SEQ ID NO 105
<211> LENGTH: 20
<212> TYPE: DNA
<213> ORGANISM: Homo sapiens
<220> FEATURE:
<223> OTHER INFORMATION: probe for human prothrombin gene

<400> SEQUENCE: 105
gcacagacgg ctgttctctt                                                   20

<210> SEQ ID NO 106
<211> LENGTH: 13
<212> TYPE: DNA
<213> ORGANISM: Homo sapiens
<220> FEATURE:
<223> OTHER INFORMATION: probe for human prothrombin gene

<400> SEQUENCE: 106
gtgactctca gcg                                                          13

<210> SEQ ID NO 107
<211> LENGTH: 13
<212> TYPE: DNA
<213> ORGANISM: Artificial Sequence
```

```
<220> FEATURE:
<223> OTHER INFORMATION: Description of Artificial Sequence:match to
      mutant prothrombin; complementary to wild-type 9 from 3'

<400> SEQUENCE: 107
gtgactctca gca                                                          13

<210> SEQ ID NO 108
<211> LENGTH: 13
<212> TYPE: DNA
<213> ORGANISM: Artificial Sequence
<220> FEATURE:
<223> OTHER INFORMATION: Description of Artificial Sequence:match to
      wild-type prothrombin; mismatch 9 from 3'

<400> SEQUENCE: 108
gtgattctca gcg                                                          13

<210> SEQ ID NO 109
<211> LENGTH: 13
<212> TYPE: DNA
<213> ORGANISM: Artificial Sequence
<220> FEATURE:
<223> OTHER INFORMATION: Description of Artificial Sequence:match to
      mutant prothrombin; mismatch 9 from 3'

<400> SEQUENCE: 109
gtgattctca gca                                                          13

<210> SEQ ID NO 110
<211> LENGTH: 22
<212> TYPE: DNA
<213> ORGANISM: Homo sapiens
<220> FEATURE:
<223> OTHER INFORMATION: probe for human Factor V gene

<400> SEQUENCE: 110
gacaaaatac ctgtattcct cg                                                22

<210> SEQ ID NO 111
<211> LENGTH: 22
<212> TYPE: DNA
<213> ORGANISM: Homo sapiens
<220> FEATURE:
<223> OTHER INFORMATION: probe for human Factor V gene

<400> SEQUENCE: 111
gacaaaatac ctgtattcct tg                                                22

<210> SEQ ID NO 112
<211> LENGTH: 20
<212> TYPE: DNA
<213> ORGANISM: Homo sapiens
<220> FEATURE:
<223> OTHER INFORMATION: probe for human cystic fibrosis gene

<400> SEQUENCE: 112
cattcacagt agcttaccca                                                   20

<210> SEQ ID NO 113
<211> LENGTH: 20
<212> TYPE: DNA
<213> ORGANISM: Homo sapiens
<220> FEATURE:
<223> OTHER INFORMATION: probe for human cystic fibrosis gene

<400> SEQUENCE: 113
```
gcagagtacc tgaaacagga                                                    20

<210> SEQ ID NO 114
<211> LENGTH: 19
<212> TYPE: DNA
<213> ORGANISM: Homo sapiens
<220> FEATURE:
<223> OTHER INFORMATION: probe for human cystic fibrosis gene

<400> SEQUENCE: 114
catcatagga aacaccaag                                                     19

<210> SEQ ID NO 115
<211> LENGTH: 19
<212> TYPE: DNA
<213> ORGANISM: Homo sapiens
<220> FEATURE:
<223> OTHER INFORMATION: probe for human cystic fibrosis gene

<400> SEQUENCE: 115
catcatagga aacaccaat                                                     19

<210> SEQ ID NO 116
<211> LENGTH: 24
<212> TYPE: DNA
<213> ORGANISM: Homo sapiens
<220> FEATURE:
<223> OTHER INFORMATION: probe for human cystic fibrosis gene

<400> SEQUENCE: 116
ggcaccatta aagaaaatat catt                                               24

<210> SEQ ID NO 117
<211> LENGTH: 49
<212> TYPE: DNA
<213> ORGANISM: Homo sapiens
<220> FEATURE:
<223> OTHER INFORMATION: probe for human cystic fibrosis gene

<400> SEQUENCE: 117
ctggcaccat taaagaaaat atcattggtg tttcctatga tgaatatag                    49

<210> SEQ ID NO 118
<211> LENGTH: 49
<212> TYPE: DNA
<213> ORGANISM: Homo sapiens
<220> FEATURE:
<223> OTHER INFORMATION: probe for human cystic fibrosis gene

<400> SEQUENCE: 118
ctatattcat cataggaaac accaatgata ttttctttaa tggtgccag                    49

<210> SEQ ID NO 119
<211> LENGTH: 52
<212> TYPE: DNA
<213> ORGANISM: Homo sapiens
<220> FEATURE:
<223> OTHER INFORMATION: target for wild-type cystic fibrosis gene

<400> SEQUENCE: 119
ctggcaccat taaagaaaat atcatctttg gtgtttccta tgatgaatat ag                52

<210> SEQ ID NO 120
<211> LENGTH: 52
<212> TYPE: DNA

```
<213> ORGANISM: Homo sapiens
<220> FEATURE:
<223> OTHER INFORMATION: target for mutant cystic fibrosis gene

<400> SEQUENCE: 120
ctatattcat cataggaaac accaaagatg atattttctt taatggtgcc ag        52

<210> SEQ ID NO 121
<211> LENGTH: 50
<212> TYPE: DNA
<213> ORGANISM: Homo sapiens
<220> FEATURE:
<223> OTHER INFORMATION: target for human prothrombin wild-type gene

<400> SEQUENCE: 121
tcccaataaa agtgactctc agcgagcctc aatgctccca gtgctattca            50

<210> SEQ ID NO 122
<211> LENGTH: 50
<212> TYPE: DNA
<213> ORGANISM: Homo sapiens
<220> FEATURE:
<223> OTHER INFORMATION: target for human prothrombin mutant gene

<400> SEQUENCE: 122
tcccaataaa agtgactctc agcaagcctc aatgctccca gtgctattca            50

<210> SEQ ID NO 123
<211> LENGTH: 16
<212> TYPE: DNA
<213> ORGANISM: Homo sapiens
<220> FEATURE:
<223> OTHER INFORMATION: probe for human prothrombin gene

<400> SEQUENCE: 123
ggagcattga ggctcg                                                 16

<210> SEQ ID NO 124
<211> LENGTH: 16
<212> TYPE: DNA
<213> ORGANISM: Homo sapiens
<220> FEATURE:
<223> OTHER INFORMATION: probe for human prothrombin gene

<400> SEQUENCE: 124
ggagcattga ggcttg                                                 16

<210> SEQ ID NO 125
<211> LENGTH: 40
<212> TYPE: DNA
<213> ORGANISM: Homo sapiens
<220> FEATURE:
<223> OTHER INFORMATION: native bcr

<400> SEQUENCE: 125
cagtacttac ttgaactctg cttaaatcca gtggctgagt                       40

<210> SEQ ID NO 126
<211> LENGTH: 41
<212> TYPE: DNA
<213> ORGANISM: Homo sapiens
<220> FEATURE:
<223> OTHER INFORMATION: bcr/abl translocation

<400> SEQUENCE: 126
ctgaagggct tttgaactct gcttaaatcc agtggctgag t                     41
```

```
<210> SEQ ID NO 127
<211> LENGTH: 22
<212> TYPE: DNA
<213> ORGANISM: Homo sapiens
<220> FEATURE:
<223> OTHER INFORMATION: probe for native bcr

<400> SEQUENCE: 127
tggatttaag cagagttcaa gt                                              22

<210> SEQ ID NO 128
<211> LENGTH: 22
<212> TYPE: DNA
<213> ORGANISM: Homo sapiens
<220> FEATURE:
<223> OTHER INFORMATION: probe for bcr/abl translocation

<400> SEQUENCE: 128
tggatttaag cagagttcaa aa                                              22

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence:probe for
      Rice genome (with phosphorothioate linkages)
<223> OTHER INFORMATION: phosphothioate linkages between first five
      bases

<400> SEQUENCE: 129
cccaacacct tacagaaatt agc                                             23

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence:probe for
      Rice genome

<400> SEQUENCE: 130
tctcaagaca caaataactg cag                                             23

<210> SEQ ID NO 131
<211> LENGTH: 15
<212> TYPE: DNA
<213> ORGANISM: Artificial Sequence
<220> FEATURE:
<223> OTHER INFORMATION: Description of Artificial Sequence:probe for
      "G" allele of Rice

<400> SEQUENCE: 131
agaacatctg caagg                                                      15

<210> SEQ ID NO 132
<211> LENGTH: 15
<212> TYPE: DNA
<213> ORGANISM: Artificial Sequence
<220> FEATURE:
<223> OTHER INFORMATION: Description of Artificial Sequence:probe for
      "T" allele of Rice

<400> SEQUENCE: 132
agaacatctg caagt                                                      15
```

```
<210> SEQ ID NO 133
<211> LENGTH: 22
<212> TYPE: DNA
<213> ORGANISM: Homo sapiens
<220> FEATURE:
<223> OTHER INFORMATION: probe for prohibitin mutant

<400> SEQUENCE: 133
caggaacgta ggtcggacac gt                                              22

<210> SEQ ID NO 134
<211> LENGTH: 58
<212> TYPE: DNA
<213> ORGANISM: Artificial Sequence
<220> FEATURE:
<223> OTHER INFORMATION: Description of Artificial Sequence:THO locus
      with 6x CATT repeat
<223> OTHER INFORMATION: THO locus with 6x CATT repeat

<400> SEQUENCE: 134
ggtgaatgaa tgaatgaatg aatgaatgag ggaaataagg gaggaagagg ccaatggg      58

<210> SEQ ID NO 135
<211> LENGTH: 62
<212> TYPE: DNA
<213> ORGANISM: Artificial Sequence
<220> FEATURE:
<223> OTHER INFORMATION: Description of Artificial Sequence:THO locus
      with 7x CATT repeat
<223> OTHER INFORMATION: THO locus with 7x CATT repeat

<400> SEQUENCE: 135
ggtgaatgaa tgaatgaatg aatgaatgaa tgagggaaat aagggaggaa gaggccaatg    60
gg                                                                    62

<210> SEQ ID NO 136
<211> LENGTH: 70
<212> TYPE: DNA
<213> ORGANISM: Artificial Sequence
<220> FEATURE:
<223> OTHER INFORMATION: Description of Artificial Sequence:THO locus
      with 8x CATT repeat
<223> OTHER INFORMATION: THO locus with 8x CATT repeat

<400> SEQUENCE: 136
ggtaggtgaa tgaatgaatg aatgaatgaa tgaatgaatg agggaaataa gggaggaaga    60
ggccaatggg                                                            70

<210> SEQ ID NO 137
<211> LENGTH: 58
<212> TYPE: DNA
<213> ORGANISM: Artificial Sequence
<220> FEATURE:
<223> OTHER INFORMATION: Description of Artificial Sequence:primer for
      THO1 locus with 6x CATT repeats

<400> SEQUENCE: 137
cccattggcc tgttcctccc ttatttccct cattcattca ttcattcatt cattcacc      58

<210> SEQ ID NO 138
<211> LENGTH: 62
<212> TYPE: DNA
<213> ORGANISM: Artificial Sequence
<220> FEATURE:
<223> OTHER INFORMATION: Description of Artificial Sequence:probe for
      THO1 locus with 7x CATT repeats
```

<400> SEQUENCE: 138
cccattggcc tgttcctccc ttatttccct cattcattca ttcattcatt cattcattca    60
cc    62

<210> SEQ ID NO 139
<211> LENGTH: 66
<212> TYPE: DNA
<213> ORGANISM: Artificial Sequence
<220> FEATURE:
<223> OTHER INFORMATION: Description of Artificial Sequence:probe for
      THO1 locus with 8x CATT repeats

<400> SEQUENCE: 139
cccattggcc tgttcctccc ttatttccct cattcattca ttcattcatt cattcattca    60
ttcacc    66

<210> SEQ ID NO 140
<211> LENGTH: 54
<212> TYPE: DNA
<213> ORGANISM: Artificial Sequence
<220> FEATURE:
<223> OTHER INFORMATION: Description of Artificial Sequence:probe for
      THO1 locus with 5x CATT repeats

<400> SEQUENCE: 140
cccattggcc tgttcctccc ttatttccct cattcattca ttcattcatt cacc    54

<210> SEQ ID NO 141
<211> LENGTH: 58
<212> TYPE: DNA
<213> ORGANISM: Artificial Sequence
<220> FEATURE:
<223> OTHER INFORMATION: Description of Artificial Sequence:probe for
      THO1 locus with 6x CATT repeats

<400> SEQUENCE: 141
cccattggcc tgttcctccc ttatttccct cattcattca ttcattcatt cattcacc    58

<210> SEQ ID NO 142
<211> LENGTH: 62
<212> TYPE: DNA
<213> ORGANISM: Artificial Sequence
<220> FEATURE:
<223> OTHER INFORMATION: Description of Artificial Sequence:probe for
      THO1 locus with 7x CATT repeats

<400> SEQUENCE: 142
cccattggcc tgttcctccc ttatttccct cattcattca ttcattcatt cattcattca    60
cc    62

<210> SEQ ID NO 143
<211> LENGTH: 66
<212> TYPE: DNA
<213> ORGANISM: Artificial Sequence
<220> FEATURE:
<223> OTHER INFORMATION: Description of Artificial Sequence:probe for
      THO1 locus with 8x CATT repeats

<400> SEQUENCE: 143
cccattggcc tgttcctccc ttatttccct cattcattca ttcattcatt cattcattca    60
ttcacc    66

```
<210> SEQ ID NO 144
<211> LENGTH: 70
<212> TYPE: DNA
<213> ORGANISM: Artificial Sequence
<220> FEATURE:
<223> OTHER INFORMATION: Description of Artificial Sequence:probe for
      THO1 locus with 9x CATT repeats

<400> SEQUENCE: 144
cccattggcc tgttcctccc ttatttccct cattcattca ttcattcatt cattcattca      60
ttcattcacc                                                             70

<210> SEQ ID NO 145
<211> LENGTH: 58
<212> TYPE: DNA
<213> ORGANISM: Artificial Sequence
<220> FEATURE:
<223> OTHER INFORMATION: Description of Artificial Sequence:probe for
      THO locus with 2 base pair mismatch

<400> SEQUENCE: 145
cccattggcc tgttcctccc ttatttccct cattcattca ttcattcatt cattcagc        58

<210> SEQ ID NO 146
<211> LENGTH: 58
<212> TYPE: DNA
<213> ORGANISM: Artificial Sequence
<220> FEATURE:
<223> OTHER INFORMATION: Description of Artificial Sequence:probe to THO
      locus with A to C mutation 3 from 3' terminus

<400> SEQUENCE: 146
cccattggcc tgttcctccc ttatttccct cattcattca ttcattcatt cattcccc        58

<210> SEQ ID NO 147
<211> LENGTH: 58
<212> TYPE: DNA
<213> ORGANISM: Artificial Sequence
<220> FEATURE:
<223> OTHER INFORMATION: Description of Artificial Sequence:probe to THO
      locus with A to G mutation 3 from 3' terminus

<400> SEQUENCE: 147
cccattggcc tgttcctccc ttatttccct cattcattca ttcattcatt cattcgcc        58

<210> SEQ ID NO 148
<211> LENGTH: 58
<212> TYPE: DNA
<213> ORGANISM: Artificial Sequence
<220> FEATURE:
<223> OTHER INFORMATION: Description of Artificial Sequence:probe to THO
      locus with additional base pair mismatches 4 from
      3' terminus

<400> SEQUENCE: 148
cccattggcc tgttcctccc ttatttccct cattcattca ttcattcatt cattgacc        58

<210> SEQ ID NO 149
<211> LENGTH: 58
<212> TYPE: DNA
<213> ORGANISM: Artificial Sequence
<220> FEATURE:
<223> OTHER INFORMATION: Description of Artificial Sequence:probe for
      THO locus with additional base pair mismatches 4 from
      3' terminus

<400> SEQUENCE: 149
```

```
cccattggcc tgttcctccc ttatttccct cattcattca ttcattcatt cattaacc      58

<210> SEQ ID NO 150
<211> LENGTH: 48
<212> TYPE: DNA
<213> ORGANISM: Artificial Sequence
<220> FEATURE:
<223> OTHER INFORMATION: Description of Artificial Sequence:TPOX allele

<400> SEQUENCE: 150
ggcacttagg gaaccctcac tgaatgaatg aatgaatgaa tgaatatt                 48

<210> SEQ ID NO 151
<211> LENGTH: 52
<212> TYPE: DNA
<213> ORGANISM: Artificial Sequence
<220> FEATURE:
<223> OTHER INFORMATION: Description of Artificial Sequence:TPOX allele

<400> SEQUENCE: 151
ggcacttagg gaaccctcac tgaatgaatg aatgaatgaa tgaatgaata tt            52

<210> SEQ ID NO 152
<211> LENGTH: 56
<212> TYPE: DNA
<213> ORGANISM: Artificial Sequence
<220> FEATURE:
<223> OTHER INFORMATION: Description of Artificial Sequence:TPOX allele

<400> SEQUENCE: 152
ggcacttagg gaaccctcac tgaatgaatg aatgaatgaa tgaatgaatg aatatt        56

<210> SEQ ID NO 153
<211> LENGTH: 60
<212> TYPE: DNA
<213> ORGANISM: Artificial Sequence
<220> FEATURE:
<223> OTHER INFORMATION: Description of Artificial Sequence:TPOX allele

<400> SEQUENCE: 153
ggcacttagg gaaccctcac tgaatgaatg aatgaatgaa tgaatgaatg aatgaatatt    60

<210> SEQ ID NO 154
<211> LENGTH: 63
<212> TYPE: DNA
<213> ORGANISM: Unknown
<220> FEATURE:
<223> OTHER INFORMATION: :

<400> SEQUENCE: 154
gcacttaggg aaccctcact gaatgaatga atgaatgaat gaatgaatga atgaatgaat    60
att                                                                  63

<210> SEQ ID NO 155
<211> LENGTH: 68
<212> TYPE: DNA
<213> ORGANISM: Artificial Sequence
<220> FEATURE:
<223> OTHER INFORMATION: Description of Artificial Sequence:TPOX allele

<400> SEQUENCE: 155
ggcacttagg gaaccctcac tgaatgaatg aatgaatgaa tgaatgaatg aatgaatgaa    60
tgaatatt                                                             68
```

<210> SEQ ID NO 156
<211> LENGTH: 72
<212> TYPE: DNA
<213> ORGANISM: Artificial Sequence
<220> FEATURE:
<223> OTHER INFORMATION: Description of Artificial Sequence:TPOX allele

<400> SEQUENCE: 156
ggcacttagg gaaccctcac tgaatgaatg aatgaatgaa tgaatgaatg aatgaatgaa    60
tgaatgaata tt                                                       72

<210> SEQ ID NO 157
<211> LENGTH: 76
<212> TYPE: DNA
<213> ORGANISM: Artificial Sequence
<220> FEATURE:
<223> OTHER INFORMATION: Description of Artificial Sequence:TPOX allele

<400> SEQUENCE: 157
ggcacttagg gaaccctcac tgaatgaatg aatgaatgaa tgaatgaatg aatgaatgaa    60
tgaatgaatg aatatt                                                   76

<210> SEQ ID NO 158
<211> LENGTH: 241
<212> TYPE: DNA
<213> ORGANISM: Homo sapiens
<220> FEATURE:
<223> OTHER INFORMATION: target allele 6 with 6 TGAA repeats

<400> SEQUENCE: 158
ggcacttagg gaaccctcac tgaatgaatg aatgaatgaa tgaatgtttg ggcaaataaa    60
cgctgacaag gacagaaggg cctagcggga agggaacagg agtaagacca gcgcacagcc   120
cgacttgtgt tcagaagacc tgggattgga cctgaggatt caattttgga tgaatctctt   180
aattaacctg tgtggttccc agttcctccc ctgagcgccc aggacagtag agtcaacctc   240
a                                                                  241

<210> SEQ ID NO 159
<211> LENGTH: 245
<212> TYPE: DNA
<213> ORGANISM: Homo sapiens
<220> FEATURE:
<223> OTHER INFORMATION: target allele 7 with 7 TGAA repeats

<400> SEQUENCE: 159
ggcacttagg gaaccctcac tgaatgaatg aatgaatgaa tgaatgaatg tttgggcaaa    60
taaacgctga caaggacaga agggcctagc gggaagggaa caggagtaag accagcgcac   120
agcccgactt gtgttcagaa gacctgggat tggacctgag gattcaattt tggatgaatc   180
tcttaattaa cctgtgtggt tcccagttcc tcccctgagc gcccaggaca gtagagtcaa   240
cctca                                                              245

<210> SEQ ID NO 160
<211> LENGTH: 249
<212> TYPE: DNA
<213> ORGANISM: Homo sapiens
<220> FEATURE:
<223> OTHER INFORMATION: target allele 8 with 8 TGAA repeats

<400> SEQUENCE: 160
ggcacttagg gaaccctcac tgaatgaatg aatgaatgaa tgaatgaatg aatgtttggg    60

```
caaatAaacg ctgacaagga cagaagggcc tagcgggaag ggaacaggag taagaccagc    120
gcacagcccg acttgtgttc agaagacctg ggattggacc tgaggattca attttggatg    180
aatctcttaa ttaacctgtg tggttcccag ttcctcccct gagcgccag  gacagtagag    240 tcaacctca                                                            249
```

```
<210> SEQ ID NO 161
<211> LENGTH: 253
<212> TYPE: DNA
<213> ORGANISM: Homo sapiens
<220> FEATURE:
<223> OTHER INFORMATION: target allele 9 with 9 TGAA repeats

<400> SEQUENCE: 161
```

```
ggcacttagg gaaccctcac tgaatgaatg aatgaatgaa tgaatgaatg aatgaatgtt    60
tgggcaaata acgctgaca  aggacagaag ggcctagcgg gaagggaaca ggagtaagac    120
cagcgcacag cccgacttgt gttcagaaga cctgggattg gacctgagga ttcaattttg    180
gatgaatctc ttaattaacc tgtgtggttc ccagttcctc ccctgagcgc ccaggacagt    240
agagtcaacc tca                                                       253
```

```
<210> SEQ ID NO 162
<211> LENGTH: 257
<212> TYPE: DNA
<213> ORGANISM: Homo sapiens
<220> FEATURE:
<223> OTHER INFORMATION: target allele 10 with 10 TGAA repeats

<400> SEQUENCE: 162
```

```
ggcacttagg gaaccctcac tgaatgaatg aatgaatgaa tgaatgaatg aatgaatgaa    60
tgtttgggca aataaacgct gacaaggaca gaagggccta gcgggaaggg aacaggagta    120
agaccagcgc acagcccgac ttgtgttcag aagacctggg attggacctg aggattcaat    180
tttggatgaa tctcttaatt aacctgtgtg gttcccagtt cctcccctga gcgcccagga    240
cagtagagtc aacctca                                                   257
```

```
<210> SEQ ID NO 163
<211> LENGTH: 261
<212> TYPE: DNA
<213> ORGANISM: Homo sapiens
<220> FEATURE:
<223> OTHER INFORMATION: target allele 11 with 11 TGAA repeats

<400> SEQUENCE: 163
```

```
ggcacttagg gaaccctcac tgaatgaatg aatgaatgaa tgaatgaatg aatgaatgaa    60
tgaatgtttg gcaaataaa  cgctgacaag gacagaaggg cctagcggga agggaacagg    120
agtaagacca gcgcacagcc cgacttgtgt tcagaagacc tgggattgga cctgaggatt    180
caattttgga tgaatctctt aattaacctg tgtggttccc agttcctccc ctgagcgccc    240
aggacagtag agtcaacctc a                                              261
```

```
<210> SEQ ID NO 164
<211> LENGTH: 265
<212> TYPE: DNA
<213> ORGANISM: Homo sapiens
<220> FEATURE:
<223> OTHER INFORMATION: target allele 12 with 12 TGAA repeats

<400> SEQUENCE: 164
```

```
ggcacttagg gaaccctcac tgaatgaatg aatgaatgaa tgaatgaatg aatgaatgaa    60
```

```
tgaatgaatg tttgggcaaa taaacgctga caaggacaga agggcctagc gggaagggaa      120
caggagtaag accagcgcac agcccgactt gtgttcagaa gacctgggat tggacctgag      180
gattcaattt tggatgaatc tcttaattaa cctgtgtggt tcccagttcc tcccctgagc      240
gcccaggaca gtagagtcaa cctca                                           265
```

```
<210> SEQ ID NO 165
<211> LENGTH: 269
<212> TYPE: DNA
<213> ORGANISM: Homo sapiens
<220> FEATURE:
<223> OTHER INFORMATION: target allele 13 with 13 TGAA repeats

<400> SEQUENCE: 165
ggcacttagg gaaccctcac tgaatgaatg aatgaatgaa tgaatgaatg aatgaatgaa       60
tgaatgaatg aatgtttggg caaataaacg ctgacaagga cagaagggcc tagcgggaag      120
ggaacaggag taagaccagc gcacagcccg acttgtgttc agaagacctg ggattggacc      180
tgaggattca attttggatg aatctcttaa ttaacctgtg tggttcccag ttcctcccct      240
gagcgcccag gacagtagag tcaacctca                                       269
```

```
<210> SEQ ID NO 166
<211> LENGTH: 24
<212> TYPE: DNA
<213> ORGANISM: Homo sapiens
<220> FEATURE:
<223> OTHER INFORMATION: probe to E. coli

<400> SEQUENCE: 166
cactttatgc ttccggctcg tatg                                             24
```

```
<210> SEQ ID NO 167
<211> LENGTH: 26
<212> TYPE: DNA
<213> ORGANISM: Homo sapiens
<220> FEATURE:
<223> OTHER INFORMATION: probe to E. coli

<400> SEQUENCE: 167
gggataggtt acgttggtgt agatgg                                           26
```

```
<210> SEQ ID NO 168
<211> LENGTH: 20
<212> TYPE: DNA
<213> ORGANISM: Escherichia coli
<220> FEATURE:
<223> OTHER INFORMATION: common probe for E. coli lac

<400> SEQUENCE: 168
gttgggaagg gcgatcggtg                                                  20
```

```
<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence:probe to E.
      coli lac

<400> SEQUENCE: 169
gggatgtgct gcaaggcgat t                                                21
```

```
<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence:probe for
      lac deletion in E. coli

<400> SEQUENCE: 170
ggattcactg gccgtcgtgg                                              20

<210> SEQ ID NO 171
<211> LENGTH: 65
<212> TYPE: DNA
<213> ORGANISM: Cytomegalovirus
<220> FEATURE:
<223> OTHER INFORMATION: target for cytomegalovirus

<400> SEQUENCE: 171
cgtgtatgcc actttgatat tacacccatg aacgtgctca tcgacgtgaa cccgcacaac   60
gagct                                                              65

<210> SEQ ID NO 172
<211> LENGTH: 65
<212> TYPE: DNA
<213> ORGANISM: Cytomegalovirus
<220> FEATURE:
<223> OTHER INFORMATION: target for cytomegalovirus

<400> SEQUENCE: 172
cgttgtgcgg gttcacgtcg atgagcacgt tcatgggtgt aatatcaaag tggcatacac   60
gagct                                                              65

<210> SEQ ID NO 173
<211> LENGTH: 65
<212> TYPE: DNA
<213> ORGANISM: Cytomegalovirus
<220> FEATURE:
<223> OTHER INFORMATION: target for cytomegalovirus

<400> SEQUENCE: 173
cgtgtatgcc actttgatat tacacccgtg aacgtgctca tcgacgtgaa cccgcacaac   60
gagct                                                              65

<210> SEQ ID NO 174
<211> LENGTH: 65
<212> TYPE: DNA
<213> ORGANISM: Cytomegalovirus
<220> FEATURE:
<223> OTHER INFORMATION: target for mutant cytomegalovirus

<400> SEQUENCE: 174
cgttgtgcgg gttcacgtcg atgagcacgt tcacgggtgt aatatcaaag tggcatacac   60
gagct                                                              65

<210> SEQ ID NO 175
<211> LENGTH: 26
<212> TYPE: DNA
<213> ORGANISM: Cytomegalovirus
<220> FEATURE:
<223> OTHER INFORMATION: probe for cytomegalovirus

<400> SEQUENCE: 175
tcacacagga aacagctatg accatg                                       26
```

<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence:M13 forward
      probe
<223> OTHER INFORMATION: M13 forward probe

<400> SEQUENCE: 176
gcaaggcgat taagttgggt aacg                                          24

<210> SEQ ID NO 177
<211> LENGTH: 29
<212> TYPE: DNA
<213> ORGANISM: Artificial Sequence
<220> FEATURE:
<223> OTHER INFORMATION: Description of Artificial Sequence:probe which
      forms hairpin when allowed to self-anneal

<400> SEQUENCE: 177
atgaacgtac gtcggatgag cacgttcat                                     29

<210> SEQ ID NO 178
<211> LENGTH: 29
<212> TYPE: DNA
<213> ORGANISM: Artificial Sequence
<220> FEATURE:
<223> OTHER INFORMATION: Description of Artificial Sequence:probe which
      forms hairpin when allowed to self-anneal

<400> SEQUENCE: 178
gtgaacgtac gtcggatgag cacgttcat                                     29

<210> SEQ ID NO 179
<211> LENGTH: 29
<212> TYPE: DNA
<213> ORGANISM: Artificial Sequence
<220> FEATURE:
<223> OTHER INFORMATION: Description of Artificial Sequence:probe which
      forms hairpin when allowed to self-anneal

<400> SEQUENCE: 179
ataaacgtac gtcggatgag cacgttcat                                     29

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence:probe which
      forms hairpin when allowed to self-anneal

<400> SEQUENCE: 180
ataaacgtac gtcggatgag cacg                                          24

<210> SEQ ID NO 181
<211> LENGTH: 40
<212> TYPE: DNA
<213> ORGANISM: Hepatitis C virus
<220> FEATURE:
<223> OTHER INFORMATION: probe for Hepatitis C

<400> SEQUENCE: 181
ctgctagccg agtagtgttg ggtcgcgaaa ggccttgtgg                         40

```
<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence:35S promoter
      PCR primer

<400> SEQUENCE: 182
gatagtggga ttgtgcgtca                                              20

<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence:35S promoter
      PCR primer

<400> SEQUENCE: 183
gctcctacaa atgccatca                                               19

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence:NOS
      terminator PCR primer

<400> SEQUENCE: 184
ttatcctagt ttgcgcgcta                                              20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence:NOS
      terminator PCR primer

<400> SEQUENCE: 185
gaatcctgct gccggtcttg                                              20

<210> SEQ ID NO 186
<211> LENGTH: 15
<212> TYPE: DNA
<213> ORGANISM: Artificial Sequence
<220> FEATURE:
<223> OTHER INFORMATION: Description of Artificial Sequence:35S probe

<400> SEQUENCE: 186
gcaagtggat tgatg                                                   15

<210> SEQ ID NO 187
<211> LENGTH: 17
<212> TYPE: DNA
<213> ORGANISM: Artificial Sequence
<220> FEATURE:
<223> OTHER INFORMATION: Description of Artificial Sequence:35S probe

<400> SEQUENCE: 187
ccaaccacgt cttcaaa                                                 17

<210> SEQ ID NO 188
<211> LENGTH: 16
```

```
<212> TYPE: DNA
<213> ORGANISM: Artificial Sequence
<220> FEATURE:
<223> OTHER INFORMATION: Description of Artificial Sequence:NOS probe

<400> SEQUENCE: 188
tttatgagat gggttt                                                    16

<210> SEQ ID NO 189
<211> LENGTH: 15
<212> TYPE: DNA
<213> ORGANISM: Artificial Sequence
<220> FEATURE:
<223> OTHER INFORMATION: Description of Artificial Sequence:NOS probe

<400> SEQUENCE: 189
atgattagag tcccg                                                     15

<210> SEQ ID NO 190
<211> LENGTH: 30
<212> TYPE: DNA
<213> ORGANISM: Artificial Sequence
<220> FEATURE:
<223> OTHER INFORMATION: Description of Artificial Sequence:probe which
      can be used for pyrophosphorylation only if the 3' end
      of the target results from previous
      pyrophosphorylation reax.

<400> SEQUENCE: 190
ggtgcatctg tccagtgagg agaagtctgc                                     30

<210> SEQ ID NO 191
<211> LENGTH: 30
<212> TYPE: DNA
<213> ORGANISM: Artificial Sequence
<220> FEATURE:
<223> OTHER INFORMATION: Description of Artificial Sequence:probe which
      can be used for pyrophosphorylation only if the 3' end
      of the target results from a previous
      phosphorylation reax.

<400> SEQUENCE: 191
tggtgcatct gtccagtgag gagaagtctg                                     30

<210> SEQ ID NO 192
<211> LENGTH: 30
<212> TYPE: DNA
<213> ORGANISM: Artificial Sequence
<220> FEATURE:
<223> OTHER INFORMATION: Description of Artificial Sequence:probe which
      can be used for pyrophosphorylation only if the 3' end
      of the target results from a previous
      pyrophospylation reax.

<400> SEQUENCE: 192
agacttctcc tcactggaca gatgcaccat                                     30

<210> SEQ ID NO 193
<211> LENGTH: 30
<212> TYPE: DNA
<213> ORGANISM: Artificial Sequence
<220> FEATURE:
<223> OTHER INFORMATION: Description of Artificial Sequence:probe which
      can be used for pyrophosphorylation only if the 3' end
      of the target results from a previous
      pyrophosphorylation reax.

<400> SEQUENCE: 193
```

```
atggtgcatc tgtccagtga ggagaagtct                                    30

<210> SEQ ID NO 194
<211> LENGTH: 53
<212> TYPE: DNA
<213> ORGANISM: Artificial Sequence
<220> FEATURE:
<223> OTHER INFORMATION: Description of Artificial Sequence:wild-type
      target

<400> SEQUENCE: 194
ttgcagagaa agacaatata gttcttggag aaggtggaat cacactgagt gga          53

<210> SEQ ID NO 195
<211> LENGTH: 53
<212> TYPE: DNA
<213> ORGANISM: Artificial Sequence
<220> FEATURE:
<223> OTHER INFORMATION: Description of Artificial Sequence:mutant
      target

<400> SEQUENCE: 195
ttgcagagaa agacaatata gttctttgag aaggtggaat cacactgagt gga          53

<210> SEQ ID NO 196
<211> LENGTH: 89
<212> TYPE: DNA
<213> ORGANISM: Artificial Sequence
<220> FEATURE:
<223> OTHER INFORMATION: Description of Artificial Sequence:probe to
      wild-type targets 10870 and 10994

<400> SEQUENCE: 196
gaactatatt gtctttctct gattctgact cgtcatgtct cagctttagt ttaatacgac   60
tcactatagg gctcagtgtg attccacct                                     89

<210> SEQ ID NO 197
<211> LENGTH: 23
<212> TYPE: DNA
<213> ORGANISM: Artificial Sequence
<220> FEATURE:
<223> OTHER INFORMATION: Description of Artificial Sequence:probe which
      hybridizes to 10870 and 10994

<400> SEQUENCE: 197
ctaaagctga gacatgacga gtc                                           23

<210> SEQ ID NO 198
<211> LENGTH: 22
<212> TYPE: DNA
<213> ORGANISM: Artificial Sequence
<220> FEATURE:
<223> OTHER INFORMATION: Description of Artificial Sequence:probe which
      hybridizes to only to wild-type target

<400> SEQUENCE: 198
ctcagtgtga ttccacttca cc                                            22

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence:probe which
      hybridizes only to mutant target

<400> SEQUENCE: 199
```

```
ctcagtgtga ttccaccttc aca                                              23

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence:CAH reverse
      probe (CYP21 only)

<400> SEQUENCE: 200
ccagagcagg gagtagtctc                                                  20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence:CAH forward
      probe

<400> SEQUENCE: 201
gcatatagag catggctgtg                                                  20

<210> SEQ ID NO 202
<211> LENGTH: 19
<212> TYPE: DNA
<213> ORGANISM: Artificial Sequence
<220> FEATURE:
<223> OTHER INFORMATION: Description of Artificial Sequence:CAH forward
      probe (CYP21 only)

<400> SEQUENCE: 202
cctgtccttg ggagactac                                                   19

<210> SEQ ID NO 203
<211> LENGTH: 18
<212> TYPE: DNA
<213> ORGANISM: Artificial Sequence
<220> FEATURE:
<223> OTHER INFORMATION: Description of Artificial Sequence:CAH reverse
      probe

<400> SEQUENCE: 203
cccagttcgt ggtctagc                                                    18

<210> SEQ ID NO 204
<211> LENGTH: 18
<212> TYPE: DNA
<213> ORGANISM: Artificial Sequence
<220> FEATURE:
<223> OTHER INFORMATION: Description of Artificial Sequence:CAH reverse
      probe

<400> SEQUENCE: 204
tcctcactca tccccaac                                                    18

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence:CAH forward
      probe

<400> SEQUENCE: 205
```

```
gaaatacgga cgtcccaagg c                                          21
```

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence:CAH reverse
      probe (CYP21 only)

<400> SEQUENCE: 206

```
ctttccagag cagggagtag                                            20
```

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence:CAH forward
      probe (CYP21 only)

<400> SEQUENCE: 207

```
ccggacctgt ccttgggaga                                            20
```

<210> SEQ ID NO 208
<211> LENGTH: 40
<212> TYPE: DNA
<213> ORGANISM: Homo sapiens
<220> FEATURE:
<223> OTHER INFORMATION: CAH target 1; mutation site 1

<400> SEQUENCE: 208

```
agaagcccgg ggcaagaggc aggaggtgga ggctccggag                      40
```

<210> SEQ ID NO 209
<211> LENGTH: 40
<212> TYPE: DNA
<213> ORGANISM: Homo sapiens
<220> FEATURE:
<223> OTHER INFORMATION: CAH target 2; mutation site 2

<400> SEQUENCE: 209

```
agcttgtctg caggaggagc tggggctgg agggtgggaa                       40
```

<210> SEQ ID NO 210
<211> LENGTH: 40
<212> TYPE: DNA
<213> ORGANISM: Homo sapiens
<220> FEATURE:
<223> OTHER INFORMATION: CAH target 3; mutation site 3

<400> SEQUENCE: 210

```
tccgaaggtg aggtaacagt tgatgctgca ggtgaggaga                      40
```

<210> SEQ ID NO 211
<211> LENGTH: 40
<212> TYPE: DNA
<213> ORGANISM: Homo sapiens
<220> FEATURE:
<223> OTHER INFORMATION: CAH target 4; mutation site 4

<400> SEQUENCE: 211

```
tccactgcag ccatgtgcaa gtgcccttcc aggagctgtc                      40
```

<210> SEQ ID NO 212
<211> LENGTH: 40

```
<212> TYPE: DNA
<213> ORGANISM: Homo sapiens
<220> FEATURE:
<223> OTHER INFORMATION: CAH target 5; mutation site 5

<400> SEQUENCE: 212
tcgtggtcta gctcctccta cagtcgctgc tgaatctggg                    40

<210> SEQ ID NO 213
<211> LENGTH: 40
<212> TYPE: DNA
<213> ORGANISM: Homo sapiens
<220> FEATURE:
<223> OTHER INFORMATION: CAH target 6; mutation site 6

<400> SEQUENCE: 213
gctaagggca caacgggcca caggcgcagc acctcggcga                    40

<210> SEQ ID NO 214
<211> LENGTH: 40
<212> TYPE: DNA
<213> ORGANISM: Homo sapiens
<220> FEATURE:
<223> OTHER INFORMATION: CAH target 7; mutation site 2

<400> SEQUENCE: 214
cagcttgtct gcaggaggag ttgggggctg gagggtggga                    40

<210> SEQ ID NO 215
<211> LENGTH: 40
<212> TYPE: DNA
<213> ORGANISM: Homo sapiens
<220> FEATURE:
<223> OTHER INFORMATION: CAH target 8; mutation site 6

<400> SEQUENCE: 215
ggctaagggc acaacgggcc gcaggcgcag cacctcggcg                    40

<210> SEQ ID NO 216
<211> LENGTH: 18
<212> TYPE: DNA
<213> ORGANISM: Homo sapiens
<220> FEATURE:
<223> OTHER INFORMATION: CAH oligo 6 for mutation site 1

<400> SEQUENCE: 216
cggagcctcc acctcccg                                            18

<210> SEQ ID NO 217
<211> LENGTH: 18
<212> TYPE: DNA
<213> ORGANISM: Homo sapiens
<220> FEATURE:
<223> OTHER INFORMATION: CAH oligo 2 for mutation site 2

<400> SEQUENCE: 217
caccctccag cccccagc                                            18

<210> SEQ ID NO 218
<211> LENGTH: 18
<212> TYPE: DNA
<213> ORGANISM: Homo sapiens
<220> FEATURE:
<223> OTHER INFORMATION: CAH oligo 1 for mutation site 1

<400> SEQUENCE: 218
```

```
cggagcctcc acctcctg                                                    18

<210> SEQ ID NO 219
<211> LENGTH: 19
<212> TYPE: DNA
<213> ORGANISM: Homo sapiens
<220> FEATURE:
<223> OTHER INFORMATION: CAH oligo 3 for mutation site 3

<400> SEQUENCE: 219
cctcacctgc agcatcaac                                                   19

<210> SEQ ID NO 220
<211> LENGTH: 18
<212> TYPE: DNA
<213> ORGANISM: Homo sapiens
<220> FEATURE:
<223> OTHER INFORMATION: CAH oligo 7 for mutation site 2

<400> SEQUENCE: 220
caccctccag cccccaac                                                    18

<210> SEQ ID NO 221
<211> LENGTH: 19
<212> TYPE: DNA
<213> ORGANISM: Homo sapiens
<220> FEATURE:
<223> OTHER INFORMATION: CAH oligo 8 for mutation site 3

<400> SEQUENCE: 221
cctcacctgc agcatcatc                                                   19

<210> SEQ ID NO 222
<211> LENGTH: 15
<212> TYPE: DNA
<213> ORGANISM: Homo sapiens
<220> FEATURE:
<223> OTHER INFORMATION: CAH oligo 4 for mutation site 4

<400> SEQUENCE: 222
cctggaaggg cactt                                                       15

<210> SEQ ID NO 223
<211> LENGTH: 15
<212> TYPE: DNA
<213> ORGANISM: Homo sapiens
<220> FEATURE:
<223> OTHER INFORMATION: CAH oligo site 9 for mutation site 4

<400> SEQUENCE: 223
cctggaaggg cacgt                                                       15

<210> SEQ ID NO 224
<211> LENGTH: 18
<212> TYPE: DNA
<213> ORGANISM: Homo sapiens
<220> FEATURE:
<223> OTHER INFORMATION: CAH oligo 5 for mutation site 5

<400> SEQUENCE: 224
gattcagcag cgactgta                                                    18

<210> SEQ ID NO 225
<211> LENGTH: 18
<212> TYPE: DNA
<213> ORGANISM: Homo sapiens
```

```
<220> FEATURE:
<223> OTHER INFORMATION: CAH oligo 10 for mutation site 5

<400> SEQUENCE: 225
gattcagcag cgactgca                                              18

<210> SEQ ID NO 226
<211> LENGTH: 18
<212> TYPE: DNA
<213> ORGANISM: Homo sapiens
<220> FEATURE:
<223> OTHER INFORMATION: CAH oligo 11 for mutation site 6

<400> SEQUENCE: 226
cgaggtgctg cgcctgcg                                              18

<210> SEQ ID NO 227
<211> LENGTH: 18
<212> TYPE: DNA
<213> ORGANISM: Homo sapiens
<220> FEATURE:
<223> OTHER INFORMATION: CAH oligo 12 for mutation site 6

<400> SEQUENCE: 227
cgaggtgctg cgcctgtg                                              18

<210> SEQ ID NO 228
<211> LENGTH: 20
<212> TYPE: DNA
<213> ORGANISM: Homo sapiens
<220> FEATURE:
<223> OTHER INFORMATION: CAH oligo 23 for mutation site 7

<400> SEQUENCE: 228
gggatcacat cgtggagatg                                            20

<210> SEQ ID NO 229
<211> LENGTH: 20
<212> TYPE: DNA
<213> ORGANISM: Homo sapiens
<220> FEATURE:
<223> OTHER INFORMATION: CAH oligo 24 for mutation site 7

<400> SEQUENCE: 229
gggatcacaa cgaggagaag                                            20

<210> SEQ ID NO 230
<211> LENGTH: 51
<212> TYPE: DNA
<213> ORGANISM: Artificial Sequence
<220> FEATURE:
<223> OTHER INFORMATION: Description of Artificial Sequence:primer for
      PstI restriction site

<400> SEQUENCE: 230
gcttaagctg caggcatat gtggtgatga tatcgtgggt gagttcattt a           51

<210> SEQ ID NO 231
<211> LENGTH: 51
<212> TYPE: DNA
<213> ORGANISM: Artificial Sequence
<220> FEATURE:
<223> OTHER INFORMATION: Description of Artificial Sequence:primer for
      PstI restriction site

<400> SEQUENCE: 231
```
gcttaagctg cagggccatg gtggtgatga tatcgtgggt gagttcattt t        51

<210> SEQ ID NO 232
<211> LENGTH: 34
<212> TYPE: DNA
<213> ORGANISM: Artificial Sequence
<220> FEATURE:
<223> OTHER INFORMATION: Description of Artificial Sequence:probe for
      oligo 53

<400> SEQUENCE: 232
ctggaaaatg aactcaccca cgatatcatc acca                           34

<210> SEQ ID NO 233
<211> LENGTH: 42
<212> TYPE: DNA
<213> ORGANISM: Artificial Sequence
<220> FEATURE:
<223> OTHER INFORMATION: Description of Artificial Sequence:probe for
      oligo 53

<400> SEQUENCE: 233
agcttggtga tgatatcgtg ggtgagttca ttttccaggt ac                  42

<210> SEQ ID NO 234
<211> LENGTH: 34
<212> TYPE: DNA
<213> ORGANISM: Artificial Sequence
<220> FEATURE:
<223> OTHER INFORMATION: Description of Artificial Sequence:probe for
      oligo 54

<400> SEQUENCE: 234
ctggtaaatg aactcaccca cgatatcatc acca                           34

<210> SEQ ID NO 235
<211> LENGTH: 42
<212> TYPE: DNA
<213> ORGANISM: Artificial Sequence
<220> FEATURE:
<223> OTHER INFORMATION: Description of Artificial Sequence:probe for
      oligo 54

<400> SEQUENCE: 235
agcttggtga tgatatcgtg ggtgagttca tttaccaggt ac                  42

<210> SEQ ID NO 236
<211> LENGTH: 29
<212> TYPE: DNA
<213> ORGANISM: Artificial Sequence
<220> FEATURE:
<223> OTHER INFORMATION: Description of Artificial Sequence:contains
      PstI restriction site

<400> SEQUENCE: 236
atgatgctgc agcaggaaac agctatgac                                 29

<210> SEQ ID NO 237
<211> LENGTH: 29
<212> TYPE: DNA
<213> ORGANISM: Artificial Sequence
<220> FEATURE:
<223> OTHER INFORMATION: Description of Artificial Sequence:contains
      PstI restriction site

<400> SEQUENCE: 237
atgatgctgc aggttttccc agtcacgac                                 29

<210> SEQ ID NO 238
<211> LENGTH: 82
<212> TYPE: DNA
<213> ORGANISM: Artificial Sequence
<220> FEATURE:
<223> OTHER INFORMATION: Description of Artificial Sequence:circular
      probe

<400> SEQUENCE: 238
acaacgtcgt gactaggatc acgctaatgc ttcagcctga tgagtccgat cagcctgatg      60
agtccgatct ggccgtcgtt tt                                               82

<210> SEQ ID NO 239
<211> LENGTH: 30
<212> TYPE: DNA
<213> ORGANISM: Artificial Sequence
<220> FEATURE:
<223> OTHER INFORMATION: Description of Artificial Sequence:wt target

<400> SEQUENCE: 239
cagtcacgac gttgtaaaac gacggccagt                                       30

<210> SEQ ID NO 240
<211> LENGTH: 30
<212> TYPE: DNA
<213> ORGANISM: Artificial Sequence
<220> FEATURE:
<223> OTHER INFORMATION: Description of Artificial Sequence:mutant
      target

<400> SEQUENCE: 240
cagtcacgac gttgtgaaac gacggccagt                                       30

<210> SEQ ID NO 241
<211> LENGTH: 16
<212> TYPE: DNA
<213> ORGANISM: Artificial Sequence
<220> FEATURE:
<223> OTHER INFORMATION: Description of Artificial Sequence:extension
      probe

<400> SEQUENCE: 241
agcattagcg tgatcc                                                      16

<210> SEQ ID NO 242
<211> LENGTH: 16
<212> TYPE: DNA
<213> ORGANISM: Artificial Sequence
<220> FEATURE:
<223> OTHER INFORMATION: Description of Artificial Sequence:
      complementary probe

<400> SEQUENCE: 242
cagcctgatg agtccg                                                      16

<210> SEQ ID NO 243
<211> LENGTH: 24
<212> TYPE: DNA
<213> ORGANISM: Artificial Sequence
<220> FEATURE:
<223> OTHER INFORMATION: Description of Artificial Sequence:
      complementary to 11195 (wt) and 11194 (mutant) lacI

<400> SEQUENCE: 243
ttgtgccacg cggttgggaa tgta                                             24

<210> SEQ ID NO 244
<211> LENGTH: 25
<212> TYPE: DNA
<213> ORGANISM: Artificial Sequence
<220> FEATURE:
<223> OTHER INFORMATION: Description of Artificial Sequence:wild-type
      lacI

<400> SEQUENCE: 244
tacattccca accgcgtggc acaac                                          25

<210> SEQ ID NO 245
<211> LENGTH: 25
<212> TYPE: DNA
<213> ORGANISM: Artificial Sequence
<220> FEATURE:
<223> OTHER INFORMATION: Description of Artificial Sequence:mutant lacI

<400> SEQUENCE: 245
tacattccca accgcgtggc acaat                                          25

<210> SEQ ID NO 246
<211> LENGTH: 25
<212> TYPE: DNA
<213> ORGANISM: Artificial Sequence
<220> FEATURE:
<223> OTHER INFORMATION: Description of Artificial Sequence:
      complementary to 11193 (wt) and 11194 (mut) lacI

<400> SEQUENCE: 246
aactggcggg caaacagtcg ttgct                                          25

<210> SEQ ID NO 247
<211> LENGTH: 26
<212> TYPE: DNA
<213> ORGANISM: Artificial Sequence
<220> FEATURE:
<223> OTHER INFORMATION: Description of Artificial Sequence:wild-type
      lacI

<400> SEQUENCE: 247
agcaacgact gtttgcccgc cagttg                                         26

<210> SEQ ID NO 248
<211> LENGTH: 26
<212> TYPE: DNA
<213> ORGANISM: Artificial Sequence
<220> FEATURE:
<223> OTHER INFORMATION: Description of Artificial Sequence:mutant lacI

<400> SEQUENCE: 248
agcaacgact gtttgcccgc cagtta                                         26

<210> SEQ ID NO 249
<211> LENGTH: 17
<212> TYPE: DNA
<213> ORGANISM: Artificial Sequence
<220> FEATURE:
<223> OTHER INFORMATION: Description of Artificial Sequence:probe to
      wild-type lacI

<400> SEQUENCE: 249
tttgcccgcc agttgtt                                                   17

<210> SEQ ID NO 250

<211> LENGTH: 17
<212> TYPE: DNA
<213> ORGANISM: Artificial Sequence
<220> FEATURE:
<223> OTHER INFORMATION: Description of Artificial Sequence:probe to
      mutant lacI

<400> SEQUENCE: 250
tttgcccgcc agttatt                                                    17

<210> SEQ ID NO 251
<211> LENGTH: 15
<212> TYPE: DNA
<213> ORGANISM: Artificial Sequence
<220> FEATURE:
<223> OTHER INFORMATION: Description of Artificial Sequence:probe to
      Alu1 human gene

<400> SEQUENCE: 251 agacccatc tctaa                                                       15

<210> SEQ ID NO 252
<211> LENGTH: 17
<212> TYPE: DNA
<213> ORGANISM: Artificial Sequence
<220> FEATURE:
<223> OTHER INFORMATION: Description of Artificial Sequence:probe to
      Alu2 human gene

<400> SEQUENCE: 252
gcctgggtga cagagca                                                    17

<210> SEQ ID NO 253
<211> LENGTH: 68
<212> TYPE: DNA
<213> ORGANISM: Artificial Sequence
<220> FEATURE:
<223> OTHER INFORMATION: Description of Artificial Sequence:probe to
      Alu which forms a hairpin

<400> SEQUENCE: 253
ctccagcctc ggtgacagag caagaccctg tctcaaaaaa aaagcctcgg tgcagggtct     60
tgctctgt                                                              68

<210> SEQ ID NO 254
<211> LENGTH: 69
<212> TYPE: DNA
<213> ORGANISM: Artificial Sequence
<220> FEATURE:
<223> OTHER INFORMATION: Description of Artificial Sequence:probe to
      Alu which forms a hairpin

<400> SEQUENCE: 254
ctccagcctg agcaacacag caagaccctg tctcaaaaca aaacgcctga gccagggtct     60
tgctgtgtt                                                             69

<210> SEQ ID NO 255
<211> LENGTH: 34
<212> TYPE: DNA
<213> ORGANISM: Artificial Sequence
<220> FEATURE:
<223> OTHER INFORMATION: Description of Artificial Sequence:probe for
      cytochrome B

<400> SEQUENCE: 255
aaactgcagc ccctcagaat gatatttgtc ctca                                 34

```
<210> SEQ ID NO 256
<211> LENGTH: 35
<212> TYPE: DNA
<213> ORGANISM: Artificial Sequence
<220> FEATURE:
<223> OTHER INFORMATION: Description of Artificial Sequence:probe for
      cytochrome B

<400> SEQUENCE: 256
aaaaagcttc catccaacat ctcagcatga tgaaa                               35

<210> SEQ ID NO 257
<211> LENGTH: 12
<212> TYPE: DNA
<213> ORGANISM: Homo sapiens
<220> FEATURE:
<223> OTHER INFORMATION: Description of Artificial Sequence:human
      cytochrome B
<223> OTHER INFORMATION: human cytochrome B

<400> SEQUENCE: 257
ccagacgcct ca                                                        12

<210> SEQ ID NO 258
<211> LENGTH: 12
<212> TYPE: DNA
<213> ORGANISM: Homo sapiens
<220> FEATURE:
<223> OTHER INFORMATION: human cytochrome B

<400> SEQUENCE: 258
accttcacgc ca                                                        12

<210> SEQ ID NO 259
<211> LENGTH: 11
<212> TYPE: DNA
<213> ORGANISM: Unknown
<220> FEATURE:
<223> OTHER INFORMATION: Description of Unknown Organism:common probe to
      cytochrome B

<400> SEQUENCE: 259
tgccgagacg t                                                         11

<210> SEQ ID NO 260
<211> LENGTH: 12
<212> TYPE: DNA
<213> ORGANISM: chicken
<220> FEATURE:
<223> OTHER INFORMATION: Description of Artificial Sequence:chicken
      cytochrome B
<223> OTHER INFORMATION: chicken cytochrome B

<400> SEQUENCE: 260
gcagacacat cc                                                        12

<210> SEQ ID NO 261
<211> LENGTH: 12
<212> TYPE: DNA
<213> ORGANISM: chicken
<220> FEATURE:
<223> OTHER INFORMATION: chicken cytochrome B

<400> SEQUENCE: 261
ggaatctcca cg                                                        12
```

```
<210> SEQ ID NO 262
<211> LENGTH: 12
<212> TYPE: DNA
<213> ORGANISM: cow
<220> FEATURE:
<223> OTHER INFORMATION: bovine cytochrome B

<400> SEQUENCE: 262
acatacacgc aa                                                          12

<210> SEQ ID NO 263
<211> LENGTH: 12
<212> TYPE: DNA
<213> ORGANISM: dog
<220> FEATURE:
<223> OTHER INFORMATION: canine cytochrome B

<400> SEQUENCE: 263
atatgcacgc aa                                                          12

<210> SEQ ID NO 264
<211> LENGTH: 22
<212> TYPE: DNA
<213> ORGANISM: Homo sapiens
<220> FEATURE:
<223> OTHER INFORMATION: pcr probe for Factor V

<400> SEQUENCE: 264
tgcccagtgc ttaacaagac ca                                               22

<210> SEQ ID NO 265
<211> LENGTH: 20
<212> TYPE: DNA
<213> ORGANISM: Homo sapiens
<220> FEATURE:
<223> OTHER INFORMATION: probe for Factor V

<400> SEQUENCE: 265
tgttatcaca ctggtgctaa                                                  20

<210> SEQ ID NO 266
<211> LENGTH: 22
<212> TYPE: DNA
<213> ORGANISM: Homo sapiens
<220> FEATURE:
<223> OTHER INFORMATION: probe for wild-type Factor V

<400> SEQUENCE: 266
gacaaaatac ctgtattcct cg                                               22

<210> SEQ ID NO 267
<211> LENGTH: 22
<212> TYPE: DNA
<213> ORGANISM: Homo sapiens
<220> FEATURE:
<223> OTHER INFORMATION: Factor V Leiden mutant

<400> SEQUENCE: 267
gacaaaatac ctgtattcct tg                                               22

<210> SEQ ID NO 268
<211> LENGTH: 13
<212> TYPE: DNA
<213> ORGANISM: Homo sapiens
<220> FEATURE:
<223> OTHER INFORMATION: probe for Prothrombin mutant
```

<400> SEQUENCE: 268
gtgattctca gca                                                    13

<210> SEQ ID NO 269
<211> LENGTH: 13
<212> TYPE: DNA
<213> ORGANISM: Homo sapiens
<220> FEATURE:
<223> OTHER INFORMATION: probe for wild-type Prothrombin

<400> SEQUENCE: 269
gtgattctca gcg                                                    13

<210> SEQ ID NO 270
<211> LENGTH: 22
<212> TYPE: DNA
<213> ORGANISM: Homo sapiens
<220> FEATURE:
<223> OTHER INFORMATION: probe for wild-type Factor V

<400> SEQUENCE: 270
gacaaaatac ctgtattcct cg                                          22

<210> SEQ ID NO 271
<211> LENGTH: 16
<212> TYPE: DNA
<213> ORGANISM: Human Immunodeficiency Virus
<220> FEATURE:
<223> OTHER INFORMATION: HIV wild-type probe; site 1

<400> SEQUENCE: 271
ccatttagta ctgtct                                                 16

<210> SEQ ID NO 272
<211> LENGTH: 16
<212> TYPE: DNA
<213> ORGANISM: Human Immunodeficiency Virus
<220> FEATURE:
<223> OTHER INFORMATION: HIV mutant probe; site 1

<400> SEQUENCE: 272
ccatttagta ctgttt                                                 16

<210> SEQ ID NO 273
<211> LENGTH: 16
<212> TYPE: DNA
<213> ORGANISM: Human immunodeficiency virus
<220> FEATURE:
<223> OTHER INFORMATION: HIV wild-type probe; site 2

<400> SEQUENCE: 273
ctagttttct ccattt                                                 16

<210> SEQ ID NO 274
<211> LENGTH: 16
<212> TYPE: DNA
<213> ORGANISM: Human immunodeficiency virus
<220> FEATURE:
<223> OTHER INFORMATION: HIV mutant probe; site 2

<400> SEQUENCE: 274
ctagttttct ccatct                                                 16

<210> SEQ ID NO 275

```
<211> LENGTH: 16
<212> TYPE: DNA
<213> ORGANISM: Human immunodeficiency virus
<220> FEATURE:
<223> OTHER INFORMATION: HIV wild-type probe; site 3

<400> SEQUENCE: 275
ttctctgaaa tctact                                                         16

<210> SEQ ID NO 276
<211> LENGTH: 16
<212> TYPE: DNA
<213> ORGANISM: Human immunodeficiency virus
<220> FEATURE:
<223> OTHER INFORMATION: HIV mutant probe; site 3

<400> SEQUENCE: 276
ttctctgaaa tctatt                                                         16

<210> SEQ ID NO 277
<211> LENGTH: 50
<212> TYPE: DNA
<213> ORGANISM: Human immunodeficiency virus
<220> FEATURE:
<223> OTHER INFORMATION: HIV wild-type target

<400> SEQUENCE: 277
aaaaaagaca gtactaaatg gagaaaacta gtagatttca gagaacttaa                    50

<210> SEQ ID NO 278
<211> LENGTH: 50
<212> TYPE: DNA
<213> ORGANISM: Human immunodeficiency virus
<220> FEATURE:
<223> OTHER INFORMATION: HIV mutant target, site 1

<400> SEQUENCE: 278
aaaaaaaaca gtactaaatg gagaaaacta gtagatttca gagaacttaa                    50

<210> SEQ ID NO 279
<211> LENGTH: 50
<212> TYPE: DNA
<213> ORGANISM: Human immunodeficiency virus
<220> FEATURE:
<223> OTHER INFORMATION: HIV mutant target, site 2

<400> SEQUENCE: 279
aaaaaagaca gtactagatg gagaaaacta gtagatttca gagaacttaa                    50

<210> SEQ ID NO 280
<211> LENGTH: 50
<212> TYPE: DNA
<213> ORGANISM: Human immunodeficiency virus
<220> FEATURE:
<223> OTHER INFORMATION: HIV mutant target; site 3

<400> SEQUENCE: 280
aaaaaagaca gtactaaatg gagaaaacta atagatttca gagaacttaa                    50

<210> SEQ ID NO 281
<211> LENGTH: 22
<212> TYPE: DNA
<213> ORGANISM: Human immunodeficiency virus
<220> FEATURE:
<223> OTHER INFORMATION: prohibitin wild-type probe

<400> SEQUENCE: 281
```

```
ctgaacatgc ctgccaaaga cg                                              22
```

<210> SEQ ID NO 282
<211> LENGTH: 22
<212> TYPE: DNA
<213> ORGANISM: Human immunodeficiency virus
<220> FEATURE:
<223> OTHER INFORMATION: prohibitin mutant probe

<400> SEQUENCE: 282

```
ctgaacatgc ctgccaaaga tg                                              22
```

<210> SEQ ID NO 283
<211> LENGTH: 11
<212> TYPE: DNA
<213> ORGANISM: Human immunodeficiency virus
<220> FEATURE:
<223> OTHER INFORMATION: probe for 'colirep' sequence from E. coli

<400> SEQUENCE: 283

```
agtgactggg g                                                          11
```

<210> SEQ ID NO 284
<211> LENGTH: 21
<212> TYPE: DNA
<213> ORGANISM: Human immunodeficiency virus
<220> FEATURE:
<223> OTHER INFORMATION: probe for wild-type cytomegalovirus

<400> SEQUENCE: 284

```
gtacccacat tatagtttca c                                               21
```

<210> SEQ ID NO 285
<211> LENGTH: 21
<212> TYPE: DNA
<213> ORGANISM: Human immunodeficiency virus
<220> FEATURE:
<223> OTHER INFORMATION: probe for mutant cytomegalovirus

<400> SEQUENCE: 285

```
gtgcccacat tatagtttca c                                               21
```

<210> SEQ ID NO 286
<211> LENGTH: 41
<212> TYPE: DNA
<213> ORGANISM: Artificial Sequence
<220> FEATURE:
<223> OTHER INFORMATION: Description of Artificial Sequence:
      hypothetical example

<400> SEQUENCE: 286

```
agctaaggtc acaaccggtt tgccgcttta ttataccggg g                         41
```

<210> SEQ ID NO 287
<211> LENGTH: 62
<212> TYPE: DNA
<213> ORGANISM: Artificial Sequence
<220> FEATURE:
<223> OTHER INFORMATION: Description of Artificial Sequence:
      hypothetical example

<400> SEQUENCE: 287

```
cccggagaga cctccttaag gggccatatt atttcgtcga ttccagtgtt ggccaaacgg     60
at                                                                    62
```

```
<210> SEQ ID NO 288
<211> LENGTH: 77
<212> TYPE: DNA
<213> ORGANISM: Artificial Sequence
<220> FEATURE:
<223> OTHER INFORMATION: Description of Artificial Sequence:
      hypothetical example

<400> SEQUENCE: 288
gggcctctct ggaggaattc cccggtataa taaagcagct aaggtcacaa ccggtttgcc      60
gctttattat accgggg                                                    77

<210> SEQ ID NO 289
<211> LENGTH: 16
<212> TYPE: DNA
<213> ORGANISM: Artificial Sequence
<220> FEATURE:
<223> OTHER INFORMATION: Description of Artificial Sequence:
      hypothetical example

<400> SEQUENCE: 289
cccggagaga cctcct                                                     16

<210> SEQ ID NO 290
<211> LENGTH: 77
<212> TYPE: DNA
<213> ORGANISM: Artificial Sequence
<220> FEATURE:
<223> OTHER INFORMATION: Description of Artificial Sequence:
      hypothetical example

<400> SEQUENCE: 290
cccggagaga cctccttaag gggccatatt atttcgtcga ttccagtgtt ggccaaacgg     60
cgaaataata tggcccc                                                    77
```

DETECTION OF NUCLEIC ACID HYBRIDS

CROSS-REFERENCE TO RELATED APPLICATIONS

This application is a continuation of allowed U.S. patent application Ser. No. 09/358,972 filed Jul. 21, 1999, which is a continuation-in-part of U.S. patent application Ser. No. 09/252,436 filed Feb. 18, 1999, now U.S. Pat. No. 6,159,693 issued Dec. 12, 2000, which is a continuation-in-part of allowed Ser. No. 09/042,287, filed Mar. 13, 1998.

FIELD OF THE INVENTION

The invention relates to nucleic acid detection. More specifically, the invention relates to the detection of targeted, predetermined nucleic acid sequences in nucleic acid target hybrids, and the various applications of their detection.

BACKGROUND OF THE INVENTION

Methods to detect nucleic acids and to detect specific nucleic acids provide a foundation upon which the large and rapidly growing field of molecular biology is built. There is constant need for alternative methods and products. The reasons for selecting one method over another are varied, and include a desire to avoid radioactive materials, the lack of a license to use a technique, the cost or availability of reagents or equipment, the desire to minimize the time spent or the number of steps, the accuracy or sensitivity for a certain application, the ease of analysis, or the ability to automate the process.

The detection of nucleic acids or specific nucleic acids is often a portion of a process rather than an end in itself. There are many applications of the detection of nucleic acids in the art, and new applications are always being developed. The ability to detect and quantify nucleic acids is useful in detecting microorganisms, viruses and biological molecules, and thus affects many fields, including human and veterinary medicine, food processing and environmental testing. Additionally, the detection and/or quantification of specific biomolecules from biological samples (e.g. tissue, sputum, urine, blood, semen, saliva) has applications in forensic science, such as the identification and exclusion of criminal suspects and paternity testing as well as medical diagnostics.

Some general methods to detect nucleic acids are not dependent upon a priori knowledge of the nucleic acid sequence. A nucleic acid detection method that is not sequence specific, but is RNA specific is described in U.S. Pat. No. 4,735,897, where RNA is depolymerized using a polynucleotide phosphorylase (PNP) in the presence of phosphate or using a ribonuclease. PNP stops depolymerizing when a double-stranded RNA segment is encountered, sometimes as the form of secondary structure of single-stranded RNA, as is common in ribosomal RNA, transfer RNA, viral RNA, and the message portion of MRNA. PNP depolymerization of the polyadenylated tail of mRNA in the presence of inorganic phosphate forms ADP. Alternatively, depolymerization using a ribonuclease forms AMP. The formed AMP is converted to ADP with myokinase, and ADP is converted into ATP by pyruvate kinase or creatine phosphokinase. Either the ATP or the byproduct from the organophosphate co-reactant (pyruvate or creatine) is detected as an indirect method of detecting mRNA.

In U.S. Pat. No. 4,735,897, ATP is detected by a luciferase detection system. In the presence of ATP and oxygen, luciferase catalyzes the oxidation of luciferin, producing light that can then be quantified using a luminometer. Additional products of the reaction are AMP, pyrophosphate and oxyluciferin.

Duplex DNA can be detected using intercalating dyes such as ethidium bromide. Such dyes are also used to detect hybrid formation.

Hybridization methods to detect nucleic acids are dependent upon knowledge of the nucleic acid sequence. Many known nucleic acid detection techniques depend upon specific nucleic acid hybridization in which an oligonucleotide probe is hybridized or annealed to nucleic acid in the sample or on a blot, and the hybridized probes are detected.

A traditional type of process for the detection of hybridized nucleic acid uses labeled nucleic acid probes to hybridize to a nucleic acid sample. For example, in a Southern blot technique, a nucleic acid sample is separated in an agarose gel based on size and affixed to a membrane, denatured, and exposed to the labeled nucleic acid probe under hybridizing conditions. If the labeled nucleic acid probe forms a hybrid with the nucleic acid on the blot, the label is bound to the membrane. Probes used in Southern blots have been labeled with radioactivity, fluorescent dyes, digoxygenin, horseradish peroxidase, alkaline phosphatase and acridinium esters.

Another type of process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe. PCR-based methods are of limited use for the detection of nucleic acid of unknown sequence.

In a PCR method, the amplified nucleic acid product may be detected in a number of ways, e.g. incorporation of a labeled nucleotide into the amplified strand by using labeled primers. Primers used in PCR have been labeled with radioactivity, fluorescent dyes, digoxygenin, horseradish peroxidase, alkaline phosphatase, acridinium esters, biotin and jack bean urease. PCR products made with unlabeled primers may be detected in other ways, such as electrophoretic gel separation followed by dye-based visualization.

Fluorescence techniques are also known for the detection of nucleic acid hybrids. U.S. Pat. No. 5,691,146 describes the use of fluorescent hybridization probes that are fluorescence-quenched unless they are hybridized to the target nucleic acid sequence. U.S. Pat. No. 5,723,591 describes fluorescent hybridization probes that are fluorescence-quenched until hybridized to the target nucleic acid sequence, or until the probe is digested. Such techniques provide information about hybridization, and are of varying degrees of usefulness for the determination of single base variances in sequences. Some fluorescence techniques involve digestion of a nucleic acid hybrid in a 5'→3' direction to release a fluorescent signal from proximity to a fluorescence quencher, for example, TaqMan® (Perkin Elmer; U.S. Pat. Nos. 5,691,146 and 5,876,930).

Enzymes having template-specific polymerase activity for which some 3'→5' depolymerization activity has been reported include *E. coli* DNA Polymerase (Deutscher and Kornberg, *J. Biol. Chem.*, 244(11): 3019–28 (1969)), T7 DNA Polymerase (Wong et al., *Biochemistry* 30:526–37 (1991); Tabor and Richardson, *J. Biol. Chem.* 265: 8322–28

(1990)), *E. coli* RNA polymerase (Rozovskaya et al., *Biochem. J.* 224:645–50 (1994)), AMV and RLV reverse transcriptases (Srivastava and Modak, *J. Biol. Chem.* 255:2000–4 (1980)), and HIV reverse transcriptase (Zinnen et al., *J. Biol. Chem.* 269:24195–202 (1994)). A template-dependent polymerase for which 3' to 5' exonuclease activity has been reported on a mismatched end of a DNA hybrid is phage 29 DNA polymerase (de Vega, M. et al. *EMBO J.*, 15:1182–1192, 1996)

A variety of methodologies currently exist for the detection of single nucleotide polymorphisms (SNPs) that are present in genomic DNA. SNPs are DNA point mutations or insertions/deletions that are present at measurable frequencies in the population. SNPs are the most common variations in the genome.

SNPs occur at defined positions within genomes and can be used for gene mapping, defining population structure, and performing functional studies. SNPs are useful as markers because many known genetic diseases are caused by point mutations and insertions/deletions.

In rare cases where an SNP alters a fortuitous restriction enzyme recognition sequence, differential sensitivity of the amplified DNA to cleavage can be used for SNP detection. This technique requires that an appropriate restriction enzyme site be present or introduced in the appropriate sequence context for differential recognition by the restriction endonuclease. After amplification, the products are cleaved by the appropriate restriction endonuclease and products are analyzed by gel electrophoresis and subsequent staining. The throughput of analysis by this technique is limited because samples require processing, gel analysis, and significant interpretation of data before SNPs can be accurately determined.

Single strand conformational polymorphism (SSCP) is a second technique that can detect SNPs present in an amplified DNA segment (Hayashi, K. *Genetic Analysis: Techniques and Applications* 9:73–79, 1992). In this method, the double stranded amplified product is denatured and then both strands are allowed to reanneal during electrophoresis in non-denaturing polyacrylamide gels. The separated strands assume a specific folded conformation based on intramolecular base pairing. The electrophoretic properties of each strand are dependent on the folded conformation. The presence of single nucleotide changes in the sequence can cause a detectable change in the conformation and electrophoretic migration of an amplified sample relative to wild type samples, allowing SNPs to be identified. In addition to the limited throughput possible by gel-based techniques, the design and interpretation of SSCP based experiments can be difficult. Multiplex analysis of several samples in the same SSCP reaction is extremely challenging. The sensitivity required in mutation detection and analysis has led most investigators to use radioactively labeled PCR products for this technique.

In the amplification refractory mutation system (ARMS, also known as allele specific PCR or ASPCR), two amplification reactions are used to determine if a SNP is present in a DNA sample (Newton et al. *Nucl Acids Res* 17:2503, 1989; Wu et al. PNAS 86:2757, 1989). Both amplification reactions contain a common primer for the target of interest. The first reaction contains a second primer specific for the wild type product which will give rise to a PCR product if the wild type gene is present in the sample. The second PCR reaction contains a primer that has a single nucleotide change at or near the 3' end that represents the base change that is present in the mutated form of the DNA. The second primer, in conjunction with the common primer, will only function in PCR if genomic DNA that contains the mutated form of genomic DNA is present. This technique requires duplicate amplification reactions to be performed and analyzed by gel electrophoresis to ascertain if a mutated form of a gene is present. In addition, the data must be manually interpreted.

Single base extension (GBA®) is a technique that allows the detection of SNPs by hybridizing a single strand DNA probe to a captured DNA target (Nikiforov, T. et al. *Nucl Acids Res* 22:4167–4175). Once hybridized, the single strand probe is extended by a single base with labeled dideoxynucleotides. The labeled, extended products are then detected using calorimetric or fluorescent methodologies.

A variety of technologies related to real-time (or kinetic) PCR have been adapted to perform SNP detection. Many of these systems are platform based, and require specialized equipment, complicated primer design, and expensive supporting materials for SNP detection. In contrast, the process of this invention has been designed as a modular technology that can use a variety of instruments that are suited to the throughput needs of the end-user. In addition, the coupling of luciferase detection sensitivity with standard oligonucleotide chemistry and well-established enzymology provides a flexible and open system architecture. Alternative analytical detection methods, such as mass spectroscopy, HPLC, and fluorescence detection methods can also be used in the process of this invention, providing additional assay flexibility.

SNP detection using real-time amplification relies on the ability to detect amplified segments of nucleic acid as they are during the amplification reaction. Three basic real-time SNP detection methodologies exist: (i) increased fluorescence of double strand DNA specific dye binding, (ii) decreased quenching of fluorescence during amplification, and (iii) increased fluorescence energy transfer during amplification (Wittwer, C. et al. *Biotechniques* 22:130–138, 1997). All of these techniques are non-gel based and each strategy will be briefly discussed.

A variety of dyes are known to exhibit increased fluorescence in response to binding double stranded DNA. This property is utilized in conjunction with the amplification refractory mutation system described above to detect the presence of SNP. Production of wild type or mutation containing PCR products are continuously monitored by the increased fluorescence of dyes such as ethidium bromide or SYBER Green as they bind to the accumulating PCR product. Note that dye binding is not selective for the sequence of the PCR product, and high non-specific background can give rise to false signals with this technique.

A second detection technology for real time PCR, known generally as exonuclease primers (TaqMan® probes), utilizes the 5' exonuclease activity of thermostable polymerases such as Taq to cleave dual-labeled probes present in the amplification reaction (Wittwer, C. et al. *Biotechniques* 22:130–138, 1997; Holland, P et al *PNAS* 88:7276–7280, 1991). While complementary to the PCR product, the probes used in this assay are distinct from the PCR primer and are dually-labeled with both a molecule capable of fluorescence and a molecule capable of quenching fluorescence. When the probes are intact, intramolecular quenching of the fluorescent signal within the DNA probe leads to little signal. When the fluorescent molecule is liberated by the exonuclease activity of Taq during amplification, the quenching is greatly reduced leading to increased fluorescent signal.

An additional form of real-time PCR also capitalizes on the intramolecular quenching of a fluorescent molecule by use of a tethered quenching moiety. The molecular beacon technology utilizes hairpin-shaped molecules with an internally-quenched fluorophore whose fluorescence is restored by binding to a DNA target of interest (Kramer, R. et al. *Nat. Biotechnol.* 14:303–308, 1996). Increased binding of the molecular beacon probe to the accumulating PCR product can be used to specifically detect SNPs present in genomic DNA.

A final general fluorescent detection strategy used for detection of SNP in real time utilizes synthetic DNA segments known as hybridization probes in conjunction with a process known as fluorescence resonance energy transfer (FRET) (Wittwer, C. et al. Biotechniques 22:130–138, 1997; Bernard, P. et al. *Am. J. Pathol.* 153:1055–1061, 1998). This technique relies on the independent binding of labeled DNA probes on the target sequence. The close approximation of the two probes on the target sequence increases resonance energy transfer from one probe to the other, leading to a unique fluorescence signal. Mismatches caused by SNPs that disrupt the binding of either of the probes can be used to detect mutant sequences present in a DNA sample.

There is a need for highly sensitive, diagnostic applications that are capable of determining the number of virus molecules present in a body ("viral load"). For example, the presence of viral particles in the circulation system or in specific tissues is a means of monitoring the severity of viral infection. Several methods are currently used in the art for determining viral load. U.S. Pat. No. 5,667,964 discloses a method for the determination of the number of HIV-1 infected patient cells using reactive oxygen-intermediate generators. U.S. Pat. No. 5,389,512 discloses a method for determining the relative amount of a viral nucleic acid segment in a sample using PCR.

G. Garinis et al., *J. Clin. Lab. Anal.* 13:122–5 (1999) compare the determination of viral load results using an enzyme-linked immunosorbant assay (ELISA), a recombinant immunoblot assay (RIBA), and a reverse transcriptase polymerase chain reaction method (RT-PCR) in the detection of hepatitis C virus (HCV) infection in haemodialysis patients. The quantitative hepatitis HCV RT-PCR assay had a detection level of about 2,000 viral copies/mL serum. Holguin et al., *Eur. J. Clin. Microbiol. Infect. Dis.* 18:256–9 (1999) compare plasma HIV-1 RNA levels using several commercially available assays, namely the second-generation HIV-1 branched DNA assay, the Nuclisens assay, the Amplicor® Monitor reverse transcriptase polymerase chain reaction assay, and the Ultradirect Monitor. Differing values were noted in comparing results among these various assays. Boriskin et al., *Arch. Dis. Child.* 80:132–6 (1999) used a nested polymerase chain reaction to measure HIV-1 proviral DNA and CMV genomic DNA in peripheral blood leukocytes of children infected with HIV-1. There remains a need for a reliable means to detect and quantify viral load. There is a demand for methods to determine viral load when the quantities of viral particles are very low.

In summary, there is a need for alternative methods for the detection of nucleic acid hybrids. There is a demand for highly sensitive methods that are useful for determining the presence or absence of specific nucleic acid sequences, for example methods to determine viral load that are able to reliably detect as few as 10 copies of a virus present in a body, tissue, fluid, or other biological sample. There is a great demand for such methods to determine the presence or absence of nucleic acid sequences that differ slightly from sequences that might otherwise be present. There is a great demand for methods to determine the presence or absence of sequences unique to a particular species in a sample. There is also a great demand for methods that are more highly sensitive than the known methods, highly reproducible and automatable.

It would be beneficial if another method were available for detecting the presence of a sought-after, predetermined target nucleotide sequence or allelic variant. It would also be beneficial if such a method were operable using a sample size of the microgram to picogram scale. It would further be beneficial if such a detection method were capable of providing multiple analyses in a single assay (multiplex assays). The disclosure that follows provides one such method.

BRIEF SUMMARY OF THE INVENTION

A method of this invention is used to determine the presence or absence of a predetermined (known) nucleic acid target sequence in a nucleic acid sample. Such a method utilizes an enzyme that can depolymerize the 3'-terminus of an oligonucleotide probe hybridized to a nucleic acid target sequence to release one or more identifier nucleotides whose presence can then be determined.

One embodiment of the invention contemplates a method for determining the presence or absence of a predetermined nucleic acid target sequence in a nucleic acid sample. Thus, the presence or absence of at least one predetermined nucleic acid target sequence is sought to be determined. More than one such predetermined target sequence can also be present in the sample being assayed, and the presence or absence of more than one predetermined nucleic acid target sequence can be determined. The embodiment comprises the following steps.

A treated sample is provided that may contain a predetermined nucleic acid target sequence hybridized with a nucleic acid probe that includes an identifier nucleotide in the 3'-terminal region. The treated sample is admixed with a depolymerizing amount of an enzyme whose activity is to release one or more nucleotides from the 3'-terminus of a hybridized nucleic acid probe to form a treated reaction mixture. The treated reaction mixture is maintained under depolymerizing conditions for a time period sufficient to permit the enzyme to depolymerize hybridized nucleic acid and release identifier nucleotides therefrom. The presence of released identifier nucleotides is analyzed to obtain an analytical output, the analytical output indicating the presence or absence of the nucleic acid target sequence. The analytical output obtained by various techniques as discussed herein.

An analytical output is obtained by analyzing for the presence or absence of released identifier nucleotide. The analytical output indicates the presence or absence of the nucleotide at the predetermined region, and, thereby, the presence or absence of a first nucleic acid target. The analytical output is obtained by various techniques as discussed herein.

It is contemplated that an analytical output of the methods of the invention can be obtained in a variety of ways. The analytical output can be ascertained by luminescence spectroscopy. In some preferred embodiments, analysis for released 3'-terminal region indicator nucleotides comprises the detection of ATP, either by a luciferase detection system (luminescence spectroscopy) or an NADH detection system (absorbance spectroscopy). In particularly preferred embodiments where greater sensitivity is desired, ATP molecules are formed by a phosphate transferring step, for example using an enzyme such as NDPK in the presence of ADP, from the nucleotide triphosphates produced by the depolymerizing step. In some embodiments the ATP is amplified to form a plurality of ATP molecules. In the ATP detection embodiments, typically the enzyme (NDPK) for converting nucleotides and added ADP into ATP is present in the depolymerization reaction, and thus they are denoted as a "one pot" method.

In an alternative embodiment, the analytical output is obtained by fluorescence spectroscopy. It is contemplated that an identifier nucleotide includes a fluorescent label. An identifier nucleotide can be fluorescently labeled prior to, or after, release of the identifier nucleotide. It is also contemplated that other than a released identifier nucleotide contains a fluorescent tag. In such an embodiment, the release of nucleotides in a process of the invention is ascertained by a determination of a difference in the length of the polynucleotide probe, for example by capillary electrophoresis imaged by a fluorescent tag at the 5' terminus of the probe or in a region other than the 3' terminal region.

In an alternative embodiment the analytical output is obtained by mass spectrometry. It is preferred here that an identifier nucleotide be a nucleotide analog or a labeled nucleotide and have a molecular mass that is different from the mass of a usual form of that nucleotide, although a difference in mass is not required. It is also noted that with a fluorescently labeled identifier nucleotide, the analytical output can also be obtained by mass spectrometry. It is also contemplated that the analysis of released nucleotide be conducted by ascertaining the difference in mass of the probe after a depolymerization step of a process of the invention.

In another alternative embodiment, the analytical output is obtained by absorbance spectroscopy. Such analysis monitors the absorbance of light in the ultraviolet and visible regions of the spectrum to determine the presence of absorbing species. In one aspect of such a process, released nucleotides are separated from hybridized nucleic acid and other polynucleotides by chromatography (e.g. HPLC or GC) or electrophoresis (e.g. PAGE or capillary electrophoresis). Either the released identifier nucleotide or the remainder of the probe can be analyzed for to ascertain the release of the identifier nucleotide in a process of the invention. In another aspect of such a process a label may be incorporated in the analyzed nucleic acid.

In a contemplated embodiment, a sample to be assayed is admixed with one or more nucleic acid probes under hybridizing conditions to form a hybridization composition. The 3'-terminal region of the nucleic acid probe hybridizes with partial or total complementarity to the nucleic acid target sequence when that sequence is present in the sample. The 3'-terminal region of the nucleic acid probe includes an identifier nucleotide. The hybridization composition is maintained under hybridizing conditions for a time period sufficient to form a treated sample that may contain said predetermined nucleic acid target sequence hybridized with a nucleic acid probe. The treated sample is admixed with a depolymerizing amount of an enzyme whose activity is to release one or more nucleotides from the 3'-terminus of a hybridized nucleic acid probe to form a treated reaction mixture. The treated reaction mixture is maintained under depolymerizing conditions for a timer period sufficient to permit the enzyme to depolymerize hybridized nucleic acid and release identifier nucleotides therefrom. The presence of released identifier nucleotides is analyzed to obtain an analytical output, the analytical output indicating the presence or absence of the nucleic acid target sequence. The analytical output may be obtained by various techniques as discussed above.

One method of the invention contemplates interrogating the presence or absence of a specific base in a nucleic acid target sequence in a sample to be assayed, and comprises the following steps.

A hybridization composition is formed by admixing a sample to be assayed with one or more nucleic acid probes under hybridizing conditions. The sample to be assayed may contain a nucleic acid target sequence to be interrogated. The nucleic acid target comprises at least one base whose presence or absence is to be identified. The hybridization composition includes at least one nucleic acid probe that is substantially complementary to the nucleic acid target sequence and comprises at least one predetermined nucleotide at an interrogation position, and an identifier nucleotide in the 3'-terminal region.

A treated sample is formed by maintaining the hybridization composition under hybridizing conditions for a time period sufficient for base pairing to occur when a probe nucleotide at an interrogation position is aligned with a base to be identified in the target sequence. A treated reaction mixture is formed by admixing the treated sample with an enzyme whose activity is to release one or more identifier nucleotides from the 3'-terminus of a hybridized nucleic acid probe to depolymerize the hybrid. The treated reaction mixture is maintained under depolymerizing conditions for a time period sufficient to permit the enzyme to depolymerize the hybridized nucleic acid and release an identifier nucleotide.

An analytical output is obtained by analyzing for the presence or absence of released identifier nucleotides. The analytical output indicates the presence or absence of the specific base or bases to be identified. The analytical output is obtained by various techniques, as discussed herein. Preferably, an identifier nucleotide is at the interrogation position.

In one aspect of a method of the invention, the nucleic acid target sequence is selected from the group consisting of deoxyribonucleic acid and ribonucleic acid. The method that identifies the particular base present at an interrogation position, optionally comprises a first probe, a second probe, a third probe, and a fourth probe. An interrogation position of the first probe comprises a nucleic acid residue that is a deoxyadenosine or adenosine residue. An interrogation position of the second probe comprises a nucleic acid residue that is a deoxythymidine or uridine residue. An interrogation position of the third probe comprises a nucleic acid residue that is a deoxyguanosine or guanosine residue. An interrogation position of the fourth nucleic acid probe comprises a nucleic acid residue that is a deoxycytosine or cytosine residue.

In another aspect of the invention, the sample containing a plurality of target nucleic acid sequences is admixed with a plurality of the nucleic acid probes. Several analytical outputs can be obtained from such multiplexed assays. In a first embodiment, the analytical output obtained when at least one nucleic acid probes hybridizes with partial complementarity to one target nucleic acid sequence is greater than the analytical output when all of the nucleic acid probes hybridize with total complementarity to their respective nucleic acid target sequences. In a second embodiment, the analytical output obtained when at least one nucleic acid probe hybridizes with partial complementarity to one target nucleic acid sequence is less than the analytical output when all of the nucleic acid probes hybridize with total complementarity to their respective nucleic acid target sequences. In a third embodiment, the analytical output obtained when at least one nucleic acid probe hybridizes with total complementarity to one nucleic acid target sequence is greater than the analytical output when all of the nucleic acid probes hybridize with partial complementarity to their respective nucleic acid target sequences. In a fourth embodiment, the analytical output obtained when at least one nucleic acid probe hybridizes with total complementarity to one target nucleic acid sequence is less than the analytical output when all of the nucleic acid probes hybridize with partial complementarity to their respective nucleic acid target sequences. The depolymerizing enzymes are as described herein.

Yet another embodiment of the invention contemplates a method for determining the presence or absence of a first nucleic acid target in a nucleic acid sample that may contain that target or may contain a substantially identical second target. For example, the second target may have a base substitution, deletion or addition relative to the first nucleic acid target. This embodiment comprises the following steps.

A sample to be assayed is admixed with one or more nucleic acid probes under hybridizing conditions to form a hybridization composition. The first and second nucleic acid targets each comprise a region of sequence identity except for at least a single nucleotide at a predetermined position that differs between the targets. The nucleic acid probe is substantially complementary to the nucleic acid target region of sequence identity and comprises at least one nucleotide at an interrogation position. An interrogation position of the probe is aligned with the predetermined position of a target when a target and probe are hybridized. The probe also includes an identifier nucleotide in the 3'-terminal region.

The hybridization composition is maintained under hybridizing conditions for a time period sufficient to form a treated sample wherein the nucleotide at the interrogation position of the probe is aligned with the nucleotide at the predetermined position in the region of identity of the target.

A treated reaction mixture is formed by admixing the treated sample with a depolymerizing amount of an enzyme whose activity is to release one or more nucleotides from the 3'-terminus of a hybridized nucleic acid probe. The reaction mixture is maintained under depolymerization conditions for a time period sufficient to permit the enzyme to depolymerize the hybridized nucleic acid and release the identifier nucleotide.

An analytical output is obtained by analyzing for the presence or absence of released identifier nucleotides. The analytical output indicates the presence or absence of the nucleotide at the predetermined region, and; thereby, the presence or absence of a first nucleic acid target.

One aspect of the above method is comprised of a first probe and a second probe. The first probe comprises a nucleotide an interrogation position that is complementary to a first nucleic acid target at a predetermined position. The second probe comprises a nucleotide at an interrogation position that is complementary to a second nucleic acid target at a predetermined position.

In one aspect of a process of the invention, the depolymerizing enzyme, whose activity is to release nucleotides, is a template-dependent polymerase, whose activity is to depolymerize hybridized nucleic acid whose 3'-terminal nucleotide is matched, in the 3'→5' direction in the presence of pyrophosphate ions to release one or more nucleotides. Thus, the enzyme's activity is to depolymerize hybridized nucleic acid to release nucleotides under depolymerizing conditions. Preferably, this enzyme depolymerizes hybridized nucleic acids whose bases in the 3'-terminal region of the probe are matched with total complementarity to the corresponding bases of the nucleic acid target. The enzyme will continue to release properly paired bases from the 3'-terminal region and will stop when the enzyme arrives at a base that is mismatched.

In an alternative aspect of the process (method), the depolymerizing enzyme, whose activity is to release nucleotides, exhibits a 3'→5' exonuclease activity in which hybridized nucleic acids having one or more mismatched bases at the 3'-terminus of the hybridized probe are depolymerized. Thus, the enzyme's activity is to depolymerize hybridized nucleic acid to release nucleotides under depolymerizing conditions. In this embodiment, the hybrid may be separated from the free probe prior to enzyme treatment. In some embodiments, an excess of target may be used so that the concentration of free probe in the enzyme reaction is extremely low.

In still another alternative aspect of a process of the invention, the depolymerizing enzyme exhibits a 3' to 5' exonuclease activity on a double-stranded DNA substrate having one or more matched bases at the 3' terminus of the hybrid. The enzyme's activity is to depolymerize hybridized nucleic acid to release nucleotides containing a 5' phosphate under depolymerizing conditions.

In particularly preferred embodiments where greater sensitivity is desired, ATP molecules are formed by a phosphate transferring step, (e.g. using NDPK in the presence of ADP), from the dNTPs produced by the depolymerizing step. In some embodiments, the ATP can be amplified to form a plurality of ATP molecules.

In one aspect of the invention, the nucleic acid sample to be assayed is obtained from a biological sample that is a solid or liquid. Exemplary solid biological samples include animal tissues such as those obtained by biopsy or post mortem, and plant tissues such as leaves, roots, stems, fruit and seeds. Exemplary liquid samples include body fluids such as sputum, urine, blood, semen and saliva of an animal, or a fluid such as sap or other liquid obtained when plant tissues are cut or plant cells are lysed or crushed. In one aspect of the method, the predetermined nucleic acid target sequence is a microbial or viral nucleic acid.

In some preferred embodiments of the invention, the predetermined nucleic acid target sequence is a viral nucleic acid. Viral load, the amount of virus present, can be determined from the magnitude of the analytical output from a predetermined amount of biological sample such as animal fluid or tissue. In some preferred embodiments, the presence or absence of a mutation in the viral genome can be determined.

In another aspect of the method, the nucleic acid sample is obtained from a food source. In one process of the method, the food source is a plant or is derived from plant material, and the predetermined nucleic acid target sequence is a sequence not native to that plant. In one aspect of the method, the nucleic acid sequence not native to the subject plant is a transcription control sequence. In one preferred embodiment of the invention, the transcription control sequence is the promoter or the NOS terminator, or both. In another aspect of the method, the predetermined nucleic acid target sequence in a food source sample is a sequence native to the plant.

Another embodiment of the invention contemplates a method for selectively detecting poly(A)$^+$ RNA, and comprises the following steps. A hybridization composition is formed by admixing, under hybridizing conditions, a sample to be assayed with an oligo(dT) probe including a 3' terminal region identifier nucleotide. The hybridization composition is maintained under hybridizing conditions for a time period sufficient to form a treated sample that contains the poly(A)$^+$ RNA target sequence hybridized with the oligo(dT) probe. A treated reaction mixture is formed by admixing the treated sample with an enzyme whose activity is to release one or more identifier nucleotides from the 3'-terminal region of the nucleic acid hybrid. The reaction mixture is maintained under depolymerizing conditions for a time period sufficient to permit the enzyme to depolymerize the hybridized nucleic acid and release an identifier nucleotide. An analytical output is obtained by analyzing the reaction mixture for the presence of released identifier nucleotide. The analytical output indicates the presence of poly(A)$^+$ RNA.

A further embodiment of the invention, such as is used for Single Tandem Repeat (STR) detection, contemplates a method for determining the number of known sequence repeats that are present in a nucleic acid target sequence in a nucleic acid sample. A method for determining the number of known sequence repeats comprises the following steps. A plurality of separate treated samples is provided. Each treated sample contains a nucleic acid target sequence hybridized with a nucleic acid probe. The nucleic acid target sequence contains a plurality of known sequence repeats and a downstream non-repeated region. Each nucleic acid probe contains a different number of complementary repeats of the known sequence, an identifier nucleotide in the 3'-terminal region and a 5'-terminal locker sequence. The 5'-terminal locker sequence is complementary to the downstream non-repeated region of the target and comprises 1 to about 20 nucleotides, preferably 5 to 20 nucleotides, most preferably 10 to 20 nucleotides. The various probes represent complements to possible alleles of the target nucleic acid. A treated depolymerization reaction mixture is formed by admixing each treated sample with a depolymerizing amount of an enzyme whose activity is to release one or more nucleotides from the 3'-terminus of a hybridized nucleic acid probe. The treated depolymerization reaction mixture is maintained under depolymerizing conditions for a time period sufficient to permit the enzyme to depolymerize the hybridized nucleic acid probe and release an identifier nucleotide. The samples are analyzed for the presence or absence of released identifier nucleotide to obtain an analytical output. The analytical output from the sample whose probe contained the same number of sequence repeats as present in the target nucleic acid is indicative of and determines the number of sequence repeats present in the nucleic acid target.

In one aspect of the method, the nucleic acid sample contains two nucleic acid targets representing alleles, and is homozygous with respect to the number of known sequence repeats of the two alleles. In an alternative method of the invention, the nucleic acid sample is heterozygous with respect to the two alleles. In another method of the invention, an identifier nucleotide is a nucleotide that is part of the region containing a repeated sequence. In an alternative method of the invention, an identifier nucleotide of the probe sequence is part of the region containing a non-repeating sequence that is complementary to that located in the target nucleic acid 5' to the repeated known sequence. In this latter aspect of the method, the identifier nucleotide is present in a sequence containing 1 to about 20 nucleic acids that is complementary to a non-repeating sequence of the target nucleic acid located in the probe 3' to the known sequence repeats. The repeated known sequence present in a nucleic acid target sequence typically has a length of 2 to about 24 bases per repeat.

A further embodiment of the invention contemplates a method using thermostable DNA polymerase as a depolymerizing enzyme for determining the presence or absence of a at least one predetermined nucleic acid target sequence in a nucleic acid sample, and comprises the following steps.

A treated sample is provided that may contain a predetermined nucleic acid target sequence hybridized to a nucleic acid probe whose 3'-terminal region is complementary to the predetermined nucleic acid target sequence and includes an identifier nucleotide in the 3'-terminal region. A treated depolymerization reaction mixture is formed by admixing a treated sample with a depolymerizing amount of a enzyme whose activity is to release an identifier nucleotide from the 3'-terminus of a hybridized nucleic acid probe. In a preferred one-pot embodiment, the depolymerizing enzyme is thermostable and more preferably, the treated reaction mixture also contains (i) adenosine 5' diphosphate, (ii) pyrophosphate, and (iii) a thermostable nucleoside diphosphate kinase (NDPK).

The treated sample is maintained under depolymerizing conditions at a temperature of about 4° C. to about 90° C., more preferably at a temperature of about 20° C. to about 90° C., and most preferably at a temperature of about 25° C. to about 80° C., for a time period sufficient to permit the depolymerizing enzyme to depolymerize the hybridized nucleic acid probe and release an identifier nucleotide as a nucleoside triphosphate. In preferred one-pot reactions, the time period is also sufficient to permit NDPK enzyme to transfer a phosphate from the released nucleoside triphosphate to added ADP, thereby forming ATP. The presence or absence of a nucleic acid target sequence is determined from the analytical output obtained using ATP. In a preferred method of the invention, analytical output is obtained by luminescence spectrometry.

In another aspect of the thermostable enzyme one-pot method for determining the presence or absence of a predetermined nucleic acid target sequence in a nucleic acid sample, the treated sample is formed by the following further steps. A hybridization composition is formed by admixing the sample to be assayed with one or more nucleic acid probes under hybridizing conditions. The 3'-terminal region of the nucleic acid probe (i) hybridizes with partial or total complementarity to a nucleic acid target sequence when that sequence is present in the sample, and (ii) includes an identifier nucleotide. A treated sample is formed by maintaining the hybridization composition under hybridizing conditions for a time period sufficient for the predetermined nucleic acid target sequence to hybridize with the nucleic acid probe.

Preferably, the depolymerizing enzyme is from a group of thermophilic DNA polymerases comprising Tne triple mutant DNA polymerase, Tne DNA polymerase, Taq DNA polymerase, Ath DNA polymerase, Tvu DNA polymerase, Bst DNA polymerase, and Tth DNA polymerase. In another aspect of the method, the NDPK is that encoded for by the thermophilic bacteria *Pyrococcus furiosis* (Pfu).

Another embodiment of the invention contemplates a method for enhancing the discrimination of analytical output between a target/probe hybrid with a matched base at an interrogation position and a substantially identical target/probe hybrid with a mismatched base at the same interrogation position. This embodiment is useful for the determination of the presence or absence of a predetermined nucleic acid in a target nucleic acid sequence in a nucleic acid sample, and comprises the following steps.

A plurality of separate treated samples is provided. Each treated sample contains a nucleic acid target sequence that may contain the predetermined nucleic acid. Each nucleic acid target sequence is hybridized with a nucleic acid probe.

A first probe of a first treated sample comprises a 3'-terminal region sequence that is complementary to the nucleic acid target sequence. The first probe includes an identifier nucleotide. This identifier nucleotide is complementary to the first-named target nucleic acid. The first probe also contains a second sequence otherwise complementary to the nucleic acid target sequence except for a second predetermined nucleotide that is not complementary to the target sequence and is located about 2 to about 10 nucleotides upstream from the 3'-terminal nucleotide of the first probe. This second predetermined nucleotide mismatched base acts to further destabilize the hybridized probe and enhances discrimination as discussed above.

A second probe of a second treated sample contains a 3'-terminal region sequence that is complementary to the same nucleic acid target sequence as the first probe, except for an identifier nucleotide in the 3'-terminal region that is not complementary to the first predetermined nucleic acid of the first-named target nucleic acid. The second probe also contains a second sequence otherwise complementary to the target sequence except for a second predetermined nucleotide (the same second predetermined nucleotide as the first probe) that is not complementary to the target sequence and exists about 2 to about 10 nucleotides upstream from the 3'-terminal nucleotide of said probe.

Each treated sample is admixed with a depolymerizing amount of an enzyme whose activity is to release one or more nucleotides from the 3'-terminus of a hybridized nucleic acid probe to form a treated reaction mixture. The treated reaction mixtures are maintained for a time period sufficient to permit the enzyme to depolymerize a hybridized nucleic acid probe and release an identifier nucleotide therefrom.

The samples are analyzed for the presence or absence of released identifier nucleotide to obtain an analytical output. Analysis may include conversion of released identifier nucleotide to ATP by NDPK in the presence of ADP, followed by analysis of the amount of ATP present.

The ratio of the analytical output from the sample containing the first probe relative to that of the sample containing the second probe is enhanced compared to the ratio of the analytical output from a similar set of treated samples (samples 3 and 4) that contain the same target and probes as do samples 1 and 2 respectively, but whose probes do not contain the second predetermined nucleic acid that is not complementary [destabilizing mismatched base(s)] when hybridized with the target. This second predetermined nucleic acid in the first and second probes is located at about 2 to about 10 nucleotides upstream from the 3' terminal nucleotide of the probe, preferably 3 to 6 nucleotides upstream. Therefore, the third probe is identical to the first probe except that the third probe does not contain a nucleotide, located at about 2 to about 10 nucleotides upstream from the 3' terminal nucleotide, that is a mismatch when the probe is hybridized to the target sequence. Likewise, the fourth probe is identical to the second probe except that the fourth probe does not contain a nucleotide, located at about 2 to about 10 nucleotides upstream from the 3' terminal nucleotide that is a mismatch when the probe is hybridized to the target sequence. Instead, the third and fourth probes have a complementary base at the same position as the second predetermined nucleic acid that is not complementary in the first and second probes. The nucleic acid target sequence is substantially the same for all four probes.

A still further method of the invention contemplates determining whether the presence or absence of a nucleic acid target sequence in a nucleic acid sample results from a locus that is homozygous or heterozygous for the two alleles at the locus. This method is comprised of the following steps. A plurality of separate treated samples is provided. Each sample may contain a nucleic acid target sequence hybridized with a nucleic acid probe. The nucleic acid target sequence consists of either a first allele, a second allele, or a mixture of first and second alleles of the nucleic acid target. The alleles differ in sequence at an interrogation position. The nucleic acid probe contains an identifier nucleotide in the 3'-terminal region that is aligned at an interrogation nucleotide position of the target sequence when the probe and target are hybridized.

A treated reaction mixture is formed by admixing each treated sample with a depolymerizing amount of an enzyme whose activity is to release one or more nucleotides from the 3'-terminus of a hybridized nucleic acid probe. The treated reaction mixture is maintained under depolymerizing conditions for a time period sufficient to permit the enzyme to depolymerize the hybridized nucleic acid probe and release an identifier nucleotide. The samples are analyzed for the presence or absence of released identifier nucleotides to obtain an analytical output. The analytical output is quantifiable and thus determines whether the sample is homozygous or heterozygous when compared to the analytical output of appropriate controls.

A multiplexed version of this embodiment is also contemplated, wherein probes for two or more alleles are provided, each distinguishable, but preferably having the same lengths. Then, after hybridization, depolymerization, and analysis according to the invention, the relative analytical output for the various distinguishable identifier nucleotides or remaining probes will show whether the sample is homozygous or heterozygous and for which alleles. Another multiplexed version of this embodiment is contemplated, wherein probes for alleles at a plurality of loci are provided. Preferably, the different loci have substantially different target sequences. Probes for the various alleles at each locus are preferably of the same length. Each of the probes should be distinguishable either by analysis of the released identifier nucleotide or the remaining probe after depolymerization.

A still further embodiment of the invention contemplates determining the presence or absence of a nucleic acid target sequence in a nucleic acid sample with a probe that is hybridized to the target and then modified to be able to form a hairpin structure. This embodiment comprises the following steps.

A treated sample is provided that contains a nucleic acid sample that may include a nucleic acid target sequence having an interrogation position hybridized with a nucleic acid probe. The probe is comprised of at least two sections. The first section contains the probe 3'-terminal about 10 to about 30 nucleotides. These nucleotides are complementary to the target strand sequence at positions beginning about 1 to about 30 nucleotides downstream of the interrogation position. The second section of the probe is located at the 5'-terminal region of the probe and contains about 10 to about 20 nucleotides of the target sequence. This sequence spans the region in the target from the nucleotide at or just upstream (5') of the interrogation position, to the nucleotide just upstream to where the 3'-terminal nucleotide of the probe anneals to the target. An optional third section of the probe, from zero to about 50, and preferably about zero to about 20 nucleotides in length and comprising a sequence that does not hybridize with either the first or second section, is located between the first and second sections of the probe.

The probe of the treated sample is extended in a template-dependent manner, as by admixture with dNTPs and a template-dependent polymerase, at least through the interrogation position, thereby forming an extended probe/target hybrid. In a preferred embodiment, the length of the probe extension is limited by omission from the extension reaction of a dNTP complementary to a nucleotide of the target sequence that is present upstream of the interrogation position and absent between the nucleotide complementary to the 3'-end of the interrogation position.

The extended probe/target hybrid is separated from any unreacted dNTPs. The extended probe/target hybrid is denatured to separate the strands. The extended probe strand is permitted to form a hairpin structure.

A treated reaction mixture is formed by admixing the hairpin structure-containing composition with a depolymerizing amount of an enzyme whose activity is to release one or more nucleotides from the 3'-terminus of an extended probe hairpin structure. The reaction mixture is maintained under depolymerizing conditions for a time period sufficient for the depolymerizing enzyme to release 3'-terminus nucleotides, and then analyzed for the presence of released identifier nucleotides. The analytical output indicates the presence or absence of the nucleic acid target sequence.

A still further embodiment of the invention, termed REAPER™, also utilizes hairpin structures. This method contemplates determining the presence or absence of a nucleic acid target sequence, or a specific base within the target sequence, in a nucleic acid sample, and comprises the following steps. A treated sample is provided that contains a nucleic acid sample that may include a nucleic acid target sequence hybridized with a first nucleic acid probe strand.

The hybrid is termed the first hybrid. The first probe is comprised of at least two sections. The first section contains the probe 3'-terminal about 10 to about 30 nucleotides that are complementary to the target nucleic acid sequence at a position beginning about 5 to about 30 nucleotides downstream of the target interrogation position. The second section of the first probe contains about 5 to about 30 nucleotides that are a repeat of the target sequence from the interrogation position to about 10 to about 30 nucleotides downstream of the interrogation position, and does not hybridize to the first section of the probe. An optional third section of the probe, located between the first and second sections of the probe, is zero to about 50, preferably up to about 20, nucleotides in length and comprises a sequence that does not hybridize to either the first or second section.

The first hybrid in the treated sample is extended at the 3'-end of the first probe, thereby extending the first probe past the interrogation position and forming an extended first hybrid whose sequence includes an interrogation position. The extended first hybrid is comprised of the original target nucleic acid and extended first probe. The extended first hybrid is then denatured in an aqueous composition to separate the two nucleic acid strands of the hybridized duplex and form an aqueous solution containing a separated target nucleic acid and a separated extended first probe.

A second probe, that is about 10 to about 2000, preferably about 10 to about 200, most preferabley about 10 to about 30 nucleotides in length and is complementary to the extended first probe at a position beginning about 5 to about 2000, preferably about 5 to about 200, nucleotides downstream of the interrogation position in extended first probe, is annealed to the extended first probe, thereby forming the second hybrid. The second hybrid is extended at the 3'-end of the second probe until that extension reaches the 5'-end of the extended first probe, thereby forming a second extended hybrid whose 3'-region includes an identifier nucleotide. In preferred embodiments the extending polymerase for both extensions does not add a nucleotide to the 3' end that does not have a corresponding complementary nucleotide in the template.

An aqueous composition of the extended second hybrid is denatured to separate the two nucleic acid strands. The aqueous composition so formed is cooled to form a "hairpin structure" from the separated extended second probe when the target sequence is present in the original nucleic acid sample.

A treated reaction mixture is formed by admixing the hairpin structure-containing composition with a depolymerizing amount of an enzyme whose activity is to release one or more nucleotides from the 3'-terminus of a nucleic acid hybrid. The reaction mixture is maintained under depolymerizing conditions for a time period sufficient to release 3'-terminal region identifier nucleotides, and then analyzed for the presence of released identifier nucleotides. The analytical output indicates the presence or absence of the nucleic acid target sequence.

A further method of the invention contemplates a method for determining the presence or absence of a restriction endonuclease recognition sequence in a nucleic acid sample that comprises the following steps. A treated sample is provided that may contain a hybridized nucleic acid target that has a cleaved restriction endonuclease recognition sequence that includes an identifier nucleotide in the restriction endonuclease recognition sequence. The treated sample is admixed with a depolymerizing amount of an enzyme whose activity is to release one or more nucleotides from the 3'-terminus of a restriction endonuclease recognition sequence to form a treated reaction mixture. The treated reaction mixture is maintained under depolymerizing conditions for a time period sufficient to permit the enzyme to depolymerize hybridized nucleic acid and release identifier nucleotide therefrom. Finally, the treated reaction mixture is analyzed for the presence of released identifier nucleotides to obtain an analytical output, the analytical output indicating the presence or absence of the restriction endonuclease recognition sequence in the nucleic acid target.

In a preferred embodiment, the process includes the further steps of forming a treated sample by providing an endonuclease cleavage reaction solution comprising a nucleic acid sample and a restriction endonuclease enzyme specific for the restriction endonuclease recognition sequence and maintaining the endonuclease cleavage reaction solution for a time period sufficient for the restriction endonuclease enzyme to cleave the restriction endonuclease recognition sequence to form a treated sample.

In a further preferred embodiment, the process includes the further step of amplifying a nucleic acid target sequence in a nucleic acid sample prior to providing the restriction endonuclease recognition sequence.

In a still further preferred embodiment, the nucleic acid target sequence of the process is amplified by the following further steps.

A crude nucleic acid sample is admixed with PCR amplification primers that are complementary to regions upstream and downstream of the nucleic acid target sequence and a template-dependent polymerase to form an amplification sample mixture wherein either the nucleic acid target sequence or the PCR amplification primers includes a restriction endonuclease recognition sequence. The amplification sample mixture is maintained under denaturing conditions for a time period sufficient to denature the nucleic acid target sequence to form a denatured amplification reaction mixture. The denatured amplification mixture is annealed under hybridization conditions for a time period sufficient for PCR amplification primers to anneal to the nucleic acid target sequence to form an amplification reaction mixture. Finally, the amplification reaction mixture is maintained for a time period sufficient to permit the template-dependent polymerase to extend the nucleic acid from the PCR primers to form an amplified nucleic acid sample. The amplification cycle is repeated as usual for PCR to obtain a PCR amplification product that has restriction endonuclease recognition sites in it. This PCR amplification product is purified and reacted with a depolymerizing enzyme as described above.

Another embodiment of the invention contemplates a method for determining the loss of heterozygosity (LOH) of a locus of an allele that comprises the following steps.

A plurality of separate treated samples is provided, each sample containing a nucleic acid target sequence hybridized with a nucleic acid probe. The nucleic acid target sequence is that of a first allele or a mixture of the first allele and a second allele of the nucleic acid target, wherein the alleles differ in sequence. The nucleic acid probe contains a 3'-terminal region that hybridizes to a target sequence when the probe and target are hybridized.

Each treated sample is admixed with a depolymerizing amount of an enzyme whose activity is to release one or more nucleotides from the 3'-terminus of a hybridized nucleic acid probe to form a treated reaction mixture. The treated reaction mixture is maintained under depolymerizing conditions for a time period sufficient to depolymerize hybridized nucleic acid probe and release identifier nucleotides. The samples are then analyzed for the quantity of released identifier nucleotides to obtain an analytical output, the analytical output indicating whether the nucleic acid target sequence in a nucleic acid sample has lost heterozygosity at the locus of the allele.

In preferred LOH embodiments, the analytical output is obtained by luminescence spectroscopy, absorbance spectrometry, mass spectrometry or fluorescence spectroscopy. In another preferred embodiment, the released identifier nucleotide includes a fluorescent label. The identifier nucleotide is optionally fluorescently labeled after release from the hybrid. It is contemplated that in the above analytical methods, either the released identifier nucleotide or the remainder of the probe can be evaluated to determine whether identifier nucleotide had been released, as described herein.

In another preferred LOH embodiment, the enzyme whose activity is to release nucleotides is a template-dependent polymerase that, in the presence of pyrophosphate ions, depolymerized hybridized nucleic acids whose bases in the 3'-terminal region are completely complementary to bases of the nucleic acid target.

In one aspect of the LOH embodiment, the quantity of the released identifier nucleotides for the first allele is substantially less than the quantity of the released identifier nucleotide for the first allele of a known heterozygous control sample, and the quantity of the released identifier nucleotides for the second allele is substantially similar to that of the released identifier nucleotide for the second allele of a known heterozygous control sample, indicating a loss of heterozygosity at the locus of the first allele.

In another aspect of the LOH embodiment, the quantity of the released identifier nucleotides for the second allele is substantially less than the quantity of the released identifier nucleotides for the second alleles of a known heterozygous control sample, and the quantity of the released identifier nucleotides for the first allele is substantially similar to that of the released identifier nucleotide for the first allele of a known heterozygous control sample, indicating a loss of heterozygosity at the locus of the second allele. The known heteozygous control has analytical output for the treated samples indicating alleles one and two are present in the sample at about a 1:1 ratio. A sample with loss of heterozygosity has an analytical output for the treated samples indicating alleles one and two are present in the sample at a 1:0 or 0:1 ratio respectively when compared to the analytical output of a known heterozygous control sample.

A still further preferred embodiment of the invention contemplates a method for determining the presence of trisomy of an allele that comprises the following steps.

A plurality of separate treated samples is provided, wherein each sample contains a nucleic acid target sequence hybridized with a nucleic acid probe. The nucleic acid target sequence is that of a first allele, a second allele or a mixture of the first and second alleles of the nucleic acid target. The alleles differ in sequence at an interrogation position. The nucleic acid probe contains a 3'-terminal region that hybridizes to a region of the nucleic acid target sequence containing the interrogation nucleotide position when the probe and target are hybridized. The nucleic acid probe also contains an identifier nucleotide.

Each treated sample is admixed with a depolymerizing amount of an enzyme whose activity, under depolymerizing conditions, is to release one or more nucleotides from the 3'-terminus of a hybridized nucleic acid probe to form a treated reaction mixture. The treated reaction mixture is maintained for a time period sufficient to depolymerize hybridized nucleic acid probe and release identifier nucleotides. The samples are analyzed for released identifier nucleotides to obtain an analytical output, the magnitude of the analytical output relative to an analytical output of an appropriate control sample indicating whether a trisomy is present in the nucleic acid target sequence.

For trisomy analysis, preferably the analytical output is obtained by luminescence spectroscopy, absorbance spectrometry, fluorescence spectroscopy, or mass spectrometry. the released identifier nucleotide preferably includes a fluorescent label. The identifier nucleotide is optionally fluorescently labeled after release from the hybrid.

In a preferred embodiment for trisomy analysis, the enzyme whose activity is to release nucleotides is a template-dependent polymerase, that, in the presence of pyrophosphate ions, depolymerizes hybridized nucleic acids whose bases in the 3' terminal region are completely complementary to bases of said nucleic acid target.

In one embodiment, the quantity of the released identifier nucleotide for the first allele is substantially greater than the quantity of the released identifier nucleotide of a control sample homozygous for the first allele, indicating that the nucleic acid target sequence has a trisomy. Preferably, the quantity of released identifier is expressed as a ratio. For example, a normal heterozygote has about a 1:1 ratio of the analytical output for the two alleles. If the trisomy is homozygous for either allele, the ratio is about three times the value for that allele in a normal heterozygote that has none of the other allele. If the trisomy is heterozygous, then the ratio is about 2:1 of one allele to the other when compared to the analytical output of a control heterozygote.

An embodiment of the invention contemplates a process to determine the presence or absence of a predetermined single-stranded nucleic acid target sequence. Such a process comprises the following steps.

A depolymerization reaction mixture is provided that comprises a pair of first and second nucleic acid probes and a hybrid between a third probe and the nucleic acid target sequence. The first and second nucleic acid probes are complementary and form 3'-overhangs on both ends of the duplex formed when each of the pair of complementary nucleic acid probes is hybridized with the other. The first of those probes is complementary to the nucleic acid target sequence, whereas the second has the sequence of the nucleic acid target. A hybrid between a third probe and the nucleic acid target sequence is present in the depolymerization reaction mixture when the nucleic acid target sequence is present in the nucleic acid sample. Each of the first and third probes has an identifier nucleotide in its 3'-terminal region. The reaction mixture further comprises a depolymerizing amount of an enzyme whose activity is to release nucleotides from the 3'-terminus of a hybridized nucleic acid.

The reaction mixture is maintained under depolymerization conditions for a time period sufficient to permit the enzyme to depolymerize the 3'-terminal region of the hybridized third probe to release identifier nucleotides and form a first treated reaction mixture.

The products of the first treated reaction mixture are denatured to form a denatured treated reaction mixture.

The denatured treated reaction mixture is maintained under hybridizing conditions for a time period sufficient to form a second depolymerization reaction mixture. That second depolymerization reaction mixture comprises two components. The first is a hybrid formed between the first probe and the nucleic acid target sequence, when the nucleic acid target sequence is present in the nucleic acid sample. The second component is a hybrid formed between the 3'-terminal-depolymerized third probe and the second nucleic acid probe. One end of that second hybrid has a blunt end or a 5'-overhang, as well as an identifier nucleotide in the 3'-terminal region.

The first and second hybrid components of the second reaction mixture are depolymerized to release identifier nucleotide from the 3'-terminal regions of the hybrids to form a second treated reaction mixture. The second treated reaction mixture is analyzed for the presence of released identifier nucleotide to obtain an analytical output, the analytical output indicating the presence or absence of said nucleic acid target sequence.

In preferred practice, the first and third probes are the same. In addition, the denaturation, annealing and depolymerization steps are preferably repeated to further increase the number of nucleic acid hybrids from which identifier nucleotides are released prior to analysis of the amplification reaction mixture to detect released identifier nucleotide. Most preferably, the depolymerizing enzyme is thermostable.

A related embodiment of the invention contemplates a process to determine the presence or absence of a predetermined double-stranded nucleic acid target sequence. The process comprises the following steps.

A first reaction mixture comprises first and second nucleic acid probes, third and fourth nucleic acid probes, and a depolymerizing enzyme. The first and second complementary nucleic acid probes form 3'-overhangs on both ends of the duplex formed when each of the complementary nucleic acid probes is hybridized with the other. Each of those probes is complementary to one or the other strand of the nucleic acid target sequence and has an identifier nucleotide in its 3'-terminal region. Hybrids between a third and fourth probe and each of the two strands of the nucleic acid target sequence are present when the nucleic acid target sequence is present in the nucleic acid sample. The third and fourth probes each have an identifier nucleotide in its 3'-terminal region. Also present is a depolymerizing amount of a depolymerizing enzyme whose activity is to release nucleotides from the 3'-terminus of a hybridized nucleic acid.

The first reaction mixture is maintained for a time period sufficient to permit the enzyme to depolymerize hybridized nucleic acid to release identifier nucleotide from the 3'-terminal region of the hybridized third and fourth probes and form a treated first reaction mixture. The products of the treated first reaction mixture are denatured to form a denatured treated reaction mixture.

The denatured treated reaction mixture is maintained under hybridizing conditions for a time period sufficient to form a second reaction mixture. That second reaction mixture comprises two components. A first component is comprised of hybrids that lack a 3'-overhang between each of the strands of the target nucleic acid and each of the first and second probes, when the nucleic acid target sequence is present in the nucleic acid sample. A second component is comprised of hybrids between each of the first and second probes and 3'-terminal region-depolymerized third and fourth probes. Each of the hybrids of each of the components contains one end that is blunt or has a 5'-overhang, as well as an identifier nucleotide in the 3'-terminal region.

The hybrids of the first and second components above are depolymerized to release identifier nucleotide from the 3'-terminus of the hybridized probes to form a second treated reaction mixture. The second treated reaction mixture is analyzed for the presence of released identifier nucleotide to obtain an analytical output, the analytical output indicating the presence or absence of said nucleic acid target sequence.

In preferred practice, the first and third probes are the same. In addition, the denaturation, annealing and depolymerization steps are preferably repeated to further increase the number of nucleic acid hybrids from which identifier nucleotides are released prior to analysis of the amplification reaction mixture to detect released identifier nucleotide.

A further embodiment of the invention contemplates an isolated and purified nucleotide diphosphate kinase (NDPK) enzyme that exhibits higher NDPK activity at a temperature of about 50 to about 90 degrees C relative to the NDPK activity at 37 degrees C. Such an NDPK is from Pfu and comprises the amino acid sequence of SEQ ID NO:90. Preferably, the isolated and purified NDPK enzyme has a DNA sequence shown in SEQ ID NO:91.

In a contemplated amplification and interrogation process of the invention, the presence or absence of a predetermined nucleic acid target sequence is determined, comprising the following steps. A ligation reaction solution is provided, comprising a ligating amount of a ligase, a nucleic acid sample and an open circle probe. The nucleic acid sample may contain the predetermined nucleic acid target sequence. The nucleic acid target sequence has a 3'-portion and a 5'-portion. The open circle probe has an open circle probe 3'-terminal region, a linker region, and an open circle probe 5'-terminal region. The open circle probe further comprises a detection primer target and an amplification primer target. The amplification primer target is downstream of the detection primer target.

Upon hybridization between the open circle probe and the predetermined nucleic acid target sequence, the open circle probe 3'-terminal region is complementary to a sequence of the 3' portion of the nucleic acid target sequence. Similarly, the open circle probe 5'-terminal region is complementary to a sequence of the 5' portion of the nucleic acid target sequence.

The ligation reaction solution optionally further comprises a polymerizing amount of a DNA polymerase and deoxynucleoside triphosphates. Preferably, this is when the hybridized open circle probe 3'-terminus is not adjacent and ligatable to the hybridized open circle probe 5'-terminus and a gap is present between those termini.

The ligation reaction solution is maintained for a time period sufficient to permit the filling-in of the gap when DNA polymerase is present, and also for a time period sufficient for ligation of the termini of the open circle probe to form a closed circular probe, and thus a treated ligation reaction solution.

The closed circular probe is admixed with an amplification primer, which hybridizes with the amplification primer target, nucleoside triphosphates, and a polymerizing amount of a DNA polymerase to form a replication reaction mixture. The replication reaction mixture is maintained for a time period sufficient to permit the extension of a nucleic acid strand from the amplification primer. The extension product nucleic acid strand comprises an interrogation target to form a treated replication mixture.

An interrogation probe is admixed with the treated replication mixture. The interrogation probe is complementary to the interrogation target, and comprises an identifier nucleotide in its 3'-terminal region. The treated replication mixture is denatured before, during or after addition of the probe to form a denatured mixture. Preferably, the treated replication mixture is denatured after addition of the probe. The denatured mixture is annealed to permit the formation of a hybrid between the interrogation probe and the interrogation target, when present, thus forming an interrogation solution. A depolymerizing amount of an enzyme, whose activity is to release one or more nucleotides from the $_3$'-terminus of a hybridized nucleic acid probe, is admixed with the interrogation solution, thus forming a depolymerization reaction mixture. The depolymerization and analysis for released identifier nucleotide is as described above.

Preferably, the depolymerizing enzyme is thermostable. In a preferred embodiment, the free nucleotide triphosphates are separated from the treated replication mixture prior to the depolymerization step.

Optionally, in the above process wherein there is a gap present between the termini of the hybridized open circle probe, the portion of the predetermined nucleic acid target sequence between the 3'- and 5'-termini of the hybridized open circle probe that is opposite the gap contains three or fewer nucleotides and only nucleoside triphosphates complementary to the three or fewer nucleotides are present in the ligation reaction solution. Preferably, a polymerizing amount of a DNA polymerase and nucleoside triphosphates are present in the ligation reaction solution. Optionally, the open circle probe comprises a plurality of detection primer targets. Preferably, in the above process, the presence or absence of a plurality of predetermined nucleic acid targets is determined using a plurality of detection probes comprising different identifier nucleotides. Analysis of the released identifier nucleotide is preferably done according to methods disclosed elsewhere herein.

Another embodiment of the invention contemplates an amplification and interrogation process to determine the presence or absence of a predetermined nucleic acid target sequence having a 3'-portion and a 5'-portion comprising the following steps.

A ligation reaction solution is provided, comprising (i) a ligating amount of a ligase, (ii) a nucleic acid sample that may contain a predetermined nucleic acid target sequence wherein the nucleic acid target sequence has a 3'-portion and a 5'-portion, (iii) a pair of ligation probes, the ligation probe further including a detection primer target and an amplification primer target, the amplification primer target being downstream of the detection primer target, wherein upon hybridization between the open circle probe and the nucleic acid target sequence, the open circle probe 3'-terminal region is complementary to a sequence of the 3'-portion of the predetermined nucleic acid target sequence, and the open circle probe 5'-terminal region is complementary to a sequence of the 5'-portion of said predetermined nucleic acid target sequence, and (iv) optionally further comprising a polymerizing amount of a DNA polymerase and deoxynucleoside triphosphates when the hybridized open circle probe 3'-terminus is not adjacent and ligatable to the hybridized open circle probe 5'-terminus and a gap is present between those termini The ligation reaction solution is maintained for a time period sufficient to permit filling-in of the gap, when present, and ligation of the termini of the open circle probe to form a closed circular probe and a treated ligation reaction solution.

The closed circular probe is admixed with an amplification primer that hybridizes with the amplification primer target, nucleoside triphosphates, and a polymerizing amount of a DNA polymerase to form a replication reaction mixture.

The replication reaction mixture is maintained for a time period sufficient to permit extension of a nucleic acid strand from the amplification primer, wherein the extension product nucleic acid strand comprises a interrogation target to form a treated replication mixture.

An interrogation probe is admixed with the treated replication mixture, wherein the interrogation probe is complementary to the interrogation target and comprises an identifier nucleotide in the 3'-terminal region.

The treated replication mixture is denatured to form a denatured mixture.

The denatured mixture is annealed to form a hybrid between the interrogation probe and the interrogation target when present to form an interrogation solution.

A depolymerizing amount of an enzyme whose activity is to release one or more nucleotides from the 3'-terminus of a hybridized nucleic acid probe is admixed with the interrogation solution to form a depolymerization reaction mixture.

The depolymerization reaction mixture is maintained under depolymerizing conditions for a time period sufficient to permit the enzyme to depolymerize hybridized nucleic acid and release identifier nucleotide therefrom. The presence of released identifier nucleotide is analyzed to obtain an analytical output, the analytical output indicating the presence or absence of the predetermined nucleic acid target sequence.

Preferably, the depolymerizing enzyme is thermostable. In one embodiment of the process, free nucleotide triphosphates are separated from the treated replication mixture prior to step admixing a depolymerizing amount of an enzyme whose activity is to release one or more nucleotides from the 3'-terminus of a hybridized nucleic acid probe with the interrogation solution to form a depolymerization reaction mixture. In another embodiment of the process, there is a gap present between the termini of the hybridized open circle probe, the portion of the predetermined nucleic acid target sequence between the 3'- and 5'-termini of the hybridized open circle probe that is opposite the gap contains three or fewer nucleotides and only nucleoside triphosphates complementary to the three or fewer nucleotides are present in the ligation reaction solution. Preferably, a polymerizing amount of a DNA polymerase and nucleoside triphosphates are present in the ligation reaction solution.

Optionally, the open circle probe comprises a plurality of detection primer targets. Preferably, the presence or absence of a plurality of predetermined nucleic acid targets is determined using a plurality of detection probes comprising different identifier nucleotides.

Optionally, analysis of the released identifier nucleotides is by mass spectrometry.

The present invention has many benefits and advantages, several of which are listed below.

One benefit of the invention is that, in some embodiments, nucleic acid hybrids can be detected with very high levels of sensitivity without the need for radiochemicals or electrophoresis.

An advantage of the invention is that the presence or absence of one or more target nucleic acid(s) can be detected reliably, reproducibly, and with great sensitivity.

A further benefit of the invention is that quantitative information can be obtained about the amount of a target nucleic acid sequence in a sample.

A further advantage of the invention is that very slight differences in nucleic acid sequence are detectable, including single nucleotide polymorphisms (SNPs).

Yet another benefit of the invention is that the presence or absence of a number of target nucleic acid sequences can be determined in the same assay.

Yet another advantage of the invention is that the presence or absence of a target nucleic acid can be determined with a small number of reagents and manipulations.

Another benefit of the invention is that the processes lend themselves to automation.

Still another benefit of the invention is its flexibility of use in many different types of applications and assays including, but not limited to, detection of mutations, translocations, and SNPs in nucleic acid (including those associated with genetic disease), determination of viral load, species identification, sample contamination, and analysis of forensic samples.

Still further benefits and advantages of the invention will become apparent from the specification and claims that follow.

BRIEF DESCRIPTION OF THE DRAWING

In the drawings forming a portion of this disclosure,

FIG. 1 illustrates the annealing of the 10865 oligonucleotide (SEQ ID NO:196) to 10870 wild type (SEQ ID NO:194) and 10994 mutant (SEQ ID NO:195) oligonucleotides utilized in rolling circle amplification as FIG. 1A and FIG. 1B, respectively. Also shown are the annealing (hybridization) of oligonucleotide 10866 to oligonucleotide 10865, as well as the hybridization of oligonucleotide probe 10869 (SEQ ID NO:198) to oligonucleotide 10870 and of oligonucleotide probe 10989 (SEQ ID NO:199) to oligonucleotide 10994 as representations of the binding of those probes to the respective amplified sequences. Arcuate lines in oligonucleotide 10865 are used to help illustrate the shape that oligonucleotide 10865 can assume when hybridized with either of oligonucleotides 10870 or 10994.

FIG. 2. illustrates the Reaper™ assay as illustrated in Example 89. FIG. 2A illustrates the first hybrid formed by the annealing of nucleic acid target SEQ ID NO:286 (286) to first probe SEQ ID NO: 287 (287). An arrow points to an interrogation position in 286.

FIG. 2B illustrates the first extended hybrid formed by the annealing of 286 to the extended 287. Extended 287 is first extended probe SEQ ID NO: 288 (288).

FIG. 2C illustrates the second hybrid formed by annealing of 288 from the denatured nucleic acid molecule shown in FIG. 2B to the second probe denoted SEQ ID NO: 289 (289). An arrow points to the interrogation position in 288.

FIG. 2D illustrates the extended second hybrid formed by the annealing of 288 and the extended 289 strand denoted SEQ ID NO: 290 (290).

FIG. 2E illustrates the 290 strand denatured from FIG. 2D and forming a hairpin structure. An arrow points to the interrogation position at the 3'-terminus of the hybrid.

DEFINITIONS

To facilitate understanding of the invention, a number of terms are defined below.

"Nucleoside", as used herein, refers to a compound consisting of a purine [guanine (G) or adenine (A)] or pyrimidine [thymine (T), uridine (U) or cytidine (C)] base covalently linked to a pentose, whereas "nucleotide" refers to a nucleoside phosphorylated at one of its pentose hydroxyl groups. "XTP", "XDP" and "XMP" are generic designations for ribonucleotides and deoxyribonucleotides, wherein the "ITP" stands for triphosphate, "DP" stands for diphosphate, and "MP" stands for monophosphate, in conformity with standard usage in the art. Subgeneric designations for ribonucleotides are "NMP", "NDP" or "NTP", and subgeneric designations for deoxyribonucleotides are "dNMP", "dNDP" or "dNTP". Also included as "nucleoside", as used herein, are materials that are commonly used as substitutes for the nucleosides above such as modified forms of these bases (e.g. methyl guanine) or synthetic materials well known in such uses in the art, such as inosine.

A "nucleic acid," as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides. A "polynucleotide," as used herein, is a nucleic acid containing a sequence that is greater than about 100 nucleotides in length. An "oligonucleotide," as used herein, is a short polynucleotide or a portion of a polynucleotide. An oligonucleotide typically contains a sequence of about two to about one hundred bases. The word "oligo" is sometimes used in place of the word "oligonucleotide".

A base "position" as used herein refers to the location of a given base or nucleotide residue within a nucleic acid.

A "nucleic acid of interest," as used herein, is any particular nucleic acid one desires to study in a sample.

The term "isolated" when used in relation to a nucleic acid or protein, refers to a nucleic acid sequence or protein that is identified and separated from at least one contaminant (nucleic acid or protein, respectively) with which it is ordinarily associated in its natural source. Isolated nucleic acid or protein is present in a form or setting that is different from that in which it is found in nature. In contrast, non-isolated nucleic acids or proteins are found in the state they exist in nature.

As used herein, the term "purified" or "to purify" means the result of any process which removes some contaminants from the component of interest, such as a protein or nucleic acid. The percent of a purified component is thereby increased in the sample.

The term "wild-type," as used herein, refers to a gene or gene product that has the characteristics of that gene or gene product that is most frequently observed in a population and is thus arbitrarily designated the "normal" or "wild-type" form of the gene. In contrast, the term "modified" or "mutant" as used herein, refers to a gene or gene product that displays modifications in sequence and/or functional properties (i.e., altered characteristics) when compared to the wild-type gene or gene product.

Nucleic acids are known to contain different types of mutations. As used herein, a "point" mutation refers to an alteration in the sequence of a nucleotide at a single base position. A "lesion", as used herein, refers to site within a nucleic acid where one or more bases are mutated by deletion or insertion, so that the nucleic acid sequence differs from the wild-type sequence.

A "single nucleotide polymorphism" or SNP, as used herein, is a variation from the most frequently occurring base at a particular nucleic acid position.

Homologous genes or alleles from different species are also known to vary in sequence. Regions of homologous genes or alleles from different species can be essentially identical in sequence. Such regions are referred to herein as "regions of identity." It is contemplated herein that a "region of substantial identity" can contain some "mismatches," where bases at the same position in the region of identity are different. This base position is referred to herein as "mismatch position." DNA molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a nucleic acid sequence, even if internal to a larger oligonucleotide or polynucleotide, also can be said to have 5'- and 3'-ends. For example, a gene sequence located within a larger chromosome sequence can still be said to have a 5'- and 3'-end.

As used herein, the 3'-terminal region of the nucleic acid probe refers to the region of the probe including nucleotides within about 10 residues from the 3'-terminal position.

In either a linear or circular DNA molecule, discrete elements are referred to as being "upstream" or "5'" relative to an element if they are bonded or would be bonded to the 5'-end of that element. Similarly, discrete elements are "downstream" or "3'" relative to an element if they are or would be bonded to the 3'-end of that element. Transcription proceeds in a 5' to 3' manner along the DNA strand. This means that RNA is made by the sequential addition of ribonucleotide-5'-triphosphates to the 3'-terminus of the growing chain (with the elimination of pyrophosphate).

As used herein, the term "target nucleic acid" or "nucleic acid target" refers to a particular nucleic acid sequence of interest. Thus, the "target" can exist in the presence of other nucleic acid molecules or within a larger nucleic acid molecule.

As used herein, the term "nucleic acid probe" refers to an oligonucleotide or polynucleotide that is capable of hybridizing to another nucleic acid of interest. A nucleic acid probe may occur naturally as in a purified restriction digest or be produced synthetically, recombinantly or by PCR amplification. As used herein, the term "nucleic acid probe" refers to the oligonucleotide or polynucleotide used in a method of the present invention. That same oligonucleotide could also be used, for example, in a PCR method as a primer for polymerization, but as used herein, that oligonucleotide would then be referred to as a "primer". Herein, oligonucleotides or polynucleotides may contain a phosphorothioate bond.

As used herein, the terms "complementary" or "complementarity" are used in reference to nucleic acids (i.e., a sequence of nucleotides) related by the well-known base-pairing rules that A pairs with T and C pairs with G. For example, the sequence 5'-A-G-T-3', is complementary to the sequence 3'-T-C-A-5'. Complementarity can be "partial," in which only some of the nucleic acid bases are matched according to the base pairing rules. On the other hand, there may be "complete" or "total" complementarity between the nucleic acid strands when all of the bases are matched according to base pairing rules. The degree of complementarity between nucleic acid strands has significant effects on the efficiency and strength of hybridization between nucleic acid strands as known well in the art. This is of particular importance in detection methods that depend upon binding between nucleic acids, such as those of the invention. The term "substantially complementary" refers to any probe that can hybridize to either or both strands of the target nucleic acid sequence under conditions of low stringency as described below or, preferably, in polymerase reaction buffer (Promega, M195A) heated to 95° C. and then cooled to room temperature. As used herein, when the nucleic acid probe is referred to as partially or totally complementary to the target nucleic acid, that refers to the 3'-terminal region of the probe (i.e. within about 10 nucleotides of the 3'-terminal nucleotide position).

As used herein, the term "hybridization" is used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol), the molarity of the hybridizing strands and the G:C content of the nucleic acid strands.

As used herein, the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together. The art knows well that numerous equivalent conditions can be employed to comprise low stringency conditions.

As used herein, the term "$T_m$" is used in reference to the "melting temperature". The melting temperature is the temperature at which 50% of a population of double-stranded nucleic acid molecules becomes dissociated into single strands. The equation for calculating the $T_m$ of nucleic acids is well-known in the art. The $T_m$ of a hybrid nucleic acid is often estimated using a formula adopted from hybridization assays in 1 M salt, and commonly used for calculating $T_m$ for PCR primers: [(number of A+T)×2° C.+(number of G+C)× 4° C]. C. R. Newton et al. PCR, $2^{nd}$ Ed., Springer-Verlag (New York: 1997), p. 24. This formula was found to be inaccurate for primers longer that 20 nucleotides. Id. Other more sophisticated computations exist in the art which take structural as well as sequence characteristics into account for the calculation of $T_m$. A calculated $T_m$ is merely an estimate; the optimum temperature is commonly determined empirically.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous."

When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency.

When used in reference to a single-stranded nucleic acid sequence, the term "substantially homologous," as used herein, refers to a probe that can hybridize to (i.e., is the complement of) the single-stranded nucleic acid template sequence under conditions of low stringency.

The term "interrogation position," as used herein, refers to the location of a given base of interest within a nucleic acid probe. For example, in the analysis of SNPs, the "interrogation position" in the probe is in the position that would be complementary to the single nucleotide of the target that may be altered from wild type. The analytical output from a method of the invention provides information about a nucleic acid residue of the target nucleic acid that is complementary to an interrogation position of the probe. An interrogation position is within about ten bases of the actual 3'-terminal nucleotide of the nucleic acid probe, although not necessarily at the 3'-terminal nucleotide position. The interrogation position of the target nucleic acid sequence is opposite the interrogation position of the probe, when the target and probe nucleic acids are hybridized.

The term "identifier nucleotide," as used herein, refers to a nucleotide whose presence is to be detected in a process of the invention to identify that a depolymerization reaction has occurred. The particular application of a method of the invention affects which residues are considered an identifier nucleotide. For a method using ATP detection (e.g. luciferase/luciferin or NADH) wherein, during analysis, all nucleotides released in the depolymerization are "converted" to ATP with an enzyme such as NDPK, all nucleotides released are identifier nucleotides. Similarly, for a method using absorbance detection that does not distinguish between nucleotides, all released nucleotides are identifier nucleotides. For a mass spectrometric detection wherein all the released nucleotides are analyzed, all released nucleotides can be identifier nucleotides; alternatively a particular nucleotide (e.g. a nucleotide analog having a distinctive mass) can be detected. For fluorescence detection, a fluorescently-labeled nucleotide is an identifier nucleotide. The nucleotide may be labeled prior to or after release from the nucleic acid. For radiographic detection, a radioactively-labeled nucleotide is an identifier nucleotide. In some cases, the release of identifier nucleotide is deduced by analyzing the remainder of the probe after a depolymerization step of the invention. Such analysis is generally by a determination of the size or mass of the remaining probe and can be by any of the described analytical methods (e.g. a fluorescent tag on the 5'-terminus of the probe to monitor its molecular weight following capillary electrophoresis).

As used herein, the terms "restriction endonucleases" and "restriction enzymes" refer to a class of enzymes, each of which cut double-stranded DNA. Some restriction endonucleases cut double strand DNA at or near a specific nucleotide sequence, such as the enzyme commonly referred to as BamH I that recognizes the double strand sequence 5' GGATCC 3'. However, other representatives of such enzymes cut DNA in a non-specific manner such as the DNA endonuclease DNase I.

The term "sample," as used herein, is used in its broadest sense. A sample suspected of containing a nucleic acid can comprise a cell, chromosomes isolated from a cell (e.g., a spread of metaphase chromosomes), genomic DNA, RNA, cDNA and the like.

The term "detection," as used herein, refers to quantitatively or qualitatively identifying a nucleotide or nucleic acid within a sample.

The term "depolymerization," as used herein, refers to the removal of a nucleotide from the 3' end of a nucleic acid.

The term "allele," as used herein, refers to an alternative form of a gene and the term "locus," as used herein, refers to a particular place on a nucleic acid molecule.

DETAILED DESCRIPTION OF THE INVENTION

A method of this invention is used to determine the presence or absence of at least one predetermined (known) nucleic acid target sequence in a nucleic acid sample. A nucleic acid target is "predetermined" in that its sequence must be known to design a probe that hybridizes with that target. However, it should be noted that a nucleic acid target sequence, as used with respect to a process of this invention, may merely act as a reporter to signal the presence of a different nucleic acid whose presence is desired to be determined. That other nucleic acid of interest does not have to have a predetermined sequence. Furthermore, a process of the invention is useful in determining the identity of base within a target where only enough of the sequence is known to design a probe that hybridizes to that target with partial complementarity at the 3'-terminal region of the probe.

Such a method utilizes an enzyme that can depolymerize the 3'-terminus of an oligonucleotide probe hybridized to the nucleic acid target sequence to release one or more identifier nucleotides whose presence or absence can then be determined as an analytical output that indicates the presence or absence of the target sequence.

A nucleic acid target sequence is predetermined (or known) in that a nucleic acid probe is provided to be partially or totally complementary to that nucleic acid target sequence. A nucleic acid target sequence is a portion of nucleic acid sample with which the probe hybridizes if that target sequence is present in the sample.

A first step of the method is admixing a sample to be assayed with one or more nucleic acid probes. The admixing of the first step is typically carried out under low stringency hybridizing conditions to form a hybridization composition. In such a hybridization composition, the 3'-terminal region of the nucleic acid probe(s) (i) hybridizes with partial or total complementarity to a nucleic acid target sequence that may be present in the sample; and (ii) includes an identifier nucleotide in the 3'-terminal region.

Preferably, the nucleic acid probe is designed to not hybridize with itself to form a hairpin structure in such a way as to interfere with hybridization of the 3'-terminal region of the probe to the target nucleic acid. Parameters guiding probe design are well known in the art.

The hybridization composition is maintained under hybridizing conditions for a time period sufficient to form a treated sample that may contain at least one predetermined nucleic acid target sequence hybridized with a nucleic acid probe.

In the event that the sample to be assayed does not contain a target sequence to which the probe hybridizes, no hybridization takes place. When a method of the present invention is used to determine whether a particular target sequence is present or absent in a sample to be assayed, the resulting treated sample may not contain a substrate for the enzymes of the present invention. As a result, a 3' terminal region identifier nucleotide is not released and the analytical output is at or near background levels.

The treated sample is admixed with a depolymerizing amount of an enzyme whose activity is to release one or more identifier nucleotides from the 3'-terminal region of the probe that is hybridized to the nucleic acid target to form a depolymerization reaction mixture. The choice of enzyme used in the process determines if a match or mismatch at the 3'-terminal nucleotide results in release of that 3'-terminal nucleotide. Further information regarding specific enzyme reaction conditions is discussed in detail hereinafter.

The depolymerization reaction mixture is maintained under depolymerizing conditions for a time period sufficient to permit the enzyme to depolymerize hybridized nucleic acid and release identifier nucleotides therefrom to form a treated reaction mixture.

The presence or absence of released identifier nucleotides is then determined to obtain an analytical output. The analytical output indicates the presence or absence of at least the one nucleic acid target sequence.

Processes of the invention can also be concerned with the degree of hybridization of the target to the 3'-terminal region of the probe. Examples hereinafter show that the distinction between a matched and mismatched base becomes less notable as a single mismatch is at a position further upstream from the 3'-terminal region position. There is very little discrimination between a match and mismatch when a single mismatch is ten to twelve residues from the 3'-terminal nucleotide position, whereas great discrimination is observed when a single mismatch is at the 3'-terminus. Therefore, when the degree of complementarity (partial or total complementarity) of a nucleic acid probe hybridized to a target nucleic acid sequence is referred to herein in regard to an identifier nucleotide, this is to be understood to be referring to within the 3'-terminal region, up to about ten residues of the 3'-terminal position.

In particular embodiments of the invention, it is desirable to include a destabilizing mismatch in or near the 3'-terminal region of the probe. In an example of such an embodiment, the goal is to determine whether a nucleotide at an interrogation position is a match or a mismatch with the target. Better discrimination between match and mismatch at the interrogation position is observed when an intentional mismatch is introduced about 2 to about 10 nucleotides from the interrogation position or preferably about 2 to about 6 nucleotides from the interrogation position.

The distinction of the analytical output between matched and mismatched nucleotides when there is more than a single base that is mismatched within the 3'-terminal region can be evident even if mismatches are beyond position 10 from the terminus, for example at position 11 and 12 upstream of the 3'-terminal nucleotide. Thus, the phrases "about 10" and "3'-terminal region" are used above. The 3'-terminal region therefore comprises the approximately 10 residues from the 3'-terminal nucleotide (or 3' terminus) position of a nucleic acid.

The sufficiency of the time period for hybridization can be empirically ascertained for a control sample for various hybridizing conditions and nucleic acid probe/target combinations. Exemplary maintenance times and conditions are provided in the specific examples hereinafter and typically reflect low stringency hybridization conditions. In practice, once a suitable set of hybridization conditions and maintenance time periods are known for a given set of probes, an assay using those conditions provides the correct result if the nucleic acid target sequence is present. Typical maintenance times are about 5 to about 60 minutes.

The conditions and considerations with respect to hybridization of PCR primers to template nucleic acid in PCR are applicable to the hybridization of nucleic acid probes to target sequences in a process of the invention. Such hybridization conditions are well known in the art, and are a matter of routine experimentation depending on factors including the sequence of the nucleic acid probe and the target nucleic acid [sequence identity (homology), length and G+C content] molar amounts of nucleic acid present, buffer, salt content and duplex $T_m$ among other variables.

Processes of the invention are sensitive and hybridization conditions of low stringency (e.g. temperature of 0–4° C.) are sufficient, but moderate stringency conditions (i.e. temperatures of 40–60° C.) also permit hybridization and provide acceptable results. This is true for all processes of the invention.

In one contemplated embodiment of the invention, the enzyme whose activity is to depolymerize hybridized nucleic acid to release nucleotides from the probe 3'-terminal end is a template-dependent polymerase. In such an embodiment, the reverse of a polymerase reaction is used to depolymerize a nucleic acid probe, and the identifier nucleotide is released when the 3'-terminal nucleotide of the nucleic acid probe hybridizes with total complementarity to its nucleic acid target sequence. A signal confirms the presence of a nucleic acid target sequence that has the sequence sufficiently complementary to the nucleic acid probe to be detected by the process of the invention.

In an embodiment that uses a 3'→5' exonuclease activity of a polymerase, such as Klenow or T4 DNA polymerase (but not limited to those two enzymes), to depolymerize a nucleic acid probe, an identifier nucleotide is released when the 3'-terminal residue of the nucleic acid probe is mismatched and therefore there is only partial complementarity of the 3'-terminus of the nucleic acid probe to its nucleic acid target sequence. In this embodiment, to minimize background, the hybrid is typically purified from the un-annealed nucleic acid prior to the enzyme reaction, which releases identifier nucleotides. A signal confirms the presence of a nucleic acid target sequence that is not totally complementary to the nucleic acid probe.

In an embodiment that uses a 3'→5' exonuclease activity of Exonuclease III to depolymerize a nucleic acid probe, an identifier nucleotide is released when the 3'-terminal residue of the nucleic acid probe is matched to the target nucleic acid. A signal confirms the presence of a nucleic acid target that is complementary at the released identifier nucleotide.

It is thus seen that hybridization and depolymerization can lead to the release of an indicator nucleotide or to little or no release of such a nucleotide, depending upon whether the probe:target hybrid is matched or mismatched at the 3'-terminal region. This is also dependent on the type of enzyme used and the type of end, matched or mismatched, that the enzyme requires for depolymerization activity.

The magnitude of a contemplated analytical output under defined conditions is dependent upon the amount of released nucleotides. Where an identifier nucleotide is released, an analytical output can be provided that has a value greater than background. Where an identifier nucleotide is not released either because the target sequence was not present in the original sample or because the probe and depolymerizing enzyme chosen do not provide release of a 3'-terminal nucleotide when the target is present, or if the match/mismatch state of the 3'-terminal nucleotide did not match that required for the enzyme used to release a 3'-terminal nucleotide, the analytical output is substantially at a background level. Further discussion of computation of background levels can be found in the Examples, e.g. Example 1.

Depolymerization reactions and enzymes useful in such reactions are discussed below.

Depolymerization

Nucleic acid polymerases generally catalyze the elongation of nucleic acid chains. The reaction is driven by the cleavage of a pyrophosphate released as each nucleotide is added. Each nucleoside-5'-triphosphate has three phosphate groups linked to carbon five of the ribose or deoxyribose sugar. The addition of a nucleotide to a growing nucleic acid results in formation of an internucleoside phosphodiester bond. This bond is characterized in having a 3' linkage to carbon 3 of ribose or deoxyribose and a 5' linkage to carbon 5 of ribose or deoxyribose. Each nucleotide is added through formation of a new 3'→5' linkage, so the nucleic acid strand grows in a 5' to 3' direction.

Depolymerization in its strictest sense means the reverse of polymerization so that in the present context, an internucleotide phosphodiester bond is broken between the two 3'-terminal bases in the presence of pyrophosphate and a polymerase enzyme to form a nucleic acid that is one nucleotide shorter and a nucleoside triphosphate. A somewhat more encompassing definition is contemplated here. In accordance with that definition, the 3'-terminal nucleotide is removed from a nucleic acid in a reaction catalyzed by an enzyme, but the nucleotide formed can be a monophosphate and pyrophosphate is not always required.

The former reactions are referred to herein as pyrophosphorolysis reactions whereas the latter reactions are referred to as exonuclease reactions. These two types of depolymerization are discussed below.

It is to be understood that the depolymerization reaction of interest in the invention is that depolymerization occurring in the 3'-terminal region of the nucleic acid probe. This depolymerization reaction releases identifier nucleotide, as discussed herein.

A. Pyrophosphorolysis

In some embodiments of the present invention, a method comprises depolymerizing the nucleic acid (NA) at a 3'-terminal nucleotide by enzymatically cleaving the terminal internucleoside phosphodiester bond in the presence of pyrophosphate, or an analogue thereof, to form an XTP as illustrated by the following reaction on double-stranded DNA having a 5' overhang:

5' ... TpApCpGpGpCpT-3'OH
3' ... ApTpGpCpCpGpApCpTp-5'

↓ enzyme + PPi

5' ... TpApCpGp-3'OH
3' ... ApTpGpCpCpGpApCpTp-5'

+ dGTP + dCTP + dTTP

Several polymerases are known to catalyze the reverse of the polymerization process. This reverse reaction is called "pyrophosphorolysis." The pyrophosphorolysis activity of DNA polymerase was demonstrated by Deutscher and Kornberg, *J. Biol. Chem.*, 244:3019–28 (1969). Other template-dependent nucleic acid polymerases capable of pyrophosphorolysis include, but are not limited to, DNA polymerase α, DNA polymerase β, T4 DNA polymerase, Taq polymerase, Tne polymerase, Tne triple mutant polymerase, Tth polymerase, Tvu polymerase, Ath polymerase, Bst polymerase, *E. coli* DNA polymerase I, Klenow fragment, Klenow exo minus (exo-), AMV reverse transcriptase, RNA polymerase and MMLV reverse transcriptase. However, not all polymerases are known to possess pyrophosphorolysis activity. For example, poly(A) polymerase has been reported to not catalyze pyrophosphorylation. (See Sippel, *Eur. J. Biochem.* 37:31–40 (1973)).

A mechanism of pyrophosphorolysis has been suggested for RNA polymerase. Although understanding of the mechanism is not necessary to use the present invention, it is believed that the partial transfer of a $Mg^{2+}$ ion from the attacking pyrophosphate to the phosphate of the internucleoside phosphodiester bond of the RNA can increase the nucleophilic reactivity of the pyrophosphate and the electrophilicity of the diester as described in Rozovskaya et al., *Biochem. J.*, 224:645–50 (1984). The internucleoside phosphodiester bond is enzymatically cleaved by the addition of pyrophosphate to the nucleoside 5' phosphate and a new phosphodiester bond is formed between the pyrophosphate and the nucleoside monophosphate.

The pyrophosphorolysis reaction can be summarized as follows:

$$NA_n + PP_i \rightarrow NA_{n-1} + XTP \qquad \text{Reaction 1}$$

wherein NA is a nucleic acid, n is the number of nucleotide bases, $PP_i$ is pyrophosphate and XTP is either a DNTP molecule or NTP molecule. The reaction can then be repeated so as to produce at least two XTP molecules. It should be noted that the reaction can be repeated on the same nucleic acid molecule or on a plurality of different nucleic acid molecules.

In a preferred embodiment in the case of the reverse of polymerase activity (pyrophosphorolysis), a preferred substrate is a DNA probe hybridized to a nucleic acid target sequence with total complementarity at its 3'-terminus, including an identifier residue at the 3'-terminal region. In an example of this preferred embodiment, when the nucleic acid probe is hybridized to a nucleic acid target sequence such that there is one base mismatch at the 3'-terminal nucleotide of the nucleic acid probe, the nucleic acid probe is inefficiently depolymerized through the reverse polymerization reaction. Thus, such a substrate is not an ideal substrate for depolymerization.

The non-ideality of the substrate for depolymerization via a reverse of the polymerization reaction is recognized with a single base mismatch as far in as about 10 residues from the 31-terminus of the nucleic acid probe. With a single base mismatch 12 residues from the 3'-terminus of the probe, the depolymerization reaction can occur to approximately the same extent as when there is no mismatch and the nucleic acid probe is totally complementary to the nucleic acid target sequence.

It is thus contemplated that the reactivity of the depolymerization reaction is a continuum that is related to the efficiency of the substrate. A partially complementary hybrid is a less efficient depolymerization substrate than a totally complementary hybrid for the reverse of a polymerization reaction. It is contemplated that this differential reactivity be used to enhance the discrimination between matches and mismatches at certain positions (e.g. an interrogation position). When a substrate hybrid is totally complementary, it will give a fairly high analytical output. A mismatch can be intentionally introduced to destabilize the substrate hybrid. Such a destabilization can increase the difference in analytical output between bases substituted at an interrogation position that is different from the destabilizing base position.

Several chemical compounds are known in the art to be substitutable for pyrophosphate in pyrophosphorolysis reactions. Rozovskaya, et al., *Biochem. J.*, 224:645–650 (1984). Exemplary compounds and their released nucleotide product are shown in the table below, along with the nucleotide product (where the ribonucleoside or deoxyribonucleoside is denoted "Nuc") of pyrophosphorolysis.

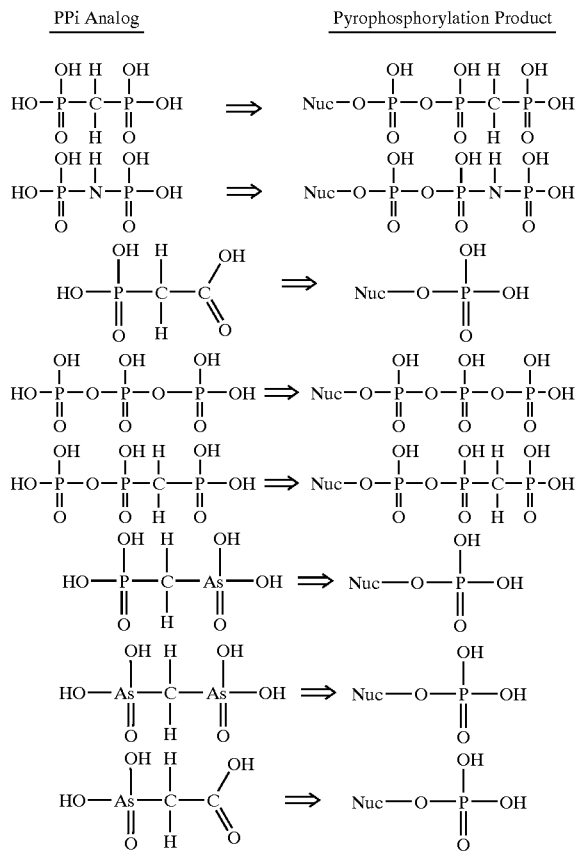

Preferred reaction mixtures for depolymerization by pyrophosphorolysis, including suitable buffers for each nucleic acid polymerase analyzed, are described in greater detail in the Examples. Typically, under these conditions, sufficient NTP or dNTP is released to accurately detect or assay extremely low amounts of nucleic acids (e.g., about 5–1000 picograms). ATP can be produced by conversion from XTP by an enzyme such as NDPK (in the presence of ADP) prior to analysis or the ATP can be further amplified prior to analysis.

Even though the preferred reaction conditions for polymerization and depolymerization by pyrophosphorolysis are similar, the rates of these reactions can vary greatly. For example, AMV and RLV reverse transcriptases catalyze pyrophosphorolysis under optimal conditions at a rate of about fifty- to one hundred-fold less than polymerization as demonstrated in Srivastavan and Modak, *J. Biol. Chem.*, 255(5): 2000–04 (1980). Thus, the high efficiency of the pyrophosphorolysis reaction was unexpected, and appears to be associated with extremely low levels of DNA substrate, in contrast to previous DNA pyrophosphorolysis studies conducted using much greater amounts of DNA.

Although not wishing to be bound by theory, a possible explanation for this effect might also be that the molar concentrations of free deoxyribonucleoside triphosphates produced at very low DNA levels would be predicted to be very low. Indeed, these levels are expected to be far below the Michaelis constant ($K_m$) of the enzyme. Thus, reincorporation of released dNTPs would be expected to be vanishingly small.

The pyrophosphorolysis activity of different nucleic acid polymerases also varies. For example, T4 polymerase and Tne DNA polymeraze possess very high pyrophosphorolysis activity as measured by a luciferase assay for ATP produced by pyrophosphorolysis. Pyrophosphorolysis using T4 polymerase resulted in about a 10 fold increase in light production as compared to MMLV-RT and a 4 fold increase in light production as compared to Taq polymerase.

During the development of the invention disclosed in the parent application, it was discovered that the detection of some types of nucleic acids at low picogram levels is generally enhanced by fragmenting or partially digesting the nucleic acid. Preferably, fragmentation is accomplished by sonication or restriction enzyme digestion of the nucleic acid in order to provide a plurality of smaller nucleic acid fragments. Although an understanding of the mechanism is not necessary in order to practice the present invention, this step probably enhances detection because the pyrophosphorolysis reaction only proceeds from the nucleic acid ends. By providing a greater number of nucleic acid ends, more reactions are allowed to occur at any one time.

It should be noted that DNA ends can be present within a molecule as well as at the end of a linear DNA fragment. For example, polymerases can catalyze pyrophosphorolysis from a gap or a nick in a DNA segment. The type of enzyme and substrate used for pyrophosphorolysis reactions determine whether fragmentation is necessary.

The type of DNA end resulting from restriction enzyme digestion also affects the pyrophosphorolysis activity of different nucleic acid polymerases. For example, Klenow exo-, MMLV-RT and Taq polymerase catalyze pyrophosphorolysis of DNA fragments with 51-overhangs and with blunt-ends, but have little or no pyrophosphorolysis activity with 3'-overhangs. In contrast, T4 DNA polymerase catalyzes both 3'- and 5'-end overhang and blunt-end mediated pyrophosphorolysis. Thus, T4 DNA polymerase is a preferred enzyme for pyrophosphorolysis of a hybrid with a 3'-overhang. When other nucleic acid polymerases are utilized for pyrophosphorolysis of restriction enzyme treated DNA, it is contemplated that care is taken to match the end specificity of the polymerase with the type of end created by the restriction endonuclease. Such care is well within the skill of those in the art.

Tabor and Richardson, *J. Biol. Chem.* 265 (14): 8322–28 (1990) reported unwanted pyrophosphorolysis mediated by T7 DNA polymerase-catalyzed DNA sequencing by the chain termination method. Those authors note that, even at the most sensitive sites, the rate of unwanted pyrophosphorolysis is at least 100,000 times slower than the rate of polymerization.

By definition, DNA sequencing is directed to ascertaining an unknown DNA sequence, rather than the detection of a known DNA sequence. In DNA sequencing by the chain termination method, oligonucleotide primers are extended by T7 DNA polymerase supplied with exogenous dNTPs and dideoxy NTPs. When a dideoxy NTP is incorporated into an elongating primer, no further polymerization can take place. These dideoxy-terminated fragments are then resolved on a DNA sequencing gel. However, in certain instances unwanted pyrophosphorolysis removes a 3'-terminal dideoxynucleotide from the elongated primer, which allows T7 DNA polymerase to catalyze additional polymerization. This additional polymerization leads to the degradation (loss) of specific dideoxynucleotide-terminated fragments on DNA sequencing gels. In other words, the resulting DNA sequencing gel will exhibit "holes" or gaps where the DNA sequence cannot be determined.

Tabor and Richardson, above, noted that when dNTPs are present in high concentrations, these pyrophosphorolysis sites occur once in several thousand nucleotides. Those authors have identified a canonical sequence, 5' dIdAdN$_1$ddN$_2$ 3', which is especially sensitive to pyrophosphorolysis when dITP is substituted for dGTP. This unwanted T7 DNA polymerase-mediated pyrophosphorolysis reaction can be avoided by the addition of pyrophosphatase, which eliminates PP$_i$ from the DNA sequencing reaction mixture. Pyrophosphatase, it is reported, eliminates the gaps in a DNA sequencing gel, permitting the accurate determination of a DNA sequence using T7 DNA polymerase-mediated dideoxy sequencing.

The present invention, in contrast, seeks to exploit DNA polymerase-mediated pyrophosphorolysis, by optimizing conditions for this reverse reaction to take place. The present invention is directed to the detection of a known sequence in a target nucleic acid, rather than ascertaining an unknown nucleic acid sequence using the polymerization activity of T7 DNA polymerase.

The pyrophosphorolysis reported by Tabor and Richardson cannot detect the presence of a specific nucleic acid sequence. In fact, DNA sequencing by the dideoxy method relies upon the incorporation of dideoxy nucleotides into an elongating primer. The T7 DNA polymerase-mediated pyrophosphorolysis reported by those authors is equally random, although there is reported a preference for the above-mentioned canonical sequence. According to Tabor and Richardson, in the absence of pyrophosphatase, one would only note gaps in a DNA sequencing gel, and those gaps would not provide any information as to the DNA sequence at those gaps. There is accordingly no method disclosed for identifying the release of 3'dideoxy nucleotides by the reported T7 DNA polymerase-mediated pyrophosphorolysis.

Further, it is contemplated that the type of polymerase used in the pyrophosphorolysis reaction is matched to the correct nucleic acid substrate in order to produce the best results. In general, DNA polymerases and reverse transcriptases are preferred for depolymerizing DNA, whereas RNA polymerases are preferred for depolymerizing RNA. Reverse transcriptases or DNA polymerases with reverse transcriptase activity are preferred for depolymerizing RNA-DNA hybrids.

In the parent application, it was surprisingly determined that poly(A) polymerase can catalyze pyrophosphorolysis, even though no such reaction had been previously reported. Indeed, poly(A) polymerase has been widely reported to not catalyze pyrophosphorolysis. (See e.g., Sippel, *Eur. J. Biochem.*, 37:31–40 (1973) and Sano and Feix, *Eur. J. Biochem.*, 71:577–83 (1976)). In these preferred embodiments of the invention disclosed in the parent application, the manganese chloride present in the previously reported buffers is omitted, the concentration of sodium chloride is decreased, and the pH value is lowered from about 8.0 to about 7.5. Furthermore, the poly(A) polymerase pyrophosphorolysis reaction buffer contains about 50 mM Tris-Cl pH 7.5, 10 mM MgCl$_2$, 50 mM NaCl, and 2 mM NaPP$_i$ (sodium pyrophosphate).

It is important to note that the depolymerization reaction is the reverse of the polymerization reaction. Therefore, as increasing amounts of free nucleoside triphosphates are produced by depolymerization, a state of equilibrium can theoretically be attained in which polymerization and depolymerization reactions are balanced. Alternatively, where small amounts of nucleic acid are detected, the reaction can go essentially to completion without reaching equilibrium, (i.e., the nucleic acid target is depolymerized into its constituent subunit nucleotides by greater than 50%). This factor is important in quantitative assays because the total amount of nucleotides released is proportional to the amount of signal generated in the detection assay.

When used for qualitative detection of nucleic acid, as long as a threshold level of nucleotides is produced, it is not necessary that the reaction reach equilibrium or go essentially to completion. In preferred embodiments, the mixture of nucleoside triphosphate molecules produced by depolymerization is preferably converted to ATP as described below. For either quantitative or qualitative detection, a detectable threshold ATP concentration of approximately $1 \times 10^{-12}$ molar in 100 $\mu$l of sample is preferably provided for detection of light in a typical luciferase assay.

In some preferred embodiments, oligonucleotide probes are typically utilized at about 100 ng to about 1 $\mu$g per 20 $\mu$L depolymerization reaction. That amount provides a probe to target weight ratio of about 200:1 to about 1,000:1.

In a preferred embodiment of the present invention, nucleic acid polymerase and pyrophosphate (PPi) or an analogue thereof, are added to a hybridized sample containing from less than about 100 tg of target nucleic acid, to less than about 10 pg of nucleic acid. Typical target nucleic acids are present at about 1 to about 5 ng in the sample to be assayed, with a target nucleic acid length of about 30 to about 1000 bp being preferred.

Next, the hybridized nucleic acid is degraded (depolymerized) by pyrophosphorolysis, releasing free NTPs or dNTPs. Enzymes useful in the pyrophosphorolysis reaction include, but are not limited to, those noted previously such as the following polymerases: AMV reverse transcriptase, MMLV reverse transcriptase, DNA polymerase alpha and beta, Taq polymerase, Tne polymerase, Ath polymerase, Tvu polymerase, Tne triple mutant polymerase, T4 DNA polymerase, *E. coli* DNA polymerase I, Klenow fragment, Klenow exo minus, Tth polymerase, and poly(A) polymerase.

Most preferably, Klenow exo minus (Klenow exo-) or Tne triple mutant polymerase is utilized for DNA pyrophosphorolysis reactions because of their efficient utilization of 5' overhanging DNA ends.

When using enzymes that utilize 5' overhang substrates, it is preferred that the 3' end of the target nucleic acid extends beyond the 5' end of the nucleic acid probe. In this way, the only 5' overhang substrate is that where the 5' end of the target nucleic acid overhangs the 3' terminal region of the nucleic acid probe. An alternative method of limiting depolymerization to the nucleic acid probe is chemical modification of the ends of other nucleic acids in the sample, such as, for example, making a phosphorothioate linkage at the 3'-terminus of the target nucleic acid.

A depolymerizing enzyme is preferably present in an amount sufficient to depolymerize a hybridized target:probe. That amount can vary with the enzyme used, the depolymerization temperature, the buffer, and the like, as are well-known in the art. For a typical reaction carried out in a 20 μL volume, about 0.25 to about 1 unit (U) of an enzyme such as Klenow exo- is used. About 1 to about 5 U of the thermostable enzymes are used for depolymerization at elevated temperatures.

Luciferase, which is part of the preferred ATP detection system, is inhibited by $PP_i$. In preferred embodiments, care is taken to avoid transferring a highly inhibiting amount of $PP_i$ to the ATP detection reaction. Preferably, the amount of $PP_i$ carried over to the ATP detection reaction results in a concentration of $PP_i$ in the luciferase detection reaction of less than about 100 μM, although less than about 10 μM is desirable. Therefore, the amount of $PP_i$ utilized in the pyrophosphorolysis reaction is determined by the size of the aliquot that is taken for use in the luciferase detection system. It is contemplated that the aliquot size can vary depending upon the test system used, but the amount of $PP_i$ transferred or carried over to the luciferase detection reaction corresponds to the $PP_i$ concentration parameters described above, so that the concentration of $PP_i$ is at least below about 100 μM, and preferably below about 10 μM.

In one preferred embodiment of the invention, the enzyme whose activity is to depolymerize is a template-dependent polymerase. The depolymerization reaction is a reverse of the polymerization reaction. In a contemplated embodiment, the polymerization reaction is reversed in the presence of pyrophosphate in a reaction referred to as pyrophosphorolysis.

In some preferred embodiments, the reaction conditions are preferably adjusted to further favor depolymerization of a nucleic acid probe that is hybridized with its target nucleic acid sequence by providing a higher concentration of nucleic acid probe than its target nucleic acid sequence.

One strategy to favor the depolymerization of a probe::target hybrid is that the probe be in excess over the nucleic acid target in the hybridization step after denaturing of duplex target nucleic acid.

Another strategy to favor the depolymerization of a probe:target hybrid is to isolate only the strand of nucleic acid target to which the probe is complementary. There are several techniques that can be used to achieve this end.

In one technique, phosphorothioate linkages are utilized at the 5'-terminus of a target nucleic acid amplifying primer sequence, e.g., at the 1 to about 10 5'-most residues. Upon PCR amplification of the target, the phosphorothioate linkages of the primer become incorporated into the amplified target nucleic acid as part of one of a pair of complementary strands. Treatment of the double-stranded resulting molecule with T7 polymerase exonuclease 6 removes the non-phosphorothioate-containing strand. This technique is illustrated in detail in the Examples hereinafter.

In another technique, strand isolation can be accomplished by amplifying the target nucleic acid using PCR primers incorporated into the extended nucleic acid strand (with which a nucleic acid probe useful herein is designed to hybridize) that are not labeled, whereas primers for the complementary strand are labeled, such as with biotin. Then, the amplified nucleic acid is denatured and added to streptavidin linked to a solid support. A useful material is Streptavidin MagneSphere® paramagnetic particles (Promega, Z548A), where a magnet can be used to separate the desired target nucleic acid strand from its biotinylated complementary strand.

B. Exonuclease Digestion

In other embodiments of the present invention, a method comprises depolymerizing the nucleic acid at a 3'-terminal nucleotide by enzymatically cleaving the terminal internucleoside phosphodiester bond to form an XMP as illustrated by the following reaction on double-stranded DNA having a 5'-overhang:

5' ... GpCpTpApApGpT-3'OH
3' ... CpGpApTpTpCpApCpTp-5'

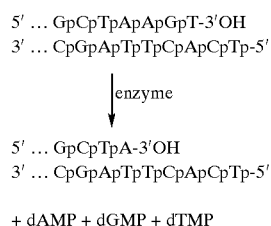

5' ... GpCpTpA-3'OH
3' ... CpGpApTpTpCpApCpTp-5'

+ dAMP + dGMP + dTMP

For example, such a hydrolysis reaction can be catalyzed by Klenow or Exonuclease III in the presence or absence of NTPs.

In some embodiments (e.g., quantitative assays for nucleic acids), the depolymerizing step is repeated essentially to completion or equilibrium to obtain at least two nucleotide molecules from a strand of minimally three nucleotides in order to increase detection sensitivity. In alternative embodiments, (e.g., qualitative detection of DNA), the depolymerizing step need not be repeated if there are sufficient nucleic acid molecules present to generate a signal.

In another embodiment of the present invention, terminally mismatched hybridized nucleic acid probes are first depolymerized into NMP or dNMP by exonuclease digestion according to the following reaction:

$$NA_n + H_2O \rightarrow NA_{n-1} + XMP \quad \text{Reaction 2}$$

wherein $NA_n$ is a nucleic acid, XMP is either a dNMP or NMP, and n is the number of nucleotides in the nucleic acid.

This depolymerization reaction is shown more specifically below in the following reaction on double-stranded DNA having a 5'-overhang and mismatched bases at the 3'-terminus:

5' ... CpTpApApGpC-3'OH
3' ... GpApTpTpCpApCpTp-5'

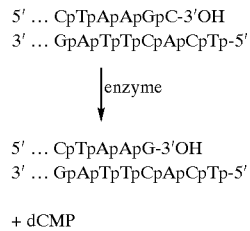

5' ... CpTpApApG-3'OH
3' ... GpApTpTpCpApCpTp-5'

+ dCMP

For example, such a depolymerization reaction can be catalyzed by bacteriophage T4 polymerase in the absence of NTPs. In preferred embodiments, the released nucleotides, XMPs, are produced by nuclease digestion.

Nuclease digestion can be accomplished by a variety of nucleases that release a nucleotide with a 5' phosphate, including Si nuclease, nuclease BAL 31, mung bean nuclease, exonuclease III and ribonuclease H. Nuclease digestion conditions and buffers are known in the art. Nucleases and buffers for their use are available from commercial sources.

In the biosynthesis of purine and pyrimidine mononucleotides, phosphoribosyl-1-pyrophosphate (PRPP) is the obligatory ribose-5'-phosphate donor. PRPP itself is formed in a reaction catalyzed by PRPP synthetase through the transfer of pyrophosphate from ATP to ribose-5'-phosphate. This reaction is known to be reversible as described in Sabina et al., Science, 223:1193–95 (1984).

In some embodiments of the present invention, the NMP or dNMP produced by nuclease digestion is preferably converted directly to NTP or dNTP by the enzyme PRPP synthetase in the following reaction:

XMP+PRPP→XTP+ribose-5'-PO$_4$                  Reaction 3 wherein XMP is either AMP or dAMP, and XTP is either ATP or DATP. Preferably, this reaction produces a threshold ATP concentration of approximately $1\times10^{-12}$ M in 100 $\mu$l of sample.

In this reaction, the pyrophosphate group of PRPP is enzymatically transferred to XMP molecules, forming XTP molecules. Examples of suitable reaction conditions and buffers are set forth elsewhere herein.

Utilization of the PRPP reaction in the nucleic acid detection system of the present invention has advantages over previously reported methods. For example, only one step is necessary to convert an AMP or dAMP to ATP or DATP, thereby simplifying the detection system. In addition, contamination of the detection reaction with exogenous ATP, ADP, or AMP is less likely using methods of the present invention, as compared to previously reported methods.

In an embodiment wherein the depolymerizing enzyme exhibits 3'→5' exonuclease activity, the substrate is a double-stranded or single-stranded nucleic acid having a 3'-hydroxyl terminus. Enzymes having 3'→5' exonuclease activity that are useful in a process of the invention include E. coli DNA polymerase I, Klenow fragment and bacteriophage T4 DNA polymerase. E. coli DNA polymerase I holoenzyme is not preferred in a process of the invention because it is preferable to avoid the 5'→3' exonuclease activity that degrades probe:target hybrids regardless of the degree of hybridization at the 3'-terminus. Bacteriophage λ exonuclease has only 5'→3' exonuclease activity, so it is not a contemplated enzyme. Similarly, Taq DNA polymerase has a very low level of 3'→5' exonuclease activity. Exonuclease III (Exo III) has 3' exonuclease activity on blunt-ended substrates or those having 5'-overhangs or nicks with 3'-hydroxyl groups, and is thus useful in a process of the invention for depolymerizing hybrids with matched 3' terminal nucleotides. However, Exo III is not limited to hybrids having only partially complementary 3'-termini, it requires a double stranded end, i.e. a matched terminal nucleotide.

In an embodiment of the invention where the enzyme's activity is a 3'→5' exonuclease activity, the hybridized nucleic acid probe is depolymerized from its 3'-terminal nucleotide. In a preferred is embodiment in the case of a 3'→5' exonuclease activity of a polymerase, the preferred substrate is a nucleic acid probe hybridized to a nucleic acid target sequence with partial complementarity at its 3'-terminal region, most preferably with a mismatch at its 3'-terminal residue that is an identifier nucleotide.

A contemplated method is particularly useful in a multiplex assay environment in which a plurality of probes is utilized to determine whether one or more of a plurality of predetermined nucleic acid sequences is present or absent in a sample. A particularly useful area for such multiplex assays is in screening assays where the usual analytical output indicates that the sought-after gene is absent.

In one illustrative embodiment, a nucleic acid sample is screened for the presence of a plurality of predetermined mutant genes. In this embodiment, the mutants usually are not present and the analytical output is, for example, at about background levels except where a mutation is present. In another embodiment, a plurality of samples is examined for the presence or absence of microbe-specific genes. Here, again, where a population of healthy individuals, animals, or presumably sterile food is sampled, the absence of the sought-after genes provides an analytical output that is about background levels, and only in the rare instance does a greater than the background output appear.

In a multiplexed embodiment of the above process, the sample is admixed with a plurality of different nucleic acid probes, preferably after amplification of the multiple nucleic acid targets as needed. In this embodiment of the invention, the analytical output for a certain result with one of the probes is distinguishable from the analytical output from the opposite result with all of the probes.

In preferred embodiments, the ATP produced via NDPK conversion of released nucleotides in the presence of ADP is detected by a luciferase detection system or an NADH detection system. In still another embodiment of the present invention, the pyrophosphate transferring step and the phosphate transferring step are performed in a single pot reaction. In other preferred embodiments, if increased sensitivity is required, the ATP molecules can be amplified.

In a contemplated multiplex embodiment, information about the presence or absence of a plurality of nucleic acid target sequences is determined using a process of the invention on a single nucleic acid sample, by admixing the sample with a plurality of nucleic acid probes for the various nucleic acid targets.

In a first multiplex embodiment of the invention, the analytical output obtained when at least one of the nucleic acid probes hybridizes with partial complementarity to its target nucleic acid sequence is greater than the analytical output when all of the nucleic acid probes hybridize with total complementarity to their respective nucleic acid target sequences. Preferably, in such an embodiment, the enzyme whose activity is to depolymerize hybridized nucleic acid to release nucleotides exhibits a 3'→5'-exonuclease activity, depolymerizing hybridized nucleic acids having one or more mismatched bases at the 3'-terminus of the hybridized probe.

In a second multiplex embodiment of the invention, the analytical output obtained when at least one of said nucleic acid probes hybridizes with partial complementarity to its target nucleic acid sequence is less than the analytical output when all of the nucleic acid probes hybridize with total complementarity to their respective nucleic acid target sequences. Preferably, in such an embodiment, the enzyme whose activity is to depolymerize hybridized nucleic acid to release nucleotides is a template-dependent polymerase.

In a third multiplex embodiment of the invention, the analytical output obtained when at least one of said nucleic acid probes hybridizes with total complementarity to its nucleic acid target sequence is greater than the analytical output when all of the nucleic acid probes hybridize with partial complementarity to their respective nucleic acid target sequences. Preferably, in such an embodiment, the enzyme whose activity is to depolymerize hybridized nucleic acid to release nucleotides is a template-dependent polymerase.

In a fourth multiplex embodiment of the invention, the analytical output obtained when at least one of said nucleic acid probes hybridizes with total complementarity to its target nucleic acid sequence is less than the analytical output when all of the nucleic acid probes hybridize with partial complementarity to their respective nucleic acid target sequences. Preferably, in such an embodiment, the enzyme whose activity is to depolymerize hybridized nucleic acid to release nucleotides exhibits a 3'→5'-exonuclease activity, depolymerizing hybridized nucleic acids having one or more mismatched bases at the 3'-terminus of the hybridized probe.

Analytical Output

The analytical output is obtained by detection of the released identifier products, either the released nucleotides or the remainder of the probe. Exemplary detection systems include the light emitting luciferase detection system, the NADH light adsorption detection system (NADH detection system), fluorescence emissions and mass spectrometry. These detection systems are discussed hereinbelow.

The fact that nucleotides were released (a qualitative determination), or even the number of nucleotides released (a quantitative determination) can be deduced through examination of the probe after depolymerization. The determination of the size of an oligonucleotide is well known in the art. For example gel separation and chromatographic separations are well known. Gel imaging techniques that take advantage of fluorescence and absorbance spectroscopy as well as radiographic methods. Mass spectrometry of oligonucleotides is also becoming more common.

A. Detection Of ATP

Luciferase detection systems are particularly useful for detecting ATP. In the presence of ATP and oxygen, luciferase catalyzes the oxidation of luciferin, producing light that can then be quantified using a luminometer. Additional products of the reaction are AMP, pyrophosphate and oxyluciferin.

In particularly preferred embodiments, ATP detection buffer referred to as L/L reagent (Promega, FF2021) is utilized. In some embodiments, Luciferase Assay Reagent (LAR) buffer (Promega, E152A) is used instead of L/L reagent. Preferably, about 5 to 10 ng of luciferase are used in the reaction. Although it is not intended that the present invention be limited to a specific concentration of luciferase, greater amounts of luciferase have a tendency to increase non-specific background.

It is contemplated that in some embodiments, the dNTPs or NTPs produced by pyrophosphorolysis or nuclease digestion are converted to XTP, which can then be used directly as substrate for luciferase, permitting detection of the nucleic acid. However, the preferred substrate for luciferase is ATP, as demonstrated by Moyer and Henderson, *Anal. Biochem.*, 131:187–89 (1983). When DNA is the initial substrate, NDPK is conveniently utilized to catalyze the conversion of dNTPs to ATP by the following general reaction:

dNTP*+ADP→DNDP+ATP*          Reaction 4 wherein dNTP is a mixture of deoxyribonucleoside triphosphates and DNDP is the corresponding deoxyribonucleoside diphosphate. In Reaction 4, the terminal 5'-triphosphate (P*) of the dNTP is transferred to ADP to form ATP.

Enzymes catalyzing this reaction are generally known as nucleoside diphosphate kinases (NDPKs). NDPKs are ubiquitous, relatively nonspecific enzymes. For a review of NDPK, see Parks and Agarwal, in *The Enzymes*, Volume 8, P. Boyer Ed. (1973).

The conversion of NTPs or dNTPs to ATP by NDPK is preferably accomplished by adding NDPK and a molar excess of ADP over the amounts of NTPs or dNTPs expected to be produced by pyrophosphorolysis or nuclease digestion, followed by pyrophosphorylation by PRPP synthetase. The utilization of ADP requires optimization of the amount of ADP added. Too much ADP results in high background levels.

NDPK (EC 2.7.4.6) preparations from several biological sources are commercially available from several suppliers. For example yeast NDPK is available from Sigma Chemical Co., St. Louis, Mo., whereas bovine NDPK is available from ICN Biochemicals, Inc., Costa Mesa, Calif. The particular NDPK selected for most uses described herein is typically a matter of choice.

A further embodiment of the invention, such as is used for Single Tandem Repeat (STR) detection, contemplates a method for determining the number of known repeated sequences that are present in a nucleic acid target sequence in a nucleic acid sample. A method for determining the number of repeated known sequences comprises the following steps. A plurality of separately treated samples is provided. Each sample contains a nucleic acid target sequence, containing a plurality of known repeated sequences and a non-repeated region, hybridized with a nucleic acid probe. Each nucleic acid probe contains a different number of complementary known repeated sequences of alleles of the target nucleic acid, an identifier nucleotide in the 3'-terminal region and a 5'-terminal locker sequence that is complementary to the non-repeated region of the target. A treated reaction mixture is formed by admixing each treated sample with a depolymerizing amount of an enzyme whose activity is to release one or more nucleotides from the 3'-terminus of a hybridized nucleic acid probe. The treated reaction mixture is maintained for a time period sufficient to permit the enzyme to depolymerize the hybridized nucleic acid probe and release an identifier nucleotide. The samples are analyzed for the presence or absence of released identifier nucleotide to obtain an analytical output. The analytical output from the sample whose probe contained the same number of sequence repeats as present in the target nucleic acid is indicative of and determines the number of sequence repeats present in the nucleic acid target.

In one aspect of the method, the target nucleic acid is homozygous with respect to the number of the repeated sequences at the two alleles. In an alternative method of the invention, the target nucleic acid is heterozygous for the repeated sequences. In another method of the invention, an identifier nucleotide is a nucleotide that is part of the region containing a repeated sequence. In an alternative method of the invention, an identifier nucleotide of the probe sequence is part of the region containing a non-repeating sequence that is complementary to that located in the target nucleic acid 5' to the repeated sequences. In this latter aspect of the method, the identifier nucleotide is present in a sequence containing 1 to about 20 nucleic acids that is complementary to a non-repeating sequence of the target nucleic acid located in the probe 3' to the repeated sequences. The repeated known sequence present in a nucleic acid target sequence typically has a length of 2 to about 24 bases per repeat. Di- and tri-nucleotide repeats are well known in the art.

As is illustrated in the Examples that follow, it can be beneficial to carry out a contemplated method at elevated temperatures, e.g., about 50° C. to about 90° C. An abovementioned NDPK has a very short half-life at these temperatures, e.g., less than about one minute, and it is preferred to use a thermostable NDPK for reactions at these elevated temperatures.

A particularly preferred thermostable NDPK was obtained by cloning the appropriate DNA of the thermophilic bacteria *Pyrococcus furiosis* (Pfu). The NDPK obtained, denoted NDPK Pfu, retains much more activity after maintenance at a temperature of 70° C. for a time period of 5 minutes than did yeast NDPK, and was found to have a half-life at a temperature of 70° C. of about 10 minutes as compared to yeast NDPK that had a half-life at that temperature of about 0.6 minutes. The recombinant enzyme contains 161 amino acid residues, whose sequence is provided as Pf5 in SEQ ID NO:91, with a corresponding DNA sense strand sequence as Pf4 in SEQ ID NO:90.

A contemplated thermostable NDPK, such as Pfu NDPK, is advantageously utilized in a so-called one-step or one-pot method of this invention. Here, a treated sample that may contain the predetermined nucleic acid target sequence hybridized with a nucleic acid probe that includes an identifier nucleotide in the 3'-terminal region is admixed with a depolymerizing amount of an enzyme whose activity in the presence of pyrophosphate is to release identifier nucleotides as nucleoside triphosphates from the hybridized nucleic acid probe, adenosine 5' diphosphate (ADP), pyrophosphate and NDPK to form a treated reaction mixture. The treated reaction mixture so formed is maintained for a time period sufficient to permit the enzyme to depolymerize the probe and to permit NDPK to convert the XTP present into ATP (as shown in reaction 4). The amount of ATP formed is determined by the production of an analytical output, with that output providing the indication of the presence or absence of the presence of the target nucleic acid sequence.

Although yeast, bovine or another NDPK can be used in these reactions, it is preferred to utilize a thermostable NDPK such as the Pfu NDPK along with a thermostable depolymerizing enzyme such as the Tne triple mutant DNA polymerase (discussed below), Bst DNA polymerase, Ath DNA polymerase, Taq DNA polymerase and Tvu DNA polymerase along with a reaction temperature of about 50° C. to about 90° C. The use of these thermostable enzymes at an above temperature can enhance the sensitivity of the method.

The Tne triple mutant DNA polymerase is described in detail in WO 96/41014, whose disclosures are incorporated by reference, and its 610 residue amino acid sequence is provided as SEQ ID NO:35 of that document. That enzyme is referred to in WO 96/41014 as Tne M284 (D323A, D389A).

Briefly, that enzyme is a triple mutant of the polymerase encoded by the thermophilic eubacterium *Thermotoga neapolitana* (ATCC 49049). The amino-terminal 283 residues of the native sequence are deleted and the aspartic acid residues at positions 323 and 389 of the native sequence are replaced by alanine residues in this recombinant enzyme. This recombinant enzyme is thus a deletion and replacement mutant of the native enzyme.

Deletion of the amino-terminal sequence removes the 5' exonuclease activity of the native enzyme, whereas replacement of the two aspartic acid residues removes a magnesium binding site whose presence facilitates exonuclease activity, and this triple mutant also exhibited no 3' exonuclease activity relative to the recombinant native enzyme. This triple mutant enzyme exhibited a half-life at 97.5° C. of 66 minutes as compared to the full length recombinant enzyme that exhibited a half-life of only 5 minutes at that temperature.

A reaction containing NDPK contains about 0.01 to 0.50 µM ADP, preferably about 0.05 µM ADP. Various useful buffers and other reaction components are set forth elsewhere. NDPK is itself present in an amount sufficient to catalyze the desired conversion of ADP to ATP. In a typical assay starting from a 20 µL depolymerization reaction, about 0.1 U of NDPK are used.

Where larger volumes of reactants are used, with the target and probe concentrations being approximately proportionately larger, the amount of NDPK or the other enzymes discussed herein can be used in a similar larger proportion relative to the amount discussed for the 20 µL reaction. Indeed, a 20 µL reaction has been successfully scaled down about two fold and scaled upwardly by a factor of about 20.

As an optional step, the NTP, DNTP, or ATP generated by the pyrophosphorolysis or nuclease digestion reactions followed by appropriate treatments can be amplified to give even greater sensitivity. For example, amplification can be required when detection systems other than luciferase are utilized or when increased levels of signal are needed for detection by a less sensitive luminometer. "Amplification of NTP" refers to a continuous reaction, wherein 1 NTP gives rise to 2 NTPs, which can be cycled to yield 4 NTPs and so on. When AMP is added to feed the amplification reaction, ATP accumulates. PCT publication WO 94/25619 and Chittock et al., *Anal. Biochem.*, 255:120–6 (1998), incorporated herein by reference, disclose amplification systems for ATP characterized by the following coupled reactions:

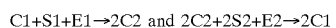
C1+S1+E1→2C2 and 2C2+2S2+E2→2C1

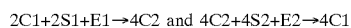
2C1+2S1+E1→4C2 and 4C2+4S2+E2→4C1

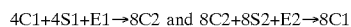
4C1+4S1+E1→8C2 and 8C2+8S2+E2→8C1                Reaction 5 wherein C1 is the target compound present in a sample to be amplified, S1 is the amplification substrate, E1 is a catalytic enzyme capable of utilizing C1 and S1 to produce C2, S2 is a high energy phosphate donating substrate, and E2 is a catalytic enzyme capable of utilizing C2 and S2 to produce C1, which then recycles through the reaction. According to this reaction scheme, each pass through the coupled reaction doubles the amount of C1, which can be subsequently detected. Patent Application GB 2,055,200 discloses an amplification system utilizing adenylate kinase and pyruvate kinase.

In providing a coupled ATP amplification reaction for use in nucleic acid detection, two main requirements should be considered. First, E1 should not be able to utilize the high energy phosphate donor utilized by E2. If E1 can utilize the high energy phosphate donor, the ATP amplification reaction proceeds in the absence of NTP or DNTP produced as a result of pyrophosphorolysis. This results in the undesirable occurrence of false positive results. Second, a molar excess of the added high energy phosphate donor is preferably provided as compared to the amount of XTP expected in the reaction. Third, E1 should be able to utilize either the NTP, dNTP, or ATP produced in step 1 by pyrophosphorolysis or nuclease digestion of the nucleic acid.

The amplification system of some preferred embodiments of the present invention can be characterized, as follows:

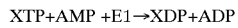
XTP+AMP +E1→XDP+ADP

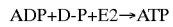
ADP+D-P+E2→ATP                        Reaction 6 wherein D-P is a high energy phosphate donor and E1 and E2 are enzymes capable of catalyzing the transfer of phosphates from an XTP to AMP and from the D-P to ADP, respectively. The ATP so produced can reenter the reaction (i.e., as XTP) and the reaction can be repeated until the substrates are exhausted or equilibrium is reached, resulting in the production of two ATPs for every ATP supplied to or generated by the reaction. When the target XTP is any nucleoside triphosphate other than ATP, the initial pass through the cycle yields only 1 ATP that then reenters the cycle to produce two ATP, both of which reenter the cycle to produce 4 ATP and so on. Preferably, the amplification reaction produces a threshold ATP concentration of approximately $1 \times 10^{-12}$ Molar in 100 $\mu$L of sample.

In some preferred embodiments, the XTP in the amplification system above is NTP or DNTP, which can preferably be ATP provided by pyrophosphorolysis (e.g., Reaction 1) or created from XTP by NDPK conversion of ADP to ATP (e.g., Reaction 4) or provided by nuclease digestion coupled with transformation of the XMPs to XTPs (e.g., Reaction 3) followed by NDPK conversion to ATP (e.g., Reaction 4). It should be appreciated, however, that when an amplification step is utilized for a DNA substrate, the step of converting dNTP to ATP is inherent in the amplification system. Therefore, a separate converting step is not required for the present invention.

A nucleoside monophosphate kinase (NMPK) or adenylate kinase is preferably utilized as enzyme 1 (E1). NMPKs occur as a family, each of which is responsible for catalyzing the phosphorylation of a particular NMP. Until recently, it was generally thought that ATP and DATP were preferred phosphate donors. However, Shimofuruya and Suzuki *Biochem. Intl.*, 26(5): 853–61 (1992) recently demonstrated that at least some NMPKs can utilize other phosphate donors such as CTP and UTP. Enzyme 2 (E2) is preferably NDPK or pyruvate kinase. NDPKs generally catalyze the transfer of the terminal 5'-triphosphate of NTPs to NDPs to form NTPs from the NDP. Pyruvate kinase catalyzes the transfer of phosphate from phosphoenolpyruvate (PEP) to ADP to form ATP. These enzymatic activities are utilized in the amplification reaction to transfer a phosphate group from a high energy phosphate donor (D-P) to either ADP or an NDP.

In particularly preferred embodiments, a high energy phosphate donor (D-P) that can be used by E2 but not by E1 is used. When E2 is NDPK, dCTP or α,β-methylene adenosine $5^1$-triphosphate (AMP-CPP) can be utilized as D-P. When E2 is pyruvate kinase, PEP is the preferred high energy phosphate donor.

Prior to the invention disclosed in the parent application, the ability of NDPK to utilize these substrates at efficiencies permitting production of minute quantities of ATP was not known. As the recent literature suggests that NMPK (E1) can utilize phosphate donors other than ATP or DATP, it is surprising that these high energy phosphate donors utilized with NMPK meet the requirements of the amplification reaction. The nonspecificity of adenylate kinase is also well known, and in the examples adenylate kinase is E-1, dCTP is not used as D-P.

The high energy phosphate donor and/or AMP is preferably provided in a molar excess as compared to the amount of ATP or dNTP expected to be present in the sample, so that the high energy phosphate donor is not recycled at an appreciable rate. Although it is not intended that the present invention be limited to any particular embodiment, various buffers and reaction components are provided in the Examples.

B. NADH Detection

In the NADH detection system, a combination of two enzymes, phosphoglycerate kinase and glyceraldehyde phosphate dehydrogenase, is used to catalyze the formation of NAD from NADH in the presence of ATP. Because NADH is fluorescent whereas NAD is not, ATP is measured as a loss in fluorescence intensity. Examples of NADH based ATP assays are disclosed in U.S. Pat. Nos. 4,735,897, 4,595,655, 4,446,231 and 4,743,561, and UK Patent Application GB 2,055,200, all of which are herein incorporated by reference.

C. Mass Spectrometric Analysis

In one method of the invention, the presence of released nucleotides is analyzed via mass spectrometry. In an embodiment of a method using mass spectrometry, the treated reaction mixture is ionized in a manner such that all components of the treated reaction mixture in the molecular weight range of the released identifier nucleotides are measured. Very small differences in molecular weight can be detected using mass spectrographic methods (different isotopes of the same atom are detectable), so any variation from a natural nucleic acid, including a single atom substitution (e.g. a fluorine in place of a hydrogen atom or a replacement of a hydrogen by a deuterium atom) in the identifier nucleotide gives rise to a detectable difference. Nucleic acid analogs used in methods of the invention should not interfere with either the hybridization of the nucleic acid probe or depolymerization of the hybridized probe.

Additionally, mass spectrometry can discriminate between individual nucleotides or nucleosides. For example, if the 3'-identifier nucleotide used in the instant invention was a G nucleotide, mass spectrometry can be used to detect the release of that G nucleotide in a method of the present invention. Similarly, mass spectrometry can detect the release of an A, T or C nucleotide, based on the differences in atomic weight of these compounds. Thus, in a multiplexing embodiment of the present invention, mass spectrometry can be used to resolve the presence of one or more of these 3'-identifier nucleotides.

In a particularly useful aspect of this embodiment, a mass spectral technique referred to as DIOS (desorption/ionization on silicon) was recently reported by Wei et al., *Nature*, 399:243(1999) that can accurately perform one or multiple assays on picogram or attagram amounts using commercially available mass spectrographs adapted with a specialized porous silicon sample well. The older, well known, MALDI mass spectrographic assay techniques can also be utilized.

In an embodiment of a multiplex method using mass spectrometry, multiple different identifier nucleotides can be used in the various nucleic acid probes. Using such a technique the presence of the different identifier nucleotides is direct evidence of the presence of the nucleic acid target sequences.

D. Fluorescence Spectroscopic Analysis

In some contemplated embodiments, the identifier nucleotide includes a fluorescent label. In one embodiment when the nucleotide is a fluorescent label, the analytical output is obtained by fluorescence spectroscopy. In an alternative embodiment when the nucleotide is a fluorescent label, the analytical output is obtained by mass spectrometry.

In a preferred embodiment of the invention, the fluorescent label is part of a fluorescent analog of a nucleotide. Fluorescent nucleotide analogs are widely known and commercially available from several sources. An exemplary source is NEN™ Life Science Products (Boston, Mass.), who offer dideoxy-, deoxy-, and ribonucleotide analogs a labeled with fluorescein, coumarin, tetramethylrhodamine, naphthofluorescein, pyrene, Texas Red@, and Lissamine™TM. Other suppliers include Amersham Pharmacia Biotech (Uppsala, Sweden; Piscataway, N.J.) and MBI Fermentas, Inc. (Amherst, N.Y.).

An advantage to using fluorescent labels and fluorescence spectroscopy analysis is that there are multiple different labels. Such different labels would be particularly useful in a multiplex embodiment of the invention. Different fluorescent labels would be used in different probes, so that the detection of a particular fluorescently-labeled nucleotide analog as a released identifier nucleotide could be used to deduce which nucleic acid targets are present.

For example, fluorescein has a 488 nm excitation and 520 nm emission wavelength, whereas rhodamine (in the form of tetramethyl rhodamine) has 550 nm excitation and 575 nm emission wavelength. A fluorescence detector provides an excitation source and an emission detector. The emission wavelengths of 520 nm and 575 nm are easily distinguishable using fluorescence spectroscopy.

On a per molecule basis, fluorescence spectroscopy is about 10-fold more sensitive than absorbance spectroscopy. A very wide variety of fluorescence spectroscopy-based detectors are commercially available for reading fluorescence values of single tubes, flow cells and multi-well plates, among others. For example, Labsystems Multiskan models of microplate readers are widely available with a spectral range of 400 to 750 nm, and filters for 340, 405, 414, 450, 492, 540, 620, and 690 nm (e.g. Fisher Scientific, Pittsburgh, Pa.).

It is contemplated that a released identifier nucleotide could be labeled before or after depolymerization using cross-linking chemistry well known in the art with commercially available reagents. For example, fluorescein isothiocyanate and rhodamine B isothiocyanate are both available from Aldrich Chemical Company (Milwaukee, Wis.). References to fluorescein isothiocyanate's use in labeling biological molecules include *Nature*, 193:167 (1962), *Methods Enzymol.* 26:28 (1972), *Anal. Biochem.*, 57:227 (1974), *Proc. Natl. Acad. Sci., U.S.*, 72:459 (1975).

It is contemplated that for many embodiments of the invention, it is useful to separate released fluorescent identifier nucleotides from those bound to an oligonucleotide, such as a probe. Thus, the separation techniques well known in the art and discussed above are useful with such an embodiment, including HPLC fitted with a fluorescence detector. The enhanced sensitivity of fluorescence relative to other spectroscopic techniques can be used to increase the sensitivity of a detection or quantification process of the invention.

E. Absorbance Spectroscopic Analysis

An absorbance spectrographic analysis step is contemplated to provide an analytical output, thereby provide for the determination of the presence or absence released identifier nucleotide, and indicate the presence or absence of said nucleic acid target sequence. This embodiment contemplates the chromatographic separation of a reaction mixture that has been treated with a depolymerizing amount of an enzyme whose activity is to release one or more nucleotides from the 3'-terminus of a hybridized nucleic acid.

In an illustrative embodiment, a multiplexed assay for the presence of several different nucleic acid target sequences in a sample is analyzed by absorbance spectroscopy. Several labeled probes to various nucleic acid target sequences are added to a nucleic acid sample. The labels on the probes may be various nucleotide analogs, a different one for each probe. A depolymerizing enzyme is added, such as Klenow exo-, releasing the labeled nucleotides and other nucleotides from the 3'-termini of probes hybridized to target sequences when the 3' terminal nucleotide is matched.

The reaction solution is loaded onto a pre-equilibrated High Pressure Liquid Chromatography (HPLC) column and eluted under conditions that separate the nucleotide analogs from the natural nucleotides. Useful media for chromatographic separation of nucleotides, bases, and nucleosides include reverse phase media, such as a reverse phase C18 column or ODS-80T$_M$ or ODS-120T TSK-GEL by TosoHaas (Montgomeryville, Pa.), anion exchange media, such as DEAE-25SW or SP-25W TSK-GEL by TosoHaas (Montgomeryville, Pa.), or affinity media, such as Boronate-5PW TSK-GEL by TosoHaas (Montgomeryville, Pa.). Example 65 illustrates an embodiment of the present invention using HPLC.

The HPLC column is fitted with an absorbance detector to monitor the column effluent. Hence, "absorbance spectroscopy" for this type of analysis. Typical wavelengths for monitoring HPLC detection of nucleotides are 250 nm, 260 nm and 280 nm. Such separations of nucleotides and nucleotide analogs are well known in the art. Revich et al., *J. Chromatography*, 317:283–300 (1984), and Perrone & Brown, *J. Chromatography*, 317:301–310 (1984) provide examples of the HPLC separation of dNTPs.

Identification of the separated nucleotide analogs can be accomplished by comparison of the retention times (as monitored by absorbance of effluent at various times) of standards of the nucleotide analogs separated on the same HPLC column under the same conditions. Alternatively, the identity of the nucleotide analogs collected in separate fractions (as determined by continually monitoring the absorbance of the column effluent) can be determined by other standard analytical methods, such as nuclear magnetic resonance or atomic analysis (H,C,N).

In this illustrative example using depolymerization with Klenow exo-, the presence of a released identifier nucleotide from a particular probe indicates the presence of the target sequence that hybridize with that probe.

In an alternative embodiment, the released nucleotides from a depolymerization reaction mixture are separated on a gas chromatograph fitted with an absorbance detector to monitor column effluent.

Coupled Reactions

In some embodiments, certain of the above reactions can be performed as single pot reactions. A "single pot reaction" is a reaction wherein at least two enzymes (i.e., E1 and E2) with catalytic activity are present in the same reaction mix and act on one or more substrate(s) (i.e., S1 and S2). In some embodiments, the reactions catalyzed by the enzymes occur simultaneously where E1 acts on S1 and E2 acts on S2. Alternatively, the reactions catalyzed by E1 and E2 can occur in a step-wise or coupled manner (e.g., where E1 acts on S1 to produce an intermediate S2$_i$ and E2 then acts on S2$_i$). Of course, in yet other embodiments, such a coupled reaction can also be essentially simultaneous.

The ability to utilize combinations or mixtures of the enzymes of the present invention in single pot reactions is surprising, in light of the extremely low levels of nucleic acid detection that are achieved using the present invention. This low level detection is possible even though some enzymes are used under suboptimal conditions. As previously described, it was found to be necessary to optimize the concentration of PP$_i$ utilized in the pyrophosphorolysis reactions to minimize inhibition of luciferase. Therefore, aliquots from the NMP-, dNMP-, NTP-, dNTP- and ATP-producing reactions can be directly added to L/L Reagent for luciferase detection without any purification of the reaction products. The luciferase reaction is not poisoned or otherwise quenched by the components of the reactions. This desirable feature permits automation and high throughput analysis with a minimal amount of time and effort, and it also permits great flexibility in the design of the overall detection schemes. However, it is not intended that the present invention be limited to any particular reaction condition, reagents, or embodiments.

In some preferred embodiments, the pyrophosphorolysis reaction producing DNTP and the NDPK catalyzed reaction in which the NTPs or dNTPs are converted to ATP are performed in a single pot reaction in the nucleic acid polymerase buffer in these embodiments. NDPK activity is sufficient to convert dNTP to ATP, even though the polymerase buffer conditions are suboptimal for NDPK activity.

The polymerase enzyme and NDPK can both be present initially in the reaction, or the NDPK can be added directly to the reaction after an incubation period sufficient for the production of NTP or dNTP. Alternatively, a nucleic acid polymerase and NDPK can be provided in the same vessel or mixture for use in the reactions described above. The mixture preferably contains the nucleic acid polymerase and NDPK in a concentration sufficient to catalyze the production of ATP when in the presence of a nucleic acid, pyrophosphate and ADP.

Preferably, the polymerase is provided in a concentration of about 0.1 to 100 U/reaction (i.e., where "U" is units) most preferably at about 0.5 U/reaction. Preferably, the NDPK is provided in a concentration of 0.1 to 100 U/reaction, most preferably at about 0.1 U/reaction. In further preferred embodiments, the mixture is substantially free of contaminating ATP.

Similarly, the PRPP synthetase and NDPK reactions can be carried out in a single pot reaction in the PRPP synthetase buffer. Again, in these embodiments, NDPK activity is sufficient even though conditions for NDPK activity are suboptimal.

The nuclease-digested sample containing free NMPs and dNMPs can be added to a reaction mix initially containing PRPP synthetase and NDPK, or added to a PRPP synthetase reaction followed by addition to a reaction mix containing NDPK. By way of example, certain preferred buffers and reaction components can be found in the Examples. However, it is not intended that the present invention be limited to specific buffers or reaction components.

PRPP synthetase and NDPK can be provided in the same vessel or mixture for use in the reactions described above. The mixture preferably contains the PRPP synthetase and NDPK in a concentration sufficient to catalyze the production of ATP when in the presence of PRPP and ADP. Preferably, the NDPK is provided in a concentration of 0.1 to 100 U/reaction, most preferably at about 0.1 U/reaction. Preferably, the PRPP synthetase is provided in a concentration of 0.001 to 10 U/reaction, most preferably at about 0.01 U/reaction. If amplification is desired, the PRPP synthetase reaction is preferably heat inactivated, otherwise the PRPP synthetase converts the added AMP to ATP.

The pyrophosphorolysis reaction and amplification reaction can also be performed in a single pot reaction. In this single pot reaction, poly(A) polymerase or any suitable template-dependent polymerase can be used, including, but not limited to, AMV reverse transcriptase, MMLV reverse transcriptase, DNA polymerase alpha or beta, Taq polymerase, Tth polymerase, Tne polymerase, Tne triple mutant polymerase, Tvu polymerase, Ath polymerase, *E. coli* DNA polymerase I, T4 DNA polymerase, Klenow fragment, Klenow exo minus, or poly(A) polymerase.

In some embodiments, a first enzyme for converting AMP to ADP can be myokinase (e.g., adenylate kinase) or NMPK, and in other embodiments, a second enzyme for converting ADP to ATP can be pyruvate kinase or NDPK. In addition, in preferred embodiments, the reaction is fed AMP. In particularly preferred embodiments, apyrase-treated AMP is utilized to reduce background due to contaminating ADP and ATP. Preferably 1 μL of 1 U/μL apyrase is added to 19 μL of 10 mM AMP, followed by incubation at room temperature for 30 minutes and heat inactivation of the apyrase by incubation at 70° C. for 10 minutes.

High energy phosphate donors are also added to the reaction. In preferred embodiments, when pyruvate kinase is utilized, PEP is added. In other preferred embodiments, when NDPK is utilized, dCTP is added. Preferably, the high energy phosphate donor is added about 15 minutes after a pre-incubation with the polymerase, although this is not necessary. These reactions can be characterized as follows:

$$NA_n + PP_i \rightarrow NA_{n-1} + XTP$$

$$XTP + AMP \rightarrow ADP + XDP$$

$$ADP + D\text{-}P \rightarrow ATP + D \qquad \text{Reaction 7:}$$

wherein NA is a nucleic acid, XTP is a nucleoside triphosphate (either a deoxynucleoside or ribonucleoside triphosphate), XDP is a nucleoside diphosphate (either a deoxynucleoside or ribonucleoside diphosphate), and D-P is a high energy phosphate donor. It should be appreciated that this reaction produces ATP, the preferred substrate for luciferase, from dNTPs.

The amplification reaction proceeds as described in reaction 7 to produce a threshold ATP concentration of approximately $1 \times 10^{-12}$ Molar in 100 μL of sample. Preferably, the polymerase is provided in a concentration of about 0.1 to 100 U/reaction, most preferably at about 0.5 U/reaction. Preferably, the NDPK is provided in a concentration of 0.1 to 100 U/reaction, most preferably at about 0.1 U/reaction. Preferably, the mixture is substantially free of contaminating ATP.

Probe-Mediated Specific Nucleic Acid Detection

Depolymerization reactions can be used to interrogate the identity of a specific base in a nucleic acid. For example, the identity of single base point mutations, deletions, or insertions in a nucleic acid can be determined as follows.

In one embodiment, a nucleic acid probe is synthesized that is substantially complementary to a target nucleic acid containing or suspected of containing a point mutation. It will be recognized that various hybridization conditions can be used, so as to vary the stringency at which hybridization occurs. Thus, depending upon the system utilized, the complementarity of the probe can be varied. Depending on the length of the probe, the GC content, and the stringency of the hybridization conditions, the probe can have as many as 10 base mismatches with the target nucleic acid, and preferably less than 5 mismatches. Most preferably, the probe has only one base mismatch with the target nucleic acid or is completely complementary to the target nucleic acid.

The nucleic acid probe comprises single-stranded nucleic acid (e.g., DNA or RNA). The probe can be of varying lengths, preferably from about 10 to 100 bases, most preferably about 10 to 30 bases. In particularly preferred embodiments, the probe is complementary to the target at all bases between an interrogation position and 3' end of the nucleic acid probe.

In preferred embodiments, the probe is designed to have a predetermined nucleotide at an interrogation position. When the complementary probe base pairs or hybridizes to the target nucleic acid, the base at an interrogation position aligns with the base in the nucleic acid target whose identity is to be determined under conditions such that base pairing can occur. It is contemplated that an interrogation position can be varied within the probe. For example, in some preferred embodiments, an interrogation position is preferably within 10 bases of the 3' end of the nucleic acid probe. In still other preferred embodiments, an interrogation position is within 6 bases of the 3' end of the nucleic acid probe. In particularly preferred embodiments, an interrogation position is at the next to last or last base at the 3' end of the nucleic acid probe.

In some preferred embodiments, four different probes of equal length are synthesized, each having a different nucleotide at an interrogation position. Accordingly, it is contemplated that in some embodiments, a set of DNA probes includes a first probe with a deoxyadenosine residue at an interrogation position, a second probe with a deoxythymidine residue at an interrogation position, a third probe with a deoxyguanosine residue at an interrogation position, and a fourth probe with a deoxycytosine residue at an interrogation position. Likewise, it is also contemplated that a set of RNA probes includes a first probe with an adenosine residue at an interrogation position, a second probe with a uridine residue at an interrogation position, a third probe with a guanosine residue at an interrogation position, and a fourth probe with a cytosine residue at an interrogation position.

In the next step of some embodiments, the probe or probes are hybridized to the target nucleic acid in separate reactions so that a probe nucleic acid-target nucleic acid complex is formed. It is contemplated that hybridization conditions can vary depending on the length and base composition of the probe. In the probe-target nucleic acid complex, the nucleotide at an interrogation position is aligned with the specific base to be identified in the nucleic acid. In embodiments in which a set of probes is utilized, a different reaction is performed with each probe. In a multiplex embodiment, the set of probes can be used simultaneously. Because the probes differ at an interrogation position, only one of the probes is complementary to the specific base in the target nucleic acid which is aligned with an interrogation position.

In the next step of some embodiments, the nucleic acid probe-target nucleic acid complexes are individually reacted under conditions permitting depolymerization of the probe. The preferred reaction conditions for depolymerization are described above and in the following Examples. The nucleotides are then detected. In preferred embodiments, the reaction mix also contains reagents necessary to catalyze the conversion of XTP to ATP equivalents as described in reaction 4 and in the following Examples. In some preferred embodiments, the nucleotides and/or ATP produced by the depolymerization reaction are then detected by either a luciferase or NADH detection system. Complementarity of the base at an interrogation position of the nucleic acid probe to the corresponding base in the nucleic acid target is characterized by detection of a signal generated from ATP following depolymerization.

In particularly preferred embodiments, the identity of the specific base is determined by comparing the amount of ATP produced in each reaction. Depolymerization of the probe proceeds from its 3' end. When the base at an interrogation position is not complementary to the specific base in the nucleic acid, very little or no ATP is produced, and thus no signal results. In alternative embodiments, this method can be practiced with from one to four probes. It is contemplated that utilizing multiple probes, (e.g., each with a different base at an interrogation position), may prove unnecessary if a positive signal is produced (e.g., with the first probe tested).

In yet another preferred embodiment, the probe-mediated specific nucleic acid detection method of the present invention can be used to simply identify or detect a nucleic acid of interest. For this method, a nucleic acid probe (e.g., DNA or RNA) is utilized which is substantially complementary to the target nucleic acid, which can be RNA or DNA. In a particularly preferred embodiment, the nucleic acid probe is entirely complementary to the target nucleic acid. The nucleic acid probe comprises single-stranded nucleic acid (e.g., DNA or RNA). The probe can be of varying lengths, preferably from about 10 to about 1000 bases, most preferably about 10 to 100 bases. Detection is carried out as described above. The nucleic acid probe-nucleic acid target complex is exposed to conditions permitting depolymerization of the probe, which results in the production of XTPs. Detection of the nucleic acid of interest is characterized by a difference in the signal generated by the XTPs produced. Preferably, the XTPs are converted to ATP as described above and the ATP detected by a luciferase or NADH detection system.

In another embodiment, the presence or absence of a lesion in the target nucleic acid can be detected. A lesion may either be an insertion mutation or a deletion mutation in the wild-type target nucleic acid. The wild-type target nucleic acid contains a region of complementarity, to which the nucleic acid probe can hybridize. Thus, the region of complementarity in the wild-type target nucleic acid is defined by the 5' and 3' ends of the nucleic acid probe. When the region of complementarity contains a lesion, the nucleic acid probe may still hybridize to the target nucleic acid, but the hybridization is only partial. Depending on the size and nature of the lesion, either the 5' or 3' end of the probe may hybridize to the target nucleic acid, or a hybridization structure characterized by the presence of a loop may be formed. In each of these cases, depolymerization will be prevented. Preferably, the nucleic acid probe is designed so that the lesion to be detected begins about less than ten bases from 3' end of the probe, preferably less than about 6 bases. The nucleic acid probe comprises single-stranded nucleic acid (e.g., DNA or RNA). The probe can be of varying lengths, preferably from about 10 to about 1000 bases, most preferably about 10 to 100 bases. Detection of a nucleic acid containing a lesion is characterized by the difference of a signal generated from the XTP produced. Preferably, the XTPs are converted to ATP as described above and the ATP detected by a luciferase or NADH detection system.

It is contemplated that an increase in the signal (analytical output) produced by the probe-mediated specific nucleic acid detection methods of the invention can be realized by a novel cycling method. In this embodiment of the invention, two probes are designed that are complementary to each other and have a 3' overhang at each end when they hybridize to one another. In preferred embodiments, the probes are designed so that the 3' overhang is a single base overhang. In alternative embodiments, the probes also can hybridize to a target nucleic acid. In particularly preferred embodiments, a polymerase that acts from the 3' end of nucleic acids and does not recognize 3' overhangs is utilized for the depolymerization reaction, such as Klenow exo-.

In preferred embodiments, the first step of the reaction involves hybridization of an excess of one of the probes to the target nucleic acid in the presence of the polymerase and under conditions permitting depolymerization as described above. In some embodiments, no 3' overhang exists, and the depolymerase reaction proceeds from the 3' end of the probe. In some embodiments, the reaction is terminated by separating the probe from the target nucleic acid by heating the probe-target nucleic acid complexes. On average, as few as one base is removed from probes that were bound to the target nucleic acid, and fractions of shortened probes are created.

In the second step, an excess of the second probe is added to the reaction. Due to the law of mass action, the shortened probes produced in the first step have a tendency to bind to the newly added complementary probes, whereas the non-shortened probes bind to the target nucleic acid. The shortened probes that bind to the complementary probes produce a complex with no 3' overhang on one end, and are depolymerized. This effectively doubles the amount of substrate available for the depolymerization reaction. Steps one and two can be repeated additional times until the desired level of detection is achieved. In an alternative preferred embodiment, the reactions can be coupled with NDPK as described above, to produce ATP equivalents that are detectable by a luciferase-based or NADH-based assay system.

The ability to interrogate the identity of a specific base in a nucleic acid also permits discrimination between nucleic acids from different species, or even from different alleles. The ability to detect and discriminate between nucleic acids of related or unrelated species also permits the identification of species contained within a given nucleic acid-containing sample. For example, the method can be used to determine which species of several related bacteria are contained within a sample (e.g., clinical samples, environmental samples, or samples from non-human animals).

In preferred embodiments of this method, nucleic acids with substantially identical sequences from at least two species or alleles are detected. The region of identity (target nucleic acid sequence) contains at least a single nucleotide mismatch between the species or alleles in at least one predetermined position and also contains a 3' end and a 5' end or the identification of a nucleic acid sequence unique to each species to be identified.

Next, in some embodiments, an RNA or DNA probe that is substantially complementary to the region of identity is synthesized. The probe can be of varying lengths, preferably from about 10 to 1000 bases, most preferably about 10 to 100 bases. As above, this complementary probe includes an interrogation position.

An interrogation position can be varied within the probe. For example, an interrogation position is preferably within 10 bases of the 3' end of the nucleic acid probe. More preferably, an interrogation position is within 6 bases of the 3' end of the nucleic acid probe. Most preferably, an interrogation position is at the next to last or last base of the 3' end of the nucleic acid probe.

The nucleic acid probes are designed so that the base at an interrogation position is complementary to the nucleotide at the predetermined position of one species or allele, but not another due to the mismatch. Likewise, a second probe can be synthesized that is complementary at an interrogation position to the nucleotide at the predetermined position of a second species or allele.

This same procedure can be employed to identify the presence or absence of multiple species within a given sample. In these embodiments, all that is required is the identification of substantially identical sequences between species that contain base mismatches or the identification of a nucleic acid sequence unique to each species to be identified. Similarly, this procedure can be used for quantitative analysis of the number of alleles at a loci in a sample. By comparing the quantity of analytical output relative to an appropriate internal or external control, the number of alleles at a locus can be determined. These comparative quantities can be expressed in terms of the ratio of one allele to the other in one sample versus that same ratio measurement in a control sample. In this process, events such as loss of heterozygosity or trisomy can be detected.

For example, a normal heterozygous control has a ratio of about 1:1 with respect to the two alleles that make up the heterozygote. That is, each allele of the heterozygote can be detected when a nucleic acid probe is used to detect the presence of that allele. If the quantity of analytical output obtained by the release of identifier nucleotide when the first and second alleles are detected is expressed as a ratio, the relative amounts of the first and second allele would be about the same for a sample which is heterozygous at that locus. When a sample has lost heterozygosity, one of the two alleles is not detectable. If the first allele is lost, then the first allele will not be detected in the sample if the sample is assayed using a nucleic acid probe for the first allele. The second allele will, however, be present at a similar amount as would be present in a known heterozygous control sample, so assaying the sample with a nucleic acid probe for the second allele will provide an analytical output. If the quantity of the analytical output for the first and second alleles for a sample having a loss of heterozygosity of the first allele is expressed as a ratio, the ratio will be about 0:1, indicating the absence of the first allele. Conversely, where the second allele is lost, the ratio of the quantity of analytical output for the first and second allele would be about 1:0, indicating the absence of the second allele.

The presence of trisomy of an allele is detected in a similar fashion. In a trisomy event, four outcomes are possible with respect to a first and second allele. The trisomy can be homozygous for the first allele, in which case three copies of the first allele will be present and no copies of the second allele will be present. Thus, the ratio of the quantity of analytical output for the first and second allele will be 3:0. If the trisomy is homozygous for the second allele, three copies of the second allele will be present. The ratio of the quantity of analytical output for the first and second allele will be 0:3. Two cases of heterozygous trisomy are possible: two copies of allele one and one copy of allele two, or one copy of allele one and two copies of allele two. These two heterozygous trisomy outcomes can be detected by determining the ratios of the quantity of analytical output for the first and second alleles, preferably in comparison to a known heterozygous control sample. If the ratio is 2:1, then the heterozygous trisomy has two copies of the first allele and one copy of the second allele. If the ratio is 1:2, then the heterozygous trisomy has one copy of the first allele and two copies of the second allele.

The use of an appropriate control, for example a heterozygous control, allows the appropriate interpretation of the ratios obtained from the analysis of a sample suspected of having a loss of heterozygosity or of trisomy.

In the next step of some embodiments, separate reactions are performed utilizing each probe. The probes are hybridized to the target nucleic acid to form a probe nucleic acid-target nucleic acid complex. In the probe nucleic acid-target nucleic acid complex, the nucleotide at an interrogation position of the probe is aligned with the nucleotide at the predetermined position in the nucleic acid, so that base pairing occurs. The probe-target nucleic acid complex is then reacted under conditions permitting depolymerization of the probe from its 3' end.

Preferred conditions for depolymerization (depolymerization conditions) are described herein. The nucleotides are then detected. In some preferred embodiments, the nucleotides are converted to ATP equivalents as described in reaction 4 and in the Examples. In preferred embodiments, the ATP is detected by luciferase or NADH detection systems.

These embodiments of the present invention permit discrimination between nucleic acids from different species or alleles, as NTPs are produced by depolymerization only when the nucleotide at an interrogation position of the probe is complementary to the nucleotide at the predetermined position of the nucleic acid from the species. As described above, significant depolymerization proceeds only if the base at an interrogation position is complementary to the base at the predetermined position in the target nucleic acid. The NTP concentration, including the ATP concentration, differs when a mismatch is present as compared to when a mismatch is not present. These differences can be detected (e.g., by either an ATP or NADH detection system).

A method contemplated by the present invention has wide applicability in assaying nucleic acids. In some aspects, an endogenous nucleic acid is assayed to determine whether a particular native or mutant sequence is present or absent. This type of analysis is sometimes referred to as genotyping because the genetic makeup of the subject from which the nucleic acid sample is obtained is determined. Speciation, the identity of an organism, such as the identification of a human, dog, chicken, bovine or the like can be determined by use of species-specific nucleic acid probes such as probes to selected regions of the gene encoding cytochrome B.

Using a contemplated method, one can illustratively determine whether a human patient, for example, has the Leiden V mutation, a mutant β-globin gene, the cystic fibrosis-related gene in the region of the delta 508 allele, a mutation in a prothrombin gene, congenital adrenal hyperplasia, a translocation that takes place in the region of the bcr gene along with involvement of a segment of the abl gene, the number of repeated sequences in a gene such as are present in THO 1 alleles or the TPOX alleles, as well as the loss of heterozygosity of the locus of certain alleles as is found in certain cancers and also allelic trisomy. Genomic typing can also be used to assay plant genomes such as that of rice, soy or maize, and the genomes of microbes such as *Campylobacter jejuni*, cytomegalovirus (CMV) or human immunodeficiency virus (HIV) to determine whether a drug-resistant strain is present in a sample.

A contemplated method can also be utilized to assay for the presence or absence of nucleic acid that is exogenous to the source of the sample. For example, a contemplated method can be used to assay for the presence of viruses such as hepatitis C virus (HCV), cytomegalovirus (CMV), human immunodeficiency virus (HIV), as well as to determine the viral load in an organism with a disease, such as a human or a plant A contemplated method can also be used to identify the presence of an exogenous nucleic acid sequence in a plant such as maize, soy or rice. A contemplated method can also be used to assay for the presence of microorganisms such as *Listeria monocytogenes*, Campylobacter spp., Salmonella spp., Shigella spp. or *Escherichia coli* (including *E. coli* E0157) in foodstuffs such as meats, dairy products, and fruit juices.

The determination of an appropriate nucleic acid target sequence useful for designing nucleic acid probes for use in a method of the invention is within the skill of the art. Databases of genetic sequences, such as Genbank, can be used to ascertain the uniqueness of the selected nucleic acid target. Commercially available software for designing PCR primers can be used to assist in the design of probes for use in the invention.

Determination of Repeated Sequences

A process of the invention is useful for determining the presence of repeated sequences in a nucleic acid sample. The repeated known sequence present in a nucleic acid target sequence typically has a length of 2 to about 24 bases per repeat. Di-and tri-nucleotide repeats are well known in the art. An application of this process is Single Tandem Repeat (STR) detection. Typically, different alleles of the target nucleic acid have different numbers of the repeated sequences, so the determination of the number of repeats is useful in genotyping. Such methods have important applications in the forensic sciences in identity testing. A method for determining the number of repeated known sequences is as follows.

Special nucleic acid probes are designed and obtained that contain multiples of a known repeating sequence. Each probe contains a different number of a repeated sequence that is complementary to that of the nucleic acid target sequence. Each probe has a 5'-terminal locker sequence that is complementary to the non-repeated region of the target that is downstream of the repeated region in the target. The probes typically have an identifier nucleotide in the 3'-terminal region, but as described herein, the release of nucleotides from the 3' terminus during a depolymerization step of the invention can alternatively be ascertained by the size of the remaining probe.

The use of a 5'-terminal locker sequence fixes the 5'-terminus of the probe relative to the repeated region. Thus, for example when the probe has fewer repeats than the target, it is not free to hybridize anywhere throughout the repeated region, but only along the first matching group of repeats. in this embodiment, the probe will be completely complementary to the target sequence, even though it is shorter than the target. However, when the probe has more repeats than the target, the probe extends into the adjacent non-repeated region and is mismatched at its 3'-terminal region.

In some cases, it is desirable to determine the number of repeats by comparison with standard nucleic acid samples having known numbers of repeats (and how they respond to the various probes). In other cases, the number of repeats can be deduced by the shape of the curve of a graph having its ordinate (x-) axis be the number of repeats in the probe and its abscissa (y-) axis be the analytical output indicating the number of nucleotides released, such as light output in luminescence spectroscopic analysis of all of the released nucleotide converted to ATP.

In such a graph, for example when the depolymerizing enzyme is a template-dependent polymerase or exoIII, the output is greater when the probe has the same or fewer repeats than the target, relative to the output when the probe has more repeats than the target. The S-shaped curve changes most rapidly after the number of repeats in the probe surpasses the number of repeats in the target. Thus, the derivative of the curve is greatest at that point. Similar results when the depolymerizing enzyme preferentially releases nucleotides from mismatched substrates, except that the output is less when the probe has the same or fewer repeats than the target.

Thus, in a preferred embodiment of a process to determine the number of repeats of a known sequence, a plurality of separately treated samples is provided. Each sample contains a nucleic acid target sequence, containing a plurality of known repeated sequences and a downstream non-repeated region on the target relative to the repeated sequences. The sample is hybridized with an above-described nucleic acid probe.

A treated reaction mixture is formed by admixing each treated sample with a depolymerizing amount of an enzyme whose activity is to release one or more nucleotides from the 3'-terminus of a hybridized nucleic acid probe. The treated reaction mixture is maintained for a time period sufficient to permit the enzyme to depolymerize the hybridized nucleic acid probe and release an identifier nucleotide.

The samples are analyzed for the presence or absence of released identifier nucleotide to obtain an analytical output. The analytical output from the sample whose probe contained the same number of sequence repeats as present in the target nucleic acid is indicative of and determines the number of sequence repeats present in the nucleic acid target. The analytical output is obtained by luminescence spectroscopy, mass spectroscopy, fluorescence spectroscopy or absorption spectroscopy, including visualization of the remaining probe, as described herein with regard to the general method of the invention.

In one aspect of the method, the target nucleic acid is homozygous with respect to the number of the repeated sequences at the two alleles. In an alternative method of the invention, the target nucleic acid is heterozygous for the repeated sequences.

In one method of the invention, an identifier nucleotide is a nucleotide that is part of the region containing a repeated sequence. In an alternative method of the invention, the nucleic acid probe further comprises a second non-repeating sequence that is located downstream of the repeated sequences in the probe (3' of them). This second non-repeating sequence is complementary to a non-repeating sequence located in the target nucleic acid 5' to its repeated sequences. In this embodiment, it is contemplated that an identifier nucleotide of the probe sequence is part of the region containing the second non-repeating sequence. Thus, the identifier nucleotide is present in a sequence containing 1 to about 20 nucleic acids that is complementary to a non-repeating sequence of the target nucleic acid located in the probe 3' to the repeated sequences.

Extension-Mediated Detection of Known Sequences

One common PCR-based method for determining the presence or absence of a specific known nucleic acid sequence, such as a mutation (e.g. a genetic polymorphism), is called an amplification refractory mutation system (ARMS), also known as allele-specific PCR (ASP), PCR amplification of specific alleles (PASA) or allele-specific amplification (ASA). In a typical ARMS assay two PCR reactions using different PCR primers are conducted on the same nucleic acid sample. Each of the two PCR primers is designed to have a residue at the 3'-terminus of the primer that is complementary to one of the two allelic variants and not to the other. The PCR reaction does not extend from a primer having a 3'-terminal mismatched base, unless the polymerase used has a 3' to 5' proofreading activity that removes the mismatched base and inserts the correct base. Proofreading repairs the PCR primer and destroys the extension discrimination between the two alleles. Therefore, a polymerase lacking a 3' to 5' proofreading activity, such as Taq DNA polymerase, is used in such an ARMS assay. The extension products are typically ascertained after agarose gel electrophoresis with ethidium bromide staining.

In the art, it is known that the discrimination between specificity of PCR extension from the allele-specific ARMS primers is enhanced by the introduction of deliberate mismatches near the 3'-terminal nucleotide, although possibly also decreasing overall PCR extension product yield. Other factors known to affect the stability of the hybridization of PCR primers in an ARMS assay include the position of additional mismatches in the primer, the GC content of the 5 or 6 nucleotides preceding the 3' nucleotide, and the discriminatory 3'-terminal nucleotide, depending on the difference between the alleles and the type of mismatch. The destabilization is greater when the second mismatch is nearer to the 3'-terminal nucleotide. The destabilizing effect of additional mismatches on ARMS has been ranked qualitatively (CC>CT>GG=AA=AC>GT).

A process of the invention can be used to ascertain matched or mismatched bases at the discriminatory 3'-terminal nucleotides in place of conducting PCR extension, as demonstrated in Example 58. It is contemplated that similar factors will affect the stability of hybrids in a process of the invention as has been noted with ARMS, so preferably, such considerations are taken into effect when designing probes for use in process of the invention.

A contemplated method can be used to determine the presence or absence in a nucleic acid sample of a restriction endonuclease recognition sequence that cleaves double-stranded DNA leaving a 5' overhang or a blunt end. The cleavage product is a nucleic acid target that is a substrate for an enzyme whose activity is to release one or more nucleotides from the 3'-terminus in a process of the invention.

The use of restriction enzymes known at the time of practicing the invention to leave 5' overhangs or a blunt end after cleavage are contemplated for use in a claimed process. Such restriction enzymes are currently well known in the art. The enzymes are commercially available from several companies, including Promega Corp. in Madison, Wis. A list of some such enzymes can be found in Sambrook et al., *Molecular Cloning: A Laboratory Manual*, $2^{nd}$ Ed., Cold Spring Harbor Laboratory Press (Plainview, N.Y.: 1989).

A process of the invention contemplates the detection of a restriction endonuclease site to detect the presence or absence of a certain nucleic acid within a sequence, such as an SNP. In such a process, the sequence adjacent downstream of an SNP in a nucleic acid target is used to design a PCR primer for a PCR amplification that is complementary to the downstream sequence SNP in a first region of the PCR primer. Preferably, the 3'-terminal of the PCR primer is used to determine the presence or absence of the SNP. Thus, the 3'-terminal residue of the PCR primer either matches or mismatches with the SNP. Preferably, a destabilizing mismatch is incorporated into this PCR primer, as described above, to enhance the specificity of PCR extension from the PCR primer when the 3'-terminal residue matches the SNP. A second region of the PCR primer forces the introduction of a restriction endonuclease recognition site into the PCR products. The restriction endonuclease recognition sequence is selected to provide a substrate for a depolymerization reaction of the invention. The PCR reaction is conducted and the product purified. The PCR product is treated with the restriction endonuclease to cleave at its recognition site leaving a restriction endonuclease cleavage product containing an identifier nucleotide. A depolymerizing enzyme of the invention is admixed with the PCR product either before or after restriction endonuclease cleavage. The admixture is analyzed for the release of identifier nucleotide after maintaining the admixture under depolymerizing conditions for a time period sufficient for depolymerization. As noted herein, the identifier nucleotide need not be a nucleotide analog, but it is possible if a nucleotide analog, including a fluorescently labeled nucleotide, were present in the original PCR primer that became the restriction endonuclease recognition sequence. As discussed herein, the release of identifier nucleotide is ascertained by analyzing the released nucleotide or the remaining probe.

Amplification of the Sample Target or a Detection Target

A target nucleic acid sequence is typically amplified prior to use of a contemplated method. However, where a sufficient number of repeated nucleotide sequences are present in the native sample as in the human Alu sequence or the *E. coli* rep sequence, amplification is often not needed prior to carrying out a contemplated method.

Several methods are known in the art to amplify a region of DNA. These include polymerase chain reaction, ligase chain reaction, repair chain reaction, amplification of transcripts, self-sustained sequence replication (3SR), ligation activated transcription (LAT), strand displacement amplification (SDA) and rolling circle replication. A claimed process contemplates prior treatment of a nucleic acid sample using any amplification method known in the art at the time of practicing a claimed process to detect the presence of a nucleic acid target in the sample.

Polymerase chain reaction (PCR) is very widely known in the art. For example, U.S. Pat. Nos. 4,683,195, 4,683,202, and 4,800,159, the disclosures of which are incorporated herein by reference, describe processes to amplify a nucleic acid sample target using PCR amplification primers which hybridize with the sample target.

As the PCR amplification primers are extended, using a DNA polymerase (preferably thermostable), more sample target is made so that more primers can be used to repeat the process, thus amplifying the sample target sequence. Typically, the reaction conditions are cycled between those conducive to hybridization and nucleic acid polymerization, and those that result in the denaturation of duplex molecules.

To briefly summarize, in the first step of the reaction, the nucleic acid molecules of the sample are transiently heated, and then cooled, in order to denature any double stranded molecules that may be present. Amplification and target primers are added to the amplification reaction mixture at an excess concentration relative to the sample target. When the sample is incubated under conditions conducive to hybridization and polymerization, the amplification primer hybridizes to the nucleic acid of the sample at a position 3' to the sequence of the desired sample target to be amplified. If the nucleic acid molecule of the sample was initially double stranded, the target primer will hybridize to the complementary strand of the nucleic acid molecule at a position 3' to the sequence of the region desired to be amplified that is the complement of the sequence whose amplification is desired. Upon addition of a polymerase, the 3' ends of the amplification and (if the nucleic acid molecule was double stranded) target primers are extended. The extension of the amplification primer results in the synthesis of a DNA molecule having the exact sequence of the complement of the desired nucleic acid sample target. Extension of the target primer results in the synthesis of a DNA molecule having the exact sequence of the desired nucleic acid sample target.

The PCR reaction is capable of exponentially amplifying the desired nucleic acid sequences, with a near doubling of the number of molecules having the desired sequence in each cycle. Thus, by permitting cycles of hybridization, polymerization, and denaturation, an exponential increase in the concentration of the desired nucleic acid molecule can be achieved. Reviews of the technique include K. Mullis, *Cold Spring Harbor Symp. Quant. Biol.*, 51:263–273 (1986); C. R. Newton & A. Graham, *Introduction to Biotechniques: PCR*, $2^{nd}$ Ed., Springer-Verlag (New York: 1997).

Ligase chain reaction (LCR) is described in European Patent No. 0,320,308. In LCR, two adjacent amplification primers, as well as two others that are complementary to them, are present in excess in the amplification reaction, which contains DNA ligase. The amplification primers hybridize to the complementary sequence in the sample target, such that the adjacent primers are substrates for ligase only when hybridized to the sample target. Ligase links the two adjacently hybridized amplification probes. In a succession of temperature cycles, preferably with use of a thermostable ligase, the linked probes separate from the target and can in turn serve as target sequence for other amplification probes (Barany, *Proc. Natl. Acad. Sci., USA*, 88:189–193 1991). In a contemplated embodiment of the invention, an LCR method is used to amplify a detection target nucleic acid prior to or simultaneously with hybridization of a detection probe (interrogation probe) of the invention and depolymerization to release identifier nucleotides.

In another aspect, the nucleic acid of interest is amplified from the crude nucleic acid sample using a repair chain reaction (RCR) method prior to detection of the target. In a RCR method of amplification, two oligonucleotide amplification primers that are complementary to the amplification target and two other primers are provided in excess in the presence of a thermostable DNA ligase and a thermostable DNA polymerase. When a nucleic acid sample target sequence is present, the amplification primers hybridize to the nucleic acid sample at either side of the amplification target leaving a gap between the otherwise adjacently hybridized primers. The gap is filled in with DNA polymerase and then ligated with DNA ligase to form a complete complementary copy of the amplification target with the primer on either end. By a succession of temperature cycles, as in PCR and LCR, the extended primers linked to the amplification primers can in turn serve as target for new primers. International patent application publication number WO 90/01069.

In another contemplated embodiment of the invention, the nucleic acid of interest is amplified from the crude nucleic acid sample using an amplification of transcripts (TAS) method prior to detection of the target. In a TAS amplification method, such as that described in international patent application publication number WO 88/10315, an amplification cycle comprises three stages.

In the first stage, a cDNA is synthesized from RNA in the presence of reverse transcriptase and a complementary primer also containing an RNA polymerase promoter, such as a phage RNA promoter. Following thermal denaturation of the RNA/cDNA heteroduplex, the single-stranded cDNA is replicated by reverse transcriptase in the presence of an antisense amplification primer. The DNA homoduplex thus obtained during this second stage contains a double-stranded promoter to which a phage DNA-dependent RNA polymerase can bind. The third stage then consists of transcribing RNA molecules (from 30 to 1000 per template) which can serve as template for the synthesis of additional cDNA to continue the amplification cycle. Davis et al., *J. Infect. Dis.*, 162:13–20 (1990).

In another contemplated embodiment of the invention, the nucleic acid of interest is amplified from the crude nucleic acid sample using a method similar to TAS, such as self-sustained sequence replication (3SR), nucleic acid sequence-based amplification (NASBA), and single primer sequence replication (SPSR), as an amplification method prior to detection of the target using depolymerization according to the invention. 3SR is described in international patent application publication number WO 90/06995. NASBA is described in European Patent No. 0,373,960. SPSR is described in U.S. Pat. No. 5,194,370, the disclosures of which are herein incorporated by reference. These three methods use RNA- and DNA-dependent DNA polymerases (reverse transcriptase), ribonuclease H (RNase H; *Escherichia coli* enzyme and/or enzymatic activity associated with reverse transcriptase) and DNA-dependent RNA polymerase (T7 bacteriophage RNA polymerase).

Briefly, at a fixed temperature (37–47° C.), a continuous process of reverse transcription and transcription reactions are conducted by methods well-known in the art in order to replicate an RNA target via cDNA. The RNA polymerase binding site (e.g. T7 phage RNA polymerase site) is introduced by the primer used for the reverse transcription stage. The isothermal denaturation of the RNA/cDNA heteroduplex is effected by specific hydrolysis of the RNA using RNase H activity. The free cDNA is replicated from a second oligonucleotide by reverse transcriptase. The resulting DNA/DNA homoduplex is transcribed into RNA by, for example, T7 RNA polymerase. The product RNA can serve as a template to repeat the amplification cycle.

In another contemplated embodiment of the invention, the nucleic acid of interest is amplified from the crude nucleic acid sample using a ligation activated transcription (LAT) method prior to detection of the target. LAT is described in U.S. Pat. No. 5,194,370, whose disclosures are incorporated herein by reference.

Rolling circle replication is described in U.S. Pat. No. 5,854,033, the disclosures of which are incorporated herein by reference. Rolling circle replication reporter systems are useful in detecting the presence of nucleic acid molecules of interest, and in amplifying target sequences—either of the nucleic acid sequence of interest or of a reporter signifying its presence. In a contemplated embodiment of the present invention, such amplification and reporter systems are used in conjunction with a hybridization analysis process of the present invention.

Several methods of the invention contemplate the determination of the presence or absence of a predetermined nucleic acid target in a nucleic acid sample using an open circle primer. The predetermined nucleic acid sample target has a 5' region and a 3' region and will be considered a "sense" strand for reference purposes.

An open circle first probe has three regions. The open circle probe has a 5'-terminal region (the first region of the open circle probe) that hybridizes to a 3' region of a nucleic acid sample target and a 3'-terminal region (the third region of the open circle probe) that hybridizes to a 5' region of a nucleic acid sample target that may be RNA or DNA. The second region is between the 3'-and 5'-terminal regions. The circular detection probe is DNA that is antisense relative to the nucleic acid sample target.

The proper hybridization of the 5'- and 3'-terminal regions of the open circle probe to the predetermined nucleic acid sample target brings the 5'- and 3'-terminal ends of the open circle probe into proximity of each other. The two ends of the open circle probe can be linked together using ligase, or if there are several bases between the two ends a process of the invention contemplates that the intervening bases can be filled in using DNA polymerase or an oligo and then linked using ligase. The linkage of the two ends of the open circle probe results in a closed circular probe that is hybridized to the predetermined nucleic acid sample target. If the predetermined nucleic acid sample target is absent, then the open circle probe is unaffected by ligase.

An amplification primer hybridizes to a portion of the second region of the closed circular probe. In a contemplated amplification step, a DNA chain (sense) is extended from the amplification primer using a DNA polymerase that has displacement activity. An extension product from the amplification primer is complementary to the second region of the closed circular probe.

If the open circle probe has not been ligated, amplification will only proceed through the 5'-terminal region (the first region) of the open circle probe. DNA complementary to the portion of the open circle primer from 3'-terminal region (the third region) through the portions of the second region up to the amplification primer hybridization site is not made unless open circle primer has been ligated to form a closed circular primer.

With a closed circular probe, DNA complementary to the entire closed circular probe is replicated, including a detection target sequence that is complementary to the detection probe (sometimes referred to as an interrogation probe). Hybridization of the detection probe to the replicated detection target sequence is ascertained in a process of the invention by depolymerization of the hybridized nucleic acid to release identifier nucleotides and analyzing for the presence of those identifier nucleotides.

Such processes of the invention using circular probes contemplate three target sequences: a predetermined nucleic acid sample target, an amplification target and a detection target. A sequence complementary to the detection target is typically designed into the open circle probe. A process contemplates that the detection target complement is not in the first region of the open circle probe (the 5'-terminal region), but is either in the second or third region that will only be replicated if the open circle probe has been ligated to a closed circle primer.

In an alternative contemplated amplification step, an RNA transcription origin is located in the circular probe at a position upstream (in the 5' direction) of the closed circle probe relative to a region that is complementary to a detection target. Transcription from this origin occurs in the 5' to 3' direction of the transcript, which makes RNA complementary to the first region of the open circular transcript and then stops unless the circle has been ligated. If the circle were ligated to a closed circular probe, then the RNA transcript will run around the circle and transcribe a region complementary to the detection target. No stop codons should be in the region of the closed circular primer between the region complementary to the detection target and the transcription origin.

An embodiment of the invention contemplates a process to determine the presence or absence of a predetermined single-stranded nucleic acid target sequence. Such a process comprises the following steps.

A nucleic acid target sequence can be RNA or DNA. Several methods are known in the art to obtain single-stranded nucleic acid. For example, the individual strands of double-stranded DNA can be separated by melting and one strand removed from the composition by binding with a biotin-labeled probe and binding of that hybrid to streptavidin-containing conjugate, and by other means well-known in the art, some of which are illustrated elsewhere herein. mRNA, on the other hand, is single-stranded. A preferred process of the invention provides a means to analyze a total mRNA preparation for the presence of a specific mRNA sequence within that mixture.

A reaction mixture is provided comprising a pair of complementary nucleic acid probes that form 3'-overhangs on both ends of the duplex formed when hybridized with each other. The first of the probes is complementary to the nucleic acid target sequence. The second probe that is complementary to the first probe thus essentially has the same sequence as the nucleic acid target sequence.

A probe can be RNA or DNA, and may include nucleotide analogs. Preferably, a probe is DNA. In the case of the detection of a specific mRNA, the probe is preferably DNA, and the depolymerizing enzyme is preferably a reverse transcriptase, such as MMLV RT.

In some embodiments of the invention, it is preferable that the 3'-terminal region of a probe hybridizes with total complementarity to the nucleic acid target sequence. However, it is also contemplated to conduct an interrogation of the presence or absence of a particular base at an interrogation position within the target as described hereinabove. In some embodiments of the invention, it is preferable that the 3'-terminal region of a probe hybridizes with partial complementarity—even in the case of depolymerization with an enzyme whose maximum activity is to release nucleotides from nucleic acid hybrid having totally complementarity. As shown in Example 30, the intentional introduction of a destabilizing base mismatch at one position enhances the discrimination between a match and mismatch at another position.

The first probe has an identifier nucleotide in its 3'-terminal region. The second probe can also contain an identifier nucleotide in its 3'-terminal region. The identifier nucleotide used depends on the desired method of analysis for released nucleotide, as discussed hereinabove.

A hybrid can form between a first probe and the nucleic acid target sequence when the nucleic acid target sequence is present in the nucleic acid sample. Typically, a designed probe that can be the same or different from the first probe and is therefore referred to as the third probe can be added to a nucleic acid sample and permitted to anneal to the designed probe to form a hybrid with the target nucleic acid sequence.

The first reaction mixture also comprises a depolymerizing amount of an enzyme whose activity is to release one or more nucleotides from a 3'-terminus of a hybridized nucleic acid. As discussed hereinabove, the particular enzyme used is based on the substrates to be depolymerized and the goals of the analysis. The first reaction mixture is similar to the above-discussed depolymerization reaction mixtures as far as preferred sample and enzyme concentrations and other reaction conditions.

The first reaction mixture is maintained for a time period sufficient to permit the enzyme to depolymerize hybridized nucleic acid to release an identifier nucleotide from the 3'-terminal region of the first probe, and form a treated reaction mixture. The general step is discussed in greater detail hereinabove. In a contemplated process where the original nucleic acid target is RNA, and the probe is DNA, the effect may be noticed that a DNA/DNA homoduplex is depolymerized at a faster rate or to a greater extent than a DNA/RNA heteroduplex. This effect depends upon the enzyme and its relative affinity for various substrates.

The treated first reaction mixture is denatured by subjecting the treated reaction mixture to denaturing conditions and maintaining the treated reaction mixture for a time period sufficient to denature the nucleic acid hybrids and form a denatured treated reaction mixture. The precise conditions required for denaturation are a function of several factors as is discussed hereinabove. Preferably, the reaction will be heated to a temperature of 90–95° C. for 2–5 minutes.

The denatured treated reaction mixture is subjected to annealing (hybridizing) conditions and maintained for a time period sufficient to form a second reaction mixture that comprises hybrids formed between the first probe and the 3'-terminal-depolymerized third nucleic acid probe. Because of the 3'-terminal depolymerization of the third probe, the hybrid formed with the first probe have one end that is blunt or that has a 5'-overhang (i.e., lacks a 3'-overhang on one end of the duplex). The hybrid formed between the first probe and a nucleic acid target sequence when the nucleic acid target sequence is present in the nucleic acid sample also has a 5'-overhang.

Further depolymerization as before provides a second treated reaction mixture that contains a further quantity of identifier nucleotides in addition to those provided by the first depolymerization step. That further quantity of identifier nucleotides can be about twice the original amount so that the total identifier present is about three-times the original amount.

The second treated reaction mixture is analyzed for the presence of released identifier nucleotide to obtain an analytical output. The analytical output indicates the presence or absence of the single-stranded nucleic acid target sequence.

The first and third probes are preferably the same. Preferably, prior to analysis of the first reaction mixture to detect released identifier nucleotide, the denaturation, annealing and depolymerization steps are repeated to further amplify the number of nucleic acid hybrids from which identifier nucleotides are released.

Not wishing to be bound by theory, it is theorized that in an above process, the first probe (that is complementary to the single-stranded target) is depolymerized, either when it is hybridized to the initial single stranded nucleic acid target sequence or when it is hybridized to its complementary probe sequence. Thus, the effective concentration of target/probe hybrid increases linearly at each progressive cycle of depolymerization. Eventually, a first probe can become too short to hybridize effectively as more and more nucleotides are released from its 3'-terminus.

A related embodiment of the invention contemplates a process to determine the presence or absence of a predetermined double-stranded nucleic acid target sequence. A process differs from the single-strand target process by (i) the presence of a double-stranded nucleic acid target sequence and (ii) third and fourth probes hybridized to separate sequences of DNA that results in an exponential rise in the amount of identifier nucleotide rather than a linear rise as noted before.

As with the single-strand target method, the first and third probes are preferably the same. Preferably, prior to analysis of the amplification reaction mixture to detect released identifier nucleotide, the denaturation, annealing and depolymerization steps are repeated to further amplify the number of nucleic acid hybrids from which identifier nucleotides are released.

It should also be apparent that the single-strand or double strand method can also be carried out by addition of the first and second probes after one has carried out a depolymerization reaction of a treated reaction mixture and before analysis of identifier nucleotides. Both methods are also particularly useful where a before-mentioned thermostable polymerase is used for depolymerization, as well as where a thermostable polymerase and a thermostable NDPK are used in a one-pot reaction.

Assays Using Hairpin Structures

Although it is preferred that the probes be constructed to be free of hairpin structures, assays in which hairpin structures are constructed are also useful. An embodiment of the invention, such as demonstrated in Example 50, contemplates use of a hairpin structure for determining the presence or absence of a nucleic acid target sequence in a nucleic acid sample with a probe that is hybridized to the target and then modified to be able to form a hairpin structure. This embodiment comprises the following steps.

A treated sample is provided that contains a nucleic acid sample that may include a nucleic acid target sequence having an interrogation position. The target sequence, if present in the nucleic acid sample is hybridized with a nucleic acid probe. The probe is comprised of at least two sections. The first section contains the probe 3'-terminal about 10 to about 30 nucleotides. These nucleotides are complementary to the target strand sequence at positions beginning about 1 to about 30 nucleotides downstream of the interrogation position. The second section of the probe is located at the 5'-terminal region of the probe and contains about 10 to about 20 nucleotides of the target sequence. This same sequence, therefore, exists in both the target and the probe in the same 5' to 31 orientation. This sequence spans the region in the target from the nucleotide at or just upstream (5') of the interrogation position, to the nucleotide just upstream to where the 3'-terminal nucleotide of the probe anneals to the target. An optional third section of the probe, from zero to about 50, preferably from zero to about 20, nucleotides in length and comprising a sequence that does not hybridize with either the first or second section, is located between the first and second sections of the probe.

The probe of the treated sample is extended in a template-dependent manner, by admixture with dNTPs and a template-dependent polymerase, at least through the interrogation position, thereby forming an extended probe/target hybrid. In a preferred embodiment, the length of the probe extension is limited by omission from the extension reaction of a dNTP complementary to a nucleotide of the target sequence that is present upstream of the interrogation position and absent between the nucleotide complementary to the 3'-end of the interrogation position.

The extended probe/target hybrid is separated from any unreacted dNTPs; i.e., purified at least to the degree needed to use the extended probe strand to determine the presence or absence of the interrogation region in the sample or the identity of the base at the interrogation position. The extended probe/target hybrid is denatured to separate the strands. The extended probe strand is permitted to form a hairpin structure.

It is preferred that the polymerase enzyme utilized for an extension reaction be a template-dependent polymerase that is free of activity that adds a 3'-terminal deoxyadenosine in a template-nonspecific manner. Thus, it is preferred to use other than a polymerase such as Taq for a contemplated extension.

A treated reaction mixture is formed by admixing the hairpin structure-containing composition with a depolymerizing amount of an enzyme whose activity is to release one or more nucleotides from the 3'-terminus of an extended probe hairpin structure. The reaction mixture is maintained under depolymerizing conditions for a time period sufficient for the depolymerizing enzyme to release 3'-terminus nucleotides, and then analyzed for the presence of released identifier nucleotides. The analytical output indicates the presence or absence of the nucleic acid target sequence. That analytical output can be determined as discussed elsewhere herein.

A still further embodiment of the invention, such as that termed REAPER™ and demonstrated in Example 89 and FIG. 2, also contemplates use of hairpin structures in determining the presence or absence of a nucleic acid target sequence, or a specific base within the target sequence, in a nucleic acid sample, and comprises the following steps. A treated sample is provided that contains a nucleic acid sample that may include a nucleic acid target sequence hybridized with a first nucleic acid probe strand (FIG. 2A).

The hybrid is termed the first hybrid. The first probe is comprised of at least two sections. The first section contains the probe 3'-terminal about 10 to about 30 nucleotides that are complementary to the target nucleic acid sequence at a position beginning about 5 to about 30 nucleotides downstream of the target interrogation position. The second section of the first probe contains about 5 to about 30 nucleotides that are a repeat of the target sequence from the interrogation position to about 10 to about 30 nucleotides downstream of the interrogation position, and does not hybridize to the first section of the probe. That is, the second sequence is a repeat of the region in the target sequence from the interrogation position downstream to the position where the 3'-terminal nucleotide of the first probe aligns with the target. An optional third section of the probe, located between the first and second sections of the probe, is zero to about 50, preferably to about 20, nucleotides in length and comprises a sequence that does not hybridize to either the first or second section.

The first hybrid in the treated sample is extended at the 3'-end of the first probe, thereby extending the first probe past the interrogation position and forming an extended first hybrid (FIG. 2B) whose sequence includes an interrogation position. The extended first hybrid is comprised of the original target nucleic acid and extended first probe. The extended first hybrid is then denatured in an aqueous composition to separate the two nucleic acid strands of the hybridized duplex and form an aqueous solution containing a separated target nucleic acid and a separated extended first probe.

A second probe, that is about 10 to about 2000, more preferably about 10 to about 200, most preferably about 10 to about 30 nucleotides in length and is complementary to the extended first probe at a position beginning about 5 to about 2000, preferably about 5 to about 200, nucleotides downstream of the interrogation position in extended first probe, is annealed to the extended first probe, thereby forming the second hybrid (FIG. 2C). The second hybrid is extended at the 3'-end of the second probe until that extension reaches the 5'-end of the extended first probe, thereby forming a second extended hybrid (FIG. 2D) whose 3'-region includes an identifier nucleotide.

It is preferred that the polymerase enzyme utilized for an extension reaction be a template-dependent polymerase that is free of activity that adds a 3'-terminal deoxyadenosine in a template-nonspecific manner. Thus, it is preferred to use other than a polymerase such as Taq for a contemplated extension.

An aqueous composition of the extended second hybrid is denatured to separate the two nucleic acid strands; i.e., the extended second probe and the extended first probe. The aqueous composition so formed is cooled to form a "hairpin structure" from the separated extended second probe (FIG. 2E) when the target sequence is present in the original nucleic acid sample. Thus, when the target sequence is present in the original nucleic acid sample, the 3'-terminal sequence of the second extended probe in the second extended hybrid hybridizes with the sequence of the second extended probe from a region comprising the interrogation position and nucleotides downstream from the interrogation position of second extended probe to the nucleotide position where the 3'-terminal nucleotide of the original (first-named) probe annealed to the original target.

A treated reaction mixture is formed by admixing the hairpin structure-containing composition with a depolymerizing amount of an enzyme whose activity is to release one or more nucleotides from the 3'-terminus of a nucleic acid hybrid. The reaction mixture is maintained under depolymerizing conditions for a time period sufficient to release 3'-terminal region identifier nucleotides, and then analyzed for the presence of released identifier nucleotides. The analytical output indicates the presence or absence of the nucleic acid target sequence. Again, the analytical output can be determined by one of the several methods discussed elsewhere herein.

As was the case in the previous embodiment, dNTPs are utilized in the extension reactions. It is preferred that the hairpin structures be separated from the dNTPs prior to depolymerization to enhance the analysis for the identifier nucleotide.

Kits

Other embodiments of the invention contemplate a kit for determining the presence or absence of a predetermined nucleic acid target sequence in a nucleic acid sample. Such a kit comprises an enzyme whose activity is to release one or more nucleotides from the 3' terminus of a hybridized nucleic acid probe and at least one nucleic acid probe, said nucleic acid probe being complementary to nucleic acid target sequence. The kit optionally further comprises a nucleoside diphosphate kinase. Preferably, the nucleoside diphosphate kinase is that encoded by *Pyrococcus furiosis*. The kit optionally further comprises instructions for detecting said nucleic acid by depolymerization. Preferably the enzyme whose activity is to release nucleotides in the kit is a template dependent polymerase that, in the presence of pyrophosphate ions, depolymerizes hybridized nucleic acids whose bases in the 3'-terminal region are matched with total complementarity. Alternatively, the enzyme whose activity is to release nucleotides in the kit exhibits a 3' to 5' exonuclease activity, depolymerizing hybridized nucleic acids having one or more mismatched bases at the 3' terminus of the hybridized probe.

It is to be understood that such a kit is useful for any of the methods of the present invention. The choice of particular components is dependent upon the particular method the kit is designed to carry out. Additional components can be provided for detection of the analytical output, as measured by the release of identifier nucleotide, or by detection of the remaining probe after depolymerization. For example, ethidium bromide can be provided in the kits of the invention for detection of a probe that has had identifier nucleotide released from the 3'-terminal region.

The instructions present in such a kit instruct the user on how to use the components of the kit to perform the various methods of the present invention. These instructions can include a description of the detection methods of the invention, including detection by luminescence spectroscopy, mass spectrometry, fluorescence spectroscopy, and absorbance spectroscopy.

In another embodiment, the invention contemplates a kit for determining the presence or absence of at least one predetermined nucleic acid target sequence in a nucleic acid sample comprising the following components: an enzyme whose activity in the presence of pyrophosphate is to release identifier nucleotide as a nucleoside triphosphate from hybridized nucleic acid probe; adenosine 5' diphosphate; pyrophosphate; a nucleoside diphosphate kinase; and at least one nucleic acid probe, wherein the nucleic acid probe is complementary to the predetermined nucleic acid target sequence.

Preferably, the enzyme whose activity in the presence of pyrophosphate is to release identifier nucleotides is selected from the group consisting of the Tne triple mutant DNA polymerase, Klenow exo-, Klenow, T4 DNA polymerase, Ath DNA polymerase, Taq DNA polymerase and Tvu DNA polymerase. Preferably, the nucleoside diphosphate kinase is that encoded by *Pyrococcus furiosis*.

The kit optionally comprises instructions for use.

In another embodiment, the invention contemplates a kit for determining the presence or absence of a predetermined nucleic acid target sequence in a nucleic acid sample comprising an enzyme whose activity is to release one or more nucleotides from the 3' terminus of a hybridized nucleic acid probe and instructions for use. Such a kit optionally comprises a nucleoside diphosphate kinase. Preferably, the nucleoside diphosphate kinase is that encoded by *Pyrococcus furiosis*. The kit further optionally comprises a nucleic acid probe complementary to the predetermined nucleic acid target sequence.

In other embodiments of the present invention, nucleic acid detection test kits are provided for performing a depolymerization method contemplated by this invention, and particularly a depolymerization detection method.

In one embodiment, the kit includes a vessel containing an enzyme capable of catalyzing pyrophosphorolysis, including, but not limited to Taq polymerase, Tne polymerase, Tne triple mutant polymerase, Tth polymerase, Tvu polymerase, Ath polymerase, T4 DNA polymerase, Klenow fragment, Klenow exo minus, *E. coli* DNA polymerase I, AMV reverse transcriptase, MMLV reverse transcriptase, or poly(A) polymerase. In another embodiment, the kit contains a vessel that contains an exonuclease such as S1 nuclease, nuclease BAL 31, mung bean nuclease, exonuclease III and ribonuclease H.

Either of the above enzyme types is utilized in a contemplated method in a depolymerizing effective amount. That is, the enzyme is used in an amount that depolymerizes the hybridized probe to release an identifier nucleotide. This amount can vary with the enzyme used and also with the temperature at which depolymerization is carried out. An enzyme of a kit is typically present in an amount of about 0.1 to 100 U/reaction; in particularly preferred embodiments, the concentration is about 0.5 U/reaction. An amount of enzyme sufficient to carry out at least one assay, with its controls is provided.

As noted elsewhere, the preferred analytical output for determining the presence or absence of identifier nucleotide is luminescence caused by the reaction of ATP with luciferin in the presence of luciferase. A kit containing a pyrophosphorylation enzyme for use in DNA detection using luminescence also preferably includes a vessel containing NDPK and a vessel containing ADP. Similarly, a kit containing an exonuclease enzyme for use in DNA detection using luminescence also preferably includes a vessel containing PRPP synthetase and a vessel containing ADP. The NDPK or PRPP synthetase is provided in concentration of about 0.01 to 100 U/reaction, preferably about 0.1 to about 1.0 U/reaction.

Preferably, these reagents, and all of the reagents utilized in the kits discussed herein, are free of contaminating ATP and adenylate kinase. Some of the contaminants can be removed from the enzymes by dialysis treatment.

Optionally, the kit contains vessels with reagents for amplification of dNTPs or NTP to ATP. Amplification reagents include, but are not limited to pyruvate kinase, adenylate kinase, NMPK, NDPK, AMP (e.g., as the amplification enzymes and substrate), and dCTP or AMP-CPP (e.g., as high-energy phosphate donors). In particularly preferred embodiments, the kit can be packaged in a single enclosure including instructions for performing the assay methods. In some embodiments, the reagents are provided in containers and are of a strength suitable for direct use or use after dilution. In alternative preferred embodiments, a standard set can also be provided in order to permit quantification of results. In yet other preferred embodiments, test buffers for optimal enzyme activity are included.

In yet other embodiments, a contemplated kit comprises a nuclease, PRPP synthetase, PRPP, NDPK, and ADP together with luciferase and luciferin. In preferred embodiments, the nuclease is provided in a concentration of about 1 to 500 U/reaction; in particularly preferred embodiments at a concentration of about 20 U/reaction. In a particularly preferred embodiment, the PRPP synthetase is provided in concentration of about 0.01 U/reaction to 10 U/reaction, preferably about 0.1 U/reaction. In some preferred embodiments, the kit includes all these reagents with luciferase and luciferin being provided as a single reagent solution.

In other preferred embodiments, these reagents include, but are not limited to, a high energy phosphate donor which cannot be utilized by luciferase, preferably dCTP, and AMP together with luciferase and luciferin. In alternative preferred embodiments, the kit includes all these reagents with luciferase and luciferin being provided in the same solution.

In still further embodiments of the present invention, the kits described above can contain a probe or probes for probe-mediated specific nucleic acid detection. In some embodiments, the kit contains at least one nucleic acid probe for a nucleic acid target of interest. In other embodiments, the kits contain multiple probes, each of which contain a different base at an interrogation position or which are designed to interrogate different target DNA sequences.

In each of the embodiments, the kits contain instructions for use in interrogating the identity of a specific base within a nucleic acid target, for discriminating between two homologous nucleic acid targets that differ by one or more base pairs, or for determining whether a nucleic acid target contains a deletion or insertion mutation. The types of nucleic acid probes that can be included in the kits and their uses are described in greater detail below.

Detection of Endonuclease and Exonuclease Activities

The present invention may also be used to detect endonuclease or exonuclease activity in a sample suspected of containing such activity. In one embodiment, a nucleic acid substrate is added to the sample suspected of containing endonuclease or exonuclease activity. In some embodiments, the substrate is preferably a double stranded nucleic acid, most preferably DNA. The mixture is incubated for a period of time sufficient for any endonuclease or exonuclease activity present in the sample to digest the substrate. In some embodiments, the incubation may be for about 1 to 18 hours, while in preferred embodiments the incubation is for about 12 hours. After the incubation, the amount of residual nucleic acid is detected via depolymerization by pyrophosphorolysis. Accordingly, in some embodiments, an aliquot of the incubation mixture then is exposed to conditions permitting depolymerization. These conditions are described above in reaction 1 and in the Examples. Nucleotides produced by depolymerization are then detected. In some embodiments, the nucleotides produced by depolymerization are converted to ATP equivalents as described in reaction 4 and in the examples. In preferred embodiments, the ATP is detected by a luciferase or NADH detection system. Because the residual nucleic acid is being assayed, a decrease in the assay value (e.g., light units when a luciferase detection system is utilized) as compared to a "no nuclease" control characterizes the presence of endonuclease or exonuclease activities.

In another embodiment of the present, endonuclease activity may be specifically detected. Closed circular DNA is not normally a substrate for pyrophosphorolysis because there are no DNA ends from which depolymerization can initiate. Therefore, in some embodiments, a closed circular DNA substrate is added to a sample suspected of containing an endonuclease. The mixture is incubated for a period of time sufficient for any endonuclease activity present in the sample to digest the substrate (e.g., create double-stranded breaks or nicks in the substrate). In some embodiments, the incubation may be for about 1 to 18 hours, while in preferred embodiments the incubation is for about 12 hours. After incubation, an aliquot of the incubation mixture then is exposed to conditions permitting depolymerization. These conditions are described above in reaction 1 and in the Examples. Nucleotides produced by depolymerization are then detected. In some embodiments, the nucleotides produced by depolymerization are converted to ATP equivalents as described in reaction 4 and in the Examples. In preferred embodiments, the ATP is detected by a luciferase or NADH detection system. The presence of endonuclease activity is characterized by an increase in assay units as compared to a no endonuclease control (e.g., an increase in light units when a luciferase detection system is utilized).

In another embodiment of the present invention, exonuclease activity may be detected qualitatively or quantitatively by converting dNMP produced by exonuclease digestion to ATP. In some embodiments, a nucleic acid substrate, preferably DNA, is added to a sample suspected of containing exonuclease activity. The mixture is allowed to incubate for a period of time sufficient for any exonuclease present in the sample to act on the substrate. In some embodiments, the incubation period is from about 0.5 to about 4 hours, while in preferred embodiments, the incubation period is about one hour. After incubation, an aliquot of the incubation mixture is then exposed to conditions permitting the conversion of dNMPs produced by exonuclease digestion to dNTPs. This reaction requires PRPP synthetase and PRPP and is described above in reaction 3 and in the Examples. The nucleotides are then detected. In some embodiments, the dNTPs may be converted to ATP as described in reaction 4 above and in the Examples. In some embodiments, the ATP is detected by a luciferase detection system or a NADH detection system. The presence of exonuclease activity is characterized by an increase in assay units as compared to a no nuclease control (e.g., an increase in light units when a luciferase detection system is utilized).

EXAMPLE 1

Comparison of Signal Strengths During Allele Determination Using Probes that Interrogate the Same DNA Strand versus Probes that Interrogate Different Strands Because DNA normally exists in a eukaryotic genome as a double-stranded polymer; in theory, allele discrimination could be performed by:

A) using probes that are essentially identical in sequence (except for an allele discriminating base) and that hybridize to the same DNA strand; or B) using two probes that hybridize to different strands of DNA but match the sequence of only one allele of the gene at a position where the genotype is to be determined.

In this example, a comparison is made of the signal strengths of these two types of probes in distinguishing a single nucleotide polymorphism (SNP) target nucleic acid provided as a homozygous target for any known allele or as a heterozygous target containing different alleles.

Oligonucleotide PH1 (SEQ ID NO:1) is a probe that encodes a segment of the human prohibitin gene where SNP exists; it matches the "C" allele. Oligonucleotide PH2 (SEQ ID NO:2) is a probe that encodes the same segment of the human prohibitin gene but it differs in one base from PH1 and matches the "T" allele. These two oligonucleotides hybridize to the same strand of a target DNA. Oligonucleotide PH4 (SEQ ID NO:3) is a probe that encodes a segment of the human prohibitin gene where the SNP defined by PH1 and PH2 exists, however this probe is made to hybridize to the other target strand than that to which PH1 and PH2 hybridize.

Oligonucleotides PH5 (SEQ ID NO:4) and PH6 (SEQ ID NO:5), when annealed together, are a double strand segment of DNA (PH5+6), and each strand is larger than PH1, PH2 or PH4. PH5 and PH6 encode a larger region of the human prohibitin gene, and match the "C" allele. This double-stranded target was produced by dissolving PH5 and PH6 in water to a concentration of 1 mg/mL, mixing equal volumes of these solutions together, heating the mixture to 95° C. for 5 minutes and then cooling to room temperature over a period of an hour.

Oligonucleotides PH7 (SEQ ID NO:6) and PH8 (SEQ ID NO:7) form a double strand DNA segment (PH7+8) identical in sequence to PH5+6 except that it contains the "T" allele of the gene. This double-stranded DNA was produced as described above. An equal mass mixture of the double-stranded target nucleic acids produced a mixed sample with equal amounts of the two alleles, as exists for samples heterozygous for these alleles.

PH1, PH2 and PH4 were dissolved in water to a concentration of 1 mg/mL. PH5+6 and PH7+8 were also diluted to 1 μg/mL in water. Equal volumes of the double-stranded DNA target segments were diluted and mixed to produce a mixture containing equal amounts of both alleles. This solution was labeled PH(5+6)+(7+8). The following solutions were assembled.

| Soln | PH1 | PH2 | PH4 | PH5 + 6 | PH7 + 8 | PH(5 + 6) + (7 + 8) | Water |
|---|---|---|---|---|---|---|---|
| #1 | — | — | — | — | — | — | 20 μL |
| #2 | 1 μL | — | — | — | — | — | 19 μL |
| #3 | — | 1 μL | — | — | — | — | 19 μL |
| #4 | — | — | 1 μL | — | — | — | 19 μL |
| #5 | — | — | — | 1 μL | — | — | 19 μL |
| #6 | — | — | — | — | — | 1 μL | 19 μL |
| #7 | — | — | — | — | 1 μL | — | 19 μL |
| #8 | 1 μL | — | — | 1 μL | — | — | 18 μL |
| #9 | — | 1 μL | — | 1 μL | — | — | 18 μL |
| #10 | 1 μL | — | — | — | — | 1 μL | 18 μL |
| #11 | — | 1 μL | — | — | — | 1 μL | 18 μL |
| #12 | 1 μL | — | — | — | 1 μL | — | 18 μL |
| #13 | — | 1 μL | — | — | 1 μL | — | 18 μL |
| #14 | 1 μL | — | — | 1 μL | — | — | 18 μL |
| #15 | — | — | 1 μL | 1 μL | — | — | 18 μL |
| #16 | 1 μL | — | — | — | — | 1 μL | 18 μL |
| #17 | — | — | 1 μL | — | — | 1 μL | 18 μL |
| #18 | 1 μL | — | — | — | 1 μL | — | 18 μL |
| #19 | — | — | 1 μL | — | 1 μL | — | 18 μL |

These solutions were heated to 95° C. for 5 minutes then permitted to cool at room temperature for 10 minutes. The following master mix was assembled and mixed.

| Component | Amount |
|---|---|
| 10X DNA Pol Buffer (Promega, M195A) | 200 μL |
| Klenow exo- (1 U/μL) (Promega M218B) | 12.5 μL |
| 40 mM Sodium Pyrophosphate (Promega C350B) | 25 μL |
| NDPK (1 U/μL) | 10 μL |
| 10 uM ADP (Sigma A5285) | 20 μL |
| Water | 732.5 μL |

Twenty microliters of this master mix were added to solutions 1–19 above after cooling at room temperature for 10 minutes and the resulting mixtures were heated at 37° C. for 15 minutes. After this incubation, duplicate 4 μL samples of each of solutions 2–19 and a single 4 μL sample of solution 1 were removed and added to 100 μL L/L reagent (Promega, F202A) and the light produced by the reaction was measured immediately using a Turner® TD20/20 luminometer. The following results were obtained.

| | Relative light units | | |
|---|---|---|---|
| Solution | Reading 1 | Reading 2 | Avg. |
| #1 | 5.03 | | |
| #2 | 6.83 | 4.85 | 5.84 |
| #3 | 14.0 | 13.8 | 13.9 |
| #4 | 8.52 | 8.94 | 8.73 |
| #5 | 8.24 | 8.98 | 8.61 |
| #6 | 6.31 | 6.40 | 6.36 |
| #7 | 5.40 | 5.30 | 5.35 |
| #8 | 371.8 | 472.7 | 422.3 |
| #9 | 18.8 | 20.9 | 19.9 |
| #10 | 260.9 | 257.9 | 259.4 |
| #11 | 396.5 | 401.6 | 399.1 |
| #12 | 9.07 | 9.31 | 9.19 |
| #13 | 567.5 | 536.5 | 552.0 |
| #14 | 380.0 | 408.7 | 394.4 |
| #15 | 54.77 | 46.36 | 50.6 |
| #16 | 216.7 | 220.3 | 218.5 |
| #17 | 55.43 | 125.0 | 90.2 |
| #18 | 9.25 | 9.56 | 9.4 |
| #19 | 114.0 | 125.0 | 119.5 |

The net relative light values for the data above were calculated as follows. The ratios reported in this example were determined by first averaging the results from matching samples, then determining the net light production from the matching and mismatching samples and dividing the net light production from the matching reaction by that seen in the mismatch reaction. The net light production was determined by subtracting the estimated light contribution from the probes and template present in the reactions from the total light produced. The light production from the template reaction was considered to be the total of that contributed from the template specifically and that contributed by contaminating ATP from various components. The net increase from the probes alone was calculated by subtracting the average "No DNA" values from the probe values since this subtracts the contributions from contaminating ATP from the probe values. Thus, the formula used to determine the net light production from the reactions was:

Net Light=Total light−[(target alone)+(probe alone−No DNA)]

These values were used to determine the signal ratio by dividing the signal from the "C" allele probe by the signal from the "T" allele probe. The calculated values are shown below.

| | Template Genotype | | |
|---|---|---|---|
| Probe | C/C | C/T | T/T |
| | Probes Interrogate the Same DNA strand | | |
| C Probe | 412.9 | 252.2 | 3.6 |
| T Probe | 0 | 388.9 | 537.7 |
| Ratio | >400 | 1.54 | .006 |
| | Probes Interrogate | | |

-continued

| Probe | Template Genotype | | |
|---|---|---|---|
| | C/C | C/T | T/T |
| | Different DNA Strands | | |
| C Probe | 385 | 211.3 | 3.8 |
| T Probe | 38.3 | 80.1 | 110.4 |
| Ratio | 10 | 2.6 | 0.034 |

These data indicate that very different detection ratios are calculated from both sets of probes but that the signal ratios from the different target genotypes are easily distinguished from each other. In addition, the "T" allele probe PH2 gave a relatively low light signal in the absence of nucleic acid target using the low Klenow exo- additions employed in this example. If such manipulations were not used, the light signal from the probe alone would be a large contribution to the total signal of the samples containing the probe, making sensitive allele discrimination more difficult.

```
PH1   5' CTGAACATGCCTGCCAAAGACG 3'                        SEQ ID NO:1

PH2   5' CTGAACATGCCTGCCAPAGATG 3'                        SEQ ID NO:2

PH4   5' CAGGAACGTAGGTCGGACACAT 3'                        SEQ ID NO:3

PH5   5' CTGCTGGGGCTGAACATGCCTGCCAAAGACGTGTCC             SEQ ID NO:4

GACCTACGTTCCTGGCCCCCTCGAGCT 3'

PH6   5' CGAGGGGGCCAGGAACGTAGGTCGGACACGTCTTTG             SEQ ID NO:5

GCAGGCATGTTCAGCCCCAGCAGAGCT 3'

PH7   5' CTGCTGGGGCTGAACATGCCTGCCAAAGATGTGTCC             SEQ ID NO:6

GACCTACGTTCCTGGCCCCCTCGAGCT 3'

PH8   5' CGAGGGGGCCAGGAACGTAGGTCGGACACATCTTTG             SEQ ID NO:7

GCAGGCATGTTCAGCCCCAGCAGAGCT 3'
```

EXAMPLE 2

Reduction of Probe-alone Background Values for Probes Designed to Interrogate a Viral Sequence In this example, the background light values from probe-alone reactions are reduced by alteration of reaction conditions. More specifically, the values from such background reactions are reduced by lowering the Klenow exo-level in the reactions as shown in Example 43. In addition, the probes are used to assay the relative probe signal strength values for probes that hybridize to the same DNA strand versus probes that hybridize to different strands but that interrogate the same nucleotide polymorphism site.

Oligonucleotides CV11 (SEQ ID NO:8) and CV12 (SEQ ID NO:9) are a pair of single-stranded DNAs that can hybridize together to produce a segment of the genome of cytomegalovirus (CMV) in a form sensitive to the drug gancyclovir. Oligonucleotides CV13 (SEQ ID NO:10) and CV14 (SEQ ID NO:11) are a pair of single-stranded DNAs that can hybridize together to produce the same segment of the CMV genome, but differ from CV11 and CV12 in that they contain a SNP that represents a form of the virus resistant to the drug gancyclovir.

Probe oligonucleotide CV15 (SEQ ID NO:12) can hybridize with exact homology to a segment of CV12. Probe oligonucleotide CV16 (SEQ ID NO:13) is identical to CV15 except that it contains a one base change from the CV15 sequence at the site of the SNP that confers drug resistance to the virus. Probe oligonucleotide CV17 (SEQ ID NO:14) can hybridize with exact homology to CV11. Probe oligonucleotide CV18 (SEQ ID NO:15) is identical to CV17 except that it contains a one base change from the CV17 sequence at the site of the SNP that confers drug resistance to the virus.

The oligonucleotides above were dissolved in water at a concentration of 1 mg/mL and the following solutions were assembled.

| Solution | Oligonucleotide | Water |
|---|---|---|
| #1 | — | 20 µL |
| #2 | CV15, 1 µL | 19 µL |
| #3 | CV16, 1 µL | 19 µL |
| #4 | CV17, 1 µL | 19 µL |
| #5 | CV18, 1 µL | 19 µL |

These solutions were heated at 95° C. for 5 minutes, then cooled at room temperature for 10 minutes. A master mix was prepared as in Example 1, containing Klenow exo- at a concentration of 0.25 U/20 µL of solution. Twenty microliters of this solution were added to solutions 1–5 above after they had cooled, and then the resulting mixtures were heated at 37° C. for 15 minutes. After this incubation, 4 µL of each solution were added to 100 µL of L/L reagent (Promega F202A) and the light production of the resulting solution was measured immediately using a Turner® TD 20/20 luminometer. The following results were obtained.

| Solution sampled | Relative light units |
|---|---|
| #1 | 13.07 |
| #2 | 14.98 |
| #3 | 14.27 |
| #4 | 28.25 |
| #5 | 583.70 |

These results demonstrate that probes CV15–CV17 provide relatively low probe-alone light signals at 0.25U Klenow exo- per reaction but that probe CV18-alone provides a very high relative light signal. The sequence of the CV18 probe can form a hairpin structure such that the terminal 3' bases hybridize to the sequence 5' TCGTGC 3' further towards the 5' end of the segment. Although probe CV17 could form the same structure, the terminal 3' base of the resulting structure would have a mispaired base.

These data exemplify one of the guiding principles of appropriate probe design for this system: the probes should not be predicted to form stable hairpin structure and, in particular, should not be predicted to give such a structure with the 31' end of the probe producing a structure that forms a blunt end or 5' overhang in the fragment as they may act as a substrate for the depolymerizing enzyme. In addition, the probes used should not be predicted to form probe dimer structures with either blunt ends or 5' overhanging ends because such probes can produce high probe-alone signals in the system and might make them unacceptable for use.

Due to their low background, probes CV15–CV17 were then selected for further study. Equal volumes of oligonucleotides CV11 and CV12 were annealed together as described in Example 1, as were CV13 and 14. The annealed solutions of CV11 and CV12, and CV13 and CV14 were labeled CV11+12 and CV13+14, respectively. The following solutions were assembled.

|  | Relative light units | |
|---|---|---|
| Solution | Reading 1 | Reading 2 |
| #1 | 10.53 | — |
| #2 | 11.35 | 12.16 |
| #3 | 10.79 | 12.75 |
| #4 | 17.70 | 16.76 |
| #5 | 12.78 | 11.12 |
| #6 | 11.36 | 11.48 |
| #7 | 12.38 | 12.16 |
| #8 | 348.3 | 369.3 |
| #9 | 73.11 | 74.48 |
| #10 | 289.5 | 283.6 |
| #11 | 509.8 | 364.0 |
| #12 | 120.2 | 108.6 |
| #13 | 785.4 | 595.7 |
| #14 | 764.3 | 763.3 |
| #15 | 77.25 | 73.22 |
| #16 | 530.9 | 541.2 |
| #17 | 476.1 | 419.6 |
| #18 | 339.4 | 262.7 |
| #19 | 943.2 | 964.0 |

The results from the readings above were averaged and the net light units calculated as described in Example 1. These values were used to calculate ratios also as described in Example 1. The results of these calculations are presented

| Solution | CV15 | CV16 | CV17 | CV11 + 12 | CV13 + 14 | CV(11 + 12) + (13 + 14) Heterozyg Template | Water |
|---|---|---|---|---|---|---|---|
| #1 | — | — | — | — | — | — | 20 μL |
| #2 | 1 μL | — | — | — | — | — | 19 μL |
| #3 | — | 1 μL | — | — | — | — | 19 μL |
| #4 | — | — | 1 μL | — | — | — | 19 μL |
| #5 | — | — | — | 1 μL | — | — | 19 μL |
| #6 | — | — | — | — | — | 1 μL | 19 μL |
| #7 | — | — | — | — | 1 μL | — | 19 μL |
| #8 | 1 μL | — | — | 1 μL | — | — | 18 μL |
| #9 | — | 1 μL | — | 1 μL | — | — | 18 μL |
| #10 | 1 μL | — | — | — | — | 1 μL | 18 μL |
| #11 | — | 1 μL | — | — | — | 1 μL | 18 μL |
| #12 | 1 μL | — | — | — | 1 μL | — | 18 μL |
| #13 | — | 1 μL | — | — | 1 μL | — | 18 μL |
| #14 | 1 μL | — | — | 1 μL | — | — | 18 μL |
| #15 | — | — | 1 μL | 1 μL | — | — | 18 μL |
| #16 | 1 μL | — | — | — | — | 1 μL | 18 μL |
| #17 | — | — | 1 μL | — | — | 1 μL | 18 μL |
| #18 | 1 μL | — | — | — | 1 μL | — | 18 μL |
| #19 | — | — | 1 μL | — | 1 μL | — | 18 μL |

These solutions were heated at 95° C. for 5 minutes and then permitted to cool for 10 minutes at 10 room temperature. A master mix solution was assembled as in Example 1 containing Klenow exo- at a final concentration of 0.25 U/20 μL. After solutions 1–19 had cooled, 20 μL of the master mix solution were added and the resulting solution heated at 37° C. for 15 minutes. After this incubation, duplicate 4 μL samples of solutions 2–19 and a single sample of solution 1 were taken, added to 100 μL of L/L reagent (Promega, F202A) and the light production of the mixture measured immediately using a Turner® TD 20/20 luminometer. The following results were obtained.

in the tables below, wherein "WT" indicates the wild type genotype.

|  | Template Genotype | | |
|---|---|---|---|
| Probe | C/C | C/T | T/T |
|  | Probes Interrogate the Same DNA strand | | |
| WT Probe (CV15) | 345.5 | 274.0 | 100.8 |
| Mutant | 60.5 | 424.3 | 677 |

-continued

| Probe | Template Genotype | | |
|---|---|---|---|
| | C/C | C/T | T/T |
| Probe (CV16) Ratio | 5.7 | 1.5 | 0.15 |
| | Probes Interrogate Different DNA Strands | | |
| WT Probe (CV15) | 745.1 | 518.0 | 282.1 |
| Mutant Probe (CV17) | 61.9 | 435.0 | 940 |
| Ratio | 12 | 1.2 | 0.33 |

These data demonstrate that, for this particular SNP, probes that detect the polymorphism that bind to different strands provide the signal ratio closest to 1.0 when both nucleic acid targets are present in the reaction (as occurs for samples heterozygous for a particular allele). However either set of probes give clearly different signals depending upon the genotype of the sample DNA.

```
CV11
5'CGCTTCTACCACGAATGCTCGCAGACCATGCTGCACGAATACGTCAGAAAG    SEQ ID NO:8
AACGTGGAGCGTCTGTTGGAGCT 3'

CV12
5'CCAACAGACGCTCCACGTTCTTTCTGACGTATTCGTGCAGCATGGTCTGCG    SEQ ID NO:9
AGCATTCGTGGTAGAAGCQAGCT 3'

CV13
5'CGCTTCTACCACGAATGCTCGCAGATCATGCTGCACGAATACGTCAGAAA     SEQ ID NO:10
GAACGTGGAGCGTCTGTTGGAGCT 3'

CV14
5'CCAACAGACGCTCCACGTTCTTTCTGACGTATTCGTGCAGCATGATCTGCG    SEQ ID NO:11
AGCATTCGTGGTAGAAGCGAGCT 3'

CV15    5' CTACCACGAATGCTCGCAGAC 3'                        SEQ ID NO:12

CV16    5' CTACCACGAATGCTCGCAGAT 3'                        SEQ ID NO:13

CV17    5' TGACGTATTCGTGCAGCATGG 3'                        SEQ ID NO:14

CV18    5' TGACGTATTCGTGCAGCATGA 3'                        SEQ ID NO:15
```

EXAMPLE 3
Multiplex Analysis of Alleles at One Interrogation Site

For a wide variety of genetic disorders, only a very small percentage of samples will have a particular single nucleotide polymorphism (SNP) at any one site. For this reason, it can be much more efficient in these cases to screen for the presence of groups of mutant alleles and to perform secondary, single probe tests only if there is a positive signal for any of the probes designed to detect the mutant sites. Such a form of multiplex analysis will be performed in this example.

Multiple probes designed to detect a mutant form of a gene in the CMV genome are used in one reaction and the signal from this reaction is compared to that from a probe that is specific for the non-mutated sequence. In this example, the SNP sites are separated by only one base and the alleles are provided as pure nucleic acid target species.

Oligonucleotides CV19 (SEQ ID NO:16) and CV20 (SEQ ID NO:17) encode a segment of the CMV genome around position 1784 of the viral genome and these probes encode the non-mutant form of a gene. Oligonucleotides CV21 (SEQ ID NO:18) and CV22 (SEQ ID NO:19) encode the same genome segment as CV19 and CV20 but encode a form of the gene where a Leu codon in the encoded protein is altered to encode a Ser codon.

Oligonucleotides CV23 (SEQ ID NO:20) and CV24 (SEQ ID NO:21) also encode the same genome segment as CV19 and CV20, but these oligonucleotides encode a form of the genome where the same Leu codon mutated in CV21 and CV22 is altered to a Phe codon. These oligonucleotides are used here as target nucleic acids for interrogation in this example.

Oligonucleotide probe CV25 (SEQ ID NO:22) exactly matches a region of CV19 and is designed to detect the non-mutated form of the gene. Oligonucleotide probe CV26 (SEQ ID NO:23) exactly matches a segment within CV21 and is designed to detect the version of the gene where the Leu codon has been mutated to a Ser codon. Oligonucleotide probe CV27 (SEQ ID NO:24) exactly matches a segment within CV24 and is designed to detect the version of the target where the Leu codon has been mutated to a Phe codon.

The target nucleic acid pairs CV19 and CV20, CV21 and CV22, and CV23 and CV24 were dissolved at 1 mg/mL in water, annealed as described in Example 1, and subsequently diluted to 3.3 jig/mL with water. The probes CV25, CV26 and CV27 were dissolved at 1 mg/mL in water.

The following solutions were assembled.

| Solution | CV (19 + 20) | CV (21 + 22) | CV (23 + 24) | CV25 | CV26 | CV27 | Water |
|---|---|---|---|---|---|---|---|
| #1 and #2 | 1 μL | — | — | 1 μL | — | — | 18 μL |
| #3 and #4 | 1 μL | — | — | — | 1 μL | 1 μL | 17 μL |
| #5 and #6 | — | 1 μL | — | 1 μL | — | — | 18 μL |
| #7 and #8 | — | 1 μL | — | — | 1 μL | 1 μL | 17 μL |
| #9 and #10 | — | — | 1 μL | 1 μL | — | — | 18 μL |
| #11 and #12 | — | — | 1 μL | — | 1 μL | 1 μL | 17 μL |

These solutions were heated at 95° C. for three minutes then cooled at room temperature for 10 minutes.

The following master mix was assembled and mixed.

| Component | Volume |
|---|---|
| 10X DNA Polymerase Buffer (Promega, M195A) | 60 µL |
| 40 mM Sodium Pyrophosphate (Promega, C350B) | 7.5 µL |
| Klenow exo- (10 U/µL) (Promega, M218B) | 7.5 µL |
| NDPK (1 U/µL) | 3 µL |
| 10 µM ADP | 6 µL |
| Water | 216 µL |

After solutions 1–12 had cooled at room temperature, 20 µL of this master mix were added to each solution, and the solutions were heated to 37° C. for 15 minutes. After this heating step, a 4 µL sample of each solution was added to 100 µL L/L reagent (Promega, F202A) and the light produced by the resulting reaction was read immediately using a Turner® TD 20/20 luminometer. The following results were obtained.

| Solution samples | Relative Light Units |
|---|---|
| #1 | 115.7 |
| #2 | 120.9 |
| #3 | 20.85 |
| #4 | 20.10 |
| #5 | 9.99 |
| #6 | 9.41 |
| #7 | 102.4 |
| #8 | 95.2 |
| #9 | 12.56 |
| #10 | 12.54 |
| #11 | 240.3 |
| #12 | 238.9 |

The results from the duplicate solutions were averaged and are presented in the table below.

Average Signal from Probe Types

| Nucleic Acid Target | Wild Type Probe | Mutant Probes Multiplexed | Ratio* |
|---|---|---|---|
| Wild Type Target | 118.3 | 20.48 | 5.78 |
| Leu to Ser Target | 9.7 | 98.8 | 0.10 |
| Leu to Phe Target | 12.6 | 239.6 | 0.05 |

*Ratio is determined by dividing the signal from the wild type probe by the signal from the multiplexed mutant probes.

These data show that the use of both mutant probes in one reaction permits either probe to give a signal if the appropriate target is added to the reaction. The signal ratios produced by the probes designed to detect the mutant target when either probe matches the target are significantly different than from when the wild type target is used with the wild type probe. Thus, comparison of the signals as described above permits the user to know that a mutation is present in the tested target at either of the interrogation sites.

```
CV19
5' CTCTTTAAGCACGCCGGCGCGGCCTGCCGCGCGTTGGAGAACGGCAAGCTC    SEQ ID NO:16
ACGCA 3'

CV20
5' CAGCAGTGCGTGAGCTTGCCGTTCTCCAACGCGCGGCAGGCCGCGCCGGCG    SEQ ID NO:17
TGCTT 3'

CV21
5' CTCTTTAAGCACGCCGGCGCGGCCTGCCGCGCGTCGGAGAACGGCAAGCTC    SEQ ID NO:18
ACGCA 3'

CV22
5' CAGCAGTGCGTGAGCTTGCCGTTCTCCGCGCGCGGCAGGCCGCGCCGGCGT    SEQ ID NO:19
GCTT 3'

CV23
5' CTCTTTAAGCACGCCGGCGCGGCCTGCCGCGCGTTTGAGAACGGCAAGC      SEQ ID NO:20
ACGCA 3'

CV24
5' CAGCAGTGCGTGAGCTTGCCGTTCTCAAACGCGCGGCAGGCCGCGCCGG      SEQ ID NO:21
TGCTT 3'

CV25
5' GGCGCGGCCTGCCGCGCGTTG 3'                                SEQ ID NO:22

CV26
5' GGCGCGGCCTGCCGCGCGTCG 3'                                SEQ ID NO:23

CV27
5' GCGTGAGCTTGCCGTTCTCCG 3'                                SEQ ID NO:24
```

EXAMPLE 4
Multiplexed Genome Analysis on Multiple Templates

For a wide variety of genetic disorders, only a very small percentage of samples exhibit a particular single nucleotide polymorphism at any one site. For this reason, it can be more efficient in these cases to screen for the presence of groups of mutant alleles and to perform secondary, single probe tests only if there is a positive signal for any of the probes designed to detect the mutant sites. Such a form of multiplex analysis will be performed in this example.

Multiple probes designed to detect a mutant form of two different target genes are used in one reaction, and the signal from this reaction is compared to that from a probe that is specific for one of the non-mutated sequences. Thus, in this example, multiple SNP sites on multiple targets are interrogated in one reaction.

The targets and probes used in this study are: FV(1+2) (SEQ ID NO:25 and SEQ ID NO:26, respectively) FV(3+4) (SEQ ID NO:27 and SEQ ID NO:28, respectively), FV5 (SEQ ID NO:29), FV6 (SEQ ID NO:30), 9162 (SEQ ID NO:31), 9165 (SEQ ID NO:32), 9163 (SEQ ID NO:33), 9166 (SEQ ID NO:34), and CV2 (SEQ ID NO:35). A synthetic first nucleic acid target of the Factor V gene was designed to have the wild type sequence that contains a G at position 32 of FV1 (SEQ ID NO:25). The complementary strand, FV2, (SEQ ID NO:26) has 4 additional bases at its 3' terminus. A second synthetic nucleic acid target of Factor V was designed to have the Leiden mutation, an A residue at position 32 of FV3. The mutant complementary strand, FV4, also had 4 additional bases at its 3' terminus. The nucleic acid target oligonucleotides, FV1 to FV4, were separately dissolved at a concentration of one mg/mL in water. Oligonucleotides 9162 and 9163 are complementary and have a segment of the wild type CMV genome. Oligonucleotides 9163 and 9166 are complementary and have the same segment of the viral genome, but they contain a single base change present in a known drug resistant form of the virus. Equal volumes of one mg/mL 9162 and 9165 were combined to serve as wild type target for CMV. Equal volumes of one mg/mL 9163 and 9166 were combined to serve as the mutant target for CMV. Oligonucleotide CV2 represents an oligonucleotide designed to detect the drug resistant form of the CMV sequence.

All the target DNAs [FV(1+2), FV(3+4), 9162+9165, 9163+9166] were diluted to 0.3 µg/mL with water. The other oligonucleotides were dissolved to 1 mg/mL with water. These compositions were used to assemble the following solutions.

| Soln | FV5 | FV6 | CV2 | 9162 + 9165 | 9163 + 9166 | FV(1 + 2) | FV(3 + 4) | Water |
|---|---|---|---|---|---|---|---|---|
| 1  | —    | —    | —    | —    | —    | —    | —    | 20 µL |
| 2  | —    | 1 µL | —    | —    | —    | —    | —    | 19 µL |
| 3  | —    | —    | 1 µL | —    | —    | —    | —    | 19 µL |
| 4  | —    | 1 µL | 1 µL | —    | —    | —    | —    | 18 µL |
| 5  | —    | —    | —    | 1 µL | —    | —    | —    | 19 µL |
| 6  | —    | —    | —    | —    | 1 µL | —    | —    | 19 µL |
| 7  | —    | —    | —    | —    | —    | 1 µL | —    | 19 µL |
| 8  | —    | —    | —    | —    | —    | —    | 1 µL | 19 µL |
| 9  | —    | —    | —    | 1 µL | —    | 1 µL | —    | 18 µL |
| 10 | —    | —    | —    | 1 µL | —    | —    | 1 µL | 18 µL |
| 11 | —    | —    | —    | —    | 1 µL | 1 µL | —    | 18 µL |
| 12 | —    | —    | —    | —    | 1 µL | —    | 1 µL | 18 µL |
| 13 | —    | —    | —    | —    | —    | —    | —    | 20 µL |
| 14 | 1 µL | —    | —    | 1 µL | —    | 1 µL | —    | 17 µL |
| 15 | 1 µL | —    | —    | —    | 1 µL | 1 µL | —    | 17 µL |
| 16 | 1 µL | —    | —    | 1 µL | —    | —    | 1 µL | 17 µL |
| 17 | 1 µL | —    | —    | —    | 1 µL | —    | 1 µL | 17 µL |
| 18 | —    | 1 µL | 1 µL | 1 µL | —    | 1 µL | —    | 16 µL |
| 19 | —    | 1 µL | 1 µL | —    | 1 µL | 1 µL | —    | 16 µL |
| 20 | —    | 1 µL | 1 µL | 1 µL | —    | —    | 1 µL | 16 µL |
| 21 | —    | 1 µL | 1 µL | —    | 1 µL | —    | 1 µL | 16 µL |

These 21 solutions, in triplicate, were heated to 92° C. for 11 minutes, then cooled approximately 1 hour at room temperature.

The following master mix was assembled and mixed.

| Component | Volume |
|---|---|
| Water | 1008 µL |
| 10X DNA Polymerase Buffer (Promega, M195A) | 280 µL |
| Klenow exo- (1 U/µL) (Promega, M218B) | 35 µL |
| 40 mM Sodium Pyrophosphate (Promega, C350B) | 35 µL |
| 10 µM ADP | 28 µL |
| NDPK (1 U/µL) | 14 µL |

After cooling at room temperature, 20 µL of the master mix were added to each of the 21 solutions, in triplicate, and they were heated at 37° C. for 15 minutes then placed on ice.

Five microliter samples of the solutions were placed in wells of a microtiter plate such that a 5 µL sample of each solution, in triplicate, was present within each plate and three such plates were prepared. The plates were placed into a Luminoskan® microtiter plate reading luminometer and this instrument was programmed to add 100 µL of L/L reagent (Promega, F120B) to each well and immediately read the light produced by the reaction in the well. The individual readings for each solution within each plate were averaged and these averages are given below.

| | | Relative Light Units | | | |
|---|---|---|---|---|---|
| Target | Probe(s) | Plate 1 | Plate 2 | Plate 3 | Average of Plates |
| none | FV5 | 5.08 | 2.81 | 2.99 | 3.63 |
| none | FV6 | 2.85 | 2.72 | 3.59 | 3.05 |
| none | CV2 | 2.91 | 2.73 | 2.60 | 2.75 |
| none | FV6 and CV2 | 2.56 | 2.75 | 2.68 | 2.66 |
| 9162 + 9165 | none | 2.67 | 2.59 | 2.50 | 2.59 |
| 9163 + 9166 | none | 2.72 | 2.59 | 2.51 | 2.61 |
| FV (1 + 2) | none | 2.80 | 2.52 | 2.55 | 2.62 |
| FV (3 + 4) | none | 2.75 | 2.41 | 2.51 | 2.56 |
| 9162 + 9165 + FV (1 + 2) | none | 2.57 | 2.53 | 2.34 | 2.48 |
| 9162 + 9165 + FV (3 + 4) | none | 2.54 | 2.46 | 2.40 | 2.47 |
| 9163 + 9166 + FV (1 + 2) | none | 2.40 | 2.39 | 2.45 | 2.41 |
| 9163 + 9166 + FV (3 + 4) | none | 2.48 | 2.35 | 2.42 | 2.42 |
| none | none | 2.53 | 2.34 | 2.22 | 2.36 |
| 9162 + 9165 + FV (1 + 2) | FV5 | 25.61 | 28.23 | 24.08 | 25.97 |
| 9162 + 9165 + FV (1 + 2) | FV6 and CV2 | 4.75 | 4.53 | 4.32 | 4.53 |
| 9163 + 9166 + FV (1 + 2) | FV5 | 25.36 | 27.72 | 28.98 | 27.35 |
| 9163 + 9166 + FV (1 + 2) | FV6 and CV2 | 44.69 | 41.14 | 45.29 | 43.71 |
| 9162 + 9165 + FV (3 + 4) | FV5 | 3.91 | 3.93 | 4.16 | 4.00 |
| 9162 + 9165 + FV (3 + 4) | FV6 and CV2 | 32.23 | 30.57 | 36.55 | 33.12 |
| 9163 + 9166 + FV (3 + 4) | FV5 | 3.54 | 3.64 | 3.52 | 3.57 |
| 9163 + 9166 + FV (3 + 4) | FV6 and CV2 | 58.61 | 59.14 | 71.77 | 63.17 |

The light values for the reactions were adjusted from the averaged plate values above by subtracting the average No-DNA signal value and target-alone averages and probe-alone values from the total light value measured for the various target and probe combinations. Reactions involving combinations of Target/Probe were further corrected by subtracting the appropriate adjusted probe-alone and target-alone values to yield a net light value. The resulting values are shown in the table below.

| Targets | FV5 Probes | Mutant Probes |
|---|---|---|
| WT CMV, WT Factor V | 22.22 | 1.76 |
| Mutant CMV, WT Factor V | 23.68 | 41.00 |
| WT CMV, Mutant Factor V | 0.27 | 30.35 |
| Mutant CMV, Mutant Factor V | (−.12) | 60.46 |

As in the previous example, a very distinctive signal pattern is seen with the various target combinations that were studied. This indicates that using multiple mutant probes in a multiplex manner can reduce the number of reactions needed to determine if a mutant site is present within the sample. These data show for this assay system that when the signal from the mutant probe reactions approaches or is greater than that seen with the corresponding wild type probe, the sample contains a target with a mutation in at least one of the sites. In addition, if the signal for the wild type (WT) probe is far lower than that for the multiplexed mutant probes, it is likely that at least the target interrogated by the wild type probe is in the mutant form.

```
FV1
5' CTAATCTGTAAGAGCAGATCCCTGGACAGGCGAGGAATACAGAGGGCAGCA   SEQ ID NO:25
GACATCGAAGAGCT 3'

FV2
5' AGCTCTTCGATGTCTGCTGCCCTCTGTATTCCTCGCCTGTCCAGGGATCTG   SEQ ID NO:26
CTCTTACAGATTAGAGCT 3'

FV3
5' CTAATCTGTAAGAGCAGATCCCTGGACAGGCAAGGAATACAGAGGGCAGCA   SEQ ID NO:27
GACATCGAAGAGCT 3'

FV4
5' AGCTCTTCGATGTCTGCTGCCCTCTGTATTCCTTGCCTGTCCAGGGATCTG   SEQ ID NO:28
CTCTTACAGATTAGAGCT 3'

FV5 5' CTGCTGCCCTCTGTATTCCTCG 3'                             SEQ ID NO:29

FV6 5' CTGCTGCCCTCTGTATTCCTTG 3'                             SEQ ID NO:30

9162 5' CGTGTATGCCACTTTGATATTACACCCATGAACGTG                  SEQ ID NO:31
CTCATCGACGTCAACCCGCACAACGAGCT 3'
```

-continued 9165 5' CGTTGTGCGGGTTCACGTCGATGAGCACGTTCATGG
GTGTAATATCAAAGTGGCATACACGAGCT 3'    SEQ ID NO:32

9163 5' CGTGTATGCCACTTTGATATTACACCCGTGAACGTG
CTCATCGACGTCAACCCGCACAACGAGCT 3'    SEQ ID NO:33

9166 5' CGTTGTGCGGGTTCACGTCGATGAGCACGTTCACGG
GTGTAATATCAAAGTGGCATACACGAGCT 3'    SEQ ID NO:34

CV2 5' CACTTTGATATTACACCCGTG 3'    SEQ ID NO:35

EXAMPLE 5
Detection of DNA Sequences in the Genome of Listeria Species

This example provides an assay for the presence of DNA sequences present in the genome of Listeria in a gene known as the iap gene. Oligonucleotides LM1 (SEQ ID NO:36) and LM2 (SEQ ID NO: 37) encode a segment of the iap gene and are exactly complementary to each other. Oligonucleotide probe LM3 (SEQ ID NO:38) was designed to hybridize exactly with a region of target LM2, and probe LM4 (SEQ ID NO:39) was designed to hybridize exactly to target LM1.

Oligonucleotides LM1–LM4 were dissolved in TE buffer (10 mM Tris, 1 mM EDTA, pH8.0) at a concentration of 500 µg/mL and then were diluted 25-fold in TE buffer to obtain solutions at a DNA concentration of 20 ng/µL. The following solutions were assembled.

| Solution | Oligonucleotides | 1X TE Buffer |
|---|---|---|
| #1 | LM1, 10 µL | 10 µL |
| #2 | LM2, 10 µL | 10 µL |
| #3 | LM3, 10 µL | 10 µL |
| #4 | LM4, 10 µL | 10 µL |
| #5 | LM1, 10 µL; LM3, 10 µL | — |
| #6 | LM1, 10 µL; LM4, 10 µL | — |
| #7 | LM2, 10 µL; LM3, 10 µL | — |
| #8 | LM2, 10 µL; LM4, 10 µL | — |
| #9 | — | 20 µL |

These solutions were heated at 95° C. for 3 minutes, then permitted to cool at room temperature for 15 minutes.

The following master mix was assembled.

| Component | Volume/reaction |
|---|---|
| Nanopure water (Promega AA399) | 12.75 µL |
| 10X DNA Polymerase Buffer (Promega M195A) | 2 µL |
| 40 mM Sodium Pyrophosphate (Promega C113) | 0.25 µL |
| ADP, 2 µM* | 1 µL |
| NDPK, 0.1 U/µL** | 1 µL |
| Klenow Exo- 10 U/µL (Promega M218) | 1 µL |

*Made by dissolving Sigma A5285 in water.
**Made by dissolving Sigma N0379 in water.

After solutions 1–9 had cooled, 2 µL samples of the solution were added to 18 µL of the master mix, in triplicate, the resulting solutions were mixed and incubated at 37° C. for 15 minutes. After this incubation, the tubes were placed on ice. Once all the incubations were on ice, 20 µL of the contents of the tubes were added to 100 µL of L/L reagent (Promega, F202A) and the light production of the resulting reaction was measured immediately using a Turner® TD 20/20 luminometer. The following data were obtained.

| | | | Relative light units | | | |
|---|---|---|---|---|---|---|
| Solution | Target | Probe | Reading 1 | Reading 2 | Reading 3 | Avg. |
| #1 | LM1 | — | 70.3 | 69.7 | 69.0 | 69.7 |
| #2 | LM2 | — | 39.6 | 40.8 | 45.3 | 41.9 |
| #3 | — | LM3 | 12.2 | 12.4 | 13.2 | 12.6 |
| #4 | — | LM4 | 16.9 | 17.3 | 17.4 | 17.2 |
| #5 | LM1 | LM3 | 57.7 | 76.5 | 72.7 | 69.0 |
| #6 | LM1 | LM4 | 1814 | 1815 | 1761 | 1797 |
| #7 | LM2 | LM3 | 56.72 | 61.1 | 57.59 | 58.5 |
| #8 | LM2 | LM4 | 67.5 | 72.4 | 79.3 | 73.1 |

These data show that LM4 produces a strong signal in the reaction with LM1 and thus can be used to detect this DNA sequence.

Oligonucleotides LM1 and LM2 were diluted to 2 ng/µL in 1×TE buffer. These materials were also used to create the following solutions in triplicate.

| Solution | LM1 | LM2 | LM3 | LM4 | 1X TE |
|---|---|---|---|---|---|
| #1 | 5 µL | 5 µL | — | — | 10 µL |
| #2 | 5 µL | 5 µL | 10 µL | — | — |
| #3 | 5 µL | 5 µL | — | 10 µL | — |

These solutions were heated to 95° C. for 10 minutes, then permitted to cool for 15 minutes at room temperature.

A master mix was made as described earlier in this example. After cooling at room temperature, 2 µL of each solution were added to an 18 µL sample of this master mix, and the resulting solutions were incubated at 37° C. for 15 minutes. After this incubation, 2 µL of the solution were added to 100 µL of L/L reagent (Promega, F202A) and the light produced was immediately read using a Turner® TD 20/20 luminometer.

The following results were obtained

| | Relative light units | | | | |
|---|---|---|---|---|---|
| Solution | Reading 1 | Reading 2 | Reading 3 | Avg. | NLU* |
| #1 | 754.4 | 727.8 | 752.7 | 745.0 | — |
| #2 | 857.4 | 801.0 | 852.3 | 836.9 | 91.9 |
| #3 | 1185 | 1211 | 1192 | 1196 | 451 |

*Net light units (NLU) were calculated by subtracting the no probe reaction average (#1) from the specific probe reaction values.

With both DNA template strands present, both probes provide signals above background.

The sequences used were as follows:

```
LM1
5' GAAGTAAAACAAACTACACAAGCAACTACACCTGCCCCTAAAG    SEQ ID NO:36
TAGCAGAAACGAAAGAAACTCCACTAG 3'

LM2
5' CTACTCGAGTTTCTTTCGTTTCTGCTACTTTAGGCGCAGGT      SEQ ID NO:37
GTAGTTGCTTGTGTAGTTTGTTTTACTTC 3'

LM3
5' GCAACTACACCTGCGCCTAAAGTAGCAGAA 3'              SEQ ID NO:38

LM4
5' TTCTGCTACTTTAGGCGCAGGTGTAGTTCG 3'              SEQ ID NO:39
```

EXAMPLE 6

Detection of Segments of the Listeria hyl Gene

In this example, a method is described for the detection of a segment of the hyl gene from *Listeria monocyotogenes*.

Oligonucleotides LM5 (SEQ ID NO:40) and LM6 (SEQ ID NO:41) anneal exactly to create a region of the hyl gene. LM7 (SEQ ID NO:42) and LM8 (SEQ ID NO:43) oligonucleotides are used as interrogation probes with LM7 completely complementary to LM6 and LM8 completely complementary to LM5.

Oligonucleotides LM5–8 were dissolved in 1×TE buffer at a concentration of 500 μg/mL and then were diluted 25 fold in TE buffer to obtain solutions at a DNA concentration of 20 μg/AL. The following solutions were assembled.

| Solution | Oligonucleotides | 1X TE Buffer |
|---|---|---|
| #1 | LM5, 10 μL | 10 μL |
| #2 | LM6, 10 μL | 10 μL |
| #3 | LM7, 10 μL | 10 μL |
| #4 | LM8, 10 μL | 10 μL |
| #5 | LM5, 10 μL; LM7, 10 μL | — |
| #6 | LM5, 10 μL; LM8, 10 μL | — |
| #7 | LM6, 10 μL; LM7, 10 μL | — |
| #8 | LM6, 10 μL; LM8, 10 μL | — |
| #9 | — | 20 μL |

These solutions were heated at 95° C. for 3 minutes, then permitted to cool at room temperature for 15 minutes.

The following master mix was assembled.

| | Volume/reaction |
|---|---|
| Nanopure water (Promega AA399) | 12.75 μL |
| 10X DNA Polymerase Buffer (Promega M195) | 2 μL |
| 40 mM Sodium Pyrophosphate (Promega C113) | 0.25 μL |
| ADP, 2 μM* | 1 μL |
| NDPK, 0.1 U/μL** | 1 μL |
| Klenow Exo- 10 U/μL (Promega M128) | 1 μL |

*Made by dissolving Sigma A5285 in water.
**Made by dissolving Sigma N0379 in water.

After solutions 1–9 had cooled, triplicate 2 μL samples of the solution were added to 18 μL master mix and the resulting solutions were mixed and incubated at 37° C. for 15 minutes. After this incubation, the tubes were placed on ice. Once all the incubations were on ice, 20 μL of the contents of the tubes were added to 100 μL of L/L reagent (Promega F202A) and the light production of the resulting reaction was measured immediately using a Turner® TD 20/20 luminometer. The following data were obtained.

| Solution | Relative light units | | | | Net Ave |
|---|---|---|---|---|---|
| | Reading 1 | Reading 2 | Reading 3 | Avg. | |
| #1 | 28.53 | 29.62 | 30.0 | 29.41 | — |
| #2 | 81.30 | 75.12 | 74.68 | 77.03 | — |
| #3 | 19.88 | 13.12 | 12.80 | 15.26 | — |
| #4 | 1326 | 1273 | 1216 | 1271 | — |
| #5 | 37.24 | 36.40 | 36.77 | 36.80 | 3.78 |
| #6 | 2582 | 2336 | 2169 | 2362 | 1089 |
| #7 | 90.74 | 90.83 | 90.64 | 90.64 | 9.97 |
| #8 | 1596 | 1671 | 1787 | 1684 | 347.6 |
| #9 | 12.33 | 11.16 | 11.48 | 11.66 | — |

The above data indicate that at least oligonucleotide LM8 can be used to detect the target gene sequence represented in LM6.

Oligonucleotides LM5 and LM6 were diluted to 2 ng/μL in 1×TE buffer (10 mM Tris, 1 mM EDTA, pH 8.0). These materials were also used to create the following solutions in triplicate.

| Solution | LM5 | LM6 | LM7 | LM8 | 1X TE |
|---|---|---|---|---|---|
| #1 | 5 μL | 5 μL | — | — | 10 μL |
| #2 | 5 μL | 5 μL | 10 μL | — | — |
| #3 | 5 μL | 5 μL | — | 10 μL | — |

These solutions were heated to 95° C. for 10 minutes, and then cooled for 15 minutes at room temperature.

Then 2 μL of the solutions were added to triplicate 18 μL samples of the master mix and then the resulting solutions were incubated at 37° C. for 15 minutes. After this incubation, 2 μL of the solution were added to 100 μL of L/L reagent (Promega, F202A) and the light produced was immediately read using a Turner® TD 20/20 luminometer. The following results were obtained.

| Solution | Relative light units | | | | NLU* |
|---|---|---|---|---|---|
| | Reading 1 | Reading 2 | Reading 3 | Avg. | |
| #1 | 442.5 | 431.8 | 432.2 | 435.5 | — |
| #2 | 576.1 | 544.6 | 580.1 | 566.9 | 115.7 |
| #3 | 1779 | 1837 | 1908 | 1841 | 1405 |

-continued

| Relative light units | | | | | |
|---|---|---|---|---|---|
| Solution | Reading 1 | Reading 2 | Reading 3 | Avg. | NLU* |

*Net light units (NLU) determined by subtraction of probe alone values (see table above) and solution #1 values from the average light units measured.

These results demonstrate that specific detection of the segment of the hyl gene sequence from Listeria can be performed using the components described above. Because this gene sequence is specific for Listeria, this indicates that the components can be used for specific detection of Listeria DNA.

LM5
5' CATCGACGGCAACCTCGGAGACTTACGAGATATTTTGAAAAAA   SEQ ID NO:40
GGCGCTACTTTTAATCGAGAAACACCA 3'

LM6
5' TGGTGTTTCTCGATTAAAAGTAGCGCCTTTTTTCAAAATATCT   SEQ ID NO:41
CGTAAGTCTCCGAGGTTGCCGTCGATG 3'

LM7 5' CTCGGAGACTTACGAGATATTTTGAAAAAA 3'          SEQ ID NO:42

LM8 5' TTTTTTCAAAATATCTCGTAAGTCTCCGAG 3'          SEQ ID NO:43

EXAMPLE 7

Detection of a DNA Sequence from Salmonella

In this example, a method for detection of a gene sequence from Salmonella is provided.

Oligonucleotides ST1 (SEQ ID NO:44), ST2 (SEQ ID NO:45), ST3 (SEQ ID NO:46), and ST4 (SEQ ID NO:47) were dissolved in 1×TE buffer to 500 µg/µL and then were diluted 25 fold in 1× TE buffer to obtain solutions at a DNA concentration of 20 ng/µL. The following solutions were prepared.

| Solution | Oligonucleotides | 1X TE Buffer |
|---|---|---|
| #1 | ST1, 10 µL | 10 µL |
| #2 | ST2, 10 µL | 10 µL |
| #3 | ST3, 10 µL | 10 µL |
| #4 | ST4, 10 µL | 10 µL |
| #5 | ST1, 10 µL; ST3, 10 µL | — |
| #6 | ST1, 10 µL; ST4, 10 µL | — |
| #7 | ST2, 10 µL; ST3, 10 µL | — |
| #8 | ST2, 10 µL; ST4, 10 µL | — |
| #9 | — | 20 µL |

These solutions were heated at 95° C. for 3 minutes, then permitted to cool at room temperature for 15 minutes.

The following master mix was assembled.

| Component | Volume/reaction |
|---|---|
| Nanopure water (Promega AA399) | 12.75 µL |
| 10X DNA Polymerase Buffer (Promega M195) | 2 µL |
| 40 mM Sodium Pyrophosphate (Promega C113) | 0.25 µL |
| ADP, 2 µM* | 1 µL |
| NDPK, 0.1 U/µL** | 1 µL |
| Klenow Exo- 10 U/µL (Promega M128) | 1 µL |

*Made by dissolving Sigma A5285 in water.
**Made by dissolving Sigma N0379 in water.

After solutions 1–9 had cooled, three 2 µL samples of the solution were added to 18 µL of the master mix and the resulting solution was mixed and incubated at 37° C. for 15 minutes. After this incubation, the tubes were placed on ice. Once all the incubations were on ice, 20 µL of the contents of the tubes were added to 100 µL of L/L reagent, and the light production of the resulting reaction was measured immediately using a Turner® TD 20/20 luminometer. The following data were obtained.

| | Relative light units | | | | |
|---|---|---|---|---|---|
| Solution | Reading 1 | Reading 2 | Reading 3 | Avg. | Net Avg. |
| #1 | 18.28 | 18.27 | 17.97 | 18.17 | — |
| #2 | 231.9 | 211.4 | 226.3 | 223.2 | — |
| #3 | 11.58 | 12.56 | 11.34 | 11.83 | — |
| #4 | 14.00 | 14.48 | 14.88 | 14.45 | — |
| #5 | 21.31 | 21.20 | 19.44 | 20.65 | 2.18 |
| #6 | 3003 | 2943 | 2918 | 2955 | 2933 |
| #7 | 2780 | 2782 | 2641 | 2734 | 2510 |
| #8 | 256.4 | 269.9 | 271.1 | 265.8 | 39.67 |
| #9 | 11.63 | 11.39 | 11.56 | 11.52 | — |

These data indicate that both oligonucleotide probes ST3 and ST4 can give a very strong specific light signals with single strand target DNA sequence from Salmonella.

Oligonucleotides ST1 and ST2 were diluted to 2 ng/µL in 1×TE buffer (10 mM Tris, 1 mM EDTA, pH 8.0). These materials were also used to create the following solutions in triplicate.

| Solution | ST1 | ST2 | ST3 | ST4 | 1X TE |
|---|---|---|---|---|---|
| #1 | 5 µL | 5 µL | — | — | 10 µL |
| #2 | 5 µL | 5 µL | 10 µL | — | — |
| #3 | 5 µL | 5 µL | — | 10 µL | — |

These solutions were heated to 95° C. for 10 minutes, then permitted to cool for 15 minutes at room temperature.

A master mix was made as described earlier in this example. After cooling at room temperature, 2 µL of each solution were added to an 18 µL sample of this master mix, and then the resulting solutions were incubated at 37° C. for 15 minutes. After this incubation, 2 µl of the solution were added to 100 µL of L/L reagent and the light produced was immediately read using a Turner® TD 20/20 luminometer.

The following results were obtained.

|  | Relative light units | | | | |
| --- | --- | --- | --- | --- | --- |
| Solution | Reading 1 | Reading 2 | Reading 3 | Avg. | NLU * |
| #1 | 692.5 | 728.9 | 678.3 | 699.9 | — |
| #2 | 2448 | 2389 | 2311 | 2382 | 1683 |
| #3 | 1742 | 1778 | 1738 | 1752 | 1053 |

* Net light units (NLU) were determined by subtraction of probe alone values (see table above) and solution #1 values from the average light units measured.

These data demonstrate that oligonucleotide probes ST3 and ST4 provide specific detection of the DNA target sequence from Salmonella even if both DNA strands are present.

Sequences Used were as Follows:

```
ST1
5' TTTAATTCCGGAGCCTGTGTAATGAAAGAAATCACCGTCACTG      SEQ ID NO:44
AACCTGCCTTTGTCACC 3'

ST2
5' GGTGACAAAGGCAGGTTCAGTGACGGTGATTTCTTTCATTACACAGGCT SEQ ID NO:45
CCGGAATTAAA 3'

ST3
5' TGTGTAATGAAGAAATCACCGTCACTGAA 3'                SEQ ID NO:46

ST4 5' TTCAGTGACGGTGATTTCTTTCATTACACA 3'            SEQ ID NO:47
```

EXAMPLE 8

Detection of Poly(A) mRNA Using Reverse Transcriptase and NDPK

This example demonstrates a method for the detection of mRNA, particularly poly(A) MRNA. In this method, an oligo(dT) DNA probe (Promega, C110A) is hybridized to the target MRNA and the hybridized probe:target is pyrophosphorylated using a reverse transcriptase and pyrophosphate. As the pyrophosphorylation occurs, the deoxynucleoside triphosphates are used to convert ADP to ATP using the enzyme NDPK. The ATP of the final solution is then measured using luciferase.

The reactions were assembled as presented in the table below, in which all volumes are in microliters ($\mu L$). The reaction components were: Buffer, 5× MMLV-RT Buffer (Promega, M531A); mRNA, Globin MRNA (Gibco BRL cat# 18103–028 dissolved in $H_2O$); Poly(dT), 0.2 $\mu M$ oligo (dT) (50); NaPPi, 20 mM Sodium Pyrophosphate, (Promega C113A in deionized water); ADP, 10 mM ADP (Sigma A-5285); NDPK, 1 U/$\mu L$, (Sigma N-0379); MMLV-RT, (Promega Part #M531A) 200 U/$\mu L$; and 200 U/$\mu L$ Superscript II (Gibco BRL cat# 18064–014).

These reactions were incubated at 37° C. for 30 minutes and 2 $\mu L$ of the reactions were added to 300 $\mu L$ of L/L reagent (Promega, F202A). The light production of the reactions was immediately measured using a Turner® TD-20e luminometer. The data from these studies are presented in the data table below.

| Rx | Buffer (μL) | mRNA (μL) | Poly (dT) (μL) | NaPPi (μL) | ADP (μL) | NDPK (μL) | MMLV-RT (μL) | Super-Scrip II (μL) | H₂O μL |
|---|---|---|---|---|---|---|---|---|---|
| 1 | 4 | 1 of 50 ng/μl | 1 | 1 | 2 | 1 | 1 | — | 9 |
| 2 | 4 | 1 of 10 ng/μl | 1 | 1 | 2 | 1 | 1 | — | 9 |
| 3 | 4 | 1 of 2 ng/μl | 1 | 1 | 2 | 1 | 1 | — | 9 |
| 4 | 4 | 1 of 400 pg/μl | 1 | 1 | 2 | 1 | 1 | — | 9 |
| 5 | 4 | 1 of 80 pg/μl | 1 | 1 | 2 | 1 | 1 | — | 9 |
| 6 | 4 | — | 1 | 1 | 2 | 1 | 1 | — | 9 |
| 7 | 4 | 1 of 50 ng/μl | 1 | 1 | 2 | 1 | — | 1 | 9 |
| 8 | 4 | 1 of 10 ng/μl | 1 | 1 | 2 | 1 | — | 1 | 9 |
| 9 | 4 | 1 of 2 ng/μl | 1 | 1 | 2 | 1 | — | 1 | 9 |
| 10 | 4 | 1 of 400 pg/μl | 1 | 1 | 2 | 1 | — | 1 | 9 |
| 11 | 4 | 1 of 80 pg/μl | 1 | 1 | 2 | 1 | — | 1 | 9 |
| 12 | 4 | — | 1 | 1 | 2 | 1 | — | 1 | 9 |

DATA TABLE

| Rx | mRNA | Light Units |
|---|---|---|
| 1 | 5 ng | 647.2 |
| 2 | 1 ng | 425.4 |
| 3 | 0.2 ng | 113.9 |
| 4 | 40 pg | 43.56 |
| 5 | 8 pg | 23.66 |
| 6 | — | 21.52 |
| 7 | 5 ng | 648.5 |
| 8 | 1 ng | 500.4 |
| 9 | 0.2 ng | 144.2 |
| 10 | 40 pg | 45.85 |
| 11 | 8 pg | 28.17 |
| 12 | — | 19.71 |

EXAMPLE 9

Detection of a Specific Message by Use of a DNA Probe Exactly Matching the Message Sequence and Lack of a Signal when the DNA Probe is Mismatched at Its 3' End In this Example, a luciferase light signal is generated from pyrophosphorylation of a DNA probe that complements the sequence of a target RNA species. In addition, evidence is presented to demonstrate that this signal is not generated if the 3'-terminal base of the probe does not complement the RNA base in the target sequence. These data demonstrate that probe pyrophosphorylation can be used to detect the presence of specific target RNA sequences and that mutations at specific bases in the target sequence can be detected by use of probes that should match the base but that do not give a signal with the message.

A master mix was assembled that contained:

| | |
|---|---|
| Capped Kanamycin RNA (0.62 mg/mL) | 1.25 μL |
| 5X MMLV Reaction Buffer | 50 μL |
| 40 mM Sodium Pyrophosphate | 2.5 μL |
| 10 μM ADP | 2.5 μL |
| NDPK (1 U/μL) | 5 μL |
| MMLV-RT (200 U/μL) (Promega, M1701) | 12.5 μL |
| Nanopure water | 163.75 μL |

Probes one through four were dissolved at a concentration of 1 mg/ml in 1×TE buffer.

Probe 1 (SEQ ID NO:48) was designed to exactly complement a segment of the coding region of the Kanamycin RNA. Probe 2 (SEQ ID NO:49), Probe 3 (SEQ ID NO:50)and Probe 4 (SEQ ID NO:51) were designed to match the sequence of Probe 1 except that the 3'-terminal base of the probe was altered to one of each of the other three DNA bases at this position.

Nineteen microliters of the master reaction mix were placed in 10 labeled 0.5 mL microfuge tubes and the following additions were made to the tubes: Tubes 1 and 2, 1 μL 1×TE buffer; Tubes 3 and 4, 1 μL Probe 1; Tubes 5 and 6, 1 μL Probe 2; Tubes 7 and 8, 1 μL Probe 3; and Tubes 9 and 10, 1 μL Probe 4. The 10 0.5 mL microfuge tubes were incubated at 37° C. for 20 minutes to hybridize and form treated samples. Thereafter, 2 μL of the contents of the tubes were added to 100 μL L/L reagent (Promega, F202A) and the light output of the reagent was measured using a luminometer. The following data were collected.

| Solution | Relative Light Units |
|---|---|
| 1 | 3.989 |
| 2 | 3.458 |

| Solution | Relative Light Units |
|---|---|
| 3 | 49.95 |
| 4 | 52.24 |
| 5 | 3.779 |
| 6 | 3.727 |
| 7 | 4.394 |
| 8 | 4.163 |
| 9 | 7.879 |
| 10 | 7.811 |

These data show that MMLV-RT is able to pyrophosphorylate a DNA probe that hybridized to a target RNA sequence and that the free nucleoside triphosphates that are formed are converted to ATP equivalents that can be measured using luciferase. In addition, the data show that this signal is either absent or much weaker (solutions 1,2,5,6,7,8,9,10) when a probe with a 3' mismatch to the expected base is used in the reaction (compare to tubes 3 and 4).

| Probe 1 | SEQ ID NO: 48 | 5'GCAACGCTACCTTTGCCATGTTTC 3' |
| Probe 2 | SEQ ID NO: 49 | 5'GCAACGCTACCTTTGCCATGTTTG 3' |
| Probe 3 | SEQ ID NO: 50 | 5'GCAACGCTACCTTTGCCATGTTTA 3' |
| Probe 4 | SEQ ID NO: 51 | 5'GCAACGCTACCTTTGCCATGTTTT 3' |

EXAMPLE 10

Detection of a Specific RNA Globin mRNA

In this Example, the light signal produced from pyrophosphorylation of DNA probes that are complementary to two regions of globin MRNA is compared to the signals from two DNA probes that are the exact sequence of the same regions. Once again, probes that totally complement the target RNA are shown to give a signal above background, whereas those that do not complement the target RNA give little or no signal.

Probe 5 (SEQ ID NO:52), Probe 6 (SEQ ID NO:53), Probe 7 (SEQ ID NO:54), and Probe 8 (SEQ ID NO:55) were diluted to a concentration of 0.5 mg/mL in 1×TE buffer (10 mM Tris, 1 mM EDTA). Purified globin mRNA (Gibco BRL, 18103–028) as target was dissolved in 1×TE buffer (10 mM Tris, 1 mM EDTA) to a concentration of 20 ng/µL.

Hybridization solutions were assembled as follows:

| Solution 1: | 10 µL Probe 5 and 10 µL Globin mRNA |
| Solution 2: | 10 µL Probe 6 and 10 µL Globin mRNA |
| Solution 3: | 10 µL Probe 7 and 10 µL Globin mRNA |
| Solution 4: | 10 µL Probe 8 and 10 µL Globin mRNA |
| Solution 5: | 10 µL Probe 5 and 10 µL 1X TE buffer |
| Solution 6: | 10 µL Probe 6 and 10 µL 1X TE buffer |
| Solution 7: | 10 µL Probe 7 and 10 µL 1X TE buffer |
| Solution 8: | 10 µL Probe 8 and 10 µL 1X TE buffer |
| Solution 9: | 10 µL 1X TE buffer, 10 µL Globin mRNA |

These solutions were assembled in 0.5 mL tubes, heated to 50° C. for 15 minutes and permitted to cool to room temperature for 15 minutes.

The following master reaction mixture was assembled:

| Nanopure water | 346.5 µL |
| MMLV-RT 5X Reaction Buffer (Promega M195A) | 132 µL |
| Sodium pyrophosphate (Promega M531) | 16.5 µL |
| NDPK (1 U/µL) | 33 µL |
| ADP (2 µM) | 33 µL |
| MMLV-RT (adjusted to 100 U/µL) (Promega, M1701) | 33 µL |

The solution above was mixed and 18 µL placed into 27 tubes. Three two-microliter samples of each of the hybridization solutions above were added in three of the tubes containing the master reaction mix and the tubes were then incubated at 37° C. for 15 minutes and permitted to cool to room temperature to hybridize and form treated samples. The contents of the tubes were then added to 100 µL of L/L reagent and the light production of the resulting reaction was measured using a luminometer (Turner® TD20/20). The following results were obtained:

| Hybridization Solution | Light Values | | | Average |
|---|---|---|---|---|
| Probe 5 + RNA | 6.555 | 6.303 | 6.187 | 6.348 |
| Probe 5 + TE Buffer | 6.335 | 5.923 | 6.046 | 6.101 |
| Probe 6 + RNA | 137.8 | 128.5 | 169.2 | 145.2 |
| Probe 6 + TE Buffer | 10.24 | 9.429 | 9.858 | 9.842 |
| Probe 7 + RNA | 6.235 | 6.763 | 6.375 | 6.458 |
| Probe 7 + TE Buffer | 6.436 | 6.545 | 6.138 | 6.388 |
| Probe 8 + RNA | 90.34 | 95.42 | 54.7 | 80.15 |
| Probe 8 + TE Buffer | 10.21 | 12.55 | 9.372 | 10.71 |
| TE Buffer + RNA | 5.579 | 6.509 | 6.388 | 6.159 |

These data show that a strong light signal is seen when the reaction mixes containing probes 6 or 8 and target RNA were added to the L/L reagent but little signal was seen when the probes were incubated without target RNA, or when the target RNA was incubated without these probes. In addition, probes 5 and 7 provided very low signals in the presence or absence of added target RNA. Probes 6 and 8 were designed to complement two different regions in the coding region of globin mRNA. Probes 5 and 7 were made to exactly mimic the sequence of these same target RNA regions. Thus, these data provide a second example of how the pyrophosphorylation of a probe can be used to detect a specific RNA.

| Probe 5 | SEQ ID NO:52 | 5'ATGGTGCATCTGTCCAGTGAGGAGAAGTCT3' |
| Probe 6 | SEQ ID NO:53 | 5'AGACTTCTCCTCACTGGACAGATGCACCAT3' |
| Probe 7 | SEQ ID NO:54 | 5'GCTGCTGGTTGTCTACCCATGGACCC 3' |
| Probe 8 | SEQ ID NO:55 | 5'GGGTCCATGGGTAGACAACCAGCAGC 3' |

EXAMPLE 11

Specific Detection Of RNA Comparison Of Signals From RNA Species That Match Probe Sequences To Those From Random Target RNA To detect specific RNA using the pyrophosphorylation reaction described in the previous Example it is necessary that the probes not give a strong signal with target RNA species that do not contain the sequence to be detected. In this Example, the strength of the signal provided by use of probes designed to detect globin mRNA is compared to the signal seen when these probes are used in reactions with yeast total RNA as target.

Probe 6 (SEQ ID NO:53), Probe 8 (SEQ ID NO:55) and oligo(dT) (Promega, Cl1OA) were diluted to a concentration of 0.5 mg/mL in 1×TE buffer. Globin mRNA (Gibco BRL, 18103–028) was dissolved in 1×TE buffer to a concentration of 20 ng/μL. Yeast RNA (Sigma Chemical Co. R3629) was dissolved in 1×TE buffer to a concentration of 20 ng/μL.

Hybridization solutions were assembled as follows:

10 μL oligo(dT) and 10 μl Globin mRNA
10 μL Probe 6 and 10 μL Globin mRNA
10 μL Probe 8 and 10 μL Globin mRNA
10 μL 1X TE buffer and 10 μL Globin mRNA
10 μL oligo(dT) and 10 μL Yeast RNA
10 μL Probe 6 and 10 μL Yeast RNA
10 μL Probe 8 and 10 μL Yeast RNA
10 μL 1X TE buffer and 10 μL Yeast RNA These solutions were assembled in 0.5 μL tubes, heated to 50° C. for 15 minutes, and then permitted to cool to room temperature for 15 minutes to hybridize and form treated samples.

The following master reaction mixture was assembled:

| | |
|---|---|
| Nanopure water | 346.5 μL |
| MMLV-RT 5X Reaction Buffer | 132 μL |
| Sodium pyrophosphate (Promega M531) | 16.5 μL |
| NDPK (1 U/μL) | 33 μL |
| ADP (2 μM) | 33 μL |
| MMLV-RT (adjusted to 100 U/μL) | 33 μL |

The solution above was mixed, and 18 μL were placed into 24 tubes. Three two-microliter samples of each of the hybridization solutions above were added in three of the tubes containing the master reaction mix and the tubes were incubated at 37° C. for 15 minutes. The contents of the tubes were then added to 100 μL of L/L reagent and the light production of the resulting reaction was measured using a luminometer (Turner® TD20/20).

The following data were obtained:

| Hybridization Solution | | | | | |
|---|---|---|---|---|---|
| RNA | Probe | Light Units | | | Average |
| Globin RNA | Oligo(dT) | 614.1 | 680.6 | 657.7 | 650.8 |
| Globin RNA | Probe 6 | 93.29 | 92.19 | 92.9 | 92.79 |
| Globin RNA | Probe 8 | 77.13 | 61.69 | 69.89 | 69.57 |
| Globin RNA | none | 4.11 | 4.07 | 3.92 | 4.03 |
| Yeast RNA | Oligo(dT) | 2.05 | 2.13 | 2.22 | 2.13 |
| Yeast RNA | Probe 6 | 4.25 | 4.15 | 4.46 | 4.28 |
| Yeast RNA | Probe 8 | 6.21 | 4.83 | 4.37 | 5.14 |
| Yeast RNA | none | 1.97 | 1.53 | 1.97 | 1.81 |

These data show that much higher signals result when the probes are incubated with target globin MRNA than when the probes are incubated with yeast total RNA as target. Because the yeast RNA should not contain the globin sequence, the lack of a high signal is expected. The fact that oligo(dT) also provides a low signal suggests that most of the target RNA in this preparation is not MRNA, but other forms of RNA.

| | | |
|---|---|---|
| Probe 6 | SEQ ID NO:53 | 5'AGACTTCTCCTCACTGGACAGATGCACCAT3' |
| Probe 8 | SEQ ID NO:55 | 5'GGGTCCATGGGTAGACAACCAGCAGC3' |

EXAMPLE 12
Specific Detection of RNA Comparison of Signals from RNA Species that Match Probe Sequences in Reactions With and Without Added Extraneous Target RNA For the pyrophosphorylation reaction described in Example 10 to be used to detect specific target sequences, another requirement of the system is that the probes should give a very similar signal in the presence and absence of extraneous RNA. In this Example, the strength of the signal of probes designed to detect target globin MRNA in the presence of a large amount of yeast RNA is compared to the signal seen in the absence of added yeast RNA. Hybridization solutions containing various levels of yeast RNA, Probe 6 (SEQ ID NO:53) or Probe 8 (SEQ ID NO:55) and target globin mRNA (Gibco BRL, 18103–028) were assembled by adding 5 μL 500 ng/μL either probe 6 or probe 8 to 5μL 40 ng/μL of target globin mRNA and 10 μL yeast RNA (Sigma Chemical Co. R3629) in 1×TE buffer (10 mM Tris, 1 mM EDTA) to produce solutions containing total amounts of yeast RNA of 0, 2, 20, 200, 400, and 800 ng. The solutions were heated at 50° C. for 15 minutes and then permitted to cool to room temperature for 15.

Reaction master mix was assembled as in Example 10 above and 18 μL of the mix were placed in 18 tubes. After cooling 15 minutes, 2 μL of the various hybridization solutions containing probe 6 were added to the tubes and the tubes were placed in a 37° C. heating block.

After 15 minutes of incubation of the hybridization mixture with the reaction master mix, 20 μL of the solution were added to 100 μL of L/L reagent (Promega, F202A) and the light output of the resulting reaction was measured using a Turner® TD-20/20 luminometer.

After the probe 6 data were collected, an identical set of reactions was performed using the hybridization solutions containing probe 8.

The following data were obtained:

| Yeast RNA | relative light units | | | Average |
|---|---|---|---|---|
| | Probe 6 Reactions | | | |
| None | 96 | 109 | 111 | 105.3 |
| 2 ng | 98.4 | 85.0 | 118.5 | 100.7 |
| 20 ng | 117.9 | 110.9 | 82.7 | 103.65 |
| 200 ng | 56.4 | 110.1 | 93.2 | 86.6 |
| 400 ng | 115.7 | 110.7 | 124.6 | 117 |
| 800 ng | 127.6 | 128.7 | 143.1 | 133.1 |
| | Probe 8 Reactions | | | |
| None | 105.8 | 97.0 | 82.3 | 95.0 |
| 2 ng | 84.5 | 84.6 | 93.7 | 87.6 |
| 20 ng | 99.6 | 111.7 | 104.9 | 105.4 |
| 200 ng | 83.6 | 75.9 | 95.6 | 85.1 |
| 400 ng | 94.7 | 97.2 | 81.9 | 91.2 |
| 800 ng | 50.7 | 89.0 | 82.1 | 73.9 |

These data indicate that addition of very large amounts of yeast RNA to the hybridization reaction does not greatly lower the signal from hybridized probes for specific target RNA species.

| Probe 6 | SEQ ID NO:53 | 5'AGACTTCTCCTCACTGGACAGATGCACC AT3' |
|---|---|---|
| Probe 8 | SEQ ID NO:55 | 5'GGGTCCATGGGTAGACAACCAGCAGC3' |

EXAMPLE 13
Mutation Detection Using Probes to Target Glob in mRNA #1: Detection of Mismatched Bases at the 3' End of the Probe Sequence The pyrophosphorylation reactions for target RNA detection, such as shown with Probe 6 and Probe 8, require that the probe be pyrophosphorylated by an added polymerase. If the 3'-terminus of the probe contains a base that does not match the RNA, it might not be a substrate for the pyrophosphorylation reaction. If this is the case, addition of a probe that detects the presence of a target RNA species to reactions containing a sample that contains the target RNA can indicate that the RNA is altered in sequence at the base that matches the 3'-end of the probe. Substitution of a new probe that contains the complementary base to the altered target RNA sequence then provides the signal. In this way, the pyrophosphorylation reaction can be used to interrogate the sequence of RNA species in the region matching the 3'-end of the probe.

To test this concept, probes were designed that were identical in sequence to Probe 6 (SEQ ID NO:53) and Probe 8 (SEQ ID NO:55), with the exception that the 3'-terminal base of each of these probes was varied to one of each of the other three DNA bases. This Example demonstrates the use of such a probe set for confirming that the target RNA base at the 3'-end of the probe matches the expected base by providing a light signal after the pyrophosphorylation reaction but that the other probes with altered 3' bases do not provide this signal.

The probes 6 ml (SEQ ID NO:56), 6m2 (SEQ ID NO:57) and 6m3 (SEQ ID NO:58) were dissolved in 1× TE buffer to a concentration of 500 ng/µL.

Hybridization solutions containing probe 6, 6m1, 6m2 or probe 6m3, or probe 8, 8 ml (SEQ ID NO:59), 8m2 (SEQ ID NO:60) or probe 8m3 (SEQ ID NO:61) were assembled by adding 5 µL of 20 ng/µL of target globin mRNA (Gibco BRL) or Tris buffer. The solutions were heated at 50° C. for 15 minutes, then permitted to cool to room temperature for 15 minutes to hybridize and form treated samples.

Reaction master mix was assembled as in Example 10 above, and 18 µL of the mix were placed in 18 tubes. After cooling for 15 minutes, 2 µL of the various hybridization solutions containing probe 6, and probe 6 ml through probe 6m3 were added to the tubes and the tubes were placed in a 37° C. heating block.

After a 15 minute incubation at 37° C. of the hybridization mixes with the reaction master mix, 20 µL the reaction were added to 100 µL L/L reagent (Promega, F202A) and the light output of the reaction measured immediately in a Turner® TD20/20 luminometer. The following data were obtained.

| Probe | RNA (+/−) | Light Units | | | Average |
|---|---|---|---|---|---|
| Probe 6 | + | 157.3 | 150 | 130.5 | 149.9 |
| Probe 6 | − | 16.2 | 13.3 | 11.1 | 13.6 |
| Probe 6m1 | + | 7.3 | 7.4 | 7.5 | 7.4 |
| Probe 6m1 | − | 6.8 | 6.7 | 6.7 | 6.7 |
| Probe 6m2 | + | 7.9 | 8.8 | 9.2 | 8.7 |
| Probe 6m2 | − | 7.9 | 7.3 | 6.5 | 7.2 |
| Probe 6m3 | + | 6.9 | 7.4 | 7.4 | 7.2 |
| Probe 6m3 | − | 6.1 | 6.8 | 7.2 | 6.7 |
| (no probe) | + | 7.0 | 6.3 | 7.4 | 6.9 |

Reaction master mix was again assembled as in Example 10 above and 18 µL of the mix were placed in 18 tubes. After cooling for 15 minutes, 2 µL of the various hybridization solutions containing probes 8, and probes 8 ml through probe 8m3 were added to the 15 tubes and the tubes were placed in a 37° C. heating block.

After a 15 minutes incubation at 37° C. of the hybridization mixes in the reaction master mix, 20 µL of the reaction were added to 100 µL L/L reagent (Promega, F202A) and the light output of the reaction measured immediately in a Turner® TD20/20 luminometer. The following data were obtained.

| Probe | RNA (+/−) | Light Units | | | Average |
|---|---|---|---|---|---|
| Probe 8 | + | 29.1 | 28.7 | 25.2 | 27.66 |
| Probe 8 | − | 5.0 | 4.3 | 5.9 | 5.1 |
| Probe 8m1 | + | 2.5 | 2.5 | 2.5 | 2.5 |
| Probe 8m1 | − | 2.3 | 2.2 | 2.4 | 2.3 |
| Probe 8m2 | + | 7.4 | 7.1 | 5.9 | 6.8 |
| Probe 8m2 | − | 2.0 | 2.1 | 2.1 | 2.1 |
| Probe 8m3 | + | 3.4 | 2.5 | 2.4 | 2.8 |
| Probe 8m3 | − | 2.1 | 2.1 | 1.9 | 2.0 |
| (no probe) | + | 2.3 | 2.2 | 2.1 | 2.2 |

These data again demonstrate that if the 3' base of a probe is not able to hybridize to the corresponding base on an RNA target, it will not provide a strong light signal after the pyrophosphorylation reaction as described above. These data also demonstrate that this method can be used to determine if the terminal base of a probe does complement the expected base in the target RNA, and thus can be used to confirm that the target RNA base at the site of pyrophosphorylation initiation is as expected.

| Probe 6 | SEQ ID NO: 53 | 5'AGACTTCTCCTCACTGGACAGATGCACC AT3' |
|---|---|---|
| Probe 8 | SEQ ID NO: 55 | 5'GGGTCCATGGGTAGACAACCAGCAGC3' |
| Probe 6m1 | SEQ ID NO: 56 | 5'AGACTTCTCCTCACTGGACAGATGCACC AA 3' |
| Probe 6m2 | SEQ ID NO: 57 | 5'AGACTTCTCCTCACTGGACAGATGCACC AG 3' |
| Probe 6m3 | SEQ ID NO: 58 | 5'AGACTTCTCCTCACTGGACAGATGCACC AC 3' |
| Probe 8m1 | SEQ ID NO: 59 | 5'GGGTCCATGGGTAGACAACCAGCAGA3' |
| Probe 8m2 | SEQ ID NO: 60 | 5'GGGTCCATGGGTAGACAACCAGCAGG3' |
| Probe 8m3 | SEQ ID NO: 61 | 5'GGGTCCATGGGTAGACAACCAGCAGT3' |

EXAMPLE 14
Mutation Detection Using Probes to Target Globin mRNA #2: Detection of Mismatched Bases Penultimate to the 3' End of the Probe Sequence Because Example 13 shows that a mismatch at the 3' end of a probe can be detected by the absence of a light signal under conditions permitting pyrophosphorylation, a series of probes corresponding to Probe 6 (SEQ ID NO:53) and Probe 8 (SEQ ID NO:55) were made that had altered bases at the penultimate base from the 3' end of the probe sequence.

The probes 6m4, (SEQ ID NO:62), 6m5 (SEQ ID NO:63) and 6m6 (SEQ ID NO:64) were dissolved in 1× TE buffer (10 mM Tris, 1 mM EDTA) to a concentration of 500 ng/µL. Hybridization solutions containing probe 6 and probe 6m4 through probe 6m6 or probe 8 and probes 8m4 (SEQ ID NO:65), 8m5 (SEQ ID NO:66), and 8m6 (SEQ ID NO:67), were assembled by adding 5 µL of 20 ng/µL of globin mRNA (Gibco BRL cat# 18103-028) or Tris-Cl buffer. The solutions were heated at 50° C. for 15 minutes and then permitted to cool to room temperature for 15 minutes to hybridize and form a treated sample.

Reaction master mix was assembled as in Example 10 above and 18 µL of the mix were placed in 18 tubes. After cooling for 15 minutes, 2 µL of the various hybridization solutions containing probe 6 through probe 6m6 were added to the tubes and the tubes were placed in a 37° C. heating block.

After a 15 minutes incubation at 37° C. of the hybridization mixes in the reaction master mix, 20 µL of the reaction were added to 100 µL L/L reagent (Promega, F202A) and the light output of the reaction measured immediately. The following data were obtained.

| Probe | RNA (+/−) | Light Units | | | Average |
|---|---|---|---|---|---|
| Probe 6 | + | 138.6 | 111.6 | 116.0 | 122.1 |
| Probe 6 | − | 14.67 | 12.28 | 9.57 | 12.17 |
| Probe 6m4 | + | 7.21 | 6.82 | 7.46 | 7.16 |
| Probe 6m4 | − | 6.24 | 5.90 | 6.28 | 6.14 |
| Probe 6m5 | + | 19.97 | 19.30 | 16.80 | 18.69 |
| Probe 6m5 | − | 6.27 | 6.23 | 6.23 | 6.23 |
| Probe 6m6 | + | 8.22 | 6.92 | 7.02 | 7.39 |
| Probe 6m6 | − | 6.40 | 6.32 | 5.98 | 6.23 |
| (no probe) | + | 4.91 | 7.59 | 5.14 | 6.24 |

Reaction master mix was assembled as in Example 10 and 18 µl of the mix were placed in 18 tubes. After cooling 15 minutes, 2 µL of the various hybridization solutions containing probe 8 through probe 8m6 were added to the tubes and the tubes were placed in a 37° C. heating block.

After a 15 minute incubation at 37° C. of the hybridization mixes in the master mix, 20 µL of the reaction were added to 100 µL L/L reagent (Promega F202A) and the light output of the reaction measured immediately. The following data were obtained.

Data Table

| Probe | RNA (+/−) | Light Units | | | Average |
|---|---|---|---|---|---|
| Probe 8 | + | 71.24 | 55.85 | 76.33 | 67.81 |
| Probe 8 | − | 12.65 | 10.15 | 6.96 | 9.91 |
| Probe 8m4 | + | 5.10 | 5.48 | 5.31 | 5.30 |
| Probe 8m4 | − | 4.76 | 5.08 | 5.04 | 4.96 |
| Probe 8m5 | + | 5.60 | 5.06 | 5.61 | 5.42 |
| Probe 8m5 | − | 2.63 | 4.42 | 4.88 | 3.98 |

-continued

Data Table

| Probe | RNA (+/−) | Light Units | | | Average |
|---|---|---|---|---|---|
| Probe 8m6 | + | 5.68 | 6.13 | 5.79 | 5.87 |
| Probe 8m6 | − | 4.72 | 4.60 | 4.84 | 4.72 |
| (no probe) | + | 5.33 | 4.64 | 4.18 | 4.72 |

These data demonstrate that if the penultimate base to the 3' end of a probe is not able to hybridize to the corresponding base on a target RNA, very little pyrophosphorolysis occurs and a strong signal is not generated. These data also demonstrate that this method can be used to determine if the penultimate base of a probe does complement the expected base in the RNA and thus can be used to confirm that the RNA base at the site of the penultimate base of the probe is as expected.

| | | |
|---|---|---|
| Probe 6 | SEQ ID NO: 53 | 5'AGACTTCTCCTCACTGGACAGATGCACC AT3' |
| Probe 8 | SEQ ID NO: 55 | 5'GGGTCCATGQGTAGACAACCAGCAGC3' |
| Probe 6m4 | SEQ ID NO: 62 | 5'AGACTTCTCCTCACTGGACAGATGCACC CC3' |
| Probe 6m5 | SEQ ID NO: 63 | 5'AGACTTCTCCTCACTGGACAGATGCACC GC3' |
| Probe 6m6 | SEQ ID NO: 64 | 5'AGACTTCTCCTCACTGGACAGATGCACC TC3' |
| Probe 8m4 | SEQ ID NO: 65 | 5'GGGTCCATGGGTAGACAACCAGCACC3' |
| Probe 8m5 | SEQ ID NO: 66 | 5'GGGTCCATGGGTAGACAACCAGCATC3' |
| Probe 8m6 | SEQ ID NO: 67 | 5'GGGTCCATGGGTAGACAACCAGCAAC3' |

EXAMPLE 15
Effect of Mismatch Location on the Signal Derived from Pyrophosphorylation of a Probe to a Known Target RNA Because probes that are mismatched at the 3'-terminal base or the penultimate 3'-base do not give a light signal following incubation in the pyrophosphorylation reaction conditions given in Examples 13 and 14 above, the following study was performed to determine if a mismatched base further within the probe sequence could affect the light signal generated from pyrophosphorylation reactions.

Probes 6m7 (SEQ ID NO:68), 6m8 (SEQ ID NO:69), 6m9 (SEQ ID NO:70) and 6m10 (SEQ ID NO:71), and probes 8m7 (SEQ ID NO:72), 8m8 (SEQ ID NO:73) and 8m9 (SEQ ID NO:74) were dissolved and diluted in water to 1 mg/mL. Globin MRNA (Gibco BRL Product number #18103-010, lot KB6705) was dissolved in 10 mM Tris-Cl, pH 7.3 buffer at a concentration of 20 ng/µL. Ten microliter hybridization reactions were assembled by mixing 5 µL of Probes 6 (SEQ ID NO:53), 6 ml (SEQ ID NO:56), 6m6 (SEQ ID NO:64), and 6m7 through 6m10, 8, (SEQ ID NO:55), 8m3 (SEQ ID NO:61), 8m5 (SEQ ID NO:66) and 8m7-9 with 5 µL of target globin mRNA solution. Control mock hybridization solutions were also made by mixing 5 µL of the probes listed above with 5 µL 10 mM Tris-Cl pH 7.3 and an RNA alone control made by mixing 5 µL target globin mRNA solution with 10 mM Tris-Cl pH 7.3. All of these solutions were heated at 50° C. for 15 minutes, and then were permitted to cool to room temperature for 15 minutes to hybridize and form treated samples.

A master reaction mix was made that contained the following per reaction assembled:

| | |
|---|---|
| Nanopure water | 10.5 μL |
| 5X MMLV-RT Buffer | 4.0 μL |
| 40 mM Sodium Pyrophosphate | 0.5 μL |
| NDPK (0.1 U/μL) | 1.0 μL |
| ADP (2 μM) | 1.0 μL |
| MMLV-RT enzyme | 1.0 μL |

Triplicate reactions were formed for each hybridization solution, probe control solution and target globin RNA solution. Each of these solutions was formed by adding two microliters of each solution to 18 μl of master reaction mix, mixing and incubating the resulting solution at 37° C. for 20 minutes. After this incubation, each solution was added to 100 μL of L/L reagent (Promega, F202A) and the light output of the solution so formed was read immediately using a Turner® TD20/20 luminometer.

The following data were obtained:

| Hybridization Solution | Mismatch Location From Probe 3' End | Light Values | Average | Net Average |
|---|---|---|---|---|
| Probe 6 + Globin mRNA | none | 284.9, 283, 300.0 | 289.3 | 268.7 |
| Probe 6 − Globin mRNA | none | 20.5, 20.7 20.8 | 20.7 | |
| Probe 6m1 + Globin mRNA | 1 (terminal) | 6.5, 6.3 6.3 | 6.4 | 1.3 |
| Probe 6m1 − Globin mRNA | 1 (terminal) | 5.2, 5.1 5.1 | 5.1 | |
| Probe 6m6 + Globin mRNA | 2 | 10.7, 11.5 12.7 | 11.6 | 6.6 |
| Probe 6m6 − Globin mRNA | 2 | 5.2, 4.9 4.8 | 5.0 | |
| Probe 6m7 + Globin mRNA | 3 | 33.3, 30.5 31.3 | 31.7 | 27.0 |
| Probe 6m7 − Globin mRNA | 3 | 4.4, 4.9 4.7 | 4.7 | |
| Probe 6m8 + Globin mRNA | 4 | 38.7, 37.7 37.1 | 37.8 | 33.0 |
| Probe 6m8 − Globin mRNA | 4 | 4.9, 4.8 4.8 | 4.8 | |
| Probe 6m9 + Globin mRNA | 5 | 68.3, 66.1 66.8 | 67.1 | 62.1 |
| Probe 6m9 − Globin mRNA | 5 | 5.0, 4.9 5.1 | 5.0 | |
| Probe 6m10 + Globin mRNA | 6 | 37.9, 35.6 36.0 | 36.5 | 31.6 |
| Probe 6m10 − Globin mRNA | 6 | 4.9, 4.9 5.0 | 4.9 | |
| Probe 8 + Globin mRNA | none | 144.1, 159.0, 165.9 | 156.3 | 122.5 |
| Probe 8 − Globin mRNA | none | 33.7, 33.6 34.1 | 33.8 | |
| Probe 8m3 + Globin mRNA | 1 (terminal) | 6.2, 6.3 6.2 | 6.2 | 1.0 |
| Probe 8m3 − Globin mRNA | 1 (terminal) | 5.3, 5.1 5.1 | 5.2 | |
| Probe 8m5 + Globin mRNA | 2 | 6.4, 6.2 6.2 | 6.3 | 1.1 |
| Probe 8m5 − Globin mRNA | 2 | 4.9, 4.8 6.0 | 5.2 | |
| Probe 8m7 + Globin mRNA | 3 | 8.3, 8.2 7.6 | 8.0 | 3.1 |
| Probe 8m7 − Globin mRNA | 3 | 4.9, 4.9 5.0 | 4.9 | |
| Probe 8m8 + Globin mRNA | 4 | 27.12, 26.4 26.5 | 26.7 | 21.9 |
| Probe 8m8 − Globin mRNA | 4 | 4.9, 4.7 4.7 | 4.8 | |
| Probe 8m9 + Globin mRNA | 5 | 42.5, 43.7 45.3 | 43.8 | −7.3 |
| Probe 8m9 − Globin mRNA | 5 | 53.9, 50.1 49.4 | 51.1 | |
| Globin mRNA Alone | na | 5.7, 5.8 5.5 | 5.7 | |
| No Probe, No RNA | na | 5.2, 5.2 5.3 | 5.2 | |

These data indicate that even mismatches as far as 6 base pairs from the 3' end of the probe can significantly reduce the light output from probe pyrophosphorylation reactions where an RNA target and MMLV-RT are used in the reaction. Thus, such a reduction can be used to indicate that a mutation has taken place in a region of an RNA at least 6 base pairs in length.

| | | |
|---|---|---|
| Probe 6 | SEQ ID NO: 53 | 5'AGACTTCTCCTCACTGGACAGATGCACCAT3' |
| Probe 8 | SEQ ID NO: 55 | 5'GGGTCCATGGGTAGACAACCAGCAGC3' |
| Probe 6m1 | SEQ ID NO: 56 | 5'AGACTTCTCCTCACTGGACAGATGCACCAA 3' |
| Probe 6m6 | SEQ ID NO: 64 | 5'AGACTTCTCCTCACTGGACAGATGCACCTC3' |
| Probe 6m7 | SEQ ID NO: 68 | 5'AGACTTCTCCTCACTGGACAGATGCACTAT 3' |
| Probe 6m8 | SEQ ID NO: 69 | 5'AGACTTCTCCTCACTGGACAGATGCATCAT 3' |
| Probe 6m9 | SEQ ID NO: 70 | 5'AGACTTCTCCTCACTGGACAOATGCTCCAT 3' |
| Probe 6m10 | SEQ ID NO: 71 | 5'AGACTTCTCCTCACTGGACAGATGTACCAT 3' |
| Probe 8m3 | SEQ ID NO: 61 | 5'GGGTCCATGGGTAGACAACCAGCAGT3' |
| Probe 8m5 | SEQ ID NO: 66 | 5'GGGTCCATGGGTAGACAACCAGCATC3' |
| Probe 8m7 | SEQ ID NO: 72 | 5'GGGTCCATGGGTAGACAACCAGCTGC3' |
| Probe 8m8 | SEQ ID NO: 73 | 5'GGGTCCATGGGTAGACAACCAGTAGC3' |
| Probe 8m9 | SEQ ID NO: 74 | 5'GCGTCCATOOOTAGACAACCATCAGC3' |

EXAMPLE 16

Detection of Target DNA Using a Probe

This study is designed to demonstrate that lath specific target DNA sequences can be detected by denaturing the target DNA in the presence of a short oligonucleotide probe that encodes a nucleotide sequence that can hybridize to the target DNA, permitting the solution containing the denatured DNA mixture to cool to form probe:target hybrid and a treated sample, and performing a pyrophosphorylation reaction on the solution followed by transfer of the terminal phosphate of the nucleoside triphosphates produced to ADP to form ATP. The ATP produced is measured using a luciferase/luciferin reaction.

Two microliters of a 1 mg/mL DNA solution of a plasmid containing the kanamycin resistance gene was incubated with 5 μL buffer K (Promega Corp), 4 μL of Endonuclease Sph I (10 U/μL, Promega Corporation), and 39 μL nuclease-free water for 1 hour at 37° C. The solution was then incubated at 70° C. for 10 minutes to inactivate the endonuclease. The final solution was labeled as Sph I-digested PKAN (40 ng/μL).

The following solutions were assembled:
Solutions 1 and 2:
 2 µL Sph I digested pKAN
 18 µL nuclease-free water
Solutions 3 and 4:
 1 µL 1 mg/mL Probe 1 (SEQ ID NO:48)
 19 µL nuclease-free water
Solutions 5 and 6:
 2 µL Sph I digested pKAN
 1 µL 1 mg/mL Probe 1
 17 µL nuclease-free water.

These solutions were heated at 95° C. for 3 minutes, and were cooled to room temperature in approximately 10 minutes by placing them on a laboratory bench to form hybrids and treated samples.

A 2× Master Mix was assembled as follows:

40 µL 10× DNA Polymerase buffer (Promega, M195A)
10 µL 40 mM Sodium Pyrophosphate
10 µL (10 U/µL) Klenow exo minus DNA Polymerase (Promega, M128B)
2 µL NDPK at a concentration of 1 U/µL
4 µL 10 µM ADP
134 µL nuclease-free water The Master Mix components were mixed and 20 µL 2× Master Mix were added to each of the solutions heated to 95° C. after they had cooled to room temperature. The reactions were then heated to 37° C. for 20 minutes, and then 4 µL of the reaction were added to 100 µL of L/L reagent (Promega F202A) and the light produced by the reaction was immediately measured using a Turner® 20/20 luminometer. The following data were obtained.

| Reaction | Light Output |
| --- | --- |
| #1 | 5.1 |
| #2 | 4.6 |
| #3 | 2.2 |
| #4 | 2.0 |
| #5 | 423.4 |
| #6 | 430.5 |

These results show that a strong light signal can be produced from reactions containing a target DNA sequence, a probe that hybridizes to this DNA sequence, and Klenow exo minus. Note that the signal produced is far greater when all the components are present than when either the target DNA or probe is not present in the reaction.

Probe 1    SEQ ID NO: 48    5'GCAACGCTACCTTTGCCATGTTTC 3'

EXAMPLE 17
Identification of a Target DNA Sequence in Plasmid DNA by Use of Probes that Hybridize to that DNA The previous Example illustrates that a pyrophosphorylation reaction can be used to detect specific target DNA sequences with probes that hybridize to the target sequence. Previous examples demonstrate that such a reaction can also be used to detect mutations in RNA sequences if probes are designed to identify the base pair present at the 3' end of the probe. This example illustrates an analogous reaction using DNA as a target that is hybridized with a probe prior to the pyrophosphorylation reaction.

The following solutions were assembled with Probe 1 (SEQ ID NO:48), Probe 2 (SEQ ID NO:49), Probe 3 (SEQ ID NO:50), or Probe 4 (SEQ ID NO:51):

| Solution | pKAN DNA (µL) | Probe/µL | Water* (µL) |
| --- | --- | --- | --- |
| 1 and 2 | 1 | — | 19 |
| 3 and 4 | 1 | 1 µl Probe 1 | 18 |
| 5 and 6 | 1 | 1 µl Probe 2 | 18 |
| 7 and 8 | 1 | 1 µl Probe 3 | 18 |
| 9 and 10 | 1 | 1 µl Probe 4 | 18 |

*Nuclease free water.

These solutions were heated at 95° C. for 3 minutes and cooled to room temperature for 10 minutes to form hybrids and a treated sample. A 2× Master Mix was assembled and mixed as described in Example 16, and 20 µL of this Master Mix were added to each of the solutions above. These reactions were incubated at 37° C. for 20 minutes, and then 4 µL of each solution were added to 100 µL L/L reagent (Promega F202A) and the light production of the resulting reaction was immediately measured using a Turner® 20/20 luminometer. The following data were obtained.

| Reaction | Light Units |
| --- | --- |
| #1 | 2.2 |
| #2 | 2.3 |
| #3 | 227.5 |
| #4 | 225.8 |
| #5 | 28.1 |
| #6 | 27.1 |
| #7 | 17.9 |
| #8 | 18.3 |
| #9 | 21.6 |
| #10 | 21.6 |

These data demonstrate that probes that exactly match a target DNA sequence present on a plasmid give much higher light signals than do probes that contain a mismatch at the 3' end of the probe. Because the probe can be designed to match the base expected at the site, a drastic drop in this signal can indicate that the expected base is not present at the site. This system then can be used to detect mutations in target DNA that alter a base from an expected sequence to another base.

Probe 1 SEQ ID NO:48  5'GCAACGCTACCTTTGCCATGTTTC 3'

Probe 2 SEQ ID NO:49  5'GCAACGCTACCTTTGCCATGTTTG 3'

Probe 3 SEQ ID NO:50  5'GCAACGCTACCTTTGCCATGTTTA 3'

Probe 4 SEQ ID NO:51  5'GCAACGCTACCTTTGCCATGTTTT 3'

EXAMPLE 18
Initial Detection Limit for Plasmid Target DNA by Use of Probe Pyrophosphorylation In the previous two examples, plasmid target DNA was specifically detected using probes that hybridized to a target sequence in the DNA. In this example, a titration of target DNA is carried out in the pyrophosphorylation reaction to determine the level of DNA needed to obtain a signal from this reaction.

The Sph I cut target PKAN DNA (40,000 pg/µL) was serially diluted using nuclease-free water to obtain concentrations of 10,000, 2,500, 625, 156 and 39 pg/µL. Duplicate solutions containing 1 µL each of these DNA target solutions, 1 µL Probe 1 (SEQ ID NO:48) and 18 µL nuclease-free water were assembled as were a pair of solutions containing 1 µL Probe 1 and 19 µL of nuclease-free water. All of these solutions were heated at 95° C. for 3 minutes and then cooled for 10 minutes to room temperature to permit hybridization and form a treated sample. A 2× master mix was made as described in Example 16 and 20 µL of the mix were then added to all tubes and the tubes incubated at 37° C. for 20 minutes. A sample containing 4 µL of the solution was then added to 100 µL of L/L reagent (Promega, F202A) and the light measured using a Turner® 20/20 luminometer. The following results were obtained.

Data Table

| Reaction | DNA Assayed* | Light Units |
| --- | --- | --- |
| #1 | 4000 pg | 168.4 |
| #2 | 4000 pg | 169.4 |
| #3 | 1000 pg | 57.7 |
| #4 | 1000 pg | 77.9 |
| #5 | 250 pg | 19.3 |
| #6 | 250 pg | 21.1 |
| #7 | 62.5 pg | 6.3 |
| #8 | 62.5 pg | 6.4 |
| #9 | 15.6 pg | 2.4 |
| #10 | 15.6 pg | 2.3 |
| #11 | 3.9 pg | 1.4 |
| #12 | 3.9 pg | 1.4 |
| #13 | 0 pg | 1.1 |
| #14 | 0 pg | 1.4 |

*This number reflects that relative amount of DNA transferred to L/L solution.

These data demonstrate that the detection limit for DNA by this reaction under these conditions is at least about 62.5 pg of DNA and is more likely about 15.6 pg of DNA or less.

Probe 1 SEQ ID NO:84 5'GCAACGCTACCTTTGCCATGTTTC 3'

EXAMPLE 19

Detection of β-galactosidase Target Sequences in Plasmids

In this example, two probes are used that complement each other exactly. One of the probes matches the sequence of the β-galactosidase gene exactly (sense orientation) and the other probe exactly matches the complementary strand (antisense orientation) of that gene. This example demonstrates that, whereas both probes can be used to detect the presence of the target β-galactosidase gene in plasmid DNA, the level of background signal given by reactions containing only probe DNA can be very different.

Probe 23 (SEQ ID NO:75) and Probe 24 (SEQ ID NO:76) were dissolved as described above to a concentration of 500 ng/µL and then diluted in nuclease-free water to 100 and 20 ng/µL. Plasmid pGEM7zf+ (Promega) was digested with Sac I (Promega) as the target and diluted to give a solution containing 20 ng of plasmid target DNA/µL of solution.

The following solutions were assembled:

| Solution | Plasmid DNA (µL) | Probe, Concentration | H$_2$O (µL) |
| --- | --- | --- | --- |
| #1 | 1 | (none, 1 µL of 1 X TE buffer added) | 18 |
| #2 | 0 | 1 µL Probe 23, 500 ng/µL | 19 |
| #3 | 0 | 1 µL Probe 23, 100 ng/µL | 19 |
| #4 | 0 | 1 µL Probe 23, 20 ng/µL | 19 |
| #5 | 1 | 1 µl Probe 23, 500 ng/µL | 18 |
| #6 | 1 | 1 µL Probe 23, 100 ng/µL | 18 |
| #7 | 1 | 1 µL Probe 23, 20 ng/µL | 18 |
| #8 | 0 | 1 µL Probe 24, 500 ng/µL | 19 |
| #9 | 0 | 1 µL Probe 24, 100 ng/µL | 19 |
| #10 | 0 | 1 µL Probe 24, 20 ng/µL | 19 |
| #11 | 1 | 1 µL Probe 24, 500 ng/µL | 18 |
| #12 | 1 | 1 µL Probe 24, 100 ng/µL | 18 |
| #13 | 1 | 1 µL Probe 24, 20 ng/µL | 18 |

These solutions were heated at 95° C. for 3 minutes, and cooled to room temperature to form hybrids and treated samples. Then, 20 µL of 2× Master Mix made as described in Example 16 were added and the solutions incubated for another 20 minutes at 37° C. Four microliters of each solution were then added to 100 µL of L/L reagent (Promega, F202A) and the light output of the reaction immediately measured using a Turner® TD20/20 luminometer.

The following data were obtained.

| Reaction | Light Output | Net Light Output* |
| --- | --- | --- |
| #1 | 2.8 | |
| #2 | 4.0 | |
| #3 | 1.9 | |
| #4 | 1.3 | |
| #5 | 52.4 | 45.6 |
| #6 | 13.6 | 8.9 |
| #7 | 4.1 | 0 |
| #8 | 34.3 | |
| #9 | 6.6 | |
| #10 | 1.7 | |
| #11 | 59.8 | 22.7 |
| #12 | 19.3 | 9.9 |
| #13 | 6.0 | 1.5 |

*Net light output is calculated by subtracting the probe alone and DNA alone values from that obtained with both components present.

These data indicate that both probes can be used to generate a signal indicating the presence of the target region encoding the β-galactosidase gene matching the probes is present in the plasmid. They also demonstrate that the level of signal produced with a probe in the absence of target DNA can vary and that the signal from a probe and the complement of that probe are not necessarily equal.

Probe 23 SEQ ID NO:75 5'CAGTCACGACGTTGTAAAACGACGGCC
AGT3'

Probe 24 SEQ ID NO:76 5'ACTGGCCGTCGTTTTACAACGTCGTGA
CTG3'

EXAMPLE 20

Detection of Specific Target DNA Sequences on Lambda DNA

In this example, detection of the target β-galactosidase gene in the DNA of a recombinant Lambda phage is demonstrated.

Duplicate solutions were made that contained: Solution 1 and 2, 1 µL 300 ng/µL of Lambda gt11 DNA and 19 µL of nuclease-free water; Solution 3 and 4, 1 μL 500 ng/μL Probe 23 (SEQ ID NO:75) and 19 μL nuclease-free water; Solution 5 and 6, 1 μL 300 ng/μL Lambda gt11 DNA, 1 μl 500 ng/μL Probe 23, and 18 μL of nuclease-free water. All of these solutions were heated at 95° C. for 3 minutes and then cooled to room temperature for 10 minutes to permit hybridization to occur between complementary strands and form treated samples. At this point, 20 μl of 2× master mix made as described in Example 16 were added and the solutions incubated for another 20 minutes at 37° C. A 4 μL sample of each pyrophosphorolysis reaction was then taken and added to 100 μL of L/L reagent (Promega, F202A) and the light production of the solution immediately measured with a Turner® TD20/20 luminometer. The following data were obtained.

| Reaction | DNA Components | Light Units |
| --- | --- | --- |
| #1 | Target Lambda DNA | 16.5 |
| #2 | Target Lambda DNA | 7.4 |
| #3 | Probe 23 | 2.9 |
| #4 | Probe 23 | 2.9 |
| #5 | Target Lambda DNA and Probe 23 | 88.1 |
| #6 | Target Lambda DNA and Probe 23 | 70.4 |

These data indicate that the pyrophosphorylation system can be used to detect a probe hybridized to specific target sequences on lambda gt11 DNA.

| Probe 23 | SEQ ID NO:75 | 5'CAGTCACGACGTTGTAAAACGACGGCCA GT3' |
| --- | --- | --- |

EXAMPLE 21

Probe Dependent Detection of a PCR Product by Pyrophosphorolysis

A 613 bp PCR product was synthesized by reverse transcription PCR (RT-PCR) from a 1.2 kb synthetic RNA corresponding to the kanamycin resistance gene in plasmid pKanDeltaCG (Promega). The RNA was synthesized using a commercial kit from Ambion (mMESSAGE mMACHINE SP6 Kit Cat#1340) Austin, Tex. PKanDeltaCG was first linearized with EcoR I to enable a run-off transcript to be made. The plasmid was digested for one hour at 37° C. in the following reaction:

| 25 μL | 1 mg/mL pKan DeltaCG |
| --- | --- |
| 10 μL | 10X Multi-Core Buffer (Promega R999A) |
| 5 μL | 80 U/μL EcoR I (Promega R6011) |
| 60 μL | water |
| 100 μL | |

Ten microliters 5M NaCl were added to the EcoR I digested DNA and the reaction was extracted with 110 μL phenol:chloroform:isoamyl alcohol (49:49:2, Promega, Z529A). The supernatant was precipitated with two volumes ethanol, and the pellet vacuum-dried and dissolved in 30 μL of TE buffer (10 mM Tris-HCl pH 8, 1 mM EDTA). The concentration of the digested plasmid was then adjusted to 0.5 mg/mL by the addition of TE buffer.

The kanamycin transcript was generated in the following reaction:

| 16 μL | RNase-free water (Ambion, 9910G) |
| --- | --- |
| 8 μL | 10X Transcription Buffer (8153G) |
| 40 μL | 2X Ribonucleotide Mix (8055G) |
| 8 μL | EcoR I cut plasmid (4 μg) |
| 8 μL | 10X Enzyme Mix (2079G) |
| 80 μL | |

The reaction was incubated at 37° C. for one hour. Most of the synthesized RNA contains a cap structure at the 5' end (GpppG) because a cap analogue was present in the Ribonucleotide Mix. Following completion of the reaction, 4 μL DNase I (Ambion, 2226G) were added and incubation continued for another 15 minutes at 37° C. One hundred-twenty microliters of water and 100 μL of LiCl Precipitation Solution (Ambion, 9480G) were then added. The reaction was chilled at −20° C. for 30 minutes and centrifuged in a microcentrifuge at 14,000 rpm for 15 minutes. The pellet was washed once in 70% ethanol and dissolved in 50 μL of water. The concentration of the RNA was determined spectrophotometrically assuming that a 1 mg/mL solution would provide an absorbance of 25 at 260 nm.

The RNA was first prepared by attaching a small RNA oligonucleotide at the 5' end that served as a PCR anchor. In this way the entire 5' end of the RNA could be amplified by the PCR. Prior to the ligation of this RNA oligo to the kanamycin RNA, the kanamycin RNA was first treated with calf intestinal alkaline phosphatase (CIAP) and tobacco acid pyrophosphatase (TAP). The phosphatase step makes unavailable for the ligation pathway any RNA molecules that do not contain a 5' cap. Once the phosphatase is removed, the cap itself is removed with TAP. The synthetic kanamycin RNA was treated with CIAP in the following reaction:

| 0.6 μL | 850 μg/mL total Mouse Liver RNA (Promega F160A) |
| --- | --- |
| 1 μL | 5 pg/μL capped Kanamycin RNA |
| 5 μL | 10X CIAP buffer |
| 1 μL | 40 U/μL rRNasin ® (Promega N251E) |
| 2 μL | 1 U/μL CIAP |
| 40.4 μL | water |
| 50 μL | |

Following a one-hour 37° C. incubation, 250 μL water, 75 μL 10 M ammonium acetate and 375 μL phenol:chloroform:isoamyl alcohol (49:49:2) were added. The reaction was vortexed and phases separated by a 5 minute centrifugation in a microcentrifuge. The supernatant (350 μL) was removed and the extraction repeated. The supernatant was precipitated by the addition of 900 μL ethanol and centrifuged 5 minutes. Following a 70% ethanol wash, the pellet was dissolved in 43.5 μL water. To the CIAP-treated RNA were added:

| 5 μL | 10X TAP buffer (Epicentre) |
| --- | --- |
| 1 μL | 40 U/μL rRNasin ® |
| 1 μL | 0.1 U/μL TAP (Epicentre, T19500) |

Following a one-hour incubation at 37° C., the reaction was extracted and precipitated as above and the pellet dissolved in 13 μL of water. To that solution were then added:

| | |
|---|---|
| 4 µL | 10X RNA Ligase buffer |
| 1 µL | 0.25 µg/µL RNA oligo 30-mer |
| 1 µL | 40 U/µL rRNasin ® |
| 1 µL | 10 U/µL RNA Ligase (Promega, M1051) |
| 20 µL | 40% polyethylene glycol (SigmaP-2139) | and the reaction was incubated overnight (about 18 hours) at 16° C.

10× CIAP buffer: 100 mM Tris-HCl pH 8, 100 mM MgCl$_2$, 0.5 M NaCl, 10 mM DTT

10× TAP buffer: 0.5M sodium acetate pH 6, 10 mM EDTA, 1% beta-mercaptoethanol, 0.1% Triton X-100

10× RNA Ligase buffer: 0.5 M Tris-HCl pH 8, 100 mM MgCl$_2$, 0.68% beta-mercaptoethanol, 10 mM ATP Following the ligation step, 250 µL of water, 75 µL of 10 M ammonium acetate and 900 µL ethanol were added to the reaction. The mixture was vortexed and then centrifuged 20 minutes in a microcentrifuge at 14,000 rpm at 4° C. The pellet was washed in 70% ethanol and dissolved in 15 µL water. cDNA was first synthesized from the RNA prior to PCR. To the RNA was added 1 µL (50 pmoles) of a cDNA synthesis probe (SEQ ID NO:81) and the mixture heated at 70° C. for 5 minutes, then cooled to room temperature for 10 minutes. To the RNA/probe mix were added:

| | |
|---|---|
| 5 µL | 5X First Strand buffer (Promega, C121A) |
| 1 µL | 40 U/µL rRNasin ® |
| 2.5 µL | 40 mM sodium pyrophosphate (Promega, C113A) |
| 1 µL | 25 U/µL AMV reverse transcriptase (Promega, M5108) |

The reaction was incubated for 1 hour at 42° C. and then terminated by the addition of 0.5 µL of 0.5 M EDTA and 74 µL water. To 5 µL of the cDNA (SEQ ID NO:77) were added:

| | |
|---|---|
| 5 µL | 10X Thermophilic buffer (Promega, M190G) |
| 5 µL | 10X PCR dNTP |
| 5 µL | 25 mM MgCl$_2$ (Promega, A351H) |
| 1 µL | 320 µg/mL upstream probe (SEQ ID NO:78) |
| 26.5 µL | water |

The reaction was mixed and covered with 50 µL mineral oil. The mixture was put into a thermalcycler (Perkin-Elmer Model 480) at 95° C. After 2 minutes, 1 µL of 5 U/µL Taq DNA polymerase (Promega, M166B) was added and the reaction cycled 95° C. for 1 minute, 43° C. for 1 minute, 72° C. for 2 minutes for 5 cycles and then brought to 85° C. Then, 1 µL of 320 µg/ml of downstream probe (SEQ ID NO:79) was added and the reaction cycled 95° C. for 30 seconds, 55° C. for 30 seconds, 72° C. for 1 minute for 30 cycles followed by 5 minutes at 72° C. then 4° C.

10× PCR dNTP: 1 mM each of dATP, dGTP, dCTP and dTTP

The PCR reaction generated a 613 bp product. To remove unincorporated probes and DNTP, a 15 µl aliquot of the PCR reaction was purified with Promega's Wizard™ PCR Preps (A7170) according to kit instructions. The concentration of the purified PCR product was determined by a pyrophosphorolysis assay. A Master Mix (MM) was assembled containing the following components:

| | |
|---|---|
| 20 µL | 10X Buffer A (Promega, R001A) |
| 2 µL | 40 mM sodium pyrophosphate |
| 2 µL | 10 µM ADP (Sigma A5285) |
| 5 µL | 1 U/µL NDPK (Sigma N0379) |
| 151 µL | water |
| 180 µL | |

This mix was used in reactions containing control PhiX 174 HinF I DNA standard (Promega G175A) or aliquots of the PCR reaction, with and without added T4 DNAP (10 U). The PCR reaction was diluted 10× in TE buffer (10 mM Tris, 1 mM EDTA) for use in the assay. The results are shown below.

| | 1 ng/µL | PhiX DNA | PCR | T4 DNAP | LU |
|---|---|---|---|---|---|
| 1 | 18 µL | — | — | + | 0.950 |
| 2 | 18 µL | 1 µL | — | + | 44.92 |
| 3 | 18 µL | 2 µL | — | + | 68.86 |
| 4 | 18 µL | 3 µL | — | + | 90.88 |
| 5 | 18 µL | — | 1 µL | − | 1.244 |
| 6 | 18 µL | — | 2 µL | − | 1.388 |
| 7 | 18 µL | — | 1 µL | + | 47.97 |
| 8 | 18 µL | — | 2 µL | + | 68.69 |

Light units (LU) generated resulted from adding 2 µl of reaction mixes to 100 µl of L/L reagent and measuring on a Turner® TD20/20 luminometer.

As can be seen, the PhiX 174 HinF I DNA produced a light signal that was proportional to the amount of DNA added. The concentration of the ten-fold diluted PCR reaction is almost exactly that of the DNA standard, so the undiluted PCR product DNA is at a concentration of 10 ng/µL. Note that only background light units are seen for the reactions that contained the PCR product but no T4 DNAP. This indicates essentially complete removal of the dNTP's during clean-up on the Wizard™ resin.

Next, the PCR product was detected by hybridizing and pyrophosphorolyzing a probe that bound to internal sequences. The sequence of the probe was 5' GCAACGC-TACCTTTGCCATGTTTC3' (SEQ ID NO:80). For this purpose it was found most suitable to use the Klenow exopolymerase (Promega, M218B) in place of T4 DNAP. A 2× Master Mix (MM) was assembled as below:

| | |
|---|---|
| 60 µL | 10X DNAP buffer (Promega, M195A) |
| 15 µL | 40 mM Sodium Pyrophosphate |
| 15 µL | 10 U/µL Klenow exo- polymerase |
| 3 µL | 1 U/µL NDPK |
| 6 µL | 10 µM ADP |
| 201 µL | water |
| 300 µL | |

PCR product (between 0 and 20 ng) was mixed (or not) with 1 µL of 1 µg/µL probe and water as shown below. The mixtures were heated at 95° C. for 3 minutes and then permitted to cool to room temperature for 10 minutes. Then 20 µL of 2× Master Mix were added and the reactions incubated for 20 minutes at 37° C. before adding 4 µL to 100 µL of L/L reagent (Promega, F202A).

| | PCR Target | Probe | Water | LU |
|---|---|---|---|---|
| 1 | 20 ng | − | 18 μL | 37.84 |
| 2 | 20 ng | + | 17 μL | 423.2 |
| 3 | 10 ng | − | 19 μL | 16.51 |
| 4 | 10 ng | + | 18 μL | 366.1 |
| 5 | 5 ng | − | 19 μL | 7.79 |
| 6 | 5 ng | + | 18 μL | 226.0 |
| 7 | 2.5 ng | − | 19 μL | 4.994 |
| 8 | 2.5 ng | + | 18 μL | 171.2 |
| 9 | 1.25 ng | − | 19 μL | 3.176 |
| 10 | 1.25 ng | + | 18 μL | 85.6 |
| 11 | 0 ng | + | 19 μL | 2.656 |

It can be seen that substantially higher LU result when the probe is present along with the target DNA and that this signal is not due to the probe alone (reaction 11). It is surprising that only very small amount of the PCR product target has re-annealed to give a signal during the course of the assay, even at the higher DNA amounts. The light units generated represent only one tenth of the DNA that was added to the reactions and from the data it is apparent that about 10 pg of the PCR product can easily be detected in a probe-dependent manner.

```
Kanamycin RNA Oligo
5' AGAGUCUUGACGGAUCCAGGUACCAGUAAA 3'         SEQ ID NO:77

Upstream probe: 5' TGATCGTAAGAGTCTTGACGGATC 3'  SEQ ID NO:73

Downstream probe: 5' TCATTCGTGATTGCGCCTGAGCGA 3' SEQ ID NO:79

Internal Probe:
5' GCAACGCTACCTTTGCCATGTTTC 3'                SEQ ID NO:80 cDNA Synthesis Primer:
5' AAATCACTCGCATCAACCAAACCG 3'                SEQ ID NO:81
```

EXAMPLE 22

Mismatch (Mutation) Detection in a Target PCR Product

To demonstrate base interrogation, or mismatch detection, four different probes were used to hybridize with the above PCR product. The wild-type (WT) probe was the same as that used in Example 9, or Probe 1 (SEQ ID NO:48). In addition, three additional probes were used that differed in their terminal base at the 3' end.

The WT probe (Probe 1) contained a C that matched to the G present on the PCR template. Three additional probes contained either G, A or T at the 39-terminal position (Probe 2, (SEQ ID NO:49), Probe 3 (SEQ ID NO:50) and Probe 4 (SEQ ID NO:51) respectively) and thus when hybridized to the template created mismatches of GG, GA and GT, respectively. These mismatched bases substantially block pyrophosphorolysis of the hybridized probe:target, permitting determination of which base is present on the DNA template at that position.

A 2× Master Mix (2×MM) was prepared as in Example 21 and 1 μL of 10 ng/μL target PCR product were mixed with 1 μL of 1 μg/μL probe and water or TE buffer (10 mM Tris, 1 mM EDTA) as below. The mixtures were heated for 3 minutes at 95° C. then permitted to cool to room temperature for 10 minutes. Then, 20 μL of 2×MM were added, the reactions mixed and permitted to incubate for 20 minutes at 37° C. to hybridize and form treated samples prior to adding 4 μL of each to 100 μL of L/L reagent (Promega, F202A) and measuring the resulting light units produced.

| Target PCR/ Probe # | Water (μL) | TE (μL) | LU |
|---|---|---|---|
| 1 | +/− | 18 | 1 | 21.82 |
| 2 | −/1 | 19 | — | 2.628 |
| 3 | +/1 | 18 | — | 322.1 |
| 4 | +/− | 18 | 1 | 14.69 |
| 5 | −/2 | 19 | — | 3.277 |
| 6 | +/2 | 18 | — | 57.44 |
| 7 | +/− | 18 | 1 | 23.14 |
| 8 | −/3 | 19 | — | 4.861 |
| 9 | +/3 | 18 | — | 40.90 |
| 10 | +/− | 18 | 1 | 14.98 |
| 11 | −/4 | 19 | — | 5.899 |
| 12 | +/4 | 18 | — | 43.33 |

It can be seen that the greatest LU were obtained in the case of the matched probe (Probe 1). Subtracting the backgrounds of PCR product alone and probe alone, the following LU were obtained in the case of the matched and mismatched probes:

| Probe And Template Resulting In | LU |
|---|---|
| GC match | 297.7 |
| GG mismatch | 39.47 |
| GA mismatch | 12.90 |
| GT mismatch | 22.45 |

It is clear that having a probe 3'-terminal base that mismatches with the target dramatically reduces the rate of pyrophosphorolysis of the hybridized probe.

The probe alone backgrounds seen above are low (<10 LU). However, probes have been encountered that give very high backgrounds (as much as 500 LU per 100 ng probe). Such probes are generally complementary and capable of forming either self-dimers or hairpin structures leading to double-stranded regions at their 3' ends. Such probes are to be avoided and can often be detected using various secondary structure prediction programs. If one set of probes provides high background, it may be possible to use adjacent probes to the other strand with their 3' ends interrogating the same site.

| Probe 1 | SEQ ID NO :48 | 5'GCAACGCTACCTTTGCCATGTTTC 3' |
| Probe 2 | SEQ ID NO: 49 | 5'GCAACGCTACCTTTGCCATGTTTG 3' |
| Probe 3 | SEQ ID NO: 50 | 5'GCAACGCTACCTTTGCCATGTTTA 3' |

| | | |
|---|---|---|
| Probe 4 | SEQ ID NO: 51 | 5'GCAACGCTACCTTTGCCATGTTTT 3' |

EXAMPLE 23

Mutation Detection on Pseudo-PCR Product Synthetic Targets

In order to show base interrogation on DNA targets where a base has actually been changed (mutation), synthetic oligonucleotides were made that correspond to a region of cytomegalovirus DNA in which a mutation can be present that has been shown to be responsible for resistance to the drug gancyclovir.

The upper strand of the wild type target corresponds to sequence 1 below (SEQ ID NO:82) the bottom strand corresponds to sequence 2 below (SEQ ID NO:83). The base that is mutated is indicated in bold type. The upper strand of the mutant target (sequence 3 below, (SEQ ID NO:84)) is the same as sequence 1 but the bolded base has been changed from an A to a G. The bottom strand of the mutant target (sequence 4 below, (SEQ ID NO:85)) is the same as sequence 2 but the bolded base has been changed from a T to a C.

Two oligonucleotide probes were used to interrogate the position of the mutated base, one corresponding to the wild type and the other to the mutant sequence. The sequence of the wild type interrogation probe is sequence 5 (SEQ ID NO:86) below and the sequence of the mutant interrogation probe is sequence 6 below (SEQ ID NO:35). These probes were identified by the numbers 9211 and 9212 respectively. Sequence 5 differs from sequence 6 at the position of the bolded base and for these probes, the mismatched base is three nucleotides in from the 3' end of each probe.

It was expected that the wild type probe would give the strongest signal on the wild type target and the mutant probe the strongest signal on the mutant target. This was found to be the case as demonstrated in the study detailed below.

Wild type and mutant DNA targets to be interrogated were assembled by mixing together sequence 1 with sequence 2 and sequence 3 with sequence 4 to a final concentration of 0.3 µg/mL. Interrogation probes 9211 and 9212 were both dissolved to a concentration of 1 mg/mL in TE buffer (10 mM Tris, 1 mM EDTA). Reactions were assembled as below and contained either target only, probe only or target plus probe:

| Wild Type | Target (µL) | 9211 (µL) | 9212 (µL) | Water (µL) |
|---|---|---|---|---|
| 1 and 2 | 1 | — | — | 19 |
| 3 and 4 | — | 1 | — | 19 |
| 5 and 6 | — | — | 1 | 19 |
| 7 and 8 | 1 | 1 | — | 18 |
| 9 and 10 | 1 | — | 1 | 18 |

Reactions were mixed and heated at 95° C. for 3 minutes and then permitted to cool to room temperature for 10 minutes on the bench to hybridize and form treated samples. Then 20 µL of a 2× Master Mix were added, the reactions incubated 20 minutes at 37° C. then 4 µL of each were added to 100 µL of L/L reagent and the resulting light units determined in a luminometer.

2× Master Mix:

| | |
|---|---|
| 60 µL | 10X DNAP buffer |
| 15 µL | 40 mM sodium pyrophosphate |
| 15 µL | Klenow exo- DNAP |
| 3 µL | 1 U/µL NDPK |
| 6 µL | 10 µM ADP |
| 201 µL | water |

The resulting relative light units were as follows.

| Reaction | Light Units |
|---|---|
| 1 | 1.687 |
| 2 | 1.732 |
| 3 | 4.313 |
| 4 | 3.948 |
| 5 | 10.54 |
| 6 | 10.04 |
| 7 | 220.8 |
| 8 | 206.8 |
| 9 | 49.67 |
| 10 | 37.33 |

It can be seen (1 and 2) that the DNA target itself yields very few LU as is the case for the interrogation probes alone (3 through 6). Wild type interrogation probe mixed with wild type target provided over 200 LU, whereas the mutant probe mixed with the wild type target provided less than 50 LU. After subtracting the backgrounds given by the target and probes alone, it can be seen that the wild type probe provided roughly five-fold more signal on the wild type target than did the mutant probe.

The above study was then repeated but substituting the mutant DNA target for the wild type target, The resulting LU are shown below.

| Reaction | Light Units |
|---|---|
| 1 | 1.760 |
| 2 | 1.779 |
| 3 | 4.157 |
| 4 | 4.316 |
| 5 | 11.0 |
| 6 | 10.56 |
| 7 | 34.31 |
| 8 | 29.53 |
| 9 | 241.9 |
| 10 | 264.5 |

Again, it can be seen that background light units provided by target alone and probes alone are low (1–6) and that this time the greatest signal was seen with the mutant (9212) probe instead of the wild type probe. Thus, by comparing the ratio of signals obtained with the wild type and mutant probes, one can distinguish the wild type from the mutant DNA.

| | | |
|---|---|---|
| PCR Sequence 1 | SEQ ID NO: 82 | 5'CGTGTATGCCACTTTGATATTACACCCATGAAC GTGCTCATCGACGTGAACCCGCACAACGAGCT3' |
| PCR Sequence 2 | SEQ ID NO: 83 | 5'CGTTGTGCGGGTTCACGTCGATGAGCACGTTCA TGGGTGTAATATCAAAGTGGCATACACGAGCT3' |
| PCR Sequence 3 | SEQ ID NO: 84 | 5'CGTGTATGCCACTTTGATATTACACCCGTGAAC GTGCTCATCGACGTGAACCCGCACAACGAGCT3' |
| PCR Sequence 4 | SEQ ID NO: 85 | 5'CGTTGTGCGGGTTCACGTCGATGAGCACGTTCA CGGGTGTAATATCAAAGTGGCATACACGAGCT3' |
| PCR Sequence 5 (9211) | SEQ ID NO: 86 | 5'CACTTTGATATTACACCCATG3' |
| PCR Sequence 6 (9212) | SEQ ID NO: 35 | 5'CACTTTGATATTACACCCGTG3' |

EXAMPLE 24

Cloning and Expression of a Gene Encoding a NDPK Enzyme from Thermophilic Bacteria Pyrococcus furiosis The cloning and expression of a gene from the thermophilic bacteria Pyrococcus furiosis [Pfu; Pfu-Vcl (DSM 3638)] is described in this Example. This gene encodes the nucleoside diphosphate kinase (NDPK) enzyme. The protein originates from a thermophile and remains active at elevated temperatures for a longer period of time than the corresponding protein from a mesophilic organism. The protein also remains active at room temperature longer than the corresponding mesophilic enzyme. If the protein were stable at elevated temperature, it could function in combination with a thermostable polymerase in a pyrophosphorylation reaction, thereby eliminating the need to carry out separate pyrophosphorylation and phosphate transfer steps as needed for the NDPK derived from yeast.

The amino acid sequences of known NDPKs (Gene 129:141–146, 1993 and the NCBI sequence of NDPK from Pyrococcus horikoshii) were compared and segments of high amino acid homology identified.

Two degenerate DNA primers were designed that would permit the DNA between them to be amplified. These primers, Pf1 (SEQ ID NO:87) and Pf2 (SEQ ID NO:87), are shown below, and were dissolved in TE buffer (10 mM Tris, 1 mM EDTA). A '6' in the primer sequence indicates an inosine that can hybridize to any base.

Chromosomal DNA from Pfu was isolated by resuspending frozen cell paste from a 3 mL overnight (about 18 hours) culture pellet in 1 mL TE buffer (10 mM Tris, 1 mM EDTA), lysing the cells by beating with zircon beads, followed by two phenol extractions and a chloroform extraction. The DNA in the supernatant was then ethanol precipitated, dried, and resuspended in TE buffer overnight (about 18 hours). The resuspended DNA was treated with 20 units of RNaseI, reprecipitated and resuspended in TE buffer.

The Pfu genomic DNA was used in the following DNA amplification reaction.

| | |
|---|---|
| 2 µL | 1.5 µg Pfu DNA (pre-denatured for 5 minutes at 99° C., then placed on ice) |
| 5 µL | PCR buffer |
| 4 µL | 25 mM MgCl$_2$ |
| 2 µL | each primer Pf1 and Pf2 (200 picomoles each) |
| 1 µL | 10 mM dNTP mix |
| 25 µL | water |
| 1 µL | Taq (5 units) |
| 10 µL | 5M betaine |

Different extension temperatures in the range from 41° C. to 55° C. were tested in the following PCR profile: 94° C., 2 minutes; (94° C., 15 or 40 seconds; 45° C. to 55° C., 45 or 90 seconds; 72° C., 1 or 2 minutes)×20; 72° C. 2 minutes. The profile varied for the different extension temperatures, with 41° C. and 43° C. extension temperatures having the lesser times, and the remaining extension temperatures having the longer times.

The reaction products were analyzed by gel electrophoresis on a 1.2% TBE agarose gel. The products of the reaction were detected by staining the gel with ethidium bromide and photographing the gel under UV light. A 300 bp DNA fragment was identified as the product of the reaction and was present to a greater extent when using extension temperatures from 41° C. to 47° C. The 300 bp fragment was gel purified (Promega, A7170) and cloned into pGEM-T vector (Promega, A3600).

The sequence of the insert was determined and found to encode an open reading frame. The translated amino acid sequence of this open reading frame matched the protein sequence of the Pyrococcus horikoshii NDPK gene with 94% homology.

A hybridization probe, Pf3 (SEQ ID NO:89), was designed from the sequence obtained. This probe was $^{32}$p labeled and used to identify the size of the DNA fragments encoding the corresponding gene in chromosomal digests of the DNA from Pfu using standard Southern blot hybridization methods.

A size-specific EcoR I library of DNA fragments from Pfu was produced by digesting Pfu chromosomal DNA with EcoR I, fractionating the DNA fragments using agarose gel electrophoresis, identifying the segment of the fractionated DNA that corresponded to the 2 Kb EcoR I fragment identified as containing the desired gene and isolating the DNA from the gel. The DNA isolated was cloned into plasmid pZERO2 (Invitrogen), and the resulting library was transformed into E. coli TOP10 (Invitrogen). The transformants were probed using the same probe employed during Southern hybridization and two clones were identified as potential candidate clones. From this analysis, an EcoR I fragment about 2 kb in size was identified as a target for additional cloning.

The sequences of the two candidate clones were found to contain the exact sequence present in the 300 bp DNA segments sequenced earlier in addition to DNA sequences both 5' and 3' to that sequence. The open reading frame identified earlier was found to extend significantly beyond the limits of the 300 bp segment sequenced earlier. The additional segments of the open reading frame again showed good homology with NDPK. The Pfu NDPK nucleotide sequence is identified as Sequence Pf4 (SEQ ID NO:90) and the corresponding amino acid sequence is identified as Pf5 (SEQ ID NO:91). The protein codes for 161 amino acid residues.

The coding segments of the gene were amplified using primers Pf6 (SEQ ID NO:92) and Pf7 (SEQ ID NO:93), and placed into a high protein expression vector for *E. coli* JHEX25, an IPTG inducible promoter system (Promega). Bacterial transformants were grown in LB media and induced for protein expression. Samples of the induced bacterial cultures were boiled in 2× SDS Sample buffer and loaded onto an SDS gel. After running, the gel was stained with Coomassie Blue.

After destaining in 1% acetic acid and 10% methanol, the lanes containing extracts from cells with the open reading frame were found to contain a large amount of a protein of about 14 Kd, the expected size of the gene product from the insert.

Then, a comparison of the open reading frame to the published sequence of the Pfu genome (University of Utah) was performed and the open reading frame was found to exactly match a region of the genome of this organism as expected.

EXAMPLE 25
Purification of Cloned Pfu NDPK Protein from *E. coli*

An initial fermentation of Top10 *E. coli* cells expressing the Pfu NDPK protein, as described in Example 24 yielded about 10 g of wet cell paste.

The protein purification scheme was essentially that as described in Kim, S. et al. *Molecules and Cells*, 7:630, 1997. One gram of cell paste was resuspended in 10 mL of 20 mM Tris-acetate pH 7.4/1 mM EDTA/2 µg/mL aprotinin/0.1 mg/mL lysozyme and incubated at room temperature for 10 minutes. The suspension was then sonicated for 2 minutes at 50% cycle, held on ice for 5 minutes, then sonicated an additional 2 minutes. The suspension was centrifuged at 15,000×g for 20 minutes at 4° C. and the supernatant transferred to a new tube.

The supernatant was heated to 80° C. for 20 minutes to denature non-thermostable proteins. Precipitant was pelleted by centrifugation at 14,000×g for 20 minutes at 4° C. and supernatant was transferred to a new tube.

Ten milliliters of supernatant were applied to a 5 mL ATP-sepharose (Sigma, A-9264) affinity column equilibrated with Buffer A (20 mM Tris-acetate pH 7.4/20 mM NaCl/0.1 mM EDTA/3 MM $MgCl_2$/15 mM BME).

The flow through was collected by gravity. The column was washed with 6 column volumes of Buffer A (Buffer A containing 500 mM NaCl). The bound protein was eluted in two steps: 5 mL Buffer B+1 mM dCTP (Promega, U122A) followed by 5 mL of Buffer B+1 mM ATP (Sigma, A-7699).

SDS-PAGE analysis of the purification fractions showed a large loss of total protein following the heat denaturation

```
Pf1 5' AT6ATGAA(AG)CC6GA(TC)G(GC)6GT 3'                        SEQ ID NO:87

Pf2 5' AA(AG)TC6CC6C(TG)6AT6GT6CC6GG 3'                        SEQ ID NO:88

Pf3 5' GAGAAGCACTATGAGGAGCAC 3'                                SEQ ID NO:89

Pf4
5' ATGAACGAAGTTGAAAGAACATTGGTAATCATAAAGCCCGACGCAGTAGTT          SEQ ID NO:90

AGGGGTCTAATATAGGTGATAATTATAAGCAGGTTTGAGAAGAAAGGCCTCAAGAT

TGTTGGAATGAAGATGATCTGGATAGACAGGGAGTTGGCTGAGAAGCACTATG

AGGAGCACAAAGGAAAGCCCTTCTTTGAGGCTCTCATAGATTACATAACGAAA

GCTCCAGTAGTTGTTATGGTGGTTGAGGGAAGGTATGCAGTAGAAGTAGTT

AGAAAGATGGCTGGAGCTACTGATCCAAAGGACGCAGCACCTGGGACAATTAG

GGGAGATTATGGACTTGACATAGGAGATGCAATCTACAACGTGATTCATGC

CAGTGATTCAAAGGAAAGTGCGGAGAGGGAAATAAGCCTGTACTTTAAACCTG

AAGAATTTATGAATACTGCAAAGCTGCAGATTGGTTTTACAGGGAAAAGAAG

CAGGCTAAATGCTGA 3'

Pf5
MNEVERTLVIIKPDAVVRGLIGEIISRFEKKGLKIVGTVIKMIWTDRELAEKHYE         SEQ ID NO:91

EHKGKPFFEALIDYITKAPVVVMVVEGRYAVEVVRKMAGATDPKDAAPGTTIRG

DYGLDTGDAIYNVIHASDSKESAEREISLYFKPEEIYEYCKAADWFYREKKQA

KC

Pf6
5' GGGTGCTTTTCATGAACGAAGTTGA 3'                                SEQ ID NO:92

Pf7
5' AAGGGCAAAAATTCTAGAGTTCAGCAT 3'                              SEQ ID NO:93
``` step, with the NDPK being the major band loaded on the column. About 50% of the loaded NDPK was in the flow-through fraction. Eluted NDPK appeared in both the dCTP and ATP elutions at greater than 80% purity.

EXAMPLE 26

Thermostable NDPK Activity Assays

Activity Assay

The activity assay for NDPK measures ATP created following phosphate transfer from dCTP to -ADP. A linear range for the amount of enzyme was determined using yeast NDPK in a 10 minute assay at 37° C. and was found to be 0.002–0.0002 units, or 0.012–1.2 ng protein. The optimal concentrations of ADP and dCTP in the assay were found to be 100 nM and 10 μM respectively, in order to give Turner® TD20/20 luminometer readings within a readable scale.

The Pfu NDPK activity in the dCTP and ATP eluted fractions, as described in Example 25, was examined after extensive dialysis of the fractions to remove nucleotides. Both the dCTP and ATP elutions of the purified Pfu NDPK were also passed over a De-Salt™ column (Pierce, 43230) according to manufacturer's recommendations to further remove excess nucleotides.

Activity of Pfu NDPK was measured in a 10 minute assay at both 37° C. and 70° C. Activity was observed at both temperatures. If full enzymatic activity is presumed at the 70° C. optimum, then about 40% of that activity was seen at the lower temperature. The estimated unit activity for the fractions was determined by comparison of the light output, resulting from ATP formation, of yeast NDPK at 37° C. with the light output of the Pfu NDPK at 70° C. For example: if 0.0002 units of yeast NDPK provides 7000 relative light units after 10 minutes at 37° C., then 0.0002 units of Pfu NDPK is presumed to provide 7000 relative light units after 10 minutes at 70° C.

Using this unit equivalency based on light output, the dCTP and ATP Pfu NDPK fractions were assigned a unit activity of 0.5 units/μL.

Activity Assay at Two Temperatures

The activity levels of the Pfu NDPK from both the ATP- and the dCTP-eluted fractions were compared to the activity level of the yeast NDPK at both 70° C. and 37° C. A series of 10-fold serial dilutions of the three enzyme solutions was made in Nanopure water to a final dilution of 1:10,000. The following master mix was prepared:

| | |
|---|---|
| 889 μL | Nanopure water (Promega AA399) |
| 100 μL | 10X DNAP Buffer (Promega M195A) |
| 10 μL | 10 μM ADP (Promega, A-5285) |
| 1 μL | 10 μM dCTP (Promega, U128B) |

Into each reaction tube were placed 180 μL master mix preheated to either 37° C. or 70° C. and 20 μL of each 1:10,000 NDPK dilution, and tubes were incubated at the indicated temperature. Twenty microliter samples were removed at various time points, added to 100 μL of L/L reagent (Promega, F202A) and light units read in a TMDE™ luminometer. The t=0 time point was never incubated at elevated temperatures and was placed on ice. The following data were obtained:

| | Time (minutes) | 70° C. | 37° C. |
|---|---|---|---|
| Yeast NDPK | 0 | 4896 | |
| | 1.0 | 5126 | |
| | 2.5 | 5163 | |
| | 5 | 6946 | |
| | 10 | 6687 | 7503 |
| | 15 | 6735 | |
| | 20 | 6806 | |
| | 25 | 7298 | |
| Pfu | 0 | 327 | |
| NDPK (dCTP) | 1.0 | 749 | |
| | 2.5 | 1772 | |
| | 5 | 2794 | |
| | 10 | 3191 | 111 |
| | 15 | 4364 | |
| | 20 | 5025 | |
| | 25 | 5830 | |
| Pfu NDPK (ATP) | 0 | 1255 | |
| | 1.0 | 2235 | |
| | 2.5 | 4410 | |
| | 5 | 5925 | |
| | 10 | 6039 | 973 |
| | 15 | 6828 | |
| | 20 | 7747 | |
| | 25 | 10026 | |
| No NDPK | 0 | | 56 |

The Pfu NDPK is more active at 70° C. than at 37° C. This is evident by comparing relative light units at 10 minutes activity at 37° C. and 70° C. (1:10,000 dilution). There is about 10-fold more yeast protein in the 70° C. reaction than Pfu protein as determined by a standard Bradford assay. Therefore, the Pfu NDPK enzyme may have a higher specific activity. For the 37° C. assay, the yeast NDPK was further diluted to 1:100,000 and produced 247 light units at this dilution. The light units increased slightly and then leveled off for the yeast enzyme, suggesting thermal inactivation of the enzyme at 70° C. The Pfu NDPK light output increased over time.

Thermostability of Pfu NDPK and Yeast NDPK

Yeast NDPK stock at 1 unit/μL was serially diluted in Nanopure water to a 1:100,000 final dilution. The dCTP- and ATP-eluted Pfu NDPK stock were serially diluted in Nanopure water to a 1:10,000 final dilution. This equalized the amount of protein present in the Pfu NDPK and Yeast NDPK final dilutions, as determined by standard Bradford protein assay and SDS-PAGE analysis.

Two microliters of the diluted enzymes were added to 18 μL of master mix in chilled tubes and placed on ice. These are the t=0 time points. The remainder of the diluted NDPK solutions were pre-warmed at 70° C. For each time point, a 2 μL aliquot of the enzyme dilution was added to 18 μL master mix and then placed on ice. After the t=10 minutes time point, all tubes were incubated at 37° C. for 10 minutes. Then, 100 μL of L/L reagent were added to each reaction and the relative light units measured on a TMDE™ luminometer. The following results were obtained.

| | Relative Light Units | | |
|---|---|---|---|
| Time (minutes) | Yeast | Pfu NDPK (dCTP) | Pfu NDPK (ATP) |
| 0 | 1877 | 446 | 615 |
| 1 | 263 | 358 | 400 |
| 2 | 47 | 299 | 472 |
| 3 | 42 | 319 | 446 |
| 4 | 40 | 296 | 432 |
| 5 | 38 | 315 | 353 |
| 7.5 | 36 | 241 | 339 |
| 10 | 37 | 239 | 307 |

The yeast NDPK appears to be thermolabile, whereas the Pfu NDPK is relatively thermostable. The purified Pfu NDPK had a half-life of about 10 minutes, whereas the yeast NDPK had a half-life of about 0.6 minutes.

EXAMPLE 27

Interrogation Assay at 70° C. Using Pfu NDPK and Tne Triple Mutant DNA Polymerase This Example uses thermostable NDPK and thermostable polymerase in a one-step 70° C. interrogation reaction. Synthetic CMV targets, differing at one nucleotide, were prepared by annealing single-stranded DNAs as described in Example 2. The wild-type single-stranded DNAs used were CV11 (SEQ ID NO:8) and CV12 (SEQ ID NO:9), and the mutant single-stranded DNAs used were CV 13 (SEQ ID NO:10) and CV 14 (SEQ ID NO:11). Interrogation oligonucleotides used were 9211 (SEQ ID NO:86) and 9212 (SEQ ID NO:35)

The following solutions, brought to a final volume of 20 μL with water, were assembled and assayed:

| Soln.* | CMV WT Target | CMV Mutant Target | Interrogation Oligo (1 μg) | (0.1 U Tne) | (0.2 U Tne) |
|---|---|---|---|---|---|
| 1 | — | — | — | 48 | 72 |
| 2 | 5 ng | — | — | 60 | 79 |
| 3 | — | 5 ng | — | 27 | 74 |
| 4 | — | — | 9211 | 55 | 71 |
| 5 | — | — | 9212 | 55 | 70 |
| 6 | 5 ng | — | 9211 | 374* | 599 |
| 7 | 5 ng | — | 9212 | 28* | 80 |
| 8 | — | 5 ng | 9211 | 53* | 82 |
| 9 | — | 5 ng | 9212 | 180* | 443 |

*Soln. = solution; Average of two reactions.

The solutions were heated to 95° C. for 5 minutes, then cooled to room temperature for 10 minutes. Then 20 μL 2× master mix were added to each reaction, and the reactions were incubated at 70° C. for 10 minutes. The 2× master mix contains 100 μL 10×Thermophilic DNA Pol buffer (Promega, M190A), 100 μL 25 mM $MgCl_2$ (Promega, A351B), 25 μL 40 mM NaPPi (Promega, E350B), 10 μL 10 μM ADP (Promega, A5285), 25 units Tne triple mutant (Promega), 2.5 units Pfu NDPK, and 259.4 μL Nanopure water. Each reaction contained 1 unit Tne DNA Polymerase and 0.1 units Pfu NDPK. An identical set of reactions was also performed containing 0.2 units Pfu NDPK per reaction. Four microliters of each reaction were then added to 100 μL of L/L reagent and relative light units (rlu) were measured on a TMDE™ luminometer.

The results obtained indicate that Pfu NDPK is active in this interrogation assay at 70° C. Doubling the NDPK concentration increased the light output to levels seen previously with 0.1 units yeast NDPK at 37° C.

EXAMPLE 28

One Step Interrogation on β-globin PCR Targets: Comparison of 70° C. Reaction Using Tne Triple Mutant Polymerase and Pfu NDPK to 37° C. Reaction Using Klenow exo- Polymerase and Yeast NDPK A method was carried out using a thermostable polymerase (Tne triple mutant) and thermostable NDPK (Pfu) and compared to more thermally labile polymerase (Klenow exo-) and NDPK (yeast) to assay for native and mutant sequences of β-globin. These methods were carried out at 37° C. and 70° C. As will be seen from the results that follow, use of the thermostable enzymes permit a one step (or one-pot) reaction in which depolymerization and ATP formation are carried out at an elevated temperature. The DNA interrogation probes used were 9994 (SEQ ID NO:94), 9995 (SEQ ID NO:95), 10665 (SEQ ID NO:96), and 11472 (SEQ ID NO:97). Probes 9994 and 9995 interrogate the TCTT site. Probes 10665 and 11472 interrogate the 17 (A to T) site. PCR probes used were Probe 9992 (SEQ ID NO:98) and 9993 (SEQ ID NO:99). Reaction conditions are as described in Example 31.

Two sets of the following reactions were assembled and brought to a final 20 μL volume with nanopure water:

| | | Interrogation | | |
|---|---|---|---|---|
| Reaction | Target | Oligo 1 μl/1 μg | rlu (70° C.) | rlu (37° C.) |
| 1 | — | — | 41 | 5 |
| 2 | WT* | — | 165 | 94 |
| 3 | — | WT 9994 | 51 | 12 |
| 4 | — | Mut 9995* | 42 | 6 |
| 5 | — | WT 10665 | 45 | 14 |
| 6 | — | Mut 11472 | 44 | 6 |
| 7 | WT | WT 9994 | 645* | 360* |
| 8 | WT | Mut 9995 | 199* | 109* |
| 9 | WT | WT 10665 | 525* | 233* |
| 10 | WT | Mut 11472 | 169* | 121* |

*WT = wild type; Mut = =mutant; Average of two values.

| | 2X Master Mix for 37° C. | 2X Master Mix for 70° C. |
|---|---|---|
| 10X DNAP buffer | 60 μL (Promega, M195A) | 100 μL (Promega, M190A) |
| Klenow exo- | 3.75 units | — |
| Tne triple mutant | — | 25 units |

```
CV11
5'CGCTTCTACCACGAATGCTCGCAGACCATGCTGCACGAATACGTCAGAAAG      SEQ ID NO:8

AACGTGGAGCGTCTGTTCGAGCT 3'

CV12
5'CCAACAGACGCTCCACGTTCTTTCTGACGTATTCGTGCAGCATGGTCTGCG      SEQ ID NO:9

AGCATTCGTGGTAGAAGCGAGCT 3'

CV13
5'CGCTTCTACCACGAATGCTCGCAGATCATGCTGCACGAATACGTCAGAAA       SEQ ID NO:10

GAACGTGGAGCGTCTGTTCGAGCT 3'

CV14
5'CCAACAGACGCTCCACGTTCTTTCTGACGTATTCGTGCAGCATGATCTGCG      SEQ ID NO:11

AGCATTCGTGGTAGAAGCGAGCT 3'

9211 5' CACTTTGATATTACACCCATG 3'                            SEQ ID NO:86

9212 5' CACTTTGATATTACACCCGTG 3'                            SEQ ID NO:35
```

| | -continued | |
|---|---|---|
| 40 mM NaPPi | 7.5 µL | 25 µL |
| yeast NDPK | 3 units | — |
| Pfu NDPK | — | 2.5 units |
| 10 µM ADP | 6.0 µL | 10 µL |
| Nanopure water | 219.75 µL | 259.4 µL |

Four microliters of target solution were used for the set of 37° C. reactions, 8 µL target solutions were used for the set of 70° C. reactions. The assembled reactions were heated to 95° C. for 5 minutes and then cooled to room temperature for 10 minutes. Twenty microliters of the 2× master mix were then added. The 37° C. reaction set was incubated at 37° C. for 15 minutes, the 70° C. reaction set was incubated at 70° C. for 5 minutes. Four microliters of each reaction were added to 100 µL of L/L reagent (Promega, F202A) and light output was immediately measured on a TMDE™ luminometer.

The high temperature interrogation conditions improve the discrimination ratios between wild type and mutant for the 17 (A to T) site primarily by reducing the background signal from the mismatch. Discrimination ratios at the TCTT site are essentially the same between the two temperatures.

```
Interrogation Probes:
9994  5' CCCTTGGACCCAGAGGTTCT 3'       SEQ ID NO:94

9955  5' CCCTTGGACCCAGAGGTTGA 3'       SEQ ID NO:95

10665 5' CTTCATCCACGTTCACCTTG 3'       SEQ ID NO:96

11472 5' CTTCATCCACGTTCACCTAG 3'       SEQ ID NO:97

PCR Target Probes:
9992 5' GTACGGCTGTCATCACTTAGACCTCA      SEQ ID NO:98
3'

9993 5' TGCAGCTTGTCACAAGTGCAGCTCACT    SEQ ID NO:99
3'
```

(SEQ ID NO:102) and 11450 (SEQ ID NO:103) are Campylobacter jejuni interrogation probes that bind to opposite strands of the bacterial genome represented in the synthetic target. Oligonucleotide 11451 anneals to oligonucleotide 11454. Oligonucleotide 11450 anneals to oligonucleotide 11453.

The following solutions were assembled in triplicate and nanopure water added to a final volume of 20 µL.

| Solution | 0.3 ng Target | 1 µg Probe | rlu |
|---|---|---|---|
| 1. | + | 11451 | 391 |
| 2. | + | 11450 | 241 |
| 3. | + | none | 28 |
| 4. | − | 11451 | 248 |
| 5. | − | 11450 | 30 |
| 6. | − | none | 24 |

The assembled solutions were incubated at 92° C. for 5 minutes, then cooled at room temperature for 10 minutes. Master mix was prepared as in Example 1 using 10 units Klenow exo- polymerase and 4 units NDPK. Twenty microliters of master mix were added to each tube and incubated at 37° C. for 15 minutes. Five microliters of each solution were then combined with 100 µL of L/L reagent (Promega F202A) and light output measured immediately on a Turners TD20/20 luminometer. The average relative light units (rlu) are recorded in the table above Using each of the interrogation probes with the target appears to give strong net signal. The top probe (11451) however, gives very strong signal alone, possibly due to hairpin formation, and is less suitable for interrogation. The bottom interrogation probe (11450) is the better for interrogation.

```
11453
5'CTTGAAGCATAGTTCTTGTTTTTAAACTTTGTCCATCTTGAGCCGCTTGA  SEQ ID NO:100

GTTGCCTTAGTTTTAATAGT 3'

11454
5'ACTATTAAAACTAAGGCAACTCAAGCGGCTCAAGATGGACAAAGTTTA   SEQ ID NO:101

AAAACAAGAACTATGCTTCAAG 3'

11451
5' AGTTCTTGTTTTTAAACTTTGTCCATCTTG 3'   SEQ ID NO:102

11450
5' CAAGATGGACAAAGTTTAAAAACAAGAACT 3'   SEQ ID NO:103
```

EXAMPLE 29

Detection of DNA Sequences in the Genome of Campylobacter jejuni

Oligonucleotides 11453 (SEQ ID NO:100) and 11454 (SEQ ID NO:101) are exactly complementary and can be annealed, thereby forming a synthetic target representing a 70 bp segment of Campylobacter jejuni. These two oligonucleotides were diluted in nanopure water to a final concentration of 10 µg/mL. Four microliters of each were then mixed with 232 µL 10 mM Tris pH7.3 to yield a target solution of 0.3 µg/mL of DNA. Oligonucleotides 11451

EXAMPLE 30

Enhancing Output Discrimination by Destabilizing Interrogation Probes with Internal Mismatches Prothrombin PCR fragments were interrogated to determine if they contained a single nucleotide polymorphism (SNP) associated with prothrombin as described in Example 35. The interrogation probes were designed to compare data when there is a potential for a mismatched nucleotide only at the 3'-terminal base of the interrogation probe versus an interrogation probe having this same potential mismatch and an additional mismatch 9 bases from the 3' end.

Probes PT5 and PT6 (SEQ ID NO:104 and SEQ ID NO:105, respectively) were used to PCR amplify a region of human genomic DNA spanning about 500 base pairs encoding the prothrombin gene. The PT5 probe has phosphothioate linkages between the first five bases at the 5' end. As described in Example 38, below, these linkages, present on one strand of the resulting PCR product, are resistant to cleavage with T7 Polymerase Exonuclease 6 (Exo 6). The PCR reaction was set up as follows:

| | |
|---|---|
| 10 µL | 10X PCR buffer |
| 6 µL | 25 mM MgCl2 |
| 2 µL | 10 mM dNTP mixture (2.5 mM each dNTP) |
| 2 µL | 100 pmoles probe PT5 |
| 2 µL | 100 pmoles probe PT6 |
| 4 µL | human genomic DNA (Promega, G3041) |
| 75 µL | water |
| 2.5 units | Taq (Promega, M1861) |

The PCR cycling parameters were: 94° C., 2 minutes; (94° C., 30 seconds; 60° C., 1 minute; 70° C., 1 minutes)× 35; 70° C., 7 minutes; 4° C. soak. Ten microliters of the PCR reaction were run on a 1.5% agarose gel, ethidium bromide stained, and a band of correct size was visualized under UV light. To 25 µL of the PCR reaction were added 50 units of Exo 6, and the sample was incubated at 37° C. for 15 minutes. The sample was then treated with Exo 6 as described in Example 38, below, and purified away from the free nucleotides using MagneSil™ paramagnetic particles (Promega, A1330) according to manufacturer's instructions. Four microliters of the 100 µL eluted DNA were interrogated with probes PT7 (SEQ ID NO:106), PT8 (SEQ ID NO:107), PT9 (SEQ ID NO:108), and PT10 (SEQ ID NO:109) in four separate reactions.

PT7 and PT9 differ only in the nucleotide present nine nucleotides from the 3' end. Probe PT7 has a base complementary to the wild type sequence nine bases from the 3' end, whereas probe PT9 has a mismatching base at that position. These two probes have a 3' terminal nucleotide that matches wild type prothrombin. PT8 and PT10 differ only in the nucleotide present nine nucleotides from the 3' end. Probe PT8 has a base complementary to the wild type sequence nine bases from the 3' end, whereas probe PT10 has a mismatching base at that position. These two probes have a 3'-terminal nucleotide that matches the mutant prothrombin, but is a mismatch with wild type.

The interrogation reactions were set up as follows: 4 µL target DNA were combined with 150 pmol of interrogation oligonucleotide probe (or none for control reaction) and water to a final volume of 20 µL. These samples were incubated at 95° C. for 3 minutes, followed by incubation at 37° C. for 10 minutes. Then 20 µL master mix were added, and the tube incubated at 37° C. for an additional 15 minutes. The master mix contains 71 µL water, 20 µL 10× DNA Pol buffer (Promega, M195A), 5 µL 40 mM NaPPi, 2 µL 10 µM ADP, 1 unit NDPK, and 2 units Klenow exo- (Promega, M218A). Then, 100 µL of L/L reagent (Promega, FF2021) were added and the relative light units measured immediately in a Turner⁰ TD20/20 luminometer. The control values from samples lacking an interrogation oligonucleotide were subtracted and the results are reported in the Table below.

| Reaction | Interrogation oligo | Relative Light Units |
|---|---|---|
| 1. | PT7 | 1520 |
| 2. | PT8 | 495 |
| 3. | PT9 | 1724 |
| 4. | PT10 | 219 |

The results indicate that the additional mismatch, internally located in the interrogation probe, helped to increase the level of discrimination observed between wild type and mutant probes. When the internal mismatch was not present in the interrogation probes, there was 3.1-fold discrimination, whereas when the internal mismatch was present in the interrogation probes, there was 7.9-fold discrimination.

| | | | |
|---|---|---|---|
| PT5 | 5' ATAGCACTGGGAGCATTCAGGC 3' | SEQ ID NO:104 |
| PT6 | 5' GCACAGACGGCTGTTCTCTT 3' | SEQ ID NO:105 |
| PT7 | 5' GTGACTCTCAGCG 3' | SEQ ID NO:106 |
| PT8 | 5' GTGACTCTCAGCA 3' | SEQ ID NO:107 |
| PT9 | 5' GTGATTCTCAGCG 3' | SEQ ID NO:108 |
| PT10 | 5' GTGATTCTCAGCA 3' | SEQ ID NO:109 |

EXAMPLE 31

Determination of the Presence of the Leiden Mutation of Factor V

A synthetic first nucleic acid target of the Factor V gene was designed to have the wild type sequence that contains a G at position 32 of FV1 (SEQ ID NO:25). The complementary strand, FV2, (SEQ ID NO:26) had 4 additional bases at its 3'-terminus. A second synthetic nucleic acid target of Factor V was designed to have the Leiden mutation, an A residue at position 32 of FV3 (SEQ ID NO:27). The mutant complementary strand, FV4 (SEQ ID NO:28) also had 4 additional bases at its 3'-terminus. The nucleic acid target oligonucleotides, FV1 to FV4, were separately dissolved at a concentration of one mg/mL in water.

Nucleic acid probe FV5 (SEQ ID NO:29) was synthesized to be totally complementary to one strand of the first target, FV1. The probe was synthesized to place the complementary C residue at an interrogation position penultimate to the 3'-terminal nucleotide of the probe FV5, corresponding to the G at position 32 of FV1. Similarly, a synthetic nucleic acid probe was prepared having sequence FV6 (SEQ ID NO:30) that is totally complementary to one strand of the second target, Factor V with the Leiden mutation, FV3. The probe was synthesized to place the complementary T residue at an interrogation position penultimate to the 3'-terminal nucleotide of the probe FV6, corresponding to the A at position 32 of FV3. Nucleic acid probe stock solutions had a concentration of one mg/mL in water.

The FV1 oligonucleotide was mixed with an equal amount of its complementary strand, FV2, heated to 95° C. for about 15 minutes and then cooled to room temperature to produce a first sample containing a double stranded DNA segment including the first nucleic acid target, corresponding to the wild type sequence of the Factor V gene.

The FV3 oligonucleotide was mixed with an equal amount of its complementary strand having FV4, heated to 95° C. for about 15 minutes, and then cooled to room temperature to produce a second sample that included a double stranded DNA (dsDNA) segment containing the second target, the sequence of the Factor V gene in the region of the Leiden mutation.

One microliter of the dsDNA sample to be assayed for the presence of the first or second target was admixed with 1 μL of a nucleic acid probe and 18 μL of water to form separate hybridization compositions. Controls had 1 μL of the dsDNA sample and 19 μL of water.

They were denatured by heating to 95° C. for three minutes, then maintained for 10 minutes under hybridizing conditions (in a 37° C. incubator) to form separate treated samples.

A master mix was assembled containing 10×DNA Polymerase Buffer (20 μL; Promega, M195), sodium pyrophosphate (5 μL of 40 mM Na$_4$P$_2$O$_7$ solution; Promega, C113), Klenow Exo Minus (5 μL; 5 U; Promega, M218), NDPK (1 μL of a 10U/μL solution of NDPK [Sigma, N0379], dissolved in water), ADP (2 μL of a 10 μM solution of ADP [Sigma, A5285] dissolved in water), and water (67 μL).

The hybridized, treated samples (20 gL) were each mixed with the master mix and maintained for 15 minutes at 37° C. to form a depolymerized sample.

The depolymerized sample was added to 100 μL L/L reagent (Promega, F202A), and the amount of light produced was read on a Turner® TD20/20 luminometer. A total of 8 samples and two controls were analyzed. The averaged results are shown below.

| Assay No. | Nucleic Acid Target in Sample | Nucleic Acid Probe | Average Relative Light Units |
|---|---|---|---|
| 1, 2 | Factor V | Factor V | 1063 |
| 3, 4 | Factor V | Factor V Leiden | 88.8 |
| 5 | Factor V | none | 8.652 |
| 6, 7 | Factor V Leiden | Factor V | 139.8 |
| 8, 9 | Factor V Leiden | Factor V Leiden | 1016 |
| 10 | Factor V Leiden | none | 7.587 |

The data show that the light signal is about 10 fold greater when the nucleic acid probe is exactly complementary to the nucleic acid target (Assay Nos. 1, 2, 8 and 9) than when the nucleic acid probe is partially complementary to the nucleic acid target with the mismatch at the position penultimate to the 3'-terminal nucleotide (Assay Nos. 3, 4, 6, and 7). The latter signal is in turn about 10-fold greater than the light generated when there is no probe to hybridize to the nucleic acid target (Assay Nos. 5 and 10).

Factor V gene and the Leiden allele of this gene. Oligonucleotides FV7 (SEQ ID NO:110) and FV8 (SEQ ID NO:111) were dissolved at 1 mg/mL in water. Oligonucleotides FV1 (SEQ ID NO:25), FV2 (SEQ ID NO:26), FV3 (SEQ ID NO:27) and FV4 (SEQ ID NO:28) were used as targets, and the following solutions were assembled.

| Solution | Target (μL) | Probe (μL) | Water (μL) |
|---|---|---|---|
| 1 and 2 | 1 FV1 + FV2 | 1 FV7 | 18 |
| 3 and 4 | 1 FV1 + FV2 | 1 FV8 | 18 |
| 5 | 1 FV1 + FV2 | none | 19 |
| 6 and 7 | 1 FV3 + FV4 | 1 FV7 | 18 |
| 8 and 9 | 1 FV3 + FV4 | 1 FV8 | 18 |
| 10 | 1 FV3 + FV4 | none | 19 |

The above solutions were heated to 95° C. for three minutes, then placed in a 37° C. incubator for 10 minutes. The following master mix was assembled:

| | |
|---|---|
| 10X DNA Polymerase Buffer (Promega M195) | 20 μL |
| 40 mM Sodium Pyrophosphate (Promega C113) | 5 μL |
| 10 U/μl Klenow Exo Minus (Promega M218) | 5 μL |
| NDPK (Sigma, NO379 at 10 U/μL in water) | 1 μL |
| ADP (Sigma A5285, 10 μM in water) | 2 μL |
| Water | 67 μL |
| | 100 μL |

Twenty microliters of master mix were added to each of the heated nucleotide mixes after incubation at 37° C. for 10 minutes. The resulting reactions were incubated for 15 minutes at 37° C. and then added to 100 μL L/L reagent (Promega, F202A) and the light produced was immediately read using a Turner® TD20/20 luminometer.

```
FV1
5'CTAATCTGTAAGAGCAGATCCCTGGACAGGCGAGGAATACAGAGGGCAGCAGACATCGAAGAGCT 3'          SEQ ID NO:25

FV2
5'AGCTCTTCGATGTCTGCTGCCCTCTGTATTCCTCGCCTGTCCAGGGATCTGCTCTTACAGATTAGAGCT 3'      SEQ ID NO:26

FV3
5'CTAATCTGTAAGAGCAGATCCCTGGACAGGCAAGGAATACAGAGGGCAGCAGACATCGAAGAGCT 3'          SEQ ID NO:27

FV4
5'AGCTCTTCGATGTCTGCTGCCCTCTGTATTCCTTGCCTGTCCAGGGATCTGCTCTTACAGATTAGAGCT 3'      SEQ ID NO:28

FV5  5' CTGCTGCCCTCTGTATTCCTCG 3'                                                 SEQ ID NO:29

FVG  5' CTGCTGCCCTCTGTATTCCTTG 3'                                                 SEQ ID NO:30
```

EXAMPLE 32

Determination of the Presence or Absence of a Nucleotide Sequence in a Sample Known to be Associated with the Factor V Leiden Phenotype in Humans with Additional Interrogation Probes In this Example, another pair of probes, complementary to the opposite template strand as those used in Example 31, were used to detect the gene sequences of the wild type The following results were obtained.

| Reaction | Relative Light Units |
|---|---|
| 1 | 217.9 |
| 2 | 237.9 |
| 3 | 47.76 |
| 4 | 48.33 |
| 5 | 5.903 |
| 6 | 18.79 |
| 7 | 19.19 |
| 8 | 186.8 |
| 9 | 181.5 |
| 10 | 5.837 |

These data show that probe FV7 gave a much stronger signal than FV8 on DNA containing a sequence corresponding the native Factor V gene, and thus can be used to detect this DNA sequence in a sample. Probe FV8 gave a much stronger signal than FV7 on DNA containing a sequence encoding the Factor V gene in the region of the Leiden mutation.

```
FV1
5'CTAATCTGTAAGAGCAGATCCCTGGACAGGCGAGGAATACAGAGGGCAGCAGACATCGAAGAGCT 3'        SEQ ID NO:25

FV2
5'AGCTCTTCGATGTCTGCTGCCCTCTGTATTCCTCGCCTGTCCAGGGATCTGCTCTTACAGATTAGAGCT 3'   SEQ ID NO:26

FV3
5'CTAATCTGTAAGAGCAGATCCCTGGACAGGCAAGGAATACAGAGGGCAGCAGACATCGAAGAGCT 3'       SEQ ID NO:27

FV4
5'AGCTCTTCGATGTCTGCTGCCCTCTGTATTCCTTGCCTGTCCAGGGATCTGCTCTTACAGATTAGAGCT 3'   SEQ ID NO:28

FV7 5' GACAAAATACCTGTATTCCTCG 3'                                             SEQ ID NO:110

FV8 5' GACAAAATACCTGTATTCCTTG 3'                                             SEQ ID NO:111
```

EXAMPLE 33

Detection of a Sequence in the Cystic Fibrosis Gene in the Region of the Delta 508 Mutation In this Example, an assay was performed to detect a sequence that encodes a segment of the cystic fibrosis gene spanning the mutation known as the delta F508 allele.

Oligonucleotides CF1 (SEQ ID NO:112) and CF2 (SEQ ID NO:113) were synthesized and redissolved in water at a concentration of 50 pmol/µL. These primers were used to produce an amplified segment of the human chromosomal DNA by PCR amplification. PCR reactions contained 20 ng human genomic DNA, 50 pmol each primer, 1× Promega Taq Reaction Buffer with 1.5 mM $MgCl_2$ (Promega, M188A), 200 FM dNTPs, and 1.25 U Taq DNA Polymerase (Promega M186A). Cycling conditions were 1×2 minutes at 94° C., 35×[0.5 minutes at 94° C., 1 minute at 60° C., 1 minute at 72° C.], 1×7 minutes at 72° C., 4° C. soak. The amplified DNA was purified using Wizard PCR Preps (Promega A7170) by mixing 25 FL PCR product with 1 mL resin and washing with 3×1 mL 80% isopropanol. This DNA was used to represent wild type human DNA encoding the cystic fibrosis gene spanning the delta F508 mutation.

Oligonucleotides CF6 (SEQ ID NO:117) and CF7 (SEQ ID NO:118) were dissolved in water at a concentration of 1 mg/mL, mixed and annealed to form a double strand DNA segment as described for oligonucleotide FV1 and FV2 above. This DNA was used to represent human DNA encoding the delta F508 mutation at this locus.

Oligonucleotide probes CF3 (SEQ ID NO:114), CF4 (SEQ ID NO:115) and CF5 (SEQ ID NO:116) were prepared. The sequence of probe CF3 is completely complementary to wild type cystic fibrosis gene. The sequence of probe CF4 was identical to that of probe CF3 except for the 3'-terminal nucleotide that is complementary to the nucleotide present in the delta F508 mutation, and thus was completely complementary to one strand of that mutant sequence. The sequence of probe CF5 was completely complementary to the second strand of that F508 mutant sequence, and also therefore differed from a total complement of probe CF3 at the 3-terminal nucleotide. The probes were separately dissolved in water to a concentration of 1 mg/mL. The following solutions were assembled.

| Solution | Probe (µL) | Target (µL) | Water (µL) |
|---|---|---|---|
| 1 and 2 | 1, CF3 | 4, Purified, Amplified DNA | 15 |
| 3 and 4 | 1, CF4 | 4, Purified, Amplified DNA | 15 |
| 5 and 6 | 1, CF5 | 4, Purified, Amplified DNA | 15 |
| 7 | none | 4, Purified, Amplified DNA | 16 |
| 8 and 9 | 1, CF3 | 1, Annealed (CF6 + CF7) | 18 |
| 10 and 11 | 1, CF4 | 1, Annealed (CF6 + CF7) | 18 |
| 12 and 13 | 1, CF5, | 1, Annealed (CF6 + CF7) | 18 |
| 14 | none | 1, Annealed (CF6 + CF7) | 19 |

These solutions were heated at 95° C. for 3 minutes and then placed in a 37° C. incubator for 10 minutes.

A master mix was assembled as described in Example 32 and 20 µL of this solution were added to each of solutions 1–14 above. They were incubated for another 15 minutes at 37° C.

The solutions were added to 100 µL of L/L reagent (Promega F202A)) and the light produced by the reactions was immediately measured using a Turner® TD 20/20 luminometer. The following results were obtained.

| Solution | Relative Light Units | Net Average RLU* |
|---|---|---|
| 1 | 1527 | 762 |
| 2 | 1683 | |
| 3 | 766.7 | (−48.5) |
| 4 | 823.5 | |
| 5 | 893.2 | 44.1 |
| 6 | 881.0 | |
| 7 | 843.4 | |
| 8 | 72.73 | 11.0 |
| 9 | 80.05 | |
| 10 | 310.9 | 306.5 |
| 11 | 302.1 | |
| 12 | 439.0 | 434.4 |
| 13 | 429.8 | |
| 14 | 65.90 | |

*The net value is calculated by averaging the duplicate samples and subtracting the target alone value measured for the different sets.

These data show that probe CF3 provided much higher signals with wild type DNA than were provided by either of probes CF4 or CF5 that had a mismatched nucleotide at the site of the mutation. In addition, both probes CF4 and CF5 that were completely complementary to the mutant sequence provided much higher signals with DNA encoding the delta F508 mutant than with wild type DNA.

```
CF1  5' CATTCACAGTAGCTTACCCA 3'               SEQ ID NO:112

CF2  5' GCAGAGTACCTGAAACAGGA 3'               SEQ ID NO:113

CF3  5' CATCATAGGAAACACCAAG 3'                SEQ ID NO:114

CF4  5' CATCATAGGAAACACCAAT 3'                SEQ ID NO:115

CF5  5' GGCACCATTAAAGAAAATATCATT 3'           SEQ ID NO:116

CF6
5' CTGGCACCATTAAAGAAAATATCATTGGTG            SEQ ID NO:117

TTTCCTATGATGAATATAG

CF7
5' CTATATTCATCATAGGAAACACCAATGATA            SEQ ID NO:118

TTTTCTTTAATGGTGCCAG 3'
```

EXAMPLE 34

Detection of a Sequence in the Cystic Fibrosis Gene in the Region of the Delta 508 Mutation including a Sample Containing Both the Normal and Delta F508 Alleles This Example demonstrates an assay that detects a sequence encoding a segment of the cystic fibrosis gene spanning the mutation known as the delta F508 allele. The assay is illustrated using the wild type human sequence of this gene in this region and using a sample that has both alleles. The results here demonstrate that the assay can discriminate between homozygotes for these alleles, and can be used to detect heterozygote samples in which both alleles are present together, as would be the case with a carrier for a wide variety of genetic diseases.

Oligonucleotides CF8 (SEQ ID NO:119) and CF9 (SEQ ID NO:120), a synthetic wild type target, were dissolved in water and annealed as described for Example 31. CF6 (SEQ ID NO:117) and CF7 (SEQ ID NO:118) were also used as targets. CF3 (SEQ ID NO:114) and CF4 (SEQ ID NO:115) were used as probes. The following solutions were assembled.

| Solution | Probe (μL) | Target(s) (μL) | Water (μL) |
|---|---|---|---|
| 1 and 2 | 1, CF3 | 1, Annealed (CF8 + CF9) | 18 |
| 3 and 4 | 1, CF4 | 1, Annealed (CF8 + CF9) | 18 |
| 5 | none | 1, Annealed (CF8 + CF9) | 19 |
| 6 and 7 | 1, CF3 | 1, Annealed (CF6 + CF7) and 1, Annealed (CF8 + CF9) | 17 |
| 8 and 9 | 1, CF4 | 1, Annealed (CF6 + CF7) and 1, Annealed (CF8 + CF9) | 17 |
| 10 | none | 1, Annealed (CF6 + CF7) and 1, Annealed (CF8 + CF9) | 18 |
| 11 and 12 | 1, CF3 | 1, Annealed (CF6 + CF7) | 18 |
| 13 and 14 | 1, CF4 | 1, Annealed (CF6 + CF7) | 18 |
| 15 | none | 1, Annealed (CF6 + CF7) | 19 |

The above solutions were heated at 95° C. for 3 minutes, then placed in a 37° C. incubator for 10 minutes. A master mix was made as in Example 32 and 20 μL of this solution were then added to each of tubes 1–15. The tubes were incubated at 37° C. for an additional 15 minutes, then the solutions were added to 100 μL of L/L reagent (Promega F202A) and the light produced by the reactions was read immediately using a Turner® TD20/20 luminometer. The following data were obtained.

| Sample | Relative Light Units | Adjusted Net Light Value* |
|---|---|---|
| 1 | 310.1 | 307.9 |
| 2 | 342.3 | |
| 3 | 22.45 | 4.41 |
| 4 | 23.02 | |
| 5 | 18.29 | |
| 6 | 400.2 | 346.98 |
| 7 | 393.7 | |
| 8 | 332.3 | 269.38 |
| 9 | 306.4 | |
| 10 | 49.97 | |
| 11 | 96.67 | 37.68 |
| 12 | 109.1 | |
| 13 | 371.3 | 305.4 |
| 14 | 369.8 | |
| 15 | 65.22 | |

*This value was calculated by averaging the duplicate reactions and subtracting the value measured for the appropriate target alone control reaction.

These data again show that probe CF3 provided a much stronger signal with normal (wild type; homozygous) DNA than did probe CF4, and probe CF4 provided a much stronger signal with the homozygous delta F508 mutation target than did probe CF3. In addition, when both targets were present in the sample, as in a heterozygote, signals were provided from both probes to indicate the presence of a heterozygote. Thus, the analytical output from this method illustrated whether the nucleic acid target sequence in a nucleic acid sample was homozygous or heterozygous, and when homozygous, which of the alleles was present.

| | |
|---|---|
| CF3 5' CATCATAGGAAACACCAAG 3' | SEQ ID NO:114 |
| CF4 5' CATCATAGGAAACACCAAT 3' | SEQ ID NO:115 |
| CF6 5' CTGGCACCATTAAAGAAAATAT CATTGGTGTTTCCTATGATGAATATAG 3' | SEQ ID NO:117 |
| CF7 5'CTATATTCATCATAGGAAACAC CAATGATATTTTCTTTAATGGTGCCAG 3' | SEQ ID NO:118 |
| CF8 5'CTGGCACCATTAAAGAAAATAT CATCTTTGGTGTTTCCTATGATGAATATAG 3' | SEQ ID NO:119 |
| CF9 5'CTATATTCATCATAGGAAACAC CAAAGATGATATTTTCTTTAATGGTGCCAG 3' | SEQ ID NO:120 |

EXAMPLE 35

Detection of DNA Sequences Corresponding to the Prothrombin Gene in the Region of a Single Nucleotide Polymorphism An assay for the presence or absence of a mutation in the human prothrombin gene is illustrated in this Example. This SNP is characterized by a G to A substitution in the prothrombin gene.

Oligonucleotides PT1 (SEQ ID NO:121), PT2 (SEQ ID NO:122), PT3 (SEQ ID NO:123), and PT4 (SEQ ID NO:124) were synthesized and dissolved in water to a concentration of 1 mg/mL. A sample of PT1 and PT2 were then diluted to 0.3 ng in water for use in the solutions below, and the following solutions were made.

| Solution | Probe (µL) | Target (µL) | Water (µL) |
|---|---|---|---|
| 1 and 2 | 1, PT3 | 1, PT1 | 18 |
| 3 and 4 | 1, PT4 | 1, PT1 | 18 |
| 5 | none | 1, PT1 | 19 |
| 6 and 7 | 1, PT3 | 1, PT2 | 18 |
| 8 and 9 | 1, PT4 | 1, PT2 | 18 |
| 10 | none | 1, PT2 | 19 |

These solutions were heated at 95° C. for three minutes then placed in a 37° C. incubator for 10 minutes.

A master mix was assembled as in Example 32 and 20 µL of this solution were added to each of solutions 1–10, above, and all solutions were incubated for 15 minutes at 37° C. After this incubation, these solutions were added to 100 µL of L/L reagent (Promega F202A) and the light produced by the solution immediately read using a Turner® TD 20/20 luminometer. The following results were obtained.

| Sample | Relative Light Units |
|---|---|
| 1 | 240.9 |
| 2 | 253.3 |
| 3 | 56.10 |
| 4 | 55.88 |
| 5 | 5.88 |
| 6 | 29.61 |
| 7 | 31.49 |
| 8 | 738.0 |
| 9 | 646.8 |
| 10 | 6.21 |

These data demonstrate the probe PT3 provided much higher signals with a wild type target (PT1) than does probe PT4, but that probe PT4 provided a much higher signal with mutant template (PT2) than did PT3.

| | |
|---|---|
| PT1 5' TCCCAATAAAAGTGACTCTCAGCGA GCCTCAATGCTCCCAGTGCTATTCA 3' | SEQ ID NO:121 |
| PT2 5' TCCCAATAAAAGTGACTCTCAGCAA GCCTCAATGCTCCCAGTGCTATTCA 3' | SEQ ID NO:122 |
| PT3 5' GGAGCATTGAGGCTCG 3' | SEQ ID NO:123 |
| PT4 5' GGAGCATTGAGGCTTG 3' | SEQ ID NO:124 |

EXAMPLE 36

Detection of DNA Sequences Associated with DNA Translocations

An assay is described in this Example that permits a particular type of human DNA translocation to be detected. The particular translocation takes place in the region of the bcr gene, and a segment of the abl gene is involved with the translocation.

Oligonucleotides BA1 (SEQ ID NO:125), BA2 (SEQ ID NO:126), BA3 (SEQ ID NO:127) and BA4 (SEQ ID NO:128) were synthesized and dissolved in water at a concentration of 1 mg/mL. BA1 and BA2 were diluted 1:1000 in water and the following solutions were assembled.

| Solution | Probe (µL) | Target (µL) | Water (µL) |
|---|---|---|---|
| 1 and 2 | 1, BA3 | 1, BA1 | 18 |
| 3 and 4 | 1, BA4 | 1, BA1 | 18 |
| 5 | none | 1, BA1 | 19 |
| 6 and 7 | 1, BA3 | 1, BA2 | 18 |
| 8 and 9 | 1, BA4 | 1, BA2 | 18 |
| 10 | none | 1, BA2 | 19 |

These solutions were heated at 95° C. for 3 minutes then placed in a 37° C. incubator for 10 minutes.

A master mix was assembled as described in Example 32. After solutions 1–10 were separately incubated for 10 minutes at 37° C., 20 µL of master mix were added to each, and the resulting solutions were heated for an additional 15 minutes at 37° C. After this time, the contents of the tubes were added to 100 µL of L/L reagent (Promega F202A) and the resulting light produced was read immediately using a Turner® TD 20/20 luminometer. The following results were obtained.

| Solution | Relative Light Units |
|---|---|
| 1 | 1284 |
| 2 | 1414 |
| 3 | 126.9 |
| 4 | 124.7 |
| 5 | 27.21 |
| 6 | 33.73 |
| 7 | 36.68 |
| 8 | 1061 |
| 9 | 1040 |
| 10 | 24.04 |

These data show that probe BA3 provided a much greater signal with DNA sequences corresponding to the wild type bcr gene than with mutant DNA. Conversely, probe BA4 provided a much greater signal with a DNA sequence that corresponds to the sequence from a bcr/abl translocation than with the normal DNA.

BA1
5' CAGTACTTACTTGAACTCTGCTTAAAT        SEQ ID NO:125
CCAGTGGCTGAGT 3'

BA2
5' CTGAAGGGCTTTTGAACTCTGCTTAAA        SEQ ID NO:126
TCCAGTGGCTGAGT 3'

BA3
5' TGGATTTAAGCAGAGTTCAAGT 3'           SEQ ID NO:127

BA4
5' TGGATTTAAGCAGAGTTCAAAA 3'           SEQ ID NO:128

EXAMPLE 37

Use of Chemical DNA Denaturation of Target DNA Prior to Genotype Determination

In this Example, denaturation of target DNA by chemical agents is compared to high temperature denaturatin.

An amplified DNA segment containing a segment of the Factor V gene in the region of the Leiden mutation, but from wild type DNA was produced as described in Example 32.

The amplified DNA was purified using a commercial DNA purification system (Promega, A7170) as described in Example 32. Probe FV7 (SEQ ID NO:110) and FV8 (SEQ ID NO:111) were used, and the following solutions were assembled.

| Solution | Target* (µL) | Probe (µL) | Water (µL) | Total (µL) |
|---|---|---|---|---|
| 1 and 2 | 4 | 1, FV7 150 (pmol) | 15 | 20 |
| 3 and 4 | 4 | 1, FV8 | 15 | 20 |
| 5 | 4 | none | 15 | 20 |
| 6, 7, 11, 12, 16, and 17 | 4 | 1, FV8 | 4 | 9 |
| 8, 9, 13, 14, 18 and 19 | 4 | 1, FV7 | 4 | 9 |
| 10, 15, and 20 | 4 | none | 5 | 9 |

Solutions 1–5 were heated at 95° C. for three minutes then put in a 37° C. incubator for 10 minutes. Solutions 6–10 were treated with 1 µL 0.2 N sodium hydroxide for 1–2 minutes, then 10 µL water were added. Solutions 11–15 were treated with 1 µl 0.2 N sodium hydroxide for 1–2 minutes, then 10 µL 50 mM Tris HCl pH 7.3 were added. Solutions 16–20 were treated with 1 µL 0.2 N sodium hydroxide for 1–2 minutes, then 10 µL 100 mM Tris HCl pH 7.3 were added. After these treatments, solutions 7–18 were placed in a 37° C. incubator for 5 minutes.

A master mix was assembled as in Example 32 After the treatments described above, 20 µL of master mix were added to solutions 1–18 and the solutions were then incubated for 15 minutes at 37° C. After this incubation, the contents of the tubes were added to 100 µL L/L reagent (Promega F202A) and the light production from the reactions was read immediately using a Turners TD 20/20 luminometer. The following results were obtained.

| Solution | Relative Light Units | Net Average Light Units |
|---|---|---|
| 1 | 1495 | 1343 |
| 2 | 1540 | |
| 3 | 278.7 | 100.1 |
| 4 | 269.5 | |
| 5 | 174 | 0 |
| 6 | 625 | 1383.2 |
| 7 | 1539 | |
| 8 | 305.1 | 106.9 |
| 9 | 306.3 | |
| 10 | 198.8 | 0 |
| 11 | 1629 | 1408.8 |
| 12 | 1638 | |
| 13 | 304.9 | 82.15 |
| 14 | 308.8 | |
| 15 | 224.7 | 0 |
| 16 | 1595 | 1350.2 |
| 17 | 1567 | |
| 18 | 303.2 | 76.95 |
| 19 | 312.3 | |
| 20 | 230.8 | 0 |

These data indicate that either chemical denaturation or heat denaturation can be used prior to primer pyrophosphorylation without greatly affecting the results.

FV7 5' GACAAAATACCTGTATTCCTCG 3'        SEQ ID NO:110

FV8 5' GACAAAATACCTGTATTCCTTG 3'        SEQ ID NO:111

EXAMPLE 38
Reduction of Target Background by Removal of One Strand of a Double Strand DNA Target A particular target produced by amplification of a segment of the rice genome is interrogated in this Example. It was found that this target produces high background signal values if nothing is done to eliminate one strand of the amplified DNA target and did not exhibit discrimination between two primers that were designed to detect a SNP present in some rice strains. This Example illustrates how one can purposefully destroy one of the amplified DNA strands and interrogate the other strand. For this case in particular, such manipulations result in greatly reduced background light signals from the target, permitting clear determination of the interrogation signals.

Probes RS1 (SEQ ID NO:129) and RS2 (SEQ ID NO:130) were dissolved at a concentration of 50 pmole/µL in water. Probe RS1 contained phosphorothioate linkages at the first four 5'-terminal linkages that are not cleaved by the enzyme used in the reaction. DNA was isolated from rice and was at a concentration of 10 µg/mL. The following solution was assembled in duplicate:

| Component | Volume (µL) |
|---|---|
| 10X DNA Polymerase buffer without MgCl$_2$ (Promega M190A) | 5 |
| 25 mM MgCl$_2$ (Promega A351A) | 3 |
| 10 mM dNTP mixture (Promega C114A) | 1 |
| Primer RS1 (50 pmol/µL) | 1 |
| Primer RS2 (50 pmol/µL) | 1 |
| Rice genomic DNA (10 ng/µL) | 1 |
| Water | 38 |
| Taq DNA Polymerase (Promega M186A) | 1.25U |

These solutions were heated to 94° C. for two minutes, then subjected to the following temperature cycling program for 35 cycles: 0.5 minutes, 94° C.; 1 minute, 60° C.; 1 minute, 70° C. Then the solution was held at 70° C. for 7 minutes then cooled to 4° C.

The two reaction tubes were pooled and mixed and then 3–25 µL samples were removed and placed into individual tubes. The compositions within the individual tubes were treated with T7 Exonuclease 6 (USB, E700254) as follows.

Solution 1

No Exo 6 addition or further heating

Solution 2

50 U of Exo 6 and heated for 15 minutes at 37° C.

Solution 3

50 U of Exo 6 and heated for 30 minutes at 37° C.

The DNA in the resulting solutions was purified using the following method:

1. 200 µL of a slurry containing 15 µL MagneSil™ paramagnetic particles (Promega) in solution containing 0.4 M guanidine thiocyanate and 0.08 M potassium acetate were added to each sample.
2. The MagneSil™ paramagnetic particles were mixed in the solutions and held against the side of the tube with a magnet.
3. The particles were washed twice with 200 µL of 70% ethanol by addition of the solution to the tubes, resuspension of the particles in the solution, recapture of the particles against the tube walls with the magnet and removal of the particle-free solution.
4. The particles were resuspended in fifty microliters of water.
5. 200 µL 0.4 M GTC and 0.08 M potassium acetate were added to each.
6. Step 2 was repeated as described above except that three washes with 70% ethanol were performed.
7. The particles were resuspended in 100 µL water, the particles were captured against the side of the tube, and the solution containing the purified DNA was transferred to a new tube.

A master mix was made as described in Example 32, and primers RS3 (SEQ ID NO:131) and RS4 (SEQ ID NO:132) were resuspended at a concentration of 1 mg/mL in water. Each of the purified DNAs was assembled into reaction solutions as described below.

| Solution | Probe (µL) | Purified DNA Target (µL) | Water (µL) |
|---|---|---|---|
| Wild Type (WT) Probe | 1, RS3 | 4 | 15 |
| Variant Probe | 1, RS4 | 4 | 15 |
| No Probe | none | 4 | 16 |

These solutions were heated at 95° C. for 3 minutes, then placed in a 37° C. incubator for 10 minutes. After the 10 minute incubation, 20 µL of master mix were added to all tubes and the tubes were incubated again for 15 minutes at 37° C. After this second incubation, the solutions were added to 100 µl L/L reagent (Promega, F202A) and the light produced measured immediately using a Turner® TD 20/20 luminometer.

The following results were obtained:

| | Relative Light Units Measured | | |
|---|---|---|---|
| Target | WT Probe | Variant Probe | No Probe |
| No Exo 6 Treatment | 759.0 | 776.0 | 401.6 |
| 15 min. Exo 6 Treatment | 556.6 | 138.4 | 122.3 |
| 30 min. Exo 6 Treatment | 543.2 | 257.4 | 203.0 |

Calculation of Net Light Units and Ratio of Response

| | Net Light Units* | | |
|---|---|---|---|
| Target | WT Probe | Variant Probe | Ratio** |
| No Exo 6 Treatment | 357.4 | 374.4 | 0.95 |
| 15 min. Exo 6 Treatment | 434.3 | 16.1 | 27.0 |
| 30 min. Exo 6 Treatment | 340.2 | 54.4 | 6.25 |

*Net light units are calculated by subtracting the no probe value from the other two values
**Ratio is calculated by dividing the net light units for the WT probe by the net light units for the variant reaction.

The exonuclease used in this example hydrolyzes double-stranded DNA in a 5' to 3' direction, but cannot hydrolyze the DNA if phosphorothioate linkages are present on the 5' end of the DNA to be digested. Thus, the treatment used above should eliminate one strand of the amplified DNA made by extension of primer RS2 but should not eliminate the strand made by extension of primer RS1. This treatment both reduced the response of reactions without primer and permitted the discrimination of the SNP at the interrogation site.

RS1 5'C*C*C*A*ACACCTTACAGAAATTAGC 3'     SEQ ID NO:129

(* signifies the presence of a phosphorothioate linkage between the indicated bases.)

RS2 5'TCTCAAGACACAAATAACTGCAG 3'     SEQ ID NO:130

RS3 5'AGAACATCTGCAAGG 3'     SEQ ID NO:131

RS4 5'AGAACATCTGCAAGT 3'     SEQ ID NO:132

EXAMPLE 39

Determination of SNPs in DNA Isolated from Plant Materials

The procedures detailed in Example 38 are used here to determine the genotype of rice DNAs at a known SNP site.

Five coded DNA samples and two DNA samples of known genotype (the "G" allele and the "T" allele) were obtained and subjected to amplification with probes RS1 (SEQ ID NQ: 129) and RS2 (SEQ ID NO:130)as described in the previous Example. The DNA was then treated with T7 Exonuclease 6 for 15 minutes at 37° C. and purified as in the previous Example. The resulting purified DNA was subjected to pyrophosphorylation reactions using probes RS3 (SEQ ID NO:131), RS4 (SEQ ID NO:132), or no probe and the reaction products added to L/L reagent (Promega, F202A) and light production measured as in the previous example.

The following results were obtained:

| DNA Analyzed | Relative Light Units Measured | | |
|---|---|---|---|
| | WT Probe (RS3 G Allele) | Variant Probe (RS4 T Allele) | No Probe |
| #1 | 784.5 | 307.5 | 229.9 |
| #2 | 286.3 | 882.7 | 227.9 |
| #3 | 291.5 | 862.4 | 202.9 |
| #4 | 560.4 | 195.5 | 158.2 |
| #5 | 706.8 | 235.5 | 187.7 |
| G Allele | 810.7 | 250.0 | 189.2 |
| T Allele | 416.6 | 1121 | 243.4 |

Net Light Units, Ratio and Called Genotype

| DNA Analyzed | Net Light Units* | | Ratio** | Called Genotype |
|---|---|---|---|---|
| | WT Probe | Variant Probe | | |
| #1 | 554.6 | 77.6 | 7.1 | G Allele |
| #2 | 58.4 | 654.8 | 0.09 | T Allele |
| #3 | 88.6 | 659.5 | 0.13 | T Allele |
| #4 | 402.2 | 37.3 | 10.8 | G Allele |
| #5 | 519.1 | 47.8 | 10.9 | G Allele |
| G Allele | 621.5 | 60.8 | 10.2 | G Allele |
| Std. Deviation | | | | |
| T Allele | 173.2 | 877.6 | 0.20 | T Allele |
| Std. Deviation | | | | |

*Net light units = total light units - no primer values.
**Ratio = Net light units WT primer/net light units variant primer After these results were obtained, the identity of the DNA samples was uncoded and all the called genotypes agreed with the previously determined genotype of these samples. These results demonstrate the assay described in this Example can be used to determine SNPs in plant DNA and that removal of one DNA strand of a sample can help eliminate high background signals from a template, permitting SNPs to be determined.

```
RS1 5'C*C*C*A*ACACCTTACAGAAATTAGC 3'    SEQ ID NO:129

(* signifies the presence of a phosphorothioate
linkage between the indicated bases.)

RS2 5'TCTCAAGACACAAATAACTGCAG 3'        SEQ ID NO:130

RS3 5'AGAACATCTGCAAGG 3'                SEQ ID NO:131

RS4 5'AGAACATCTGCAAGT 3'                SEQ ID NO:132
```

EXAMPLE 40
Improvement in Allele Discrimination by Varying Reaction Conditions and ATP Stability in the Pyrophosphorylation Solution after Pyrophosphorolysis As shown in several previous Examples, pairs of probes can be used to determine the genotype of a DNA segment using coupled enzymatic reactions. One way to present the discrimination of different alleles using this technology is to report the relative detection signals as a ratio, as shown in the Example above. In this Example, a study is described that illustrates that the ratio between the signals from matched and mismatched probes can be varied by alteration of the reaction conditions. In addition, the reaction solutions are incubated on ice to demonstrate that determining the amounts of ATP generated following pyrophosphorylation of the probes does not have to be performed immediately if the solutions are placed on ice.

Oligonucleotides CV1 (SEQ ID NO:86), CV2 (SEQ ID NO:35), and CV3 (SEQ ID NO:83) were dissolved to 1 mg/mL in water and CV3 was diluted to a concentration of 0.3 μg/mL in water. Oligonucleotide CV1 was designed to match a known sequence in the CMV viral genome. Oligonucleotide CV2 was designed to match the same region of the viral genome, but to hybridize exactly to a known drug resistance form of the virus that contained single base changes in this region. Oligonucleotide CV3 was designed to match a larger region of this viral DNA and is used as a target for the hybridization of probes CV1 and CV2 in the study below.

Nine samples of each of the three following solutions were assembled: Solution 1: 18 μL water, 1 μL CV3 and 1 μL Cv1; Solution 2: 18 μL water, 1 μL CV2 and 1 μL CV3; and Solution 3: 19 μL water, 1 μL CV3. These solutions were heated at 91° C. for 5 minutes, then cooled at room temperature for 10 minutes.

Three solutions of Klenow exo- were prepared by mixing the following:

| Component | Enzyme solutions | |
|---|---|---|
| | Klenow #1 | Klenow #2 |
| 1X DNA Polymerase Buffer* | 4 μL | 8 μL |
| Klenow Exo Minus (Promega M218B) | 6 μL | 2 μL |

*Made by 1:10 dilution of Promega 10X DNA Polymerase Buffer (M195A with water).

These manipulations produced solutions of Klenow exo- at concentrations of 6 U/μL and 2 U/μL for the Klenow #1 and Klenow #2 solutions, respectively.

A master mix was made by assembling the following:

| Component | Amount (μL) |
|---|---|
| 10X DNA Polymerase Buffer | 120 |
| water | 432 |
| 10 mM Sodium Pyrophosphate | 15 |
| NDPK (1 U/μL) | 6 |
| 10 μM ADP (Sigma) | 12 |

After mixing, 195 μL samples of master mix were placed into each of three separate 1.5 mL microfuge tubes labeled MM#1, MM#2 and MM#3, and 5 μL of Klenow exo minus, Klenow #1 and Klenow #2, as described above, were added to those tubes. Twenty microliter samples of each of those mixes were separately added to each of: 3 tubes of solution 1, three tubes of solution 2 and three tubes of solution 3 after the before-described solutions had cooled to room temperature. The tubes were then incubated at 37° C. for 15 minutes. Four microliters of the solution in each tube were immediately added to 100 μL of L/L reagent (Promega F202A) and the light production of the resulting solution was read immediately using a Turner® TD 20/20 luminometer. The tube containing the remaining solution was placed on ice. Periodically, four microliter samples of the remaining solution in each of the tubes were added to 100 μL of L/L reagent (Promega F120B) and the light production of the resulting solution read as before to determine if the values first seen changed over time. The average values for the triplicate readings are given below.

| Reading Time* (min) | CV1/CV3 Reactions | CV2/CV3 Reactions | No Probe Reactions | Ratio** |
|---|---|---|---|---|
| Klenow used: 5 U/reaction | | | | |
| Zero | 235.4 | 31.1 | 2.98 | 8.26 |
| 15 | 231.9 | 30.2 | 2.76 | 8.40 |
| 30 | 233.8 | 32.2 | 3.41 | 8.00 |
| 45 | 219.7 | 32.8 | 8.60 | 8.77 |
| 60 | 218.5 | 31.8 | 4.41 | 7.87 |
| Klenow used: 3 U/reaction | | | | |
| Zero | 200.8 | 26.3 | 6.27 | 9.80 |
| 15 min | 207.2 | 31.9 | 14.9 | 11.2 |
| 30 min | 191.3 | 26.3 | 7.30 | 9.71 |
| 45 min | 202.0 | 26.7 | 6.34 | 9.62 |
| 60 min | 192.8 | 25.9 | 6.03 | 9.43 |
| Klenow used: 1 U/reaction | | | | |
| Zero | 217.5 | 24.6 | 8.03 | 12.65 |
| 15 | 206.8 | 35.5 | 23.8 | 15.9 |
| 30 | 200.0 | 24.4 | 9.24 | 12.7 |
| 45 | 210.7 | 24.9 | 5.70 | 10.6 |
| 60 | 210.7 | 24.5 | 6.12 | 11.1 |

*Reading time = time from placement of the tube on ice post 37° C. incubation.
**Ratio = ratio obtained by dividing the average net CV1/CV3 reaction value by the average net CV2/CV3 reaction value. Net reaction values were calculated by subtracting the no probe reaction value from the value obtained with the indicated probe.

The ratio calculated above provides a measurement of the relative strength of the signals of perfectly matched versus mismatched probes at different enzyme levels. Because the ratio is higher as the amount of enzyme decreased, improved specificity of detection is seen at the lower enzyme amounts used than at the higher amounts used. Because the absolute signal strength of the matching probe/target substrate does not vary much over the enzyme levels used, these data illustrate that one way to improve detection specificity is through the optimization of enzyme concentrations and that the optimal concentration for the enzyme Klenow exo- can be at or below 1 U/reaction in some cases.

The readings, taken up to an hour after the placement of the reaction tubes on ice, do not show much change versus those read immediately. These results suggest that the ATP level in the reactions does not need to be measured immediately but that the measurement can be performed up to at least one hour post incubation if the solutions are placed on ice.

```
CV1 5'  CACTTTGATATTACACCCATG 3'           SEQ ID NO:85

CV2 5'  CACTTTGATATTACACCCGTG 3'           SEQ ID NO:35

CV3 5'  GCAACGCTACCTTTGCCATGTTTG 3'        SEQ ID NO: 83
```

EXAMPLE 41

Improved Allele Discrimination with Automated ATP Measurement

Improved allele discrimination is demonstrated in this Example by varying reaction conditions. In addition, the ability to automate the reading of the samples by the use of a plate luminometer that can add the needed reagent is illustrated.

Oligonucleotides FV1 (SEQ ID NO:25), FV2 (SEQ ID NO:26), FV5 (SEQ ID NO:29) and FV6 (SEQ ID NO:30) were dissolved in water at 1 mg/mL, and then FV1 and FV2 were diluted to 0.3 $\mu$g/mL in water. Solution FV1+2 is assembled from equal volumes of the diluted FV1 and FV2. FV1 and FV2 are complementary strands of a segment of the wild type Factor V gene except for a 3' overhang region of FV2. FV5 is an oligonucleotide probe spanning the wild type Factor V gene in the region where the Factor V Leiden mutation occurs in the mutant gene. FV6 is an oligonucleotide probe spanning the same region as FV5, but it is totally complementary to the Factor V mutant. Oligonucleotide FV5 is complementary to a region of FV1 and oligonucleotide FVG is complementary to FV2. FV5 and FV6 are the interrogation oligonucleotides.

Six replicates of the solutions below were assembled.

| Solution | FV5 ($\mu$L) | FV6 ($\mu$L) | FV1 + 2 ($\mu$L) | Water ($\mu$L) |
|---|---|---|---|---|
| Solution #1 | 1 | none | 1 | 18 |
| Solution #2 | none | 1 | 1 | 18 |
| Solution #3 | none | none | 1 | 19 |
| Solution #4 | 1 | none | none | 19 |
| Solution #5 | none | 1 | none | 19 |
| Solution #6 | none | none | none | 20 |

These solutions were heated at 91° C. for 7 minutes and cooled at room temperature for 15 minutes.

The following master mix was assembled.

| | ($\mu$L) |
|---|---|
| 10X DNA Polymerase Buffer (Promega M195A) | 160 |
| 40 mM Sodium Pyrophosphate (Promega L350B) | 20 |
| NDPK (1 U/$\mu$L) | 8 |
| 10 $\mu$M ADP (Sigma) | 16 |
| water | 556 |

This solution was mixed and three 253 $\mu$L samples were put into separate 1.5 mL microfuge tubes. Enzyme dilutions of Klenow exo- to concentrations of 5 and 2.5 U/$\mu$L were made as in Example 40.

A 13.5 $\mu$L aliquot of Klenow exo- at 10, 5 and 2.5 U/$\mu$L (the lower enzyme concentrations were produced by dilution of stock enzyme as in the previous Example) was added to each of the master mix samples. Each resulting solution was mixed and 20 $\mu$L samples of the resulting solutions were added to two of each of the 6 different solutions heated at 95° C. before and cooled by incubation at room temperature. The resulting reaction solutions were heated at 37° C. for 15 minutes and then placed on ice.-

A microtiter plate was taken and 5 µL samples of nanopure water (controls) added to multiple wells and replicate 5 µL samples of the various reaction mixes corresponding to the reactions performed at one enzyme concentration were also added to individual wells in the plate. The plates were then placed on ice. In total, four replicates of two separate sets of each reaction were put on the plate. In the same way, two additional plates were assembled with the other reaction mixes for the other two enzyme concentrations. The plates were then read on a Luminoskan® luminometer that was programmed to add 100 µL of L/L reagent (Promega F202A) and immediately measure the luminescence produced.

In addition, 5 µL samples of the reaction mixes on ice were read in triplicate using a Turner® TD20/20 luminometer by adding the sample to a tube containing 100 µL of L/L reagent and immediately reading the light production of the resulting solution.

The averages of the data for the results obtained were calculated and are presented below. Samples labeled 'match' contain FV1+2 wild type target and FV5 wild type interrogation probe, previously described as solution #1. Samples labeled "mismatch" contain FV1+2 wild type target and FV6 mutant interrogation probe, previously described as solution #2.

| Sample | Luminoskan Average Readings | | Turner TD 20/20 Average Readings | |
|---|---|---|---|---|
| | Relative Light Units | Ratio* | Relative Light Units | Ratio* |
| 10 U Klenow Data | | | | |
| Match #1 | 76.55 | | 179.8 | |
| Match #2 | 71.46 | | 210.7 | |
| Mismatch #1 | 3.90 | | 11.16 | |
| Mismatch #2 | 4.61 | 40 | 11.71 | 52 |
| Target #1 | 1.70 | | 5.32 | |
| Target #2 | 1.51 | | 5.16 | |
| Probe FV1 #1 | 3.89 | | 13.73 | |
| Probe FV1 #2 | 3.82 | | 11.75 | |
| Probe FV2 #1 | 2.54 | | 7.63 | |
| Probe FV2 #2 | 2.22 | | 7.06 | |
| No DNA #1 | 1.61 | | 4.37 | |
| No DNA #2 | 1.31 | | 4.90 | |
| 5 U Klenow Data | | | | |
| Match #1 | 59.33 | | 196.0 | |
| Match #2 | 75.59 | | 215.5 | |
| Mismatch #1 | 3.60 | | 11.28 | |
| Mismatch #2 | 3.47 | 54 | 10.17 | 43 |
| Target #1 | 1.77 | | 5.21 | |
| Target #2 | 1.56 | | 4.73 | |
| Probe FV1 #1 | 3.13 | | 9.89 | |
| Probe FV1 #2 | 3.12 | | 9.33 | |
| Probe FV2 #1 | 2.19 | | 6.01 | |
| Probe FV2 #2 | 2.22 | | 6.32 | |
| No DNA #1 | 1.58 | | 4.17 | |
| No DNA #2 | 1.46 | | 4.21 | |
| 2.5 U Klenow Data | | | | |
| Match #1 | 68.83 | | 235.6 | |
| Match #2 | 72.20 | | 245.8 | |
| Mismatch #1 | 3.08 | | 9.18 | |
| Mismatch #2 | 3.33 | 72 | 9.83 | 71 |
| Target #1 | 1.90 | | 5.11 | |
| Target #2 | 1.65 | | 4.35 | |
| Probe FV1 #1 | 3.11 | | 9.70 | |
| Probe FV1 #2 | 2.12 | | 10.99 | |
| Probe FV2 #1 | 2.07 | | 5.79 | |
| Probe FV2 #2 | 2.12 | | 6.08 | |
| No DNA #1 | 1.62 | | 4.14 | |
| No DNA #2 | 1.59 | | 4.64 | |

*See the text below.

The ratios reported in this Example were determined by first averaging the results from matching samples then determining the net light production from the matching and mismatching samples and dividing the net light production from the matching reaction by that seen in the mismatch reaction. The net light production was determined by subtracting the estimated light contribution from the probes and target present in the reactions from the total light produced. The light production from the target reaction was considered to be the total of that contributed from the target specifically and that contributed by contaminating ATP from various components. The net increase from the probes alone was calculated by subtracting the average No DNA values from the probe values because it subtracted the contributions from contaminating ATP from the probe values. Thus, the formula used to determine the net light production from the reactions was:

$$\text{Net Light} = \text{Total light} - [(\text{target alone}) + (\text{probe alone} - \text{no DNA})]$$

These data again indicate that improved allele detection results can be obtained by optimizing the amount of enzyme in the reaction. In addition, the results indicate that, while reading samples on a commercially available plate luminometer with automated reagent addition does not give the same readings as another instrument, the ratio of the relative signal strengths from reactions performed with matched and mismatched probes are approximately equal. Thus, automated reading of the reaction products can be used to perform allele determination.

FV1 5' CTAATCTGTAAGAGCAGATCCCTGGACAGGCGAGGAATACAGAGGGCAGCAGACAT 3'    SEQ ID NO:25

FV2 5' ATGTCTGCTGCCCTCTGTATTCCTGGCCTGTCCAGGGATCTGCTCTTACAGATTAG 3'    SEQ ID NO:26

FV5 5' CTGCTGCCCTCTGTATTCCTCG 3'    SEQ ID NO:29

FV6 5' CTGCTGCCCTCTGTATTCCTTG 3'    SEQ ID NO:30

EXAMPLE 42

The Effects of Enzyme Reduction on Allele Discrimination

Allele discrimination is further improved in this Example by further reduction in the amount of enzyme used in the pyrophosphorylation reaction. Oligonucleotides CM1 (SEQ ID NO:83), CM2 (SEQ ID NO:35) and CM3 (SEQ ID NO:86) were dissolved in water, and CM1 was then diluted to 0.3 µg/mL in water. These reagents were used to form the following solutions.

| Solution | CM1 (µL) | CM2 (µL) | CM3 (µL) | Water (µL) |
|---|---|---|---|---|
| #1 | 1 | 1 | — | 18 |
| #2 | 1 | — | 1 | 18 |
| #3 | 1 | — | — | 19 |
| #4 | — | 1 | — | 19 |
| #5 | — | — | 1 | 19 |
| #6 | — | — | — | 20 |

These solutions were heated to 91° C. for 7 minutes, then permitted to cool for 15 minutes at room temperature. A master mix was assembled as in Example 41 except that the volumes used permitted 5–390 µL samples of the final mix to be placed into 5 0.5 mL microfuge tubes.

Klenow Exo- was diluted as described in Example 40 except the dilutions were adjusted so the diluted solutions contained 20, 10, 5, and 2.5 units of enzyme per 10 µL of diluted material. Ten microliters of the diluted enzyme solutions were added to four tubes containing 390 µL of master mix. Ten microliters of 1× DNA polymerase buffer (made by 1:10 dilution of 10× DNA Polymerase buffer with water) were added to a fifth tube with master mix to serve as a no-enzyme control. Twenty microliters of each of the master mixes and control mix were added to groups of three of solutions 1–6 above and each resulting solution was heated at 37° C. for 15 minutes, then the tube was placed on ice. After all tubes were processed in this manner, 5 µL samples from each of the tubes were separately added to 100 µL of L/L reagent (Promega, F202A) and the light produced by the solution immediately read using a Turner® TD 20/20 luminometer. The results for the triplicate determinations were averaged and those averages are presented in the table below.

Relative Light Units Measured in Reactions at Various Enzyme Levels (enz/rx)

| Reaction Type | 2 U enz/rx | 1 U enz/rx | 0.5 U enz/rx | 0.25 U enz/rx | no enz |
|---|---|---|---|---|---|
| Matching probe | 279.0 | 301.3 | 306.6 | 268.3 | 3.94 |
| Mismatched probe | 24.51 | 23.95 | 25.02 | 13.70 | 4.35 |
| CM1 alone | 4.33 | 4.55 | 4.75 | 4.42 | 3.71 |
| CM2 alone | 3.90 | 4.05 | 3.91 | 4.44 | 3.75 |
| CM3 alone | 7.06 | 5.06 | 4.13 | 4.57 | 3.93 |

-continued

Relative Light Units Measured in Reactions at Various Enzyme Levels (enz/rx)

| Reaction Type | 2 U enz/rx | 1 U enz/rx | 0.5 U enz/rx | 0.25 U enz/rx | no enz |
|---|---|---|---|---|---|
| No DNA | 3.35 | 3.52 | 4.01 | 3.94 | 3.27 |
| Ratio* | 16.6 | 16.6 | 15.0 | 30.4 | (nd) |

*Ratio determined by taking the net relative light units as described in Example 41 for the matching and mismatched primers and dividing the matching probe value by the mismatched probe value.
(nd) = not determined.

These data show that a very large degree of allele discrimination can be obtained by lowering the Klenow Exo- level to 0.25 U/reaction.

CM1   5' GCAACGCTACCTTTGCCATGTTTG 3'    SEQ ID NO:83

CM2   5' CACTTTGATATTACACCCGTG 3'    SEQ ID NO:35

CM3   5' CACTTTGATATTACACCCATG 3'    SEQ ID NO:86

EXAMPLE 43

Reduction of Background Light Production by Reduction of Enzyme Concentrations

A method to reduce the signal production from probes is demonstrated in this Example. Thus, probes PH1 (SEQ ID NO:1), PH2 (SEQ ID NO:2), PH3 (SEQ ID NO:133), and PH4 (SEQ ID NO:3) were dissolved in water to a concentration of 1 mg/mL. The following solutions were assembled in duplicate.

| Solution | PH Probe (µL) | Water (µL) |
|---|---|---|
| #1 | — | 20 |
| #2 | 1, PH1 | 19 |
| #3 | 1, PH2 | 19 |
| #4 | 1, PH3 | 19 |
| #5 | 1, PH4 | 19 |

The solutions were heated at 95° C. for 5 minutes then cooled at room temperature for 10 minutes. The following two master mixes were assembled.

| Component | 0.25 U Master Mix (µL) | 5.0 U Master Mix (µL) |
|---|---|---|
| 10 X DNA Polymerase Buffer | 20 | 20 |
| Klenow Exo-(1 U/µL)* | 1.25 | — |
| Klenow exo- (10 U/µL) | — | 2.5 |
| 40 mM Sodium Pyrophosphate | 2.5 | 2.5 |
| NDPK (1 U/µL) | 1 | 1 |

-continued

| Component | 0.25 U Master Mix ($\mu$L) | 5.0 U Master Mix ($\mu$L) |
|---|---|---|
| ADP (10 $\mu$M, Sigma) | 2 | 2 |
| Water | 73.25 | 72 |
|  | 100 | 100 |

*Made by a 1:10 dilution of Klenow exo- with 1X DNA polymerase buffer (1X DNA Polymerase buffer made by 1:10 dilution of 10X DNA Polymerase Buffer).

These master mixes were mixed and 20 $\mu$L of each master mix were added to one of each of solutions 1–5 above and heated at 37° C. for 15 minutes. Duplicate four microliter samples of each solution containing DNA were added to 10 $\mu$L L/L reagent (Promega F202A) and the light produced was immediately read using a Turner® TD 20/20 luminometer. A single 4 $\mu$L sample of the reactions not containing DNA was also read by adding it to 100 $\mu$l of L/L reagent and reading as above. The following results were obtained.

| | Relative Light Units | | | | | |
|---|---|---|---|---|---|---|
| | 0.25 U Master Mix Reactions ($\mu$L)* | | | 5.0 U Master Mix Reactions ($\mu$L)* | | |
| Solution | $1^{st}$. | $2^{nd}$. | Avg. | $1^{st}$. | $2^{nd}$. | Avg. |
| #1 (no DNA) | 6.89 | | | 7.32 | | |
| #2 (PH1) | 6.82 | 6.36 | 6.60 | 8.42 | 8.63 | 8.50 |
| #3 (PH2) | 17.38 | 14.25 | 15.8 | 195.1 | 185.8 | 190.3 |
| #4 (PH3) | 20.4 | 20.4 | 20.4 | 256.6 | 381.0 | 318.8 |
| #5 (PH4) | 8.35 | 7.56 | 7.96 | 20.24 | 32.68 | 26.5 |

*Data are from a first ($1^{st}$.) and second ($2^{nd}$.) reading that are averaged (Avg.).

These data indicate that probes PH2 and PH3 produce very high probe-alone light signals when a master mix containing 5 U of Klenow exo-/reaction was used, and produced a greatly reduced light signal when 0.25 U of Klenow exo-/reaction was used. Thus, some probes that produce very high light values with one enzyme concentration can be useful in allele determination reactions if used in reactions with a lowered amount of enzyme.

PH1   5'CTCAACATGCCTGCCAAAGACG 3'   SEQ ID NO:1

PH2   5'CTGAACATGCCTGCCAAAGATG 3'   SEQ ID NO:2

PH3   5'CAGGAACGTAGGTCGGACACGT 3'   SEQ ID NO:133

PH4   5'CAGGAACGTAGGTCGGACACAT 3'   SEQ ID NO:3

EXAMPLE 44

Discrimination of Repeated DNA Sequences Using Pyrophosphorylation-Based Assay Methods This Example illustrates an assay for determining the number of repeats of a four base pair sequence in a DNA. Discrimination of such repeat sequences has been found to be very useful for identification of forensic samples. The probes in this set, TR1 (SEQ ID NO:137), TR2 (SEQ ID NO:138) and TR3 (SEQ ID NO:139) were designed to exactly match known alleles of the THO 1 locus with 6, 7, and 8 repeats respectively, of a CATT sequence.

Probes TR1–TR3 were suspended in water to a concentration of 1 mg/mL. Targets that were homozygous for THO 1 alleles with 6, 7 and 8 repeats were amplified using the protocol in the Gene Print™ System instructions (Promega).

These targets were named allele 6 (SEQ ID NO:134), allele 7 (SEQ ID NO:135) and allele 8 (SEQ ID NO:136), respectively. Gel-purified targets were PCR amplified and then further purified using the Wizard™ PCR Clean-up system (Promega, A7170) and the concentration of the DNA measured by DNAQuant (Promega). These targets were adjusted to a concentration of 1 $\mu$g/mL and to 3.3 $\mu$g/mL by the addition of deionized water. The following solutions containing probes were assembled in a final volume of 20 $\mu$L by the addition of water.

| Solution | Probe | Target (ng) |
|---|---|---|
| #1 | — | allele 6, 1 |
| #2 | TR1 | allele 6, 1 |
| #3 | TR2 | allele 6, 1 |
| #4 | TR3 | allele 6, 1 |
| #5 | — | allele 7, 1 |
| #6 | TR1 | allele 7, 1 |
| #7 | TR2 | allele 7, 1 |
| #8 | TR3 | allele 7, 1 |
| #9 | — | allele 8, 1 |
| #10 | TR1 | allele 8, 1 |
| #11 | TR2 | allele 8, 1 |
| #12 | TR3 | allele 8, 1 |
| #13 | — | allele 6, 3.3 |
| #14 | TR1 | allele 6, 3.3 |
| #15 | TR2 | allele 6, 3.3 |
| #16 | TR3 | allele 6, 3.3 |
| #17 | — | allele 7, 3.3 |
| #18 | TR1 | allele 7, 3.3 |
| #19 | TR2 | allele 7, 3.3 |
| #20 | TR3 | allele 7, 3.3 |
| #21 | — | allele 8, 3.3 |
| #22 | TR1 | allele 8, 3.3 |
| #23 | TR2 | allele 8, 3.3 |
| #24 | TR3 | allele 8, 3.3 |

These solutions were heated at 95° C. for 3 minutes, then permitted to cool by incubation at room temperature for 10 minutes.

The following master mix was made.

| Component | Amount ($\mu$L)/reaction |
|---|---|
| 10X DNA Polymerase Buffer | 4 |
| 40 mM Sodium Pyrophosphate | 0.5 |
| 10 $\mu$M ADP | 0.4 |
| Klenow exo-, 10 U/$\mu$L | 0.5 |
| NDPK, 1 U/$\mu$L | 0.2 |
| Nanopure water | 14.4 |

This solution was mixed and 20 $\mu$L of this solution were added to solutions 1–24 above, and the resulting solutions incubated for 15 minutes at 37° C. After this incubation, 4 $\mu$L of the resulting solution were added to 100 $\mu$L of L/L reagent(Promega, F202A) and the light produced was immediately measured using a Turner® TD20/20 luminometer. The following data were obtained.

| Solution | Relative Light Units |
|---|---|
| #1 | 3.97 |
| #2 | 50.79 |
| #3 | 5.94 |
| #4 | 6.03 |
| #4 | 3.79 |

-continued

| Solution | Relative Light Units |
|---|---|
| #5 | 67.23 |
| #7 | 28.94 |
| #8 | 6.73 |
| #9 | 3.19 |
| #10 | 49.52 |
| #11 | 30.99 |
| #12 | 30.63 |
| #13 | 8.62 |
| #14 | 256.90 |
| #15 | 16.74 |
| #16 | 13.83 |
| #17 | 6.73 |
| #18 | 206.5 |
| #19 | 110.2 |
| #20 | 15.35 |
| #21 | 6.49 |
| #22 | 271.9 |

Allele 6  SEQ ID NO:134
5'GGTGAATGAATGAATGAATGAATGAATGAGGGAAATAAGGGAGGAAGAGGCCAATGGG 3'

Allele 7  SEQ ID NO:135
5'GGTGAATGAATGAATGAATGAATGAATGAATGAGGGAAATAAGGGAGGAAGAGGCCAATGGG 3'

Allele 8  SEQ ID NO:136
5'GGTAGGTGAATGAATGAATGAATGAATGAATGAATGAATGAGGGAAATAAGGGAGGAAGAGGCCAATGGG 3'

TR1  SEQ ID NO:137
5'CCCATTGGCCTGTTCCTCCCTTATTTCCCTCATTCATTCATTCATTCATTCATTCACC 3'

TR2  SEQ ID NO:138
5'CCCATTGGCCTGTTCCTCCCTTATTTCCCTCATTCATTCATTCATTCATTCATTCATTCACC 3'

TR3  SEQ ID NO:139
5'CCCATTGGCCTGTTCCTCCCTTATTTCCCTCATTCATTCATTCATTCATTCATTCATTCATTCACC 3'

-continued

| Solution | Relative Light Units |
|---|---|
| #23 | 150.5 |
| #24 | 154.8 |

The values from the no probe reactions above were subtracted from the values for the various probe/target matches and the resulting values are shown in the table below.

| Allele Assayed | TR1 Probe | TR2 Probe | TR3 Probe |
|---|---|---|---|
| Relative Light Units With 1 ng of Target | | | |
| Allele 6 | 44.46 | −0.01 | −0.44 |
| Allele 7 | 61.07 | 23.17 | 0.44 |
| Allele 8 | 43.97 | 25.83 | 24.95 |
| Relative Light Units With 3.3 ng of Target | | | |
| Allele 6 | 245.08 | 4.88 | 1.73 |
| Allele 7 | 196.58 | 100.24 | 5.14 |
| Allele 8 | 262.22 | 140.78 | 144.83 |

If, in the repeat region, the probe contains the same number of repeats as the target or fewer, no mismatching bases should be present at the 3' end of the probe and a relatively strong signal is obtained. The TR1 probe shows such a signal with targets containing 6, 7 or 8 repeats. However, if the probe contains more repeats in this region than are present in the target, mismatched bases are expected at the 3' end of the probe that should greatly reduce the signal developed. As expected, the TR3 probe gave a strong signal against the allele 8 target, but gave a much weaker signal against the allele 7 and 6 targets. Because the signal generated using the various probes can be used to determine the number of repeated units in the repeat region, this method can be used to determine the alleles present in samples.

Using the above method, probes containing the same number or fewer repeated sequences as the target produced similar light output. When more repeats were present in the probe than the target, low analytical outputs were observed. The number of repeats in the target could thus accurately be determined by an indicative change in the analytical output, here, luminescence, between the separately assayed samples.

EXAMPLE 45

Discrimination of Repeated DNA Sequences Using Pyrophosphorylation Based Assay Methods Using Another Class of Probes A surprising result is presented in this Example that demonstrates that a class of probes that should only produce signals with targets of a certain class, essentially give equivalent signals with additional targets. Although these results do not match the predicted results, they can still be used to determine the allelic composition of samples.

The probes in the Example above were designed to hybridize to alleles of THO 1 that are used for genotyping humans. They were designed to hybridize as illustratively shown below for probe TR2 with targets of three alleles.

Hybridization of probe TR2 (top strand) with an Allele 6 target (bottom strand):

CCCATTGGCCTCTTCCTCCCTTATTTCCCTCATT(CATT)$_4$
CATTCATTCACC

GGGTAACCGGAGAAGGAGGGAATAAAGGGAGTAA(GTAA)$_4$
GTAAGTGG

Hybridization of probe TR2 (top strand) with an Allele 7 target (bottom strand):

CCCATTGGCCTCTTCCTCCCTTATTTCCCTCATT(CATT)$_4$
CATTCATTCACC

-continued

```
GGGTAACCGGAGAAGGAGGGAATAAAGGGAGTCC(GTAA)4
GTAAGTAAGTGG
```

Hybridization of probe TR2 (top strand) with an Allele 8 target (bottom strand):

```
CCCATTGGCCTCTTCCTCCCTTATTTCCCTCATT(CATT)4
CATTCATTCACC

GGGTAACCGGAGAAGGAGGGAATAAAGGGAGTAA(GTAA)4
GTAAGTAAGTAAGTGGATGG 5'
```

As described in Example 44, when the target contains fewer repeats than the probe, mismatched bases can occur at the 3' end of the probe, creating a double strand DNA region that is a very poor substrate for the pyrophosphorylation reaction. These predictions were verified with the results obtained.

In this Example, a new form of probe is used in the reactions. These probes are designed to extend beyond the repeat region and hybridize to the target following this DNA segment when they are hybridized to the allele with the correct number of repeat segments. The predicted hybridization segments for the allele 7 probe (TR6) with the allele 6, 7, and 8 targets are shown below.

Hybridization of probe TR6 (top strand) with an Allele 6 target (bottom strand):

```
CCCATTGGCCTCTTCCTCCCTTATTTCCCTCATT(CATT)4
CATTCATTCACC

CACCGGGTAACCGGAGAAGGAGGGAATAAAGGGAGTAA(GTAA)4
GTAAGTGGATGG
```

Hybridization of probe TR6 (top strand) with an Allele 7 target (bottom strand):

```
CCCATTGGCCTCTTCCTCCCTTATTTCCCTCATT(CATT)4
CATTCATTCACC

TCACCGGGTAACCGGAGAAGGAGGGAATAAAGGGAGTAA(GTAA)4
GTAAGTAAGTGGATGG 5'
```

Hybridization of probe TR6 (top strand) with an Allele 8 target (bottom strand):

```
CCCATTGGCCTCTTCCTCCCTTATTTCCCTCATT(CATT)4
CATTCATTCACC

TCACCGGGTAACCGGAGAAGGAGGGAATAAAGGGAGTAA(GTAA)4
GTAAGTAAGTAATGGAGTGG 5'
```

As shown above, probe TR6 was designed to form a product without 3' end mismatches with only allele 7. Thus, this probe was expected to only give a strong signal with the allele 7 target.

In order to test the actual signals that such probes would give with various targets, probes TR4 (SEQ ID NO:140), TR5 (SEQ ID NO:141), TR6 (SEQ ID NO:142), TR7 (SEQ ID NO:143) and TR8 (SEQ ID NO:144) were dissolved in water to a concentration of 1 mg/mL. These probes were used with the targets Allele 6 (SEQ ID NO:134), Allele 7 (SEQ ID NO:135) and Allele 8 (SEQ ID NO:136) to generate the following solutions. As in the Example above, the final volume of these solutions was adjusted to 20 µL by the addition of water. The probes were used at a concentration of 1 µg/reaction.

| Soln. | Probe | Target (ng) |
|---|---|---|
| #1 | — | Allele 6, 1 |
| #2 | TR4 | Allele 6, 1 |
| #3 | TR5 | Allele 6, 1 |
| #4 | TR6 | Allele 6, 1 |
| #5 | TR7 | Allele 6, 1 |
| #6 | TR8 | Allele 6, 1 |
| #7 | — | Allele 7, 1 |
| #8 | TR4 | Allele 7, 1 |
| #9 | TR5 | Allele 7, 1 |
| #10 | TR6 | Allele 7, 1 |
| #11 | TR7 | Allele 7, 1 |
| #12 | TR8 | Allele 7, 1 |
| #13 | — | Allele 8, 1 |
| #14 | TR4 | Allele 8, 1 |
| #15 | TR5 | Allele 8, 1 |
| #16 | TR6 | Allele 8, 1 |
| #17 | TR7 | Allele 8, 1 |
| #18 | TR8 | Allele 8, 1 |
| #19 | — | Allele 6, 3.3 |
| #20 | TR4 | Allele 6, 3.3 |
| #21 | TR5 | Allele 6, 3.3 |
| #22 | TR6 | Allele 6, 3.3 |
| #23 | TR7 | Allele 6, 3.3 |
| #24 | TR8 | Allele 6, 3.3 |
| #25 | — | Allele 7, 3.3 |
| #26 | TR4 | Allele 7, 3.3 |
| #27 | TR5 | Allele 7, 3.3 |
| #28 | TR6 | Allele 7, 3.3 |
| #29 | TR7 | Allele 7, 3.3 |
| #30 | TR8 | Allele 7, 3.3 |
| #31 | — | Allele 8, 3.3 |
| #32 | TR4 | Allele 8, 3.3 |
| #33 | TR5 | Allele 8, 3.3 |
| #34 | TR6 | Allele 8, 3.3 |
| #35 | TR7 | Allele 8, 3.3 |
| #36 | TR8 | Allele 8, 3.3 |

These solutions were heated at 95° C. for 3 minutes, then cooled at room temperature for 10 minutes. A master mix was assembled and added to these solutions as in the previous Example. The resulting solutions were then heated at 37° C. for 15 minutes and were sampled as in the previous Example. The samples were added to L/L reagent (Promega, F202A) and the light output was immediately measured as in the previous Example. The following results were obtained.

| Target | — | TR4 | TR5 | TR6 | TR7 | TR8 |
|---|---|---|---|---|---|---|
| Relative Light Units From Reactions Containing Probes With 1 ng of Target | | | | | | |
| Allele 6 | 2.14 | 47.40 | 33.87 | 11.45 | 7.57 | 7.98 |
| Allele 7 | 2.06 | 53.00 | 30.97 | 30.43 | 12.38 | 10.41 |
| Allele 8 | 2.51 | 21.30 | 27.54 | 30.99 | 39.04 | 14.84 |
| (none) | (nd) | 2.28 | 2.30 | 2.59 | 3.12 | 3.43 |
| Expected Allele Detected | — | A 5 | A 6 | A 7 | A 8 | A 9 |
| Relative Light Units From Reactions Containing Probes With 3.3 ng of Target | | | | | | |
| Allele 6 | 8.52 | 282.6 | 291.5 | 90.62 | 61.34 | 46.49 |
| Allele 7 | 12.23 | 276.2 | 237.8 | 286.4 | 103.4 | 74.92 |
| Allele 8 | 10.33 | 170.6 | 242.5 | 264.4 | 264.9 | 111.9 |
| (none) | (nd) | 3.56 | 3.11 | 3.25 | 3.63 | 3.60 |
| Expected Allele Detected | — | A 5 | A 6 | A 7 | A 8 | A 9 |

Surprisingly, these probes did not provide the expected detection pattern. For example, probe TR6 was expected to only give a strong signal with a target with allele 7 (A 7).

Although the probe did show a lower signal with allele 6 (A 6) than with allele 7 (90.6 vs. 286.4 units, respectively), very little difference was seen between the signals with alleles 7 and 8 (A 8) (286.4 vs. 264.4 units respectively). In general, all the probes exhibited substantially equal reactivity with any target that had the same number of repeated units or greater than the number of repeated units in the probe. These same probes showed lower signals with targets having fewer repeat units than those present in the probe, with the signal strength seen decreasing as the difference in the number of repeat units increased. Thus, although these probes clearly did not provide the expected signal patterns, they can be used to determine THO 1 alleles.

| | Relative Light Units | | |
|---|---|---|---|
| Target | Probe TR9 | Probe TR10 | Probe TR11 |
| Allele 6 | 3.51 | −7.34 | 63.14 |
| Allele 7 | −6.08 | −22.46 | 1.63 |
| Allele 8 | 1.46 | −18.72 | 20.14 |

Increasing the number of mismatched bases between the probe and target lowers the signal value measured, and in many cases decreases the values seen below those attribut-

```
Allele 6                                                                          SEQ ID NO:134
5' GGTGAATGAATGAATGAATGAATGAATGAGGGAAATAAGGGAGGAAGAAGGCCAATGGG 3'

Allele 7                                                                          SEQ ID NO:135
5' GGTGAATGAATGAATGAATGAATGAATGAATGAGGGAAATAAGGGAGGAAGAGGCCAATGGG 3'

Allele 8                                                                          SEQ ID NO:136
5' GGTAGGTGAATGAATGAATGAATGAATGAATGAATGAATGAGGGAAATAAGGGAGGAAGAGGCCAATGGG 3'

TR4                                                                               SEQ ID NO:140
5' CCCATTGGCCTGTTCCTCCCTTATTTCCCTCATTCATTCATTCATTCATTCACC 3'

TR5                                                                               SEQ ID NO:141
5' CCCATTGGCCTGTTCCTCCCTTATTTCCCTCATTCATTCATTCATTCATTCATTCACC 3'

TR6                                                                               SEQ ID NO:142
5' CCCATTGGCCTGTTCCTCCCTTATTTCCCTCATTCATTCATTCATTCATTCATTCATTCACC 3'

TR7                                                                               SEQ ID NO:143
5' CCCATTGGCCTGTTCCTCCCTTATTTCCCTCATTCATTCATTCATTCATTCATTCATTCATTCACC 3'

TR8                                                                               SEQ ID NO:144
5' CCCATTGGCCTGTTCCTCCCTTATTTCCCTCATTCATTCATTCATTCATTCATTCATTCATTCATTCACC 3'
```

EXAMPLE 46
Additional Probes for Detection of THO 1 Alleles

Additional probes are used in this Example to demonstrate that the creation of additional mismatches between THO 1 allele targets and probes can result in the formation of probe/target combinations that provide strong signals with essentially one THO 1 allele.

Probes TR 9 (SEQ ID NO:145), TR10 (SEQ ID NO:146) and TR11 (SEQ ID NO:147) were dissolved at 1 mg/mL and assembled into reactions with target at 3 ng/reaction with allele 6 (SEQ ID NO:134), allele 7 (SEQ ID NO:135), and allele 8 (SEQ ID NO:136) of THO 1 and without any target as described in the Example above. These solutions were heated and cooled as in the previous Example. The resulting solutions were treated with master mix, incubated, added to L/L reagent (Promega, F202A) and the light produced measured as in the previous Example. The following results were obtained.

| | Relative Light Units | | | |
|---|---|---|---|---|
| Target | Probe TR9 | Probe TR10 | Probe TR11 | none |
| Allele 6 | 59.74 | 35.86 | 75.78 | 8.96 |
| Allele 7 | 51.73 | 2.32 | 15.85 | 10.54 |
| Allele 8 | 58.58 | 25.37 | 33.67 | 9.85 |
| (none) | 47.27 | 34.24 | 3.676 | (nd) |

The values for the probe alone and target alone reactions were subtracted from the values for the combined reactions and are shown in the table below.

able from background reactions. In particular, probes TR9, which has a mismatch of 2 base pairs, and TR10, which has an A to C mutation 3 bases from the end of the probe, do not exhibit the ability to detect THO 1 alleles. However, probe TR11, which has a A to G change 3 bases from the end of the probe, produced a measurable signal with the allele 6 target that is greater than the signals seen with the other targets.

Probes TR12 (SEQ ID NO:148) and TR13 (SEQ ID NO:149) were then used as above. The following data were obtained.

| | Relative Light Units | |
|---|---|---|
| Target | Probe TR12 | Probe TR13 |
| Allele 6 | 9.7 | 9.8 |
| Allele 7 | 5.0 | 7.1 |
| Allele 8 | 10.4 | 12.6 |
| (none) | 3.0 | 2.9 |

These probes, having additional mismatches four base pairs from the 3' end of the probe, only provided very low light signals and apparently did not discriminate between the alleles of THO 1. Thus, these data suggest that probes that can provide allele-specific signals can be identified by designing probes with base pair mismatches placed in the probe sequence near the 3' end of the probe.

Allele 6                                                                                          SEQ ID NO:134
5'GGTGAATGAATGAATGAATGAATGAATGAGGGAAATAAGGCAGGAAGAGGCCAATGGG 3'

Allele 7                                                                                          SEQ ID NO:135
5'GGTGAATGAATGAATGAATGAATGAATGAATGAGGGAAATAAGGGAGGAAGAGGCCAATGGG 3'

Allele 8                                                                                          SEQ ID NO:136
5'GGTAGGTGAATGAATGAATGAATGAATGAATGAATGAATGAGGGAAATAAGGGAGGAAGAGGCCAATGGG 3'

TR9                                                                                               SEQ ID NO:145
5' CCCATTGGCCTGTTCCTCCCTTATTTCCCTCATTCATTCATTCATTCATTCATTCAGC 3'

TR10                                                                                              SEQ ID NO:146
5' CCCATTGGCCTGTTCCTCCCTTATTTCCCTCATTCATTCATTCATTCATTCATTCCCC 3'

TR11                                                                                              SEQ ID NO:147
5' CCCATTGGCCTGTTCCTCCCTTATTTCCCTCATTCATTCATTCATTCATTCATTCGCC 3'

TR12                                                                                              SEQ ID NO:148
5' CCCATTGGCCTGTTCCTCCCTTATTTCCCTCATTCATTCATTCATTCATTCATTGACC 3'

TR13                                                                                              SEQ ID NO:149
5' CCCATTGGCCTGTTCCTCCCTTATTTCCCTCATTCATTCATTCATTCATTCATTAACC 3'

EXAMPLE 47

Discrimination of Repeated DNA Sequences Using Pyrophosphorylation-based Assay Methods-III In this Example, PCR targets spanning between 6 to 13 copies of the TPOX four nucleotide short tandem repeat were discriminated with probes specific for the number of repeats using a pyrophosphorylation based assay. The targets were prepared by standard PCR amplification of each of the (Promega, DC5111) TPOX bands that were previously gel-purified. The PCR cycling parameters were 94° C., 1 minute (94° C., 15 seconds; 60° C., 30 seconds; 72° C., 60 seconds)×35, 68° C., 10 minutes. The correct size of the PCR products was confirmed on a 4% polyacrylamide gel electrophoresis. The PCR products were purified using Wizard™ PCR Purification System (Promega, A7170) and resuspended in water to a concentration of 10 ng/μL. The interrogation sequence probes were P6 (SEQ ID NO:150), P7 (SEQ ID NO:151), P8 (SEQ ID NO:152), P9 (SEQ ID NO:153), P10 (SEQ ID NO:154), P11 (SEQ ID NO:155), P12 (SEQ ID NO:156) and P13 (SEQ ID NO:157).

Targets containing between 6 and 13 TGAA repeats were each interrogated with each of the interrogation probes listed above. The target alleles used were A6 (SEQ ID NO:158), A7 (SEQ ID NO:159), A8 (SEQ ID NO:160), A9 (SEQ ID NO:161), A10 (SEQ ID NO:162), A11 (SEQ ID NO:163), A12 (SEQ ID NO:164) and A13 (SEQ ID NO:165), respectively. The probes were at a final concentration of 2.5 μM in the solution, 10 ng of target were used per reaction and the volume was increased to 20 μL with water. The solutions were heated at 95° C. for 2 minutes, then cooled at room temperature over 10 minutes.

Twenty microliters of master mix were added to each solution (14.7 μL water, 4 μL 10× DNA polymerization buffer, 5 μL 40 mM NaPPi, 0.4 μL 10 μM ADP, 0.2 μL NDPK (1 U/μL), 0.2 μL Klenow exo- (10 U/μL) ) and they were further incubated at 37° C. for 15 minutes. Then, 4 μL of the solution were added to 100 μL of L/L reagent and the light output read with a Turner® TD20/20 luminometer. The relative light units (rlu) obtained are reported below:

| | Raw rlu numbers | | | | | | | | |
|---|---|---|---|---|---|---|---|---|---|
| | Probe | | | | | | | | |
| Target | P6 | P7 | P8 | P9 | P10 | P11 | P12 | P13 | None |
| A6 | 57.62 | 16.80 | 15.65 | 28.51 | 23.37 | 25.31 | 26.70 | 47.48 | 14.08 |
| A7 | 23.29 | 73.44 | 22.39 | 37.28 | 20.31 | 25.01 | 26.29 | 44.24 | 25.06 |
| A8 | 25.04 | 20.82 | 54.63 | 35.78 | 20.69 | 21.02 | 22.99 | 37.51 | 18.37 |
| A9 | 28.83 | 21.60 | 25.03 | 85.98 | 30.71 | 28.55 | 29.54 | 50.86 | 21.48 |
| A10 | 27.69 | 25.53 | 30.30 | 42.38 | 61.04 | 30.21 | 27.71 | 46.30 | 32.80 |
| A11 | 30.29 | 35.07 | 30.67 | 51.20 | 40.37 | 69.92 | 39.12 | 58.52 | 30.00 |
| A12 | 35.36 | 25.43 | 29.71 | 45.14 | 28.44 | 38.76 | 63.31 | 57.05 | 40.24 |
| A13 | 39.35 | 27.67 | 29.92 | 42.56 | 33.59 | 32.80 | 36.04 | 84.37 | 32.70 |
| None | 8.67 | 6.29 | 9.15 | 27.98 | 14.18 | 16.51 | 16.22 | 32.98 | 4.66 |

The above values were adjusted for background and the negative numbers converted to zero to provide the data in the table below.

| | Probe | | | | | | | |
|---|---|---|---|---|---|---|---|---|
| Target | P6 | P7 | P8 | P9 | P10 | P11 | P12 | P13 |
| A6 | 40 | 1 | 0 | 0 | 0 | 0 | 1 | 5 |
| A7 | 0 | 47 | 0 | 0 | 0 | 0 | 0 | 0 |
| A8 | 3 | 1 | 32 | 0 | 0 | 0 | 0 | 0 |
| A9 | 3 | 0 | 0 | 41 | 0 | 0 | 0 | 1 |
| A10 | 0 | 0 | 0 | 0 | 19 | 0 | 0 | 0 |
| A11 | 0 | 3 | 0 | 0 | 1 | 28 | 0 | 0 |
| A12 | 0 | 0 | 0 | 0 | 0 | 0 | 12 | 0 |
| A13 | 3 | 0 | 0 | 0 | 0 | 0 | 0 | 23 |

The data indicate that the interrogation probes can recognize the presence of the related homozygote alleles of the TPOX locus. Similarly, heterozygote targets were assayed with the same set of interrogation probes. Ten nanograms of each purified PCR target were included in each interrogation reaction. The reaction conditions were identical to those for the homozygote targets described above. The rlu values obtained are reported below.

| | Raw rlu numbers | | | | | | | | |
|---|---|---|---|---|---|---|---|---|---|
| | Probe | | | | | | | | |
| Target | P6 | P7 | P8 | P9 | P10 | P11 | P12 | P13 | None |
| A6, A13 | 91.09 | 36.85 | 40.90 | 50.88 | 41.93 | 41.33 | 83.69 | 83.69 | 31.78 |
| A11, A12 | 55.94 | 48.13 | 54.35 | 62.64 | 50.92 | 84.19 | 80.33 | 66.41 | 54.62 |
| A9, A10 | 61.75 | 43.49 | 47.71 | 93.76 | 77.91 | 37.18 | 39.11 | 59.74 | 33.37 |
| A7, A8 | 35.66 | 76.04 | 62.03 | 36.03 | 27.92 | 30.07 | 31.92 | 51.40 | 50.52 |
| None | 6.29 | 4.87 | 6.22 | 20.83 | 10.89 | 11.86 | 12.41 | 28.64 | 4.32 |

The values were adjusted for background and the negative numbers converted to zero to provide the data in the table below.

| | Probe | | | | | | | |
|---|---|---|---|---|---|---|---|---|
| Target | P6 | P7 | P8 | P9 | P10 | P11 | P12 | P13 |
| A6, A13 | 57.35 | 4.53 | 7.23 | 2.59 | 3.58 | 2.01 | 6.45 | 27.59 |
| A11, A12 | 0 | 0 | 0 | 0 | 0 | 22.03 | 17.62 | 0 |
| A9, A10 | 26.42 | 9.58 | 12.45 | 43.88 | 37.97 | 0 | 0 | 2.05 |
| A7, A8 | 0 | 24.98 | 9.62 | 0 | 0 | 0 | 0 | 0 |

As can be seen from the results in the table above, this method accurately identified each of the heterozygote targets, although probe P6 also identified one false positive for an unknown reason.

Interrogation Probe Sequences:

```
P6  5' GGCACTTAGGGAACCCTCAC TGAA TGAA TGAA TGAA          SEQ ID NO:150
       TGAA TGAA TATT 3'

P7  5' GGCACTTAGGGAACCCTCAC TGAA TGAA TGAA TGAA          SEQ ID NO:151
       TGAA TGAA TGAA TATT 3'

P8  5' GGCACTTAGGGAACCCTCAC TGAA TGAA TGAA TGAA          SEQ ID NO:152
       TGAA TGAA TGAA TGAA TATT 3'

P9  5' GGCACTTAGGGAACCCTCAC TGAA TGAA TGAA TGAA          SEQ ID NO:153
       TGAA TGAA TGAA TGAA TGAA TATT 3'

P10 5' GCACTTAGGGAACCCTCAC TGAA TGAA TGAA TGAA           SEQ ID NO:154
       GAA TGAA TGAA TGAA TGAA TGAA TATT 3'

P11 5' GGCACTTAGGGAACCCTCAC TCAA TGAA TGAA TGAA          SEQ ID NO:155
       TGAA TGAA TGAA TGAA TGAA TGAA TATT 3'

P12 5' GGCACTTAGGGAACCCTCAC TGAA TGAA TGAA TGAA          SEQ ID NO:156
       TGAA TGAA TGAA TGAA TGAA TGAA TGAA TATT 3'

P13 5' GGCACTTAGGGAACCCTCAC TGAT TGAA TGAA TGAA          SEQ ID NO:157
       TGAA TGAA TGAA TGAA TGAA TGAA TCAA TGAA
       TGAA TATT 3'

Target Alleles:
A6:
5' GGCACTTAGGGAACCCTCACTGAATGAATGAATGAATGA              SEQ ID NO:158
ATGAATGTTTGGGCAAATAAACGCTGACAAGGACAGAAGGG
CCTAGCGGGAAGGGAACAGGAGTAAGACCAGCGCACAGCCCGACTTGTG
TTCAGAAGACCTGGGATTGGACCTGAGGATTCAATTTTGGATGAATCTC
TTAATTAACCTGTGTQGTTCCCAGTTCCTCCCCTGAGCGCCCAGGACAG
TAGAGTCAACCTCA 3'

A7:
5' GGCACTTAGGGAACCCTCACTGAATGAATGAATGAATGA              SEQ ID NO:159
ATGAATGAATGTTTGGGCAAATAAACGCTGACAAGGACAGAAGGG
CCTAGCGGGAAGGGAACAGGAGTAAGACCAGCGCACAGCCCGACTTGTG
TTCAGAAGACCTGGGATTGGACCTGAGGATTCAATTTTGGATGAATCTC
TTAATTAACCTGTGTGGTTCCCAGTTCCTCCCCTGAGCGCCCAGGACAG
TAGAGTCAACCTCA 3'

A8:
5' GGCACTTAGGGAACCCTCACTGAATGAATGAATGAATGA              SEQ ID NO:160
ATGAATGAATGAATGTTTGGGCAAATAAACGCTGACAAGGACAGAAGGG
CCTAGCGGGAAGGGAACAGGAGTAAGACCAGCGCACAGCCCGACTTGTG
TTCAGAAGACCTGGGATTGGACCTGAGGATTCAATTTTGGATGAATCTC
TTAATTAACCTGTGTGGTTCCCAGTTCCTCCCCTGAGCGCCCAGGACAG
TAGAGTCAACCTCA 3'

A9:
5' GGCACTTAGGGAACCCTCACTGAATGAATGAATGAATGA              SEQ ID NO:161
```

```
                          -continued
ATGAATGAATGAATGAATGTTTGGGCATAAACGCTGACAAGGACAGAAGGG
CCTAGCGGGAAGGGAACAGGAGTAAGACCAGCGCACAGCCCGACTTGTG
TTCAGAAGACCTGGGATTGGACCTGAGGATTCAATTTTGGATGAATCTC
TTAATTAACCTGTGTGGTTCCCAGTTCCTCCCCTGAGCGCCCAGGACAG
TAGAGTCAACCTCA 3'

A10 :
5' GGCACTTAGGGAACCCTCACTGAATGAATGAATGAATGA                SEQ ID NO:162
ATGAATGAATGAATGAATGAATGTTTGGGCAAATAAACGCTGACAAGGACAGA
AGGGCCTAGCGGGAAGGGAACAGGAGTAAGACCAGCGCACAGCCCGACTTGTG
TTCAGAAGACCTGGGATTGGACCTGAGGATTCAATTTTGGATGAATCTC
TTAATTAACCTGTGTGGTTCCCAGTTCCTCCCCTGAGCGCCCAGGACAG
TAGAGTCAACCTCA 3'

A11:
5' GGCACTTAGGGAACCCTCACTGAATGAATGAATGAATGA                SEQ ID NO:163
ATGAATGAATGAATGAATGAATGAATGTTTGGGCAAATAAACGCTGACAAGGA
CAGAAGGGCCTAGCGGGAAGGGAACAGGAGTAAGACCAGCGCACAGCCCGACT
TGTGTTCAGAAGACCTGGGATTGGACCTGAGGATTCAATTTTGGATGAATCTC
TTAATTAACCTGTGTGGTTCCCAGTTCCTCCCCTGAGCGCCCAGGACAG
TAGAGTCAACCTCA 3'

A12:
5' GGCACTTAGGGAACCCTCACTGAATGAATGAATGAATGA                SEQ ID NO:164
ATGAATGAATGAATGAATGAATGAATGAATGTTTGGGCAAATAAACGCTGACA
AGGACAGAAGGGCCTAGCGGGAAGGGAACAGGAGTAAGACCAGCGCACAGCCC
GACTTGTGTTCAGAAGACCTGGGATTGGACCTGAGGATTCAATTTTGGATGAA
TCTCTTAATTAACCTGTGTGGTTCCCAGTTCCTCCCCTGAGCGCCCAGGACAG
TAGAGTCAACCTCA 3'

A13:
5' GGCACTTAGGGAACCCTCACTGAATGAATGAATGAATGA                SEQ ID NO:165
ATGAATGAATGAATGAATGAATGAATGAATGTTTGGCCAAATAAACGCT
GACAAGGACAGAAGGGCCTAGCGGGAAGGGAACAGGAGTAAGACCAGCGCACA
GCCCGACTTGTGTTCAGAAGACCTGGGATTGGACCTGAGGATTCAATTTTGGA
TGAATCTCTTAATTAACCTGTGTGGTTCCCAGTTCCTCCCCTGAGCGCCCAGG
ACAGTAGAGTCAACCTCA 3'
```

EXAMPLE 48

Interrogation for Loss of Heterozygosity

In certain types of disease states such as some cancers, there is a change in the heterozygosity of the locus of certain alleles. For example, a non-cancerous cell may be heterozygous at a particular locus. In a cancer cell, however, one of the two alleles may be lost or deleted at the particular locus. This is referred to as loss of heterozygosity.

This type of loss of heterozygosity (LOH) reaction was created by PCR-amplifying 25 ng (1 μL) and 50 ng (2 μL) of two E. coli targets (W3110, DH5α) with probes 10730 (SEQ ID NO:166) and 10731 (SEQ ID NO:167) as described below. These probes span the ΔM15 93bp deletion present in DH5α DNA, but not present in W3110 DNA. The number of PCR cycles was optimized so amplification of the "heterozygote" target (1 μL W3110 and 1 μL DH5α) produced one-half the amount of DNA in each band as did amplification of the "homozygote" target (2 μL W3110 or 2 μL DH5α) under the same amplification conditions.

PCR targets spanning the locus of interest were created in duplicate as follows:

2 μL E. coli genomic DNA, W3110 or DH5α for homozygote sample (50 ng); 1 μL each W3110 and DH5α for the heterozygote sample; 1 μL of W3110 or DH5a for the LOH sample.

| | |
|---|---|
| 5 μL | 10X Taq buffer with 15 mM MgCl₂ (Promega, M188A) |
| 0.5 μL | Probe 10730 (50 pmol) |
| 0.5 μL | Probe 10731 (50 pmol) |
| 1 μL | 10 mM dNTPs |
| 1 μL | Taq DNA Polymerase (Promega, M186A) |
| 40 μL | water |

PCR cycling parameters were 96° C., 1 minute; (94° C., 15 seconds; 60° C., 30 seconds; 72° C., 45 seconds)×20; 72° C., 45 seconds. The PCR reaction was purified with 500 μL Wizard™ PCR Purification Resin (Promega, A7181) according to manufacturer instructions and eluted with 25 μL water.

The duplicate DNA targets (1 μL) were then interrogated in duplicate, with 1 μg (200 pmol) probe 10732 (SEQ ID NO:168), a sequence common to both W3110 and DH5α; 1 μg (200 pmol) probe 10733 (SEQ ID NO:169), a sequence completely matching only W3110 DNA; and 1 μg (200 pmol) probe 10734 (SEQ ID NO:170), a sequence completely matching only DH5αDNA. Four microliters of the interrogation reaction were combined with 100 μl L/L reagent (Promega, F202A) and the light output measured.

|  | homozygotes | | | | hetero-zygotes | | LOH | | | | oligo alone |
|---|---|---|---|---|---|---|---|---|---|---|---|
|  | W1 | W2 | D1 | D2 | W | D | W1 | W2 | D1 | D2 |  |
| No oligo | 93 | 131 | 59 | 115 | 129 | 83 | 101 | 59 | 63 | 71 | — |
| 10732 | 91 | 372 | 542 | 480 | 447 | 403 | 307 | 53 | 362 | 352 | 4 |
| 10732 | 95 | 465 | 536 | 494 | 479 | 419 | 295 | 257 | 364 | 349 | 4 |
| 10733 | 95 | 373 | 112 | 95 | 251 | 191 | 218 | 173 | 67 | 76 | 6 |
| 10733 | 86 | 353 | 108 | 88 | 245 | 187 | 204 | 158 | 77 | 68 | 6 |
| 10734 | 185 | 212 | 427 | 384 | 337 | 264 | 181 | 161 | 182 | 263 | 111 |
| 10734 | 179 | 199 | 409 | 378 | 318 | 258 | 159 | 127 | 182 | 282 | 111 |

The deletion-specific interrogation oligonucleotide (10734) gave high background. In general these data show the utility of the technology for determination of LOH. However, two samples, the first W/W homozygote and first D LOH, give aberrant data for an unknown reason.

| 10730 | 5' CACTTTATGCTTCCGGCTCGTATG 3' (lacZ) | SEQ ID NO:166 |
|---|---|---|
| 10731 | 5' GGGATAGGTTACGTTGGTGTAGATGG (lacZ) | SEQ ID NO:167 |
| 10732 | 5' GTTGGGAAGGGCGATCGGTG 3' (common lac probe) | SEQ ID NO:168 |
| 10733 | 5' GGGATGTGCTGCAAGGCGATT 3' (wt lac probe) | SEQ ID NO:169 |
| 10734 | 5' GGATTCACTGGCCGTCGTGG 3' (deletion lac probe) | SEQ ID NO:170 |

EXAMPLE 49
Interrogation For Loss of Heterozygosity—CMV

The use of an interrogation assay to determine loss of heterozygosity with a synthetic cytomegalovirus (CMV) target is demonstrated in this Example.

The CMV target was chosen because the interrogating probe oligonucleotides (9211 (SEQ ID NO:86) and 9212 (SEQ ID NO:35) had been previously used and well characterized. Oligonucleotides 10800 (SEQ ID NO:171) and 10801 (SEQ ID NO:172) were annealed to produce a synthetic target, "A", representing a fragment of the CMV genome. Likewise, oligonucleotides 10803 (SEQ ID NO:173) and 10805 (SEQ ID NO:174) were annealed to produce a synthetic target, "G" representing a fragment of the CMV genome. Targets A and G are identical except at one nucleotide position where they have the nucleotide resulting in their name. Both targets have SacI overhangs.

The targets were cloned into the SacI restriction site of pZERO-2 plasmid (Invitrogen) and transformed into TOP10 E. coli cells (Invitrogen). The presence of the correct nucleotide sequence in the A and G clones was confirmed by sequencing. However, the G clone was found to contain an unintended mutation at the nucleotide position three bases in from the 5' end of the region that anneals to the interrogation probes. Because this mismatch is near the 5' end of the interrogation probe annealing sequence, it should not affect the interrogation results.

The following five target solutions were created with the A and G clones:

1. Hetero: 125 pg A and 125 pg G/microliter
2. LOH A: 125 pg A and no G/microliter
3. LOH G: no A and 125 pg G/microliter
4. Mix Ag: 125 pg A and 62 pg G/microliter
5. Mix Ga: 62 pg A and 125 pg G/microliter These target solutions were PCR amplified with the JH67 (SEQ ID NO:175) and 11077 (SEQ ID NO: 176) probes in the following reaction:

| 2 µL | Target solution |
|---|---|
| 1 µL | Probes JH67 and 11077 (50 pmol each) |
| 1 µL | 10 mM dNTPs |
| 5 µL | 10X Taq buffer |
| 1 µL | Taq DNA polymerase |
| 240 µL | water |

The PCR cycling parameters were: 96° C., 1 minute; (94° C., 15 seconds; 60° C., 30 seconds; 72° C., 45 seconds)×15; 72° C., 45 seconds. The entire PCR reaction was then purified with 500 µL Wizard™ PCR purification resin (Promega, A7170) according to manufacturer's instructions. The DNA was eluted with 30 µL TE buffer. A standard interrogation reaction with 6 µL target and 1 µg interrogation probe, was performed with the exception that 2 units of Klenow exo- were used per reaction. Four microliters of the final reaction were combined with 100 µL of L/L reagent and the relative light units measured.

|  | Heterozygote | LOH A | | LOH G | | Mix Ag | | Mix Ga | | Oligo Alone |
|---|---|---|---|---|---|---|---|---|---|---|
| No oligo | 30 | 40 | 65 | 29 | 34 | 51 | 19 | 59 | 26 | 41 | — |
| A oligo | 279 | 340 | 74 | 329 | 27 | 27 | 258 | 309 | 50 | 164 | 5.2 |
|  | 308 | 372 | 76 | 339 | 20 | 26 | 351 | 330 | 83 | 167 | 5.2 |
| G oligo | 302 | 324 | 37 | 91 | 285 | 272 | 127 | 106 | 245 | 302 | 6.3 |
|  | 278 | 325 | 30 | 87 | 256 | 187 | 113 | 124 | 215 | 357 | 6.3 |

-continued

|  | Heterozygote | | LOH A | | LOH G | | Mix Ag | | Mix Ga | | Oligo Alone |
|---|---|---|---|---|---|---|---|---|---|---|---|
| A:G ratio | 1.01 | 1.10 | 2.26 | 3.76 | 0.09 | 0.11 | 2.54 | 2.78 | 0.29 | 0.50 | |
| G:A ratio | 0.99 | 0.91 | 0.44 | 0.27 | 11.59 | 8.71 | 0.39 | 0.36 | 3.46 | 1.99 | |

These data illustrate that LOH can be determined using this method with appropriate interrogation probes.

| 10800 | 5' CGTGTATGCCACTTTGATATTACACCCATGAACGTGCTCATCGACGTGAACCCGCACAACGAGCT 3' | SEQ ID NO:171 |
|---|---|---|
| 10801 | 5' CGTTGTGCGGGTTCACGTCGATGAQCACGTTCATGGGTGTAATATCAAAGTGGCATACACGAGCT 3' | SEQ ID NO:172 |
| 10803 | 5' CGTGTATGCCACTTTGATATTACACCCGTGAACGTGCTCATCGACGTGAACCCGCCAAACGAGCT 3' | SEQ ID NO:173 |
| 10805 | 5' CGTTGTGCGGGTTCACGTCGATGAGCACGTTCACGGGTGTAATATCAAAGTGGCATACACGAGCT 3' | SEQ ID NO:174 |
| JH67 | 5' TCACACAGGAAACAGCTATGACCATG 3' | SEQ ID NO:175 |
| 11077 | 5' GCAAGGCGATTAAGTTGGGTAACG 3' (M13 forward probe) | SEQ ID NO:176 |
| 9211 | 5' CACTTTGATATTACACCCATG 3' | SEQ ID NO:86 |
| 9212 | 5' CACTTTGATATTACACCCGTG 3' | SEQ ID NO:35 |

EXAMPLE 50

Self-annealing Interrogation Probe

This Example illustrates use of a different type of oligonucleotide probe that is used to form a hairpin structure in the interrogation technology of this invention. This study demonstrates a method for eliminating the need for adding a probe specific to the interrogation site to the interrogation reaction.

Here, the oligonucleotide probe anneals to the target strand downstream of (3' to) the interrogation position in the target strand. The oligonucleotide has at its 5' end an unannealed region of nucleotides followed by about 5 to about 20 nucleotides that are identical to the interrogation region on the target strand. The annealed 3' end of the oligonucleotide is then extended through the interrogation position of the target strand creating what is referred to as extended probe. The hybrid is denatured and a hairpin structure formed between the extended probe strand and the 5' end of the oligonucleotide probe. This region is then assayed in a standard interrogation reaction to determine if a mismatch is present or not.

Four probes were designed to represent different types of hairpin formations that an extended probe strands may assume. These probes are 10207 (SEQ ID NO:177), 10208 (SEQ ID NO:178), 10209 (SEQ ID NO:179), and 10212 (SEQ ID NO:180).

These probes are predicted to form the following self-hybridized secondary structures when allowed to self-anneal:

```
10207      5' A-T-G-A-A-C-G-T-A-C-G-T-C-G-G
           3' T-A-C-T-T-G-C-A             |
                              C-C-G-A-G-T-A
```

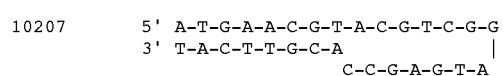

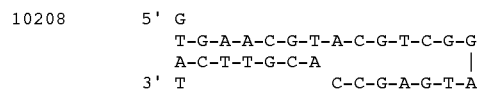

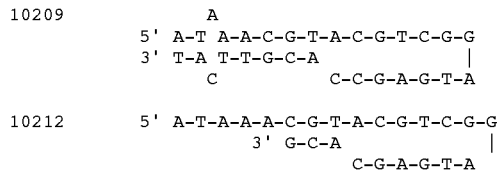

A 5 μL (5 μg) aliquot of each of the four probes was diluted to 100 μL with nanopure water. They were then sequentially diluted 1:10 to a final dilution factor of 1:100, 000. Twenty microliters of the diluted probes were heated, in separate tubes, at 95° C. for 3 minutes and cooled to room temperature for 10 minutes to permit self-annealing. Twenty microliters of Master Mix, as described in Example 1, were then added to each tube and the tubes were incubated at 37° C. for 15 minutes. Ten microliters of the solutions were added to 100 μL of L/L reagent (Promega, F202A) and relative light units measured immediately with a Turner® TD20/20 luminometer. The no-probe control resulted in 57.24 relative light units and the remaining probe results are reported below in relative light units (rlu).

| Log dilution | Probe | | | |
|---|---|---|---|---|
| | 10207 | 10208 | 10209 | 10212 |
| −5 | 44.89 | 56.22 | 57.57 | 57.80 |
| −4 | 85.21 | 64.56 | 58.26 | 63.15 |
| −3 | 297.7 | 70.53 | 79.12 | 82.65 |
| −2 | 970.5 | 108.4 | 80.06 | 106.7 |

Probe 10207 worked as an efficient target for interrogation as expected, with probe 10208 providing the anticipated negative results. Probe 10212 has only a three base match so it may be un-extended, thus resulting in the low values.

Probe 10209 likely has the 3' terminal nucleotide unannealed when the hairpin forms due to the mismatch at the third nucleotide in from the 3' end. Such an unannealed 3' terminal nucleotide would account for the low rlu values.

```
10207  5' ATGAACGTACGTCGGATGAGCACGTTCAT 3'  SEQ ID
                                            NO:177

10208  5' GTGAACGTACGTCGGATGAGCACGTTCAT 3'  SEQ ID
                                            NO:178

10209  5' ATAAACGTACGTCGGATGAGCACGTTCAT 3'  SEQ ID
                                            NO:179

10212  5' ATAAACGTACGTCGGATGAGCACG 3'       SEQ ID
                                            NO:180
```

EXAMPLE 51
Determination of Viral Load

This Example illustrates that the presence of viral nucleic acid in serum samples can be determined to a detection level of ten copies of viral nucleic acid per sample.

Hepatitis C Virus (HCV) RNA was isolated from infected or uninfected human serum samples. A two-step RT-PCR was performed using HCV-specific probes and about 1000 viral equivalents of RNA, and samples were interrogated using the interrogation probe HCV1 (SEQ ID NO:181).

Two HCV positive samples, one HCV negative sample, and a water control were analyzed in duplicate. The interrogation reaction was added to 100 μL of L/L reagent (Promega F202A) and the light output measured immediately on a Turner® TD20/20 luminometer. The average relative light unit values were as follows.

| Water control | 38.6 |
| --- | --- |
| HCV minus | 239.0 |
| HCV positive (1) | 1261.0 |
| HCV positive (2) | 1390.0 |

To determine the sensitivity of viral detection using this technology, RT-PCR was performed on HCV positive and HCV negative controls as well as samples estimated to contain 1000, 100, and 10 viral RNA copies. Twenty five microliters of each amplification reaction were purified using magnetic silica as described in Example 38 and eluted in 100 μL water. Four microliters of the eluted DNA were interrogated using the interrogation probe described above in a standard interrogation reaction as described in Example 32. The interrogation reaction was added to 100 μL of L/L reagent and the light output measured on a Turner® TD 20/20 luminometer. Ten copies of HCV are readily detected in this assay. The average relative light unit (rlu) values were as follows.

| Sample | rlu |
| --- | --- |
| Water | 49.0 |
| Water | 54.2 |
| HCV neg control | 59.4 |
| HCV neg control | 62.1 |
| HCV pos control | 653.7 |
| HCV pos control | 743.1 |
| HCV 1000 copies | 460.7 |
| HCV 1000 copies | 429.5 |
| HCV 100 copies | 405.1 |
| HCV 100 copies | 404.3 |
| HCV 10 copies | 184.9 |
| HCV 10 copies | 179.5 |

```
HCV1:                                       SEQ ID NO:181
5'CTGCTAGCCGAGTAGTGTTGGGTCGCCAAAGGCCTTGTGG 3'
```

EXAMPLE 52
Interrogation of DNA Sequences from Genetically Modified Organisms According to European Union (EU) Regulation on Novel Foods and Novel Food Ingredients, adopted in 1997, genetically modified foods must be labeled as such if they are "no longer equivalent" to their conventional counterparts. This includes when the foods have a different composition, use or nutritional value from the conventional food. The EU subsequently decided that the presence of just a fragment of genetically modified protein or DNA is enough to make the product "no longer equivalent" to conventional products for soya and maize and, therefore, such products require labeling.

Genetically modified organisms (GMO), particularly plants, are often genetically modified to include the exogenous specific DNA of interest along with an exogenous transcription sequence such as the 35S promoter and the NOS terminator. In this example, the DNA of soya and maize samples are analyzed for the presence or absence of the 35S promoter and NOS terminator. The PCR Primers 35S-1 (SEQ ID NO:182) and 35S-2 (SEQ ID NO:183) were used to prepare a 235 bp PCR product. The Primers NOS-1 (SEQ ID NO:184) and NOS-2 (SEQ ID NO:185) were used to prepare a 220 bp PCR product.

GMO positive and negative control DNA (20 ng) were PCR amplified using 50 pmol of the 35S promoter and NOS terminator PCR primer pairs. The PCR cycling profile was 94° C., 3 minutes; (94° C., 30 seconds; 54° C., 40 seconds; 72° C., 1 minute)×40; 72° C., 3 minutes. The resulting PCR products (25 μL) were purified using magnetic silica and eluted in 100 μL water as described in Example 33. Four microliters of the eluted PCR products were used in a standard interrogation assay as described in Example 32 and the relative light unit (rlu) results are detailed in the following table. The 35S interrogation probes used were 11211 (SEQ ID NO:186) and 11210 (SEQ ID NO:187). The NOS interrogation probes used were 11212 (SEQ ID NO:188) and 11213 (SEQ ID NO:189).

| DNA | PCR Oligos | Interrogation Oligos | rlu |
| --- | --- | --- | --- |
| GMO minus, soy | 35S | 11210 | 166.6 |
| GMO minus, soy | 35S | 11210 | 172.0 |
| GMO minus, soy | 35S | 11211 | 206.8 |
| GMO minus, soy | 35S | 11211 | 205.8 |
| GMO minus, soy | 35S | none | 95.7 |
| GMO minus, maize | 35S | 11210 | 245.0 |
| GMO minus, maize | 35S | 11210 | 254.3 |
| GMO minus, maize | 35S | 11211 | 271.3 |
| GMO minus, maize | 35S | 11211 | 275.7 |
| GMO minus, maize | 35S | none | 116.0 |
| GMO positive, soy | 35S | 11210 | 1456.0 |
| GMO positive, soy | 35S | 11210 | 1442.0 |
| GMO positive, soy | 35S | 11211 | 1546.0 |
| GMO positive, soy | 35S | 11211 | 1529.0 |

-continued

| DNA | PCR Oligos | Interrogation Oligos | rlu |
|---|---|---|---|
| GMO positive, soy | 35S | none | 865.0 |
| GMO positive, maize | 35S | 11210 | 1252.0 |
| GMO positive, maize | 35S | 11210 | 1299.0 |
| GMO positive, maize | 35S | 11211 | 1358.0 |
| GMO positive, maize | 35S | 11211 | 1361.0 |
| GMO positive, maize | 35S | none | 705.6 |
| GMO minus, soy | NOS | 11212 | 73.9 |
| GMO minus, soy | NOS | 11213 | 75.8 |
| GMO minus, soy | NOS | none | 76.1 |
| GMO positive, soy | NOS | 11212 | 615.0 |
| GMO positive, soy | NOS | 11213 | 616.6 |
| GMO positive, soy | NOS | none | 98.0 |

The above data demonstrate that the interrogation reaction works for the identification of presence or absence of GMO DNA in DNA samples isolated from soy and maize products. The 35S PCR product gave high background values by itself, which can be reduced by using a primer with phosphorothioate linkages near the 5'-terminus for the PCR reaction followed by exo6 treatment to remove one strand of the PCR product as described in Example 38 and below. The PCR primers 35S1 and NOS1 were resynthesized to have phosphorothioate linkages between the first five bases at the 5' end. The PCR reaction was repeated and the resulting PCR product treated with exo6 and purified as described in Example 38.

Four microliters of the purified DNA were used for the standard interrogation assay using the NOS primer 11212 and the 35S primer 11211 with 5 units of Klenow exo-. The rlu data obtained are in the table below.

| DNA | PCR oligos | Interrogation oligo | rlu |
|---|---|---|---|
| GMO minus, soy | NOS | 11212 | 52.3 |
| GMO minus, soy | NOS | 11211 | 60.2 |
| GMO minus, soy | NOS | none | 53.3 |
| GMO positive, soy | NOS | 11212 | 277.1 |
| GMO positive, soy | NOS | 11211 | 84.4 |
| GMO positive, soy | NOS | none | 75.7 |
| GMO minus, soy | 35S | 11212 | 57.8 |
| GMO minus, soy | 35S | 11211 | 66.9 |
| GMO minus, soy | 35S | none | 54.6 |
| GMO positive, soy | 35S | 11212 | 99.7 |
| GMO positive, soy | 35S | 11211 | 397.6 |
| GMO positive, soy | 35S | none | 86.0 |
| GMO positive, soy | 35S + NOS | 11212 | 249.4 |
| GMO positive, soy | 35S + NOS | 11211 | 290.1 |
| GMO positive, soy | 35S + NOS | 11211 + 11212 | 482.5 |
| GMO positive, soy | 35S + NOS | none | 70.5 |

This method greatly reduced the background from the 35S PCR product and permitted better discrimination between the GMO positive and GMO minus DNA samples. Also, this example again demonstrates the utility of the technology for multiplexing both the PCR reaction and the interrogation reaction. As seen in the last four reactions above, the data show that the use of multiple PCR probes and/or multiple interrogation probes leads to identification of GMO organisms.

```
35S promoter PCR primers:
35S-1    5' GATAGTGGGATTGTGCGTCA 3'    SEQ ID NO:182

35S-2    5' GCTCCTACAAATGCCATCA 3'     SEQ ID NO:183

NOS terminator PCR primers
NOS-1    5' TTATCCTAGTTTGCGCGCTA 3'    SEQ ID NO:184

NOS-2    5' GAATCCTGCTGCCGGTCTTG 3'    SEQ ID NO:185

35S Interrogation oligonucleotide probes:
11211    5' GCAAGTGGATTGATG 3'         SEQ ID NO:186

11210    5' CCAACCACGTCTTCAAA 3'       SEQ ID NO:187

NOS Interrogation oligonucleotide probes
11212    5' TTTATGAGATGGGTTT 3'        SEQ ID NO:188

11213    5' ATGATTAGAGTCCCG 3'         SEQ ID NO:189
```

EXAMPLE 53

Pyrophosphorylation Chain Reaction: High Sensitivity Detection Through Generation of New Targets by Probe Design Pyrophosphorylation of a DNA/DNA or a DNA/RNA hybrid with MMLV RT and Klenow Exo- does not take place when the duplex has a 3' overhang. Two probes designed to hybridize to the target exactly, but also to each other to yield 3' overhangs, do not increase the background when present in the pyrophosphorylation reaction because they are not substrates for these enzymes when hybridized to each other.

If the hybridized, treated sample is subjected to the pyrophosphorylation reaction, the ends of the probe on the target sequence are pyrophosphorylated. In this example, the presumption has been made that 5 bp are removed from these probes. After the reaction is complete, a total of "two ends worth" of nucleoside triphosphate is formed.

Heating the reaction components to 95° C. denatures the hybrids from the first round. When the reaction is cooled, the denatured hybrid strands become available for hybridization to other probes. This reaction is now subjected to a second round of pyrophosphorylation. The probes hybridized to the target sequence again pyrophosphorylate generating another "two ends worth" of nucleoside triphosphate. In addition, the original probes that have hybridized to unpyrophosphorylated probes are substrates for the reaction and also contribute "two ends worth" of nucleoside triphosphate. Thus, a total of "four ends worth" of nucleoside triphosphate are formed in this round. This is in addition to the "two ends worth" from round one, so a total of six ends worth are present after round two.

Cycling can continue for additional rounds. At the end of round 3 a total of 12 ends worth of nucleoside triphosphate are formed. At the end of round 4, a total of 20 ends worth of nucleotide triphosphate are formed and at the end of round 5, a total of 30 ends worth of nucleotide triphosphate are formed.

EXAMPLE 54

Pyrophosphorylation Chain Reaction II

The RNA concentration limit for detection is considerably higher than DNA, which can be routinely detected in lower concentrations than RNA. This study demonstrates a way to increase nucleic acid detection sensitivity using a pyrophosphorylation chain reaction.

Here, a low signal level from the initial reaction is augmented using a series of probes that can be substrates for pyrophosphorylation reaction only if the 3' end of the target is resultant from a previous pyrophosphorylation reaction. Unless there is pyrophosphorylation of the previous oligonucleotide, it would have a 3' overhang when hybridized to the second round oligonucleotide and thus would not function as a substrate for the pyrophosphorylation reaction with Klenow exo- enzyme or MMLV RT.

Two probes, 9225 (SEQ ID NO:190) and 9276 (SEQ ID NO:191), were prepared, each of which is complementary to probe 8272 (SEQ ID NO:192) and each of which is recessed on the 5' end when hybridized with probe 8272. Probe 9225 is recessed 2 bases and probe 9276 is recessed 1 base. When probe 8272 hybridizes with either 9225 or 9276, it is not a substrate for Klenow exo- or MMLV RT because there is a 3' overhang. However, if probe 8272 is previously pyrophosphorylated (e.g. when hybridized to mRNA), it will create 5' overhangs when hybridized to 9225 or 9276. Therefore, the second cycle of pyrophosphorylation enhances pyrophosphorylation values. Probe 8271 (SEQ ID NO:193) is used as a positive control, as it is an exact complement of probe 8272 and it is a pyrophosphorylation substrate for Klenow Exo- regardless of whether or not probe 8272 is previously pyrophosphorylated.

The following enzyme mix was assembled:

| | |
|---|---|
| 36 µL | 5X MMLV-RT buffer (Promega, M531A) |
| 4.5 µL | 40 mM NaPPi (Promega, C113A) |
| 9.0 µL | 200 U/µL MMLV-RT (Promega, M1701) |

First cycle pyrophosphorylation reactions were set up to include the following.

| | Reaction A | Reaction B | Reaction C |
|---|---|---|---|
| 10 mM Tris, pH 7.3 | 41.5 µL | 42.5 µL | 40.5 µL |
| 50 ng/µL Globin mRNA (Gibco BRL cat# 18103-028) | 2 µL | none | 2 µL |
| 100 ng/µL probe 8272 | none | 1 µL | 1 µL |
| enzyme mix | 16.5 µL | 16.5 µL | 16.5 µL |

The three reactions were incubated at 37° C. for 60 minutes then 15 µL of each reaction were aliquoted into 4 separate tubes. For each set of reactions, 2 µL Tris, 2 µL probe 9225, 2 µL probe 9276, or 2 µL probe 8271 were added and the tubes were then further incubated at 55° C. for 15 minutes and cooled to room temperature. This is referred to as the second cycle hybridization mix.

A master mix for the second round of pyrophosphorylation was assembled as follows:

| | |
|---|---|
| 426 µL | water |
| 80 µL | 10X Pol Buffer |
| 10 µL | 40 mM NaPPi |
| 4 µL | NDPK (1 U/µL) |
| 40 µL | 2 mM ADP (Sigma) |
| 40 µL | Klenow Exo- |

Fifteen microliters of master mix were added to 5 µL of each second cycle hybridization mix. These tubes were then incubated at 37° C. for 30 minutes. Thereafter, 100 µL of L/L reagent (Promega F202A) were added and the relative light units were measured on a Turner® TD20/20 luminometer.

The average of triplicate measurements is reported below in relative light units (avg. rlu).

| 1st cycle | 2nd cycle probe | avg. rlu |
|---|---|---|
| mRNA only | none | 22.16 |
| mRNA only | 9225 | 54.82 |
| mRNA only | 9276 | 67.28 |
| mRNA only | 8271 | 198.00 |
| Probe 8272 only | none | 42.74 |
| Probe 8272 only | 9225 | 186.13 |
| Probe 8272 only | 9276 | 910.13 |
| Probe 8272 only | 9271 | 1252.67 |
| mRNA + 8272 | none | 127.97 |
| mRNA + 8272 | 9225 | 641.17 |
| mRNA + 8272 | 9276 | 1152.67 |
| mRNA + 8272 | 9271 | 1122.33 |

Thus, after the removal of the 3' overhang due to pyrophosphorylation, probe 8272 hybridized with secondary probes becoming a substrate for $2^{nd}$ round of pyrophosphorylation. However, the results are confused due to an unknown reason by high background. Even without mRNA present, unpyrophosphorylated probe 8272, when combined with either probe 9225 or probe 9276 provided elevated $2^{nd}$ cycle rlu values.

```
9225  5' GGTGCATCTGTCCAGTGAGGAGAAGTCTGC 3' SEQ ID
                                              NO:190

9276  5' TGGTGCATCTGTCCAGTGAGGAGAAGTCTG 3' SEQ ID
                                              NO:191

8272  5' AGACTTCTCCTCACTGGACAGATGCACCAT 3' SEQ ID
                                              NO:192

8271  5' ATGGTGCATCTGTCCAGTGAGGAGAAGTCT 3' SEQ ID
                                              NO:193
```

EXAMPLE 55

Dual Probe Rolling Circle Amplification Prior to Interrogation

The amplification of target nucleic acid by means of rolling circle amplification prior to the interrogation reaction is examined in this Example as a substitute methodology for PCR amplification. A typical rolling circle amplification of a circular target using two probes is described in Lizardi, P. M. et al *Nature Genetics*, 19:227 (1998).

The wild type target used in this study is oligonucleotide 10870 (SEQ ID NO:194). The mutant target used is oligonucleotide 10994 (SEQ ID NO:195). The open circle probe which anneals to the targets is oligonucleotide 10865 (SEQ ID NO:196). Rolling circle replication primer which anneals to the open circle probe is oligonucleotide 10866 (SEQ ID NO:197). Rolling circle replication primer 10869 (SEQ ID NO:198) has a 3'-terminal residue that anneals only to the wild type target, whereas probe 10989 (SEQ ID NO:199) has a 3'-terminal residue that anneals only to the mutant target. Probes 10869 and 10989 both have a nucleotide located 3 nucleotides from the 3'-terminal nucleotide that is not complementary to either the wild type or the mutant target. This mismatched base was intentionally incorporated to provide for increased specificity in the interrogation reaction.

This Example uses a synthetic heterozygote solution containing both the 10870 and 10994 oligonucleotides as targets. The 10865 oligonucleotide anneals to both of these targets in a similar manner, forming a circular target with a seven base pair gap that needs to be filled in from the 10865

3' end and ligated in order for complete rolling circle amplification to proceed. The annealing of the 10865 oligonucleotide to 10870 wild type and 10994 mutant oligonucleotides is diagrammed in FIG. 1. In the absence of ligation, no priming can occur.

The following heterozygote solution was assembled:

| | |
|---|---|
| 2 μL | 10X ampligase buffer (Epicenter) |
| 2 μL | 2 mM dTTP, dCTP, dATP |
| 1 μL | 500 μg/mL probe 10865 (probe) |
| 0.5 μL | 500 μg/mL probe 10870 (wild type target strand) |
| 0.5 μL | 500 μg/mL probe 10994 (mutant target strand) |
| 1 μL | 5 u/μL Tfl DNA polymerase |
| 1 μL | 5 u/μL Ampligase (Thermostable ligase, Epicenter) |
| 12 μL | water |

Likewise, the homozygote solutions were assembled using either 1 μL probe 10870 and no 10994 to prepare the wild type homozygote target, or no 10870 and 1 μL 10994 to prepare the mutant homozygote target. Only three deoxynucleotides are included in the solutions to prevent strand displacement. The solutions were incubated at 65° C. for 30 minutes after which time they were estimated to have formed about $2.5 \times 10^{11}$ circular molecules per microliter. After the 30 minutes of incubation they were diluted to about 2500 circular targets per microliter. The heterozygote, the homozygote wild type and homozygote mutant gap-fill ligations were then used to assemble the following amplification reactions.

| Reaction: | 1 | 2 | 3 | 4 | 5 | 6 |
|---|---|---|---|---|---|---|
| 1 μL Target | WT* homoZ* | WT homoZ | Mut* homoZ | Mut homoZ | heteroZ* | heteroZ |
| 0.5 μL Probe | 10869 WT | 10989 Mut | 10869 WT | 10989 Mut | 10869 WT | 10989 Mut |

*WT = wild type;
*Mut = mutant;
*homoZ = homozygote; and
*heteroZ = heterozygote Additionally, each tube contained 2 μL 10× Polymerase buffer, 1 μL 10 mM dNTPs, 0.5 μL probe 10866, 1 μL 1.2 μg/μL T4 Gene 32, 1.5 μL DMSO and 18.5 μL water. The assembled components were then put on ice and 3 μL Vent exo- (2 U/μL) were added. The solutions were covered with 30 μL of mineral oil and placed at 95° C. for 3 minutes then 65° C. for 90 minutes. The free nucleotides were then removed using the Wizard™ PCR purification system (Promega, A7170) and the DNA eluted with 50 μL water.

The following Master mix was assembled.

| | |
|---|---|
| 30 μL | 10X Buffer A |
| 3.75 μL | 40 mM NaPPi |
| 15 μL | T4 DNA polymerase (10 U/μL) |
| 3 μL | NDPK (1 U/μL) |
| 3 μL | 10 μM ADP (Sigma) |
| 245 μL | water |

One microliter of the above amplification reactions was added to 19 μL master mix in duplicate tubes. The tubes were incubated for 15 minutes at 37° C., then 5 μL of the reaction were added to 100 μL of L/L reagent (Promega F202A) and light output was measured in a Turner® TD20/20 luminometer.

| | Relative light units | | | |
|---|---|---|---|---|
| Rxn* | Undiluted target | 1:4 diluted target | Second probe | Target |
| 1. | 618.6 | 458.2 | WT* | WT homoZ* |
| 1. | 621.6 | 457.7 | WT | WT homoZ |
| 2. | 282.4 | 90.2 | Mut* | WT homoZ |
| 2. | 288.4 | 100.3 | Mut | WT homoZ |
| 3. | 365.9 | 148.6 | WT | Mut homoZ |
| 3. | 379.8 | 149.9 | WT | Mut homoZ |
| 4. | 632.5 | 461.5 | Mut | Mut homoZ |
| 4. | 650.2 | 442.4 | Mut | Mut homoZ |
| 5. | 606.1 | 381.1 | WT | heteroZ* |
| 5. | 608.6 | 394.3 | WT | heteroZ |
| 6. | 631.0 | 420.1 | Mut | heteroZ |
| 6. | 637.3 | 411.4 | Mut | heteroZ |

*Rxn = reaction;
*WT = wild type;
*Mut = mutant;
*homoZ = homozygote; and
*heteroZ = heterozygote At the lower amount of target DNA, the mutant:wild type discrimination improves to 3–5 fold from the 2–3 fold exhibited when using the undiluted target DNA. This indicates that the study using the undiluted target was likely out of the linear range. The heterozygote ratio for both studies is close to the expected 1:1.

| 10870 | 5' TTGCAGAGAAGACATATAGTTCTTGGAGAAGGTGGAATCACACTGAGTGGA 3' | SEQ ID NO:194 |
|---|---|---|
| 10994 | 5' TTGCAGAGAAAGACAATATAGTTCTTTGAGAAGGTGGAATCACACTGAGTGGA 3' | SEQ ID NO:195 |
| 10865 | 5' GAACTATATTGTCTTTCTCTGATTCTGACTCGTCATGTCTCA GCTTTAGTTTAATACGACTCACTATAGGGCTCAGTGTGATTCCACCT 3' | SEQ ID NO:196 |
| 10866 | 5' CTAAAGCTGAGACATGACGAGTC 3' | SEQ ID NO:197 |
| 10869 | 5' CTCAGTGTGATTCCACCTTCACC 3' | SEQ ID NO:198 |
| 10989 | 5' CTCAGTGTGATTCCACCTTCACA 3' | SEQ ID NO:199 |

EXAMPLE 56

Tne Triple Mutant Tne Polymerase and Thermostable NDPK Used to Interrogate Congenital Adrenal Hyperplasia Congenital adrenal hyperplasia (CAH) is a group of autosomal recessive diseases resulting from a wide range of mutations in the steroid 21-hydroxylase (CYP21) gene that contains 10 exons. There is a high level of nucleic acid homology (98% in exons, 96% in introns) between CYP21, the functional gene, and CYP21P, the nonfunctional pseudogene. The many types of mutations in this gene that can lead to disease include complete gene deletions, large gene conversions, single point mutations, and a small 8 bp deletion [See, White, et al., *Hum. Mutat.*, 3:373–378, (1994)].

The majority of the CAH disease-causing mutations are sequences present in the nonexpressed CYP21P pseudogene, and arise in the CYP21 gene through recombination between CYP21P and CYP21. Thus, one mutation detection strategy specifically detects the CYP21 gene, and not the CYP21P pseudogene. The frequency of disease-carrying alleles in the population is about 1 in 50.

In this example, the CAH target was interrogated for a variety of mutations using Klenow exo- and yeast NDPK, and the results were compared to a similar analysis using Tne triple mutant thermostable DNA polymerase and a thermostable Pfu NDPK. Both wild type CAH PCR products, mutant synthetic targets, and a pseudogene PCR product amplified from the cloned CYP21P pseudogene were utilized as targets in this assay. They are listed below.

Primer pairs used in PCR amplification and the resulting products are as follows.

| Primers | Size PCR Segment | Segment Amplified |
|---|---|---|
| 10912 + 10909 | 1400 bp | 5' end CYP21 |
| 11461 + 11480 | 918 bp | 5' end CYP21 |
| 10910 + 11286 | 1492 bp | 3' end CYP21 |
| 11535 + 11286 | 1496 bp | 3' end CYP21 |
| 10912 + 10911 | 2680 bp | pseudogene (CYP21P) |

Synthetic targets and interrogation oligos utilized are listed below.

PCR reactions were assembled to amplify regions of the CAH gene with 4 different probe sets, using undigested human genomic DNA (Promega, G3041) as target (25 ng per reaction). For amplification of the pseudogene, human genomic DNA was predigested with the restriction enzyme Bcl I, which specifically cleaves the CYP21 gene upstream of the forward PCR probe, thus permitting only amplification of CYP21P [Krone, *Clinical Chem.* 44(10): 2075–2082 (1998)].

The 2680 bp PCR product was amplified from 50 ng of digested DNA and subsequently cloned into the plasmid vector pGEM-T Easy (Promega, A1380) following the manufacturer's protocol. A clone was selected and sequenced (USB Sequenase kit, US70770) to confirm it was indeed the pseudogene. The cloned CYP21P gene in the PGEM-T Easy vector was used in subsequent amplifications to obtain pure pseudogene PCR product for mutation interrogation analysis (100 pg of plasmid per PCR reaction).

All 50 µL amplification reactions contained the following reagents: genomic DNA (as described above), 1× reaction buffer (M1901), 1.0–1.5 mM magnesium chloride (all with 1.0 mM except probe pair 10912+10911 for pseudogene, which contained 1.5 mM $MgCl_2$; Promega, A3511), 200 µM each dNTP (C1141), 50 pmoles each probe, and 2.5 units Taq DNA Polymerase (M1665).

The following cycling profile was utilized for all amplifications: 5 minutes at 95° C.; 40 cycles of 30 seconds at 94° C., 1 minute at 55° C., 1 minute per kbp of product at 72° C.; 8 minutes at 68° C.; soak at 4° C. The products were analyzed on 1% agarose gels and compared to DNA molecular weight standards to confirm product sizes were correct. An aliquot of each PCR reaction (25 µL) was then treated with 50 units T7 Gene6 Exonuclease (USB, E70025Y) for 15 minutes at 37° C., followed by purification using the Wizard™ PCR Prep DNA Purification System (Promega, A7170) with 3×1 mL 80% isopropanol washes. The exonuclease-treated DNA was eluted in 100 µL of nuclease-free water.

Each interrogation assay (20 µL total volume) contained 4 µL of purified PCR product or 5 ng of synthetic target, and 1 4g interrogation oligo probe (or water for the no-oligo background control). The reactions were incubated at 95° C. for 3 minutes, followed by 10 minutes at 37° C. for Klenow exo- or 55° C. for Tne polymerase. Twenty microliters of master mix were added (2 mM sodium pyrophosphate, 0.2 µM ADP, 2× polymerase buffer (M195A for Klenow or M1901 for Tne), 5 mM magnesium chloride for Tne only, 1–2 U Klenow exo- and 0.2 U yeast NDPK or 1 U Tne triple mutant polymerase and 0.1 U Pfu NDPK) and the reaction incubated 15 minutes at 37° C. (Klenow exo-) or 55° C. (Tne). The entire reaction was then added to 100 µL of L/L reagent (Promega, FF202A) and light output read in a Turner® TD20/20 luminometer.

Although 55° C. was used in these studies with the Tne triple mutant polymerase and the Pfu NDPK, higher temperatures can also be used. The 55° C. temperature selected appeared to be a good compromise between interrogation oligo annealing and enzymatic activity. Thus, higher incubation temperatures can be beneficial if longer interrogation oligos are utilized.

The table below contains the relative light units (rlu) obtained. The data represent the combined results of many separate studies using the various enzymes. The use of the Tne triple mutant polymerase and Pfu NDPK particularly improved the discrimination ratio for the CAH wild type PCR products at mutation sites 2 and 6, whereas the thermostable enzymes improved the discrimination ratio for the mutant pseudogene PCR product at mutation sites 3, 4, and 5. The synthetic targets worked well with both enzymes, however the signals and discrimination ratios were higher for the thermostable enzymes at almost all of the mutation sites.

| | Klenow/ NDPK | Klenow/ NDPK | Klenow/ NDPK | Tne/ Pfu NDPK | Tne/ Pfu NDPK | Tne/ Pfu NDPK | |
|---|---|---|---|---|---|---|---|
| Target DNA | No oligo | WT oligo | Mutant oligo | No oligo | WT* oligo | Mutant oligo | Mut* Site |
| CAH WT 1400 bp | 176.9 | 1050.0 | 204.0 | | | | 1 |
| CAH WT 1400 bp | 176.9 | 1149 | 625.5 | | | | 2 |
| CAH WT 1492 bp | 388.9 | 496.2 | 414.7 | | | | 3 |
| CAH WT | 388.9 | 881.4 | 383.9 | | | | 4 |

|  | Klenow/ NDPK | Klenow/ NDPK | Klenow/ NDPK | Tne/ Pfu NDPK | Tne/ Pfu NDPK | Tne/ Pfu NDPK |  |
|---|---|---|---|---|---|---|---|
| CAH WT 1492 bp | 388.9 | 940.3 | 477.3 |  |  |  | 5 |
| CAH WT 1492 bp | 388.9 | 205.2 | 207.0 |  |  |  | 6 |
| CAH WT 1492 bp |  |  |  | 129.4 | 443.0 | 125.6 | 1 |
| CAH WT 918 bp |  |  |  | 129.4 | 440.9 | 134.7 | 2 |
| CAH WT 918 bp |  |  |  | 124.3 | 261.6 | 118.3 | 3 |
| CAH WT 1496 bp |  |  |  | 124.3 | 259.4 | 121.7 | 4 |
| CAH WT 1496 bp |  |  |  | 124.3 | 276.3 | 135.6 | 5 |
| CAH WT 1496 bp |  |  |  | 124.3 | 214.0 | 112.3 | 6 |
| CAH WT 1496 bp |  |  |  | 124.3 | 252.5 | 174.5 | 7 |
| Pseudo-gene 2680 bp | 15.89 | 115.7 | 109.2 | 176.1 | 419.0 | 537.3 | 1 |
| Pseudo-gene 2680 bp | 15.89 | 45.29 | 140.4 | 176.1 | 388.6 | 397.5 | 2 |
| Pseudo-gene 2680 bp | 15.89 | 129.6 | 141.6 | 176.1 | 477.8 | 772.5 | 3 |
| Pseudo-gene 2680 bp | 15.89 | 63.34 | 149.2 | 176.1 | 369.4 | 999.7 | 4 |
| Pseudo-gene 2680 bp | 15.89 | 115.8 | 91.28 | 1676.1 | 412.1 | 945.9 | 5 |
| Pseudo-gene 2680 bp |  |  |  | 176.1 | 202.7 | 945.0 | 7 |
| Synthetic Temp. 1* | 95.65 | 128.2 | 831.2 | 56.92 | 76.58 | 1499 | 1 |
| Synthetic Temp. 2 | 81.09 | 119.3 | 774.9 | 58.46 | 171.8 | 1521 | 2 |
| Synthetic Temp. 3 | 83.22 | 315.6 | 1496 | 54.05 | 171.2 | 2206 | 3 |
| Synthetic Temp. 4 | 87.71 | 85.82 | 1199 | 55.29 | 152.1 | 2829 | 4 |
| Synthetic Temp. 5 | 78.80 | 332.5 | 1071 | 57.49 | 76.91 | 837.7 | 5 |
| Synthetic Temp. 6 | 79.86 | 57.0 | 322.0 | 56.68 | 140.6 | 2328 | 6 |
| Synthetic Temp. 7 | 86.99 | 1738 | 1285 | 209.2 | 4162 | 351.3 | 2 |
| Synthetic Temp. 8 | 98.50 | 1005 | 29.24 | 212.0 | 2121 | 260.4 | 6 |

*WT = wild type;
*Mut = mutation;
*Temp. = template

PCR PRIMERS UTILIZED:

10909 5' CCAGAGCAGGGAGTAGTCTC 3'    SEQ ID NO:200
CAH reverse primer; 5' most 3 linkages
phosphorothioate (CYP21 only)

10912 5' GCATATAGAGCATGGCTGTG 3'    SEQ ID NO:201
CAH forward primer 10910 5' CCTGTCCTTGGGAGACTAC 3'     SEQ ID NO:202
CAH forward primer (CYP21 only)

10911 5' CCCAGTTCGTGGTCTAGC 3'      SEQ ID NO:203
CAH reverse primer; 5' most 3 linkages
phosphorothioate 11286 5' TCCTCACTCATCCCCAAC 3'      SEQ ID NO:204
CAH reverse primer; 5' most 3 linkages
phosphorothioate 11461 5' GAAATACGGACGTCCCAAGGC      SEQ ID NO:205
CAH forward primer 11480 5' CTTTCCAGAGCAGGGAGTAG       SEQ ID NO:206

-continued

CAH reverse primer; 5' most 3 linkages phosphorothioate (CYP21 only)

11535 5' CCGGACCTGTCCTTGGGAGA     SEQ ID NO:207
CAH forward primer (CYP21 only)

SYNTHETIC TARGETS UTILIZED:

11293 5' AGAAGCCCGGGGCAAGAGGCAGGAGGTGGAGGCTCCGGAG 3'     SEQ ID NO:208
CAH Synthetic Target 1 for Interrogator oligo 1
(pseudogene/mutant - exon 1)
Mutation site 1

11294 5' AGCTTGTCTGCAGGAGGAGCTGGGGGCTGGAGGGTGGGAA 3'     SEQ ID NO:209
CAH Synthetic Target 2 for Interrogator oligo 2
(pseudogene/mutant - intron 2)
Mutation site 2

11295 5' TCCGAAGGTGAGGTAACAGTTGATGCTGCAGGTGAGGAGA 3'     SEQ ID NO:210
CAH Synthetic Target 3 for Interrogator oligo 3
(pseudogene/mutant - exon 4)
Mutation site 3

11296 5' TCCACTGCAGCCATGTGCAAGTGCCCTTCCAGGAGCTGTC 3'     SEQ ID NO:211
CAH Synthetic Target 4 for Interrogator oligo 4
(pseudogene/mutant - exon 7)
Mutation site 4

11297 5' TCGTGGTCTAGCTCCTCCTACAGTCGCTGCTGAATCTGGG 3'     SEQ ID NO:212
CAH Synthetic Target 5 for Interrogator oligo 5
(pseudogene/mutant - exon 8)
Mutation site 5

11298 5' GCTAAGGGCACAACGGGCCACAGGCGCAGCACCTCGGCGA 3'     SEQ ID NO:213
CAH Synthetic Target 6 for Interrogator oligo 12
(pseudogene/mutant - exon 8)
Mutation site 6

11484 5' CAGCTTGTCTGCAGGAGGAGTTGGGGGCTGGAGGGTGGGA 3'     SEQ ID NO:214
CAH Synthetic Target 7 for Interrogator oligo 7
(wild type - intron 2)
Mutation site 2

11485 5' GGCTAAGGGCACAACGGGCCGCAGGCGCAGCACCTCGGCG 3'     SEQ ID NO:215
CAH Synthetic Target 8 for Interrogator oligo 11
(wild type - exon 8)
Mutation site 6

INTERROGATION OLIGOS PROBES UTILITY:

11143 5' CGGAGCCTCCACCTCCCG 3' SEQ ID NO:216
CAH interrogator oligo 6 (wild type) for mutation site 1

11085 5' CACCCTCCAGCCCCCAGC 3' SEQ ID NO:217
CAH interrogator oligo 2 (pseudogene/mutant) for mutation site 2

11084 5'CGGAGCCTCCACCTCCTG 3' SEQ ID NO:218
CAH interrogator oligo 1 (pseudogene/mutant) for mutation site 1

11086 5' CCTCACCTGCAGCATCAAC 3' SEQ ID NO:219
CAH interrogator oligo 3 (pseudogene/mutant) for mutation site 3

11144 5' CACCCTCCAGCCCCCAAC 3' SEQ ID NO:220
CAH interrogator oligo 7 (wild type) for mutation site 2

11145 5' CCTCACCTGCAGCATCATC 3' SEQ ID NO:221
CAH interrogator oligo 8 (wild type) for mutation site 3

-continued 11087 5' CCTGGAAGGGCACTT 3' SEQ ID NO:222
CAH interrogator oligo 4 (pseudogene/mutant) for mutation site 4

11146 5' CCTGGAAGGGCACGT 3' SEQ ID NO:223
CAH interrogator oligo 9 (wild type) for mutation site 4

11088 5' GATTCAGCAGCGACTGTA 3' SEQ ID NO:224
CAH interrogator oligo 5 (pseudogene/mutant) for mutation site 5

11147 5' GATTCAGCAGCGACTGCA 3' SEQ ID NO:225
CAH interrogator oligo 10 (wild type) for mutation site 5

11287 5' CGAGGTGCTGCGCCTGCG 3' SEQ ID NO:226
CAH interrogation oligo 11 (wild type) for mutation site 6

11288 5'CGAGGTGCTGCGCCTGTG 3' SEQ ID NO:227
CAH interrogation oligo 12 (pseudogene/mutant) for mutation site 6

11641 5'GGGATCACATCGTGGAGATG 3' SEQ ID NO:228
CAH interrogation oligo 23 (wild type) for mutation site 7

11642 5'GGGATCACAACGAGGAGAAG 3' SEQ ID NO:229
CAB interrogation oligo 24 (pseudogene/mutant) for mutation site 7

EXAMPLE 57

Multiplex Analysis of Congenital Adrenal Hyperplasia (CAH) Gene

The use of thermostable enzymes to interrogate the CAH gene, as described in Example 56, has also permitted the interrogation of up to 6 multiple sites within one reaction. The method used in this Example is illustrative of routine studies carried out in screening laboratories where usual results show the presence of an expected gene (or the absence of a mutant gene) in almost all of the samples, and only rarely shows the presence of a mutant gene. In the case illustrated here, a qualitative result is provided from which the exact mutation present can be determined in a subsequent assay.

Thus, equal volumes of the CAH wild type (WT) 918 bp and 1496 bp PCR products (see Example 56) were combined (to thus span the entire CAH gene) and interrogated either separately at each mutation site, or as a multiplexed group. The discrimination ratio was good both in the separate reactions for the combined PCR products, as well as the multiplexed reaction. In addition, the multiplexed reaction using the CAH wild type PCR products and either 6 wild type interrogation oligo probes or 6 mutant interrogation oligo probes was combined with an equimolar amount of synthetic target (mutant synthetic target for each mutation site; 0.2 pmoles either PCR product or synthetic target), to simulate a heterozygote sample.

| Target DNA | Tne/Pfu NDPK, No Oligo | Tne/Pfu NDPK, WT Oligo | Tne/Pfu NDPK Mutant Oligo | Probe for Mutation Site | Mutant Synthetic Target Added |
|---|---|---|---|---|---|
| CAH WT 918 bp + 1496 bp | 172.7 | 553.0 | 180.2 | 1 | |
| Same | 172.7 | 535.7 | 184.0 | 2 | |
| Same | 172.7 | 494.8 | 182.0 | 3 | |
| Same | 172.7 | 486.7 | 148.7 | 4 | |
| Same | 172.7 | 471.7 | 187.9 | 5 | |
| Same | 172.7 | 317.5 | 179.7 | 6 | |
| Same | 172.7 | 297.5 | 246.4 | 7 | |
| Same | 523.7 | 1929.0 | 499.5 | 1,2,3,4, 5 and 6 | |
| Same | 506.0 | 1882.0 | 2234.0 | 1 | 1 |
| Same | 525.4 | 1848.0 | 1505.0 | 2 | 2 |
| Same | 535.9 | 1735.0 | 2877.0 | 3 | 3 |
| Same | 547.5 | 1880.0 | 4879.0 | 4 | 4 |
| Same | 552.4 | 2000.0 | 3864.0 | 5 | 5 |
| Same | 482.9 | 1938.0 | 2189.0 | 6 | 6 |
| Same | 514.5 | 1791.0 | 4192.0 | 2 + 4 | 2 + 4 |
| Same | 537.6 | 1752.0 | 3427.0 | 5 + 6 | 5 + 6 |

Because of the large size of the CAH gene and the large number of different mutations that may be present, the use of the thermostable enzymes, and thus the increased stringency of the detection procedure, was found to be highly advantageous with this complex target. Mutation sites that interrogated poorly using Klenow exo- and yeast NDPK at 37° C., were more successfully interrogated when using the Tne triple mutant polymerase and Pfu NDPK at elevated temperatures. In addition, use of the thermostable enzymes permitted the multiplexing of numerous wild type or mutant interrogation oligos in the same interrogation assay, to obtain the rapid screening for mutations that may be present.

11143 5' CGGAGCCTCCACCTCCCG SEQ ID NO:216
CAH interrogator oligo 6 (wild type) for mutation site 1

11085 5' CACCCTCCAGCCCCCAGC 3' SEQ ID NO:217
CAH interrogator oligo 2 (pseudogene/mutant) for mutation site 2

11084 5' CGGAGCCTCCACCTCCTG 3' SEQ ID NO:218
CAH interrogator oligo 1 (pseudogene/mutant) for mutation site 1

11086 5' CCTCACCTGCAGCATCAAC 3' SEQ ID NO:219
CAH interrogator oligo 3 (pseudogene/mutant) for mutation site 3

11144 5' CACCCTCCAGCCCCCAAC 3' SEQ ID NO:220
CAH interrogator oligo 7 (wild type) for mutation site 2

11145 5' CCTCACCTGCAGCATCATC 3' SEQ ID NO:221
CAH interrogator oligo 8 (wild type) for mutation site 3

11087 5' CCTGGAAGGGCACTT 3' SEQ ID NO:222
CAH interrogator oligo 4 (pseudogene/mutant) for mutation site 4

11146 5' CCTGGAAGGGCACGT 3' SEQ ID NO:223
CAH interrogator oligo 9 (wild type) for mutation site 4

11088 5' GATTCAGCAGCGACTGTA 3' SEQ ID NO:224
CAH interrogator oligo 5 (pseudogene/mutant) for mutation site 5

11147 5' GATTCAGCAGCGACTGCA 3' SEQ ID NO:225
CAH interrogator oligo 10 (wild type) for mutation site 5

11287 5' CGAGGTGCTGCGCCTGCG 3' SEQ ID NO:226
CAH interrogation oligo 11 (wild type) for mutation site 6

11288 5' CGAGGTGCTGCGCCTGTG 3' SEQ ID NO:227
CAH interrogation oligo 12 (pseudogene/mutant) for mutation site 6

11641 5' GGGATCACATCGTGGAGATG 3' SEQ ID NO:228
CAH interrogation oligo 23 (wild type) for mutation site 7

11642 5'GGGATCACAACGAGGAGAAG 3' SEQ ID NO:229
CAH interrogation oligo 24 (pseudogene/mutant) for mutation site 7

EXAMPLE 58

Amplification-Refractory Mutation System (ARMS) Followed by Interrogation

This Example further illustrates the detection of nucleic acid produced in ARMS reactions [Newton, C. R. et al. *Nucleic Acid Res.*, 17:2503, (1989)] without running a gel to interpret results. 7 ARMS is based on a PCR probe with a 3' end mismatch at a site of mutation.

In this Example, PCR products are either made or not made with a particular probe depending on the absence or presence of a single base (SNP site) in the target. The probe with a 3'-terminal mismatch cannot amplify the product on the mutant target but can produce a product on the matched wild type target. In this example, unique restriction enzyme sites are built into the PCR probe next to the Pst I restriction site already present in the probes so that the wild type and the mutant products are uniquely identified by the restriction site incorporated.

| | |
|---|---|
| 11310<br>5' GCTTAAGCTGCAGGGCATATGTGGTGATGATATCGTGGGTGAGTTCATTTA 3' | SEQ ID NO:230 |
| 11311<br>5' GCTTAAGCTGCAGGGCCATGGTGGTGATGATATCGTGGGTGAGTTCATTTT 3' | SEQ ID NO:231 |
| 11284<br>5' CTGGAAAATGAACTCACCCACGATATCATCACCA 3' | SEQ ID NO:232 |
| 11253<br>5' AGCTTGGTGATGATATCGTGGGTGAGTTCATTTTCCAGGTAC 3' | SEQ ID NO:233 |
| 11255<br>5' CTGGTAAATGAACTCACCCACGATATCATCACCA 3' | SEQ ID NO:234 |
| 11254<br>5' AGCTTGGTGATGATATCGTGGGTGAGTTCATTTACCAGGTAC 3' | SEQ ID NO:235 |

Oligonucleotides named 11253 and 11254 were designed and cloned into Promega's pGEM-7zf vector that had been cut with Kpn I and HinD III restriction enzymes. These oligonucleotides contain a short region with a SNP. Clone 53 contains the sequences of oligonucleotides 11284 and 11253. Clone 54 contains the sequences of oligonucleotides 11255 and 11254. The sequences of clones 53 and 54 were confirmed by sequencing. Clones 53 and 54 have a unique EcoR V restriction site that provides a blunt end on cleavage. Clones 53 and 54 were digested to completion with Sca I and then diluted to 1ng/µL with water prior to use in the following PCR reactions.

PCR Master Mix:

| | |
|---|---|
| 50 µL | 10X Thermophilic buffer |
| 20 µL | 25 mM MgCl$_2$ |
| 10 µL | 10 mM each dNTP |
| 10 µL | 100 µg/mL oligo 11314 |
| 390 µL | water |

The PCR reactions were set up as follows.

| Reaction | Master Mix | Plasmid (1 µL) | Probe (1 µL) |
|---|---|---|---|
| PCR-1 | 48 µL | 53 (WT*) | 11311 (WT) |
| PCR-2 | 48 µL | 53 (WT) | 11310 (Mut*) |
| PCR-3 | 48 µL | 54 (Mut) | 11311 (WT) |
| PCR-4 | 48 µL | 54 (Mut) | 11310 (Mut) |

*WT = wild type; Mut = mutant

The oligonucleotides used for PCR amplification were 11310 and 11311. Each of those oligonucleotides contains the Pst I restriction enzyme site, as does oligonucleotide 11314. The PCR cycling parameters used were 95° C., 6 minutes. After 4.5 minutes, 1 µL (5 u/µL) of Taq DNA polymerase was added, and the reaction mixture was cycled (95° C., 30 seconds; 60° C., 2 minutes)×30; 72° C., 5 minutes.

The four PCR products were digested in standard Pst I restriction enzyme reactions, cleaned with the Wizard® PCR DNA Purification System (Promega A7170), and eluted into 50 µL of water. These Pst I-digested PCR products were then cut with either no enzyme, Nco I or Nde I in standard restriction enzyme digest reactions. Reaction 1 should cut with Nco I, but not with Nde I. Reaction 4 should cut with Nde I, but not with Nco I.

The following Interrogation Master Mix was assembled.

| | |
|---|---|
| 60 µL | 10X DNA Polymerase buffer |
| 7.5 µL | 40 mM NaPPi |
| 15 µL | 10 U/µL Klenow exo- |
| 6 µL | 1 U/µL NDPK |
| 6 µL | 10 µM ADP |
| 505.5 µL | water |

The following interrogation reactions were assembled, and incubated at 37° C. for 1 hour. Then 1 µL of the reactions was combined with 19 µL of interrogation master mix (in duplicate), incubated for 15 minutes at 37° C. and 5 µL were added to 100 µL of L/L reagent and relative light units (rlu) were measured in a Turner® TD20/20 luminometer. The results obtained are shown below.

| Reaction | cut DNA | Second digest | Avg. rlu |
|---|---|---|---|
| 1. | PCR-1 | none | 39.1 |
| 2. | PCR-1 | Nco I | 149.1 |
| 3. | PCR-1 | Nde I | 44.6 |
| 4. | PCR-2 | none | 26.5 |
| 5. | PCR-2 | Nco I | 23.9 |
| 6. | PCR-2 | Nde I | 25.2 |
| 7. | PCR-3 | none | 28.4 |
| 8. | PCR-3 | Nco I | 26.8 |
| 9. | PCR-3 | Nde I | 27.0 |
| 10. | PCR-4 | none | 43.4 |
| 11. | PCR-4 | Nco I | 54.8 |
| 12. | PCR-4 | Nde I | 116.7 |

PCR-1 is activated for detection by close to four fold by digestion with Nco I but is not activated by digestion with Nde I. PCR-4 is not substantially activated by digestion with Nco I, but is activated close to 3 fold by digestion with Nde I. Neither PCR-2 nor PCR-3 was activated by either enzyme, indicating the absence of product as anticipated.

```
11310
5' GCTTAAGCTGCAGGGCATATGTGGTGATGATATCGTGGGTGAGTTCATTTA 3'   SEQ ID NO:230

11311
5' GCTTAAGCTGCAGGGCCATGGTGGTGATGATATCGTGGGTGAGTTCATTTT 3'   SEQ ID NO:231

11284
5' CTGGAAAATGAACTCACCCACGATATCATCACCA 3'                    SEQ ID NO:232

11253
5' AGCTTGGTGATGATATCGTGGGTGAGTTCATTTTCCAGGTAC 3'            SEQ ID NO:233

11255
5' CTGGTAAATGAACTCACCCACGATATCATCACCA 3'                    SEQ ID NO:234

11254
5' AGCTTGGTGATGATATCGTGGGTGAGTTCATTTACCAGGTAC 3'            SEQ ID NO:235
```

EXAMPLE 59

Restriction Enzyme Digestion Prior to Interrogation

This Example concerns the use of two synthetic targets generated by PCR amplification with Pst I restriction enzyme sites on the probes. These targets are first digested with Pst I, which leaves 3' overhangs on both ends, making the products refractory to detection by means of interrogation using a Klenow exo- enzyme. The two PCR products differ in the presence of another unique restriction enzyme site. The ends generated by this second digest provide ends that have a 5' overhang and are permissive for interrogation.

Oligonucleotides 11315 (SEQ ID NO:236) and 11314 (SEQ ID NO:237) both contain a Pst I restriction enzyme site (CTGCAG) near the 5' end preceded by six arbitrary bases to permit efficient digestion. These oligonucleotides were used to create PCR products, about 200 base pairs in size, using the vectors pGEM-7zf(+) and pGEM-9zf(−) (Promega, P2251 and P2391, respectively) for targets and using standard PCR conditions.

Forty microliters (800 ng) of each PCR product were digested with Pst I restriction enzyme to completion and again purified with Wizard™ PCR DNA Purification System to remove the small digested fragment. Then the two different PCR products were further digested in separate reactions with BamH I, Spe I and EcoR I enzymes or with no additional enzyme. BamH I digests only the PCR product from pGEM-7zf(+) (PCR-1); Spe I digests only the PCR product from pGEM-9zf(−) (PCR-2); and EcoR I digests both PCR products. All three of these enzymes leave a 5' overhang that is responsive to interrogation.

Four microliters of the Pst I digested DNA was digested with the second enzyme, diluted two fold, and one microliter was combined with 19 µL master mix and incubated for 15 minutes at 37° C. Five microliters thereafter were added to 100 µL of L/L reagent and relative light units (rlu) read on a Turner® TD20/20 luminometer to provide the data (in duplicate) in the table below, thereby illustrating interrogations for the presence or the absence of the second digestion.

| Master Mix: | |
| --- | --- |
| 10X DNA polymerase buffer | 40 µL |
| 40 mM Sodium Pyrophosphate | 5 µL |
| 10 U/µL Klenow exo- polymerase | 10 µL |
| 1 U/µL NDPK | 4 µL |
| 10 µM ADP | 4 µL |
| Nanopure water | 337 µL |

| Reaction | DNA | Second enzyme digestion | Avg. rlu |
| --- | --- | --- | --- |
| 1. | PCR-1 | none | 38.9 |
| 2. | PCR-1 | BamH I | 325 |
| 3. | PCR-1 | Spe I | 62.2 |
| 4. | PCR-1 | EcoR I | 386.9 |
| 5. | PCR-2 | none | 26.4 |
| 6. | PCR-2 | BamH I | 37.3 |
| 7. | PCR-2 | Spe I | 265.3 |
| 8. | PCR-2 | EcoR I | 302.2 |

The PCR-1 product contains a BamH I and an EcoR I site, but no Spe I site and responds appropriately. The PCR-2 product contains a Spe I and an EcoR I site, but no BamH I site and also responds appropriately.

These data demonstrate that detection was stimulated about 10 fold by digestion with the appropriate enzyme. Furthermore, multiplexing was simulated by mixing the two PCR fragments together and detecting only one of them by digestion with the appropriate enzyme followed by interrogation. This method can thus be used to detect a single nucleotide polymorphism that destroys or creates a restriction site without running a gel.

```
11315  5' ATGATGCTGCAGCAGGAAACAGCTATGAC 3'   SEQ ID NO:236

11314  5' ATGATGCTGCAGGTTTTCCCAGTCACGAC 3'   SEQ ID NO:237
```

EXAMPLE 60

Detection of Rolling Circle Amplification Products Obtained After Circularization by Ligation In this Example, a probe (oligonucleotide 10367 (SEQ ID NO:238)) is hybridized to either no target, or to a wild type (WT; 8831 (SEQ ID NO:239)) or a mutant (10354 (SEQ ID NO:240)) target and ligated into a circle. An extension probe (10368 (SEQ ID NO:241)) is then hybridized and extended into run-around products, thereby amplifying the target. These products are detected using a complementary probe (10369 (SEQ ID NO:242)) in an interrogation reaction, with relative light unit output being used to distinguish among the possible results. In order to obtain a low, no target, background, it is beneficial to treat the ligation reaction mixture with a combination of exonucleases to remove any DNA that is not circular.

It is seen that the no target reaction gives very low light units and there is about a six fold discrimination between WT and Mutant targets. In these studies, only a single rolling circle extension probe is used and amplification is linear, not exponential. The basis for the WT/Mutant discrimination is whether or not the probe ligates into a circular molecule, because ligation is inefficient at a mismatch position.

One microliter (500 ng) of oligonucleotide 10367 was combined with 1 µL (500 ng) of either oligonucleotide 8831 or 10354 or no target in three separate tubes. Water was added to a final volume of 8 µL. The solutions were heated to 95° C. for 3 minutes, then cooled for 10 minutes at room temperature. One microliter of 10×E. coli ligase buffer (NEB) and 1 µL (10 u) E. coli ligase (NEB) were added. The solutions were further incubated for 60 minutes at 37° C. To each solution were then added:

| 0.5 µL | 50 U/µL T7 Gene 6 exonuclease (USB E700254) |
| 0.5 µL | 10 U/µL exonuclease I |
| 2 µl   | 10X Thermo Polymerase buffer |
| 7 µL   | water |

The solutions were then incubated for 15 minutes at 37° C., followed by 10 minutes at 95° C. To each solution were then added:

| 1 µL | 500 ng/µL 10368 (extension probe (SEQ ID NO: 241)) |
| 2 µL | 2 mM dNTPs |

The solutions were heated at 95° C. for 3 minutes, and then cooled for 10 minutes at room temperature to anneal the extension probe. One microliter (8 U) of Bst (LF) DNA polymerase was added and the tubes were incubated at 42° C. for 10 minutes, then 65° C. for 30 minutes to permit extension. One unit of shrimp alkaline phosphatase was added and the tubes were incubated at 37° C. for 30 minutes, and then 65° C. for 15 minutes.

To proceed with interrogation, the solutions were diluted 1:100 with water and 1 µL of each of the three reactions was combined with 1 µL (500 ng) of interrogation oligonucleotide 10369 and 18 µL water. Each composition so formed was heated at 95° C. for 3 minutes, then cooled for 10 minutes at room temperature. Twenty microliters of master mix were added, and each solution was incubated at 37° C. for 15 minutes. Then, 4 µL of each solution were combined with 100 µL of L/L reagent in duplicate, and light output read in a Turner™ TD20/20 luminometer. The results obtained were as shown below.

| Sample | average rlu |
| --- | --- |
| No target | 5.8 |
| WT target | 248.6 |
| Mutant target | 43.5 |

```
10367
5' ACAACGTCGTGACTAGGATCACGCTAATGCTTCAGCCTGATGAGT    SEQ ID NO:238
CCGATCAGCCTGATGAGTCCGATCTGGCCGTCGTTTT 3' (circle
probe)

8831 5' CAGTCACGACGTTGTAAAACGACGQCCAGT 3'             SEQ ID NO:239
(WT target)

10354 5' CAGTCACGACGTTGTGAAACGACGGCCAGT 3'            SEQ ID NO:240
(mutant target)

10368 5' AGCATTAGCGTGATCC 3'                          SEQ ID NO:241
(rolling circle extension probe)

10369 ' 5' CAGCCTGATGAGTCCG 3'                        SEQ ID NO:242
(circle interrogation probe)
```

EXAMPLE 61

Detection of Rolling Circle Amplification Products of M13 DNA

This Example uses the pUC/M13 Forward primer (17mer, Promega Q5391) to hybridize to single stranded (ss) M13mp18 DNA and synthesize rolling circle DNA using Bst LF (large fragment) thermostable DNA polymerase. The free nucleotides are then removed with Shrimp Alkaline Phosphatase (SAP) and the rolling circle products detected by pyrophosphorolysis of the probe that is complementary to this product, PUC/M13 primer, reverse (17mer) Promega Q5401.

The following reactions were assembled in duplicate:

| Sample | M13mp18 DNA (µL) | 10X Buffer (µL) | 2 µM dNTPs (µL) | Probe (µL) | Water (µL) |
| --- | --- | --- | --- | --- | --- |
| 1 | 1 (250 ng) | 2 | 2 | none | 14 |
| 2 | 1 (250 ng) | 2 | 2 | 5 | 9 |
| 3 | 1 (250 ng) | 2 | 2 | 5 | 9 |

The assembled solutions were incubated at 95° C. for 3 minutes, then cooled for 10 minutes at room temperature.

To samples 1 and 3, was added 1 µL (8 U) Bst LF DNA polymerase, and all tubes were incubated for 30 minutes at 65° C., then cooled for 2 minutes on ice. One unit of Shrimp Alkaline Phosphatase was added, the solutions incubated at 37° C. for 30 minutes, then heated to 65° C. for 15 minutes to denature the phosphatase enzyme.

One microliter of the reactions was added to 5 µL (50 ng) of pUC/M13 reverse primer, the interrogation oligonucleotide probe, and heated to 95° C. for 3 minutes, then cooled for 10 minutes at room temperature. Twenty microliters master mix were added, and the tubes were heated at 37° C. for 15 minutes. Four microliters were then combined with 100 µL of L/L Reagent, and the light output read on a Turner® TD20/20 luminometer.

| Reaction | Avg. rlu |
|---|---|
| 1. (no extension probe) | 3.5 |
| 2. (no Bst LF DNAP) | 4.1 |
| 3. (complete reaction) | 68.7 |

It can be seen that a signal of about 20 times that of the controls is dependent on the presence of both the Bst (LF) DNA thermopolymerase and the rolling circle extension probe (forward probe).

EXAMPLE 62

Ligase Chain Reaction Prior to Interrogation

In this Example, Ligase Chain Reaction (LCR) was performed to amplify wild type and mutant species of the lacI gene fragment used as an amplification control sequence in the LCR kit (Stratagene, 200520) followed by interrogation. LCR is a DNA amplification technique that utilizes a cyclic two-step reaction. Target DNA is denatured at an elevated temperature followed by the annealing of two sets of complementary oligonucleotides to the denatured DNA and their ligation with a thermostable ligase. The ligation products from one cycle serve as targets for the next cycle's ligation reaction.

Oligonucleotide 11192 (SEQ ID NO:243) is complementary to 11195 (WT) (SEQ ID NO:244) and 11196 (mutant) (SEQ ID NO:245). Oligonucleotide 11197 (SEQ ID NO:246) is complementary to 11193 (WT) (SEQ ID NO:247) and 11194 (mutant) (SEQ ID NO:248). The mutant oligonucleotide differs from its counterpart wild type oligonucleotide only at the 3'-terminal base.

The wild type and mutant targets that are present in the LCR kit were used as the targets for the LCR reaction performed according to kit instructions. The LCR product was then quantified and used as the target for interrogation. One microliter of the wild type LCR target (100 pg) was combined with 1 µg of wild type interrogation oligonucleotide (11198 (SEQ ID NO:249)), mutant interrogation oligonucleotide (11199 (SEQ ID NO:250)), or no oligonucleotide along with water to a final volume of 20 µL. A target-only reaction and a probe-only reaction were also assembled as controls. Likewise, similar solutions were assembled with the mutant LCR target. The solutions were heated at 95° C. for 8 minutes to denature the nucleic acid. LCR was performed according to manufacturer's instruction.

The following master mix was assembled.

| | |
|---|---|
| 432 µL | water |
| 120 µL | 10X DNA pol buffer (Promega, M195A) |
| 15 µL | 40 mM NaPPi |
| 15 µL | Klenow exo- (1 u/µL) |
| 6 µl | NDPK 1 U/µL |
| 12 µL | ADP 10 µM |

Twenty microliters of master mix were added to each solution, and the solutions were further incubated at 37° C. for 15 minutes. Five microliters of each solution were then combined with 100 µL of L/L reagent and light output was measured on a Turner™ TD20/20 luminometer. The results of average relative light units (Avg. rlu) are shown below:

| | Avg. rlu |
|---|---|
| Wild type target rxns | |
| Probe 11198 (WT) + target | 58.35 |
| Probe 11199 (mutant) + target | 5.29 |
| Probe 11198 only | 2.77 |
| Target only | 3.89 |
| Mutant target rxns | |
| Probe 11198 (WT) + target | 7.78 |
| Probe 11199 (mutant) + target | 77.22 |
| Probe 11199 only | 3.29 |
| Target only | 7.05 |

The data indicate that about 10-fold match/mismatch discrimination can be obtained when performing the interrogation reaction after an LCR amplification reaction.

| | | | |
|---|---|---|---|
| 11192 | 5' TTGTGCCACGCGGTTGGGAATGTA 3' | SEQ ID NO:243 |
| 11195 | 5' TACATTCCCAACCGCGTGGCACAAC 3' | SEQ ID NO:244 |
| 11196 | 5' TACATTCCCAACCGCGTGGCACAAT 3' | SEQ ID NO:245 |
| 11197 | 5' AACTGGCGGGCAAACAGTCGTTGCT 3' | SEQ ID NO:246 |
| 11193 | 5' AGCAACGACTGTTTGCCCGCCAGTTG 3' | SEQ ID NO:247 |
| 11194 | 5' AGCAACGACTGTTTGCCCGCCAGTTA 3' | SEQ ID NO:248 |
| 11198 | 5' TTTGCCCGCCAGTTGTT 3' | SEQ ID NO:249 |
| 11199 | 5' TTTGCCCGCCAGTTATT 3' | SEQ ID NO:250 |

EXAMPLE 63

Detection of Chromosomal DNA Without Amplification: I

In theory, direct detection of a single copy gene in chromosomal DNA should be possible if enough DNA can be assayed. The amount of human genomic DNA needed can be calculated as follows:

$$\frac{(1 \times 10^{-9} \text{ g DNA})(5 \times 10^9 \text{ bases/genome})}{(1 \times 10^3 \text{ bases specific target})} = \text{approximately 5 mg of DNA}$$

However, as the amount of DNA interrogated increases, nonspecific DNA signal from this DNA also increases. Therefore, chromosomal DNA in amounts approaching even 1 µg of DNA would produce very high background.

Increasing the copies of target DNA per chromosome is one way to overcome this limitation. Many such sequences are known. The absolute sequence of the repeated DNA in different species can vary as does the number of copies of the sequence in the genome. For example, there are estimated to be 500–1000 copies of a sequence known as the rep sequence in the E. coli chromosome. The Alu sequence is present in the haploid human chromosome in approximately 300,000 copies. The estimated amount of human chromosomal DNA needed to detect the Alu sequence is:

$$\frac{5 \times 10^{-3} \text{ grams DNA (single copy gene requirement)}}{3 \times 10^5 \text{ copies per genome}} =$$

$$1.7 \times 10^{-8} \text{ grams (or about 17 ng of DNA)}$$

In this example, probes to two regions of the Alu sequence (Alu 1 oligonucleotide 11597 (SEQ ID NO:251) and Alu 2 oligonucleotide 11598 (SEQ ID NQ: 252)) were used to demonstrate that direct detection of chromosomal DNA is achievable.

The genomic DNA (4.2 μg) was digested to completion (5 hours, 37° C.) with 40 units of Sph I restriction enzyme, which leaves a 3' overhang on the digested fragments. Either 40 ng or 80 ng of the digested genomic DNA was annealed to 1.0 μg of the interrogation probes 11597 and 11598 in separate reactions, and 11597 and 11598 in the same reaction with water added to a final volume of 20 μL. A negative control, without an interrogation probe, was also assembled. The solutions were heated at 92° C. for 3 minutes and cooled at room temperature for 15 minutes.

Twenty microliters of master mix, described below, were added to each annealing reaction and the tubes were further incubated at 37° C. for 20 minutes, then stored on ice. Four microliters of the reaction were added to 100 μL of L/L reagent (Promega F120B) in quadruplicate samples, and relative light units (rlu) measured on a Turner® TD20/20 luminometer. The rlu results are reported below.

| Master Mix: | |
|---|---|
| 200 μL | 10X DNA Polymerase Buffer |
| 25 μL | 40 mM NaPPi |
| 25 μL | Klenow exo- |
| 10 μL | NDPK 1 U/μL |
| 20 μL | ADP 10 μM |
| 720 μL | water |

| | Rxn* 1 | Rxn 2 | Rxn 3 | Rxn 4 | average | Net | Std Dev* |
|---|---|---|---|---|---|---|---|
| No DNA | 3.372 | 3.342 | 3.306 | 3.249 | 3.317 | 0 | 0.052898 |
| alu1 only | 3.92 | 3.625 | 3.756 | 3.799 | 3.775 | 0.458 | 0.12174 |
| alu2 only | 23.18 | 25.47 | 24.58 | 25.19 | 24.61 | 21.29 | 1.020082 |
| 40 ng DNA | 20.63 | 21.98 | 23.91 | 22.3 | 22.21 | 18.39 | 1.347504 |
| alu1 + 40 ng DNA | 53.12 | 57.05 | 52.52 | 36.5 | 49.80 | 46.03 | 9.089798 |
| alu2 + 40 ng DNA | 99.23 | 91.26 | 55.9 | 85.59 | 83.00 | 58.39 | 18.90995 |
| 80 ng DNA | 38.57 | 44.34 | 42.96 | 46.33 | 43.05 | 39.73 | 3.291454 |
| alu1 + 80 ng DNA | 89.25 | 68.01 | 91.43 | 96.14 | 86.21 | 82.44 | 12.46776 |
| alu2 + 80 ng DNA | 156.2 | 156.6 | 149.9 | 143.7 | 151.6 | 127.0 | 6.095353 |
| alu1 + alu2 | 30.65 | 23.82 | 32.57 | 27.60 | 28.66 | 25.34 | 3.820881 |
| alu1 + alu2 + 40 ng DNA | 66.49 | 101.1 | 104.9 | 104.3 | 94.1975 | 65.81 | 18.54682 |

*Std Dev = 1 standard deviation, Rxn = reaction

```
11597  5' ACACCCCATCTCTAA 3' (Alu 1)   SEQ ID NO:251
11598  5' GCCTGGGTGACAGAGCA 3'(Alu 2)  SEQ ID NO:252
```

EXAMPLE 64

Detection of Chromosomal DNA Without Amplification: II

Another method to detect the presence of the Alu sequence is to perform single probe extension reactions as described in Example 50. Probes are designed to bind to a target Alu sequence and be extended. Following extension, the probe can form a "hairpin" structure—forming a stretch of double strand DNA. This DNA is then detected in a "probeless" pyrophosphorylation assay. If the extended probe sequence extends beyond the segment of the probe designed to form one segment of the hairpin, the product is not expected to be detected because the product has a 3' overhang. In order to prevent such a situation, the probes that have been designed can be used in reactions missing one of the four DNA bases. By performing the reactions in this way, the probe is not extended beyond the region of hybridization. Scheme 1 illustrates how two such probes hybridize to an Alu sequence.

Scheme 1

Genbank#AF085897
5' CTCCAGCCTCGGTGACAGAGCAAGACCCTGTCTCAAAAAAAAA
Oligo A

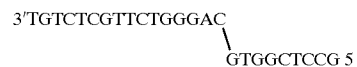

Genbank#AL022238
5' CTCCAGCCTGAGCAACACAGCAAGACCCTGTCTCAAAACAAAAC
Oligo B

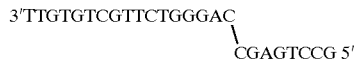

The predicted extended products of these probes and the secondary structure of the hairpins that the extended products can form are shown in Scheme 2, below.

Scheme 2

Genbank#AF085897
Extention of oligo A:
5'CTCCAGCCTCGGTGACAGAGCAAGACCCTGTCTCAAAAAAAAA
   3'CGGAGCCACTGTCTCGTTCTGGAC
                              \
                               GTGGCTCCG 5'

Hairpin
Secondary structure:

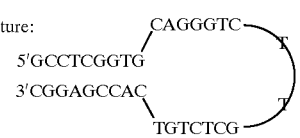

Genbank#AL022238
Extension of oligo B:
5'CTCCAGCCTGAGCAACACAGCAAGACCCTGTCTCAAAACAAAA
　　3'CGGACTCGTTGTGTCGTTCTGGGAC
　　　　　　　　　　　　　　　　　\
　　　　　　　　　　　　　　　　　CGAGTCCG5'
Hairpin
Secondary structure:

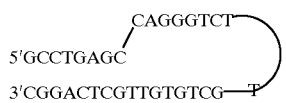

Oligo A
5'CTCCAGCCTCGGTGACAGAGCAAGACCCTGTCTCAAAAAAAAGCCTCGGT　SEQ ID NO:253
GCAGGGTCTTGCTCTGT 3'

Oligo B
5'CTCCAGCCTGAGCAACACAGCAAGACCCTGTCTCAAAACAAAACGCCTGAG　SEQ ID NO:254
CCAGGGTCTTGCTGTGTT 3'

EXAMPLE 65

HPLC Separation of dNTPs After Interrogation Assay, but Prior to Phosphate Transfer and Light Production Large-volume pyrophosphorylation assays were performed on matched and mismatched probe/target hybrids. The released nucleotides were separated by high performance liquid chromatography (HPLC) and their fractions collected. NDPK terminal phosphate transfer reactions were performed on these concentrated fractions and luciferase assays conducted to illustrate discrimination between the original matched and mismatched hybrid treated samples.

Target/probe hybrids were formed by combining 315 ng of the synthetic wild type CMV target oligonucleotide with either 10.5 μg wild type CMV probe for a matched hybrid, or 10.5 μg mutant CMV probe for a mismatched hybrid, and adding water to a final volume of 200 μL. The oligonucleotides were CV 12 (SEQ ID NO:9), CV 15 (SEQ ID NO:12), and CV 16 (SEQ ID NO:13), as previously described in Example 2. These solutions were heated to 95° C. for at least 5 minutes, then cooled at room temperature for at least 10 minutes.

The following master mix was prepared.

| | | |
|---|---|---|
| 337.5 μL | Nanopure water (Promega, AA399) | |
| 90.0 μL | 10X DNA Polymerase buffer (Promega, M195A) | |
| 11.25 μL | 40 mM NaPPi (Promega, C113) | |

Master mix (210 μL) was added to each of the above hybrid solutions and 5.8 units of Klenow exo- (Promega, M218A) were added to each. The solutions were then incubated at 37° C. for 15 minutes and stored on ice. HPLC separation of the dNTPs was performed.

HPLC separation of dATP, dCTP, dGTP and TTP was performed on a 100×4.6 mm, 3μ Luna C18 column [Perrone and Brown, J. Chromatography, 317:301–310 (1984)] from Phenomenex. The column was eluted with a linear gradient of 97 percent buffer A (100 mM triethylammonium acetate, pH 7) to 92 percent buffer A over a period of 12 minutes. The composition of buffer B is 80:20 acetonitrile: 35 mM triethylammonium acetate. Detection was monitored by absorbance at 250, 260 and 280 nm. Under these conditions, dCTP was found to elute between 4 and 4.5 minutes, TTP and dGTP eluted as two peaks between 7 and 7.5 minutes, and dATP eluted from 9 to 9.5 minutes.

The fractions containing the free dNTPs were collected and lyophilized. Fraction one contained dCTP, fraction two contained dGTP and TTP, and fraction three contained dATP.

Each fraction was reconstituted in 100 μL of nanopure water. Ten microliters of each fraction, or 10 μL of water as a control, were added to a 10 μL mixture of water, 10× DNA Polymerase Buffer, and ADP so that the final concentration was 1× DNA pol buffer and 0.1 HM ADP. NDPK (0.005 units) was added to each tube in one set of the tubes and an equal amount of water was added to each tube in the other set of tubes. Samples and controls were incubated at 37° C. for 15 minutes, 10 μL added to 100 μL of L/L reagent and the light output was measured on a Turner™ TD10/20 luminometer. The relative light units (rlu) results obtained are shown below:

| Sample | Trial 1 | Trial 2 | Trial 3 | Avg. rlu |
|---|---|---|---|---|
| Matched hybrid with NDPK | | | | |
| Fraction 1 | 206.6 | 200.6 | 205.9 | 204.4 |
| Fraction 2 | 839.4 | 851.6 | 833.9 | 841.6 |
| Fraction 3 | 1149.0 | 1150.0 | 1169.0 | 1156 |
| Mismatched hybrid with NDPK | | | | |
| Fraction 1 | 101.8 | 97.0 | 98.9 | 99.9 |
| Fraction 2 | 386.1 | 387.3 | 382.2 | 385.2 |
| Fraction 3 | 412.4 | 409.9 | 416.5 | 412.9 |
| Match hybrid without NDPK | | | | |
| Fraction 1 | 6.8 | 6.5 | — | 6.6 |
| Fraction 2 | 10.9 | 11.5 | — | 11.2 |
| Fraction 3 | 33.0 | 37.8 | — | 35.4 |
| Mismatched hybrid without NDPK | | | | |
| Fraction 1 | 6.2 | 6.7 | — | 6.4 |
| Fraction 2 | 8.3 | 8.4 | — | 8.4 |
| Fraction 3 | 13.4 | 13.5 | — | 13.4 |
| No dNTP | 7.9 | 7.5 | — | 7.7 |

As is seen from the above data, the fraction one match:mismatch ratio is 2.1, fraction 2 match:mismatch ratio is 2.2 and fraction 3 match:mismatch ratio is 2.8. The data therefore demonstrate the utility of using HPLC separation of individual nucleotides followed by NDPK conversion to ATP, the preferred substrate of luciferase. Fraction 3 provides a slightly higher match:mismatch ratio owing to the presence of dATP in the nucleotide HPLC fraction. Nevertheless, HPLC separation of identifier nucleotides is useful in the interrogation assays of the present invention.

CV12
5'CCAACAGACGCTCCACGTTCTTTCTGACGTATTCGTGCAGCATGGTCTGCG  SEQ ID NO:9

AGCATTCGTGGTAGAAOCGAGCT 3'

CV15 5' CTACCACGAATGCTCGCAGAC 3'  SEQ ID NO:12

CV16 5' CTACCACGAATGCTCGCAGAT 3'  SEQ ID NO:13

EXAMPLE 66
Mass Spectrometry for Nucleotide Detection

The mass spectrometer uses the ratio of molecular mass to charge of various molecules to identify them. Nucleic acids are made up of four different base molecules, each with a different mass to charge ratio. In this Example, the capability to use mass spectrometry for separation of the nucleotides that make up DNA is demonstrated.

The ESIMS (Electro Spray Ion Mass spectrometry) spectra of 1 μM and 0.1 μM NTP molecules were determined (Fisons Instruments, VG Platform). The samples were prepared by diluting 1:1 with acetonitrile/water/1% $NH_4OH$. A 20 μL injection was made for each sample. Therefore, 10 picomoles of each dNTP are in the 1 μM sample injection, and 1 picomole of each dNTP is in the 0.1 μM sample injection.

Each of the dNTPs is observed in the 1 μM sample along with the dNTP+$Na^+$ peaks. There was a 485 peak also present, which is an impurity in the system or samples. The peaks for each of the dNTPs are significantly diminished in the 0.1 μM sample; only the dATP peak is above the noise level. Therefore, the difference between the 1 and 0.1 μM samples can be qualitatively determined, which indicates the ability to determine the difference between interrogation samples in which the probe and target are matched and mismatched at the 3'-terminal region of the probe.

EXAMPLE 67
Speciation-Detection of Mitochondrial DNA Specific to Various Animals In this example, a segment of mitochondrial DNA comprising a segment of the cytochrome B gene was amplified from a variety of animal species using PCR primers 11590 (SEQ ID NO:255) and 11589 (SEQ ID NO:256) (PNAS 86:6196–6200). These PCR primers were diluted in 10 mM Tris, pH 7.5, to a final concentration of 0.22 μg/μL. The genomic DNAs used were bovine (Clontech, 6850-1), chicken (Clontech, 6852–1), dog (Clontech, 6950-1) and human (Promega, G1521).

The PCR reactions were assembled to include 5 μL 10× buffer with 15 mM $MgCl_2$ (Promega, M188J), 1 μL dNTPs 10 mM (Promega, C144G), 2 μL primer 11590, 2 μL primer 11589, 0.5 μL Taq polymerase 5U/μL (Promega, M186E), and 38.5 μL water. To each tube was then added 1 μL (100 ng) of genomic DNA. The PCR cycling parameters were (15 seconds, 94° C.; 15 seconds, 55° C.; 30 seconds, 72° C.)×30. The size of PCR products was confirmed by running an aliquot on an agarose gel and visualizing with ethidium bromide (EtBr) staining. The PCR products were then separated from free nucleotides (Promega, A7170) and an aliquot run on an agarose gel. All samples produced a PCR product of the same size.

Each PCR DNA was then used in an assay to determine if it could be specifically identified with a species-specific probe. One microliter of interrogation probe (1 μg/μL) and 17 μL water were combined with 2 μL of the appropriate PCR product and heated at 91° C. for 3 minutes, then cooled at room temperature for 15 minutes. Twenty microliters of master mix (described below) were added to each tube and each was further incubated at 37° C. for 15 minutes. Four microliters of the solutions were then added to 100 μL L/L reagent (Promega F120B), and the relative light output (rlu) measured on a Turner® TD20/20 luminometer. The rlu average values from two reactions, minus the DNA background values, along with the standard deviation values are listed below.

| | Master mix: |
|---|---|
| 312 μL | 10X DNA pol buffer (Promega M195A) |
| 39 μL | NaPPi 40 mM (Promega E350B) |
| 39 μL | Klenow exo minus (Promega M128B) |
| 15.6 μL | NDPK 1 U/μL |
| 31.2 μL | ADP 10 μM (Sigma) |
| 1123 μL | water (Promega AA399) |

| | Averages from 2 reactions. Net light units are calculated by subtracting the DNA background | | | | | Standard Deviations | | | | |
|---|---|---|---|---|---|---|---|---|---|---|
| Probe | No DNA | Human DNA | Chicken DNA | Cow DNA | Dog DNA | No DNA | Human DNA | Chicken DNA | Cow DNA | Dog DNA |
| comzoo | −0.096 | 44.5 | 14.25 | 119.7 | 124.6 | 0.654 | 7.000 | 23.33 | 3.465 | 8.63 |
| huzoo1 | 1.771 | 38 | −40 | −51.85 | −63.55 | 0.137 | 38.96 | 31.74 | 6.505 | 12.52 |
| huzoo2 | −0.889 | 101.6 | −23.35 | −0.05 | −48.75 | 0.761 | 3.959 | 0.141 | 8.768 | 2.19 |
| chzoo1 | 43.07 | −30.4 | 34.05 | −2.75 | −31.15 | 7.078 | 1.909 | 6.364 | 2.687 | 8.70 |
| chzoo2 | −0.361 | 57.6 | 50.7 | 33.05 | −3.25 | 0.075 | 43.77 | 29.34 | 12.59 | 21.43 |
| cozoo2 | 1.925 | 90.95 | 125.1 | 202.6 | 132.5 | 0.208 | 20.08 | 13.22 | 8.627 | 19.30 |
| dozoo2 | 0.966 | | | 71.8 | 158.7 | 0.180 | | | 9.546 | 1.98 |

The data demonstrate that the primers detect the mitochondrial PCR product. Both of the human-specific probes (11576 (SEQ ID NO:257)) and 11583 (SEQ ID NO:258)) were shown to be specific for human mitochondrial DNA. The common probe, 11582 (SEQ ID NO:259), detected all of the species, but was less efficient with chicken DNA. The chicken-specific probe, 11577 (SEQ ID NO:260), was specific for chicken mitochondrial DNA, but the other chicken-specific probe, 11584 (SEQ ID NO:261), detected all the species except dog. The cow-specific probe, 11588 (SEQ ID NO:262), gave the best detection signal for cow DNA, but also detected the other species. The dog-specific probe, 11586 (SEQ ID NO:263), was assayed only with dog and cow DNA, but detected the dog DNA better than cow DNA. A cleaner PCR product provides DNA with less background.

```
11590    zooamp2                              SEQ ID NO:255
5' AAACTGCAGCCCCTCAGAATGATATTTGTCCTCA 3'

11589    zooamp1                              SEQ ID NO:256
5' AAAAAGCTTCCATCCAACATCTCAGCATGATGAAA 3'

11576    huzoo1    5' CCAGACGCCTCA 3'        SEQ ID NO:257

11583    huzoo2    5' ACCTTCACGCCA 3'        SEQ ID NO:258

11582    comzoo    5' TGCCGAGACGT 3'         SEQ ID NO:259

11577    chzoo1    5' GCAGACACATCC 3'        SEQ ID NO:260

11584    chzoo2    5' GGAATCTCCACG 3'        SEQ ID NO:261

11588    cozoo2    5' ACATACACGCAA 3'        SEQ ID NO:262

11586    dozoo2    5' ATATGCACGCAA 3'        SEQ ID NO:263
```

EXAMPLE 68

Trisomy Detection

Detection of a simulated trisomy sample is demonstrated in this Example. The nucleic acid probes and targets were previously described in Example 49. These include the CMV probes 9211 (SEQ ID NO:86) and 9212 (SEQ ID NO:35), the p-ZERO-2 clone of the double-stranded synthetic CMV wild type target CMV-A (10800 (SEQ ID NO:171) and 10801 (SEQ ID NO:172)), and the p-ZERO-2 clone of the double-stranded synthetic CMV mutant target CMV-G (10803 (SEQ ID NO:173) and 10805 (SEQ ID NO:174)).

Each p-ZERO-2 plasmid (1 μg) was digested to completion with Pst I restriction enzyme at 37° C. for 1 hour. Ten microliters of the digest were then further diluted with 20 μL of water.

The following Master Mix was assembled.

| | |
|---|---|
| 60 μl | 10X DNA polymerase buffer (Promega M195A) |
| 7.5 μl | 40 mM NaPPi (Promega C113) |
| 1.5 μl | 10 U/μL Klenow exo- (Promega M128A) |
| 3 μL | NDPK |
| 6 μL | 10 μM ADP (Promega A5285) |
| 225 μL | water (Promega AA399) |

The following solutions were assembled using the digested and diluted templates.

| Solution | Template | Probe (μL) | Water | Simulated phenotype | rlu |
|---|---|---|---|---|---|
| 1 | 1 μL CMV-A | 1 μL 9211 | 18 | homoZ* A | 53.27 |
| 2 | 1 μL CMV-A | 1 μL 9212 | 18 | homoZ A | 7.19 |
| 3 | 1 μL CMV-G | 1 μL 9211 | 18 | homoZ G | 5.78 |
| 4 | 1 μL CMV-G | 1 μL 9212 | 18 | homoZ G | 63.84 |
| 5 | 1 μL CMV-A<br>1 μL CMV-G | 1 μL 9211 | 17 | heteroZ* 1:1 | 54.08 |
| 6 | 1 μL CMV-A<br>1 μL CMV-G | 1 μL 9212 | 17 | heteroZ 1:1 | 61.54 |
| 7 | 2 μL CMV-A<br>1 μL CMV-G | 1 μL 9211 | 16 | trisomy 2:1 (A:G) | 90.87 |
| 8 | 2 μL CMV-A<br>1 μL CMV-G | 1 μL 9212 | 16 | trisomy 2:1 (A:G) | 64.74 |
| 9 | 1 μL CMV-A<br>2 μL CMV-G | 1 μL 9211 | 16 | trisomy 1:2 (A:G) | 50.86 |
| 10 | 1 μL CMV-A<br>2 μL CMV-G | 1 μL 9212 | 16 | trisomy 1:2 (A:G) | 111.0 |

*homoZ = homozygous; heteroZ = heterozygous.

The solutions were heated at 95° C. for 3 minutes then cooled for 10 minutes at room temperature. Then, 20 μl master mix were added, and the solutions further heated at 37° C. for 15 minutes. Four microliters of the solutions were then added to 100 μL of L/L reagent (Promega F202A) and the relative light output measured immediately on a Turner® TD20/20 luminometer. The rlu values are listed above.

The rlu values demonstrate that the 1:2 (A:G) template mix exhibits a 1:2 rlu ratio, whereas the heterozygous 1:1 A:G rlu ratio is close to 1:1. A contemplated method is thus shown to be useful in detecting trisomy.

```
CMV Interrogation oligos
Wild Type CMV-A Probe: 5' CACTTTGATATTACACCCATG 3'     SEQ ID NO:86
(9211)

Mutant CMV-G probe: 5' CACTTTGATATTACACCCGTG 3'        SEQ ID NO:35
(9212)

10800 5' CGTGTATGCCACTTTG ATATTACACCCATGAACGTG         SEQ ID NO:171
CTCATCGACGTGAACCCGCA CAACGACCT 3'

10801 5' CGTTGTGCGGGTTCAC GTCGATGAGCACGTTCATGG         SEQ ID NO:172
GTGTAATATCAAAGTGGCAT ACACGAGCT 3'

10803 5' CQTGTATGCCACTTTG ATATTACACCCGTGAACGTG         SEQ ID NO:173
CTCATCGACGTGAACCCGCA CAACGOCCT 3'

10805 5' CGTTGTGCGGOTTCAC GTCGATGAGCACGTTCACGG         SEQ ID NO:174
GTGTAATATCAAAGTGGCAT ACACGAGCT 3'
```

EXAMPLE 69
Comparison of Thermophilic DNA Polymerases in a One-Step 70° C. Interrogation Reaction In this example, four different thermophilic DNA polymerases were used along with the thermophilic NDPK from Pfu in an interrogation reaction. The polymerases used were Taq (Promega, M166F), Pfu (*Pyrococcus furiosus* strain Vcl DSM3638, Promega, M774A), Tvu (*Thermoactinomyces vulgaris*, purified at Promega), and Ath (*Anaeocellum thermophilum*, purified at Promega).

Cytomegalovirus (CMV) synthetic targets were generated by combining wild type oligonucleotide primers 9162 (SEQ ID NO:31) and 9165 (SEQ ID NO:32) or mutant oligonucleotide primers 9163 (SEQ ID NO:33) and 9166 (SEQ ID NO:34). The interrogation oligonucleotides used were wild type sequence 9211 (SEQ ID NO:86) and mutant sequence 9212 (SEQ ID NO:35).

Five nanograms of either the wild type or the mutant target (2.5 ng each of 9162 and 9165 for wild type or 9163 and 9166 for mutant) were combined with 1 µg of either the wild type probe, the mutant probe, or no probe, and water to a final volume of 20 µL. The solutions were heated for 5 minutes at 95° C. then cooled for 10 minutes at room temperature. Twenty microliters of 2× master mix were then added to each solution, and each was further incubated at 70° C. for 10 minutes. Four microliters of each solution were added to 100 µL of L/L Reagent (Promega F202A) and the relative light units (rlu) measured on a Turner® TD20/20 luminometer. The various combinations of target and probe assayed and their average resulting rlu values, corrected for background values, from duplicate solutions are listed below.

|            |           |           |      | match:mismatch |
|------------|-----------|-----------|------|-------|
| Polymerase | Target    | Probe     | rlu  | ratio |
| Taq        | wild type | wild type | 129  | 128:1 |
|            | wild type | mutant    | −2   |       |
|            | mutant    | mutant    | 62   | 95:1  |
|            | mutant    | wild type | 0.65 |       |
| Pfu        | wild type | wild type | 121  | 20:1  |
|            | wild type | mutant    | 6    |       |
|            | mutant    | mutant    | 34   | 1:2   |
|            | mutant    | wild type | 54   |       |
| Tvu        | wild type | wild type | 898  | 89:1  |
|            | wild type | mutant    | 10   |       |
|            | mutant    | mutant    | 1075 | 66:1  |
|            | mutant    | wild type | 16   |       |
| Ath        | wild type | wild type | 327  | 327:1 |
|            | wild type | mutant    | 0    |       |
|            | mutant    | mutant    | 244  | 136:1 |
|            | mutant    | wild type | 1.8  |       |

```
9162  5' CGTCTATGCCACTTTGATATTACACCCATGAACGTG   SEQ ID NO:31
         CTCATCGACGTCAACCCGCACAACGAGCT 3'

9165  5' CGTTGTGCGGGTTCACGTCGATGAGCACGTTCATGG   SEQ ID NO:32
         GTGTAATATCAAAGTGGCATACACGAGCT 3'

9163  5' CGTGTATGCCACTTTGATATTACACCCGTGAACGTG   SEQ ID NO:33
         CTCATCGACGTCAACCCGCACAACGAGCT 3'

9166  5' CGTTGTGCGGGTTCACGTCGATGAGCACGTTCACGG   SEQ ID NO:34
         GTGTAATATCAAAGTGGCATACACGAGCT 3'

9211  5'CACTTTGATATTACACCCATG 3'              SEQ ID NO:86
         (wild type primer)

9212  5'CACTTTGATATTACACCCGTG 3'              SEQ ID NO:35
         (mutant primer)
```

2× Master Mix:

| 100 µL | 10X Thermophilic DNA polymerase buffer (Promega, M190A) |
| 100 µL | 15 mM MgCl$_2$ (Promega, A351B) |
| 25 µL  | 40 mM NaPPi (Promega, E350B) |
| 10 µL  | 10 µM ADP (Sigma, A-5285) |
| 5 µL   | Thermophilic polymerase (1 U enzyme/reaction) |
| 5 µL   | Pfu NDPK (0.5 U/µL) (see Example 25 for enzyme purification; 0.1 U/rxn)) |
| 275 µL | water |

EXAMPLE 70
Replicate Interrogations of One Target

This example demonstrates the amount of fluctuation when the same target is interrogated with the same probe in 30 replicates of the reaction. In this example the PCR purification is automated on a Beckman Biomek™ robot and the luciferase light output measurements are automated on an EG&G Berthold Microlumat Plus luminometer.

Ten 100 µL PCR reactions were assembled as follows.

| 10 µL  | 10X PCR buffer (Promega, M190A) |
| 8 µL   | 25 mM MgCl$_2$ |
| 2 µL   | 10 mM dNTPs |
| 2 µL   | Factor V probe 10861 (SEQ ID NO:264), 50 pmol/µL |
| 2 µL   | Factor V probe 9828 (SEQ ID NO:265), 50 pmol/µL |
| 4 µL   | human genomic DNA (40 ng) |
| 72 µL  | water |
| 2.5 U  | Taq polymerase (Promega, M186A) |

The cycling parameters were 94° C., 2 minutes; (94° C., 30 seconds; 60° C., 1 minute; 70° C., 1 minute)×35; 70° C., 5 minute; 4° C. soak. After cycling, the ten reactions were pooled together and a 10 µL aliquot was run on a 1% agarose gel to confirm that the correct size product was made.

Twenty-five microliter aliquots of the PCR product were distributed into each of 32 wells of a Dynex™ 96 well plate. The PCR product was then purified from free nucleotides on a Beckman Biomek™ robot. Two hundred fifty microliters of MagneSil™ paramagnetic particles were resuspended in 9 mL of a solution containing 0.4 M guanidine thiocyanate and 0.08 M potassium acetate. Of that suspension, 180 μL were added to each well and mixed. The samples were magnetized and the supernatant removed.

The particles were then washed three times with 100 μL of 70% ethanol. Then 50 μL of water and 150 μL of 0.4 M guanidine thiocyanate and 0.08 potassium acetate were added to each well. The samples were magnetized and the supernatant removed. Again, the particles were washed three times with 100 μL of 70% ethanol, air dried for 10 minutes and eluted into 100 μL of water, which was transferred to a new plate.

The following master mix was assembled.

| | |
|---|---|
| 3905 μL | water |
| 1100 μL | 10X DNA polymerase buffer |
| 275 μL | 40 mM NaPPi |
| 110 μL | 10 mM ADP |
| 55 μL | 1 U/μL NDPK |
| 55 μL | 10 U/μL Klenow exo- |

Ten microliters of each purified PCR product aliquot were added to 3 wells of a luminescence spectroscopy 96-well plate. To one of the replicates were added 10 μL (150 pmol) of wild type probe 11505 (SEQ ID NO:266); to another of the replicate wells were added 10 μL (150 pmol) Factor V Leiden mutant oligonucleotide 11432 (SEQ ID NO:267); and to the third well were added 10 μL of water. Sodium hydroxide (10 μL of 0.06N) was added to all wells as were 10 μL of 0.1 M Tris pH 7.3. The plate was incubated at 37° C. for 5 minutes, and then 25 μL of master mix were added to each well. The plate was further incubated at 37° C. for 15 minutes.

Then, 100 μL of L/L reagent (Promega, F202A) were added serially to each of the wells. The light output was measured in a Berthold luminometer immediately after the L/L reagent was added and before the robot added the L/L reagent to the next well. The relative light unit (rlu) results are provided below and demonstrate consistent values although some increase is obtained that is reflective of the longer time that the reaction is at 37° C. with the master mix.

| WT | Mutant | Water No Interr. |
|---|---|---|
| 96273 | 26312 | 29132 |
| 113830 | 29400 | 30506 |
| 125410 | 30445 | 31932 |
| 121334 | 30040 | 32347 |
| 136788 | 28943 | 30280 |
| 144237 | 34935 | 36664 |
| 161304 | 39844 | 41521 |
| 142979 | 34612 | 37252 |
| 157255 | 42247 | 44432 |
| 156354 | 39103 | 38966 |
| 163757 | 40294 | 40302 |
| 157427 | 39202 | 42753 |
| 163480 | 43519 | 44072 |
| 165872 | 47608 | 47560 |
| 163614 | 42507 | 43241 |
| 158910 | 37910 | 39909 |
| 164992 | 46147 | 46845 |
| 168549 | 53255 | 52263 |
| 172471 | 53922 | 52196 |
| 158835 | 40988 | 43717 |
| 169860 | 51393 | 52309 |
| 166303 | 46488 | 46870 |
| 178970 | 60475 | 58484 |
| 167606 | 46088 | 50270 |
| 171895 | 50478 | 52369 |
| 174249 | 56554 | 56536 |
| 180951 | 60283 | 54489 |
| 159357 | 37508 | 39647 |
| 176683 | 49491 | 51971 |
| 168514 | 41909 | 44462 |

PCR probe sequences:
10861   5' TGCCCAGTGCTTAACAAGACCA 3'   SEQ ID NO:264

The first four linkages at the 5' end are phosphorothioate linkages.
9828   5' TGTTATCACACTGGTGCTAA 3'   SEQ ID NO:265

11505   5' GACAAAATACCTGTATTCCTCG 3'   SEQ ID NO:266

11432   5' GACAAAATACCTGTATTCCTTG 3'   SEQ ID NO:267

EXAMPLE 71
Multiplex Determination of Nucleotide Sequences Associated with Factor V Leiden and with a Prothrombin SNP in the Same Reaction A assay is performed in this Example to determine if a human DNA sample contains the Leiden mutation of the Factor V gene, as well as a particular Prothrombin single nucleotide polymorphism (SNP). The assay for these two characteristics is performed simultaneously in the same reaction.

Probes PT5 (SEQ ID NO:104) and PT6 (SEQ ID NO:105) were used to PCR-amplify a region of human genomic DNA spanning about 500 base pairs encoding the prothrombin gene. Probes 10861 (SEQ ID NQ:264) and 9828 (SEQ ID NO:265) were used to PCR amplify a region of human genomic DNA spanning about 300 base pairs encoding the Factor V gene. Probes PT5 and 10861 have phosphorothioate linkages between the first five bases at the 5' end. The Factor V and Prothrombin fragments were co-amplified in one PCR reaction under the following conditions:

| | |
|---|---|
| 5 μL | 10X PCR buffer |
| 5 μL | 25 mM MgCl$_2$ |
| 1 μL | 10 mM dNTPs |
| 1 μL | probe PT5 (50 pmol) |
| 1 μL | probe PT6 (50 pmol) |
| 1 μL | probe 10861 (50 pmol) |
| 1 μL | probe 9828 (50 pmol) |
| 1 μL | Human genomic DNA (40 ng) |
| 36 μL | water |
| 1.25 U | Taq |

The PCR cycling parameters were as follows: 94° C., 2 minutes; (94° C., 30 seconds; 60° C., 1 minutes; 70° C., 1 minutes)×40; 70° C., 5 minutes. Fifty units of T7 gene 6 Exonuclease (USB Amersham) were added to 25 μL of the PCR reaction and the solution was incubated for 30 minutes at 37° C. Magnetic silica (Promega, A1330) was used to remove free nucleotides from the solution and the remaining DNA was eluted with 100 μL of water.

The Prothrombin interrogation probes used are 11265 (SEQ ID NO:268) that matches mutant prothrombin sequence and 11266 (SEQ ID NO:269) that matches wild type prothrombin sequence. Each of those probes has a destabilizing mutation eight bases from the 3' end as discussed in Example 30. The Factor V interrogation probes used are 9919 (SEQ ID NO:270) that matches wild types Factor V sequence and 11432 (SEQ ID NO:267) that matches Factor V Leiden mutation sequence.

Four microliters of the eluted DNA were interrogated with each interrogation probe independently and also with the Factor V and Prothrombin mutant probes conjointly in one reaction. The interrogation reactions were assembled as follows.

| | |
|---|---|
| 4 µL | DNA (PCR product, Exo6 treated and purified) |
| 150 pmol | each interrogation oligo |
| water added to a final volume of 20 µL | |

The reactions were incubated at 95° C. for 3 minutes and then at 37° C. for 10 minutes. Twenty microliters of the standard master mix was then added and the reaction incubated at 37° C. for 15 minutes. One hundred microliters of the L/L reagent were then added and the light output measured in a Turner® TD20/20 luminometer. The master mix contains the following.

| | |
|---|---|
| 71 µL | water |
| 20 µL | 10X DNA pol buffer |
| 5 µL | 40 mM NaPPi |
| 2 µL | 10 µM ADP |
| 1 µL | 1 unit/µL NDPK |
| 1 | 10 unit/µL Klenow exo- |

The light output was as follows.

| Interrogation oligo | Genomic DNA 1 | Genomic DNA 2 |
|---|---|---|
| 9919 (FV wt) | 431 | 424 |
| 11432 (FV mut) | 45 | 57 |
| 11266 (Pt wt) | 902 | 878 |
| 11265 (Pt mut) | 145 | 161 |
| 11432 + 11265 | 77 | 98 |
| no oligo | 44 | 57 |

These data indicate that the both genomic DNAs are from individuals wild type for Factor V and for wild type Prothrombin.

An additional 96 clinical genomic DNA samples were interrogated as described above. All the data fit into the following equation for calling the genotype.

$$\frac{\text{rlu both wild type probes}}{\text{rlu both wild type + rlu both mutant probes}} > 0.75$$

This equation is the analytical output from the interrogation including both wild type probes divided by the analytical output from both wild type probes added to the analytical output from both mutant probes. If that value is greater than 0.75 then the sample is homozygous wild type at both loci. If that value is less than 0.75 then there is good likelihood that at least one allele at least one of the loci is mutant and the sample should be further analyzed for the genotype at each locus separately.

| PT5 | 5' ATAOCACTGGGAGCATTGAGGC 3' | SEQ ID NO:104 |
|---|---|---|
| PT6 | 5' GCACAGACGGCTGTTCTCTT 3' | SEQ ID NO:105 |

-continued

| 10861 | 5' TGCCCAGTGCTTAACAAGACCA 3' | SEQ ID NO:264 |
|---|---|---|
| 9828 | 5' TGTTATCACACTOGTGCTAA 3' | SEQ ID NO:265 |
| 11265 | 5' GTGATTCTCAGCA 3' | SEQ ID NO:268 |
| 11266 | 5' GTGATTCTCAGCG 3' | SEQ ID NO:269 |
| 9919 | 5' GACAAAATACCTGTATTCCTCG 3' | SEQ ID NO:270 |
| 11432 | 5' GACAAAATACCTGTATTCCTTG 3' | SEQ ID NO:267 |

EXAMPLE 72

Shrimp Alkaline Phosphatase as dNTP Removal Reagent

This Example examines pretreatment of the PCR product with shrimp alkaline phosphatase to shorten the protocol using magnetic silica for purification of PCR products.

The standard protocol for purification of PCR products prior to interrogation can be broken down into the following steps.
1. Twenty five microliters PCR product are added to 175 µL Magnetic Silica (Promega, A1330)
2. Three 200 µL washes with 70% ethanol
3. Dry DNA bound to Magnetic Silica 10 minutes at room temperature
4. Elute DNA from Magnetic Silica with 50 µL water
5. Add 150 µL Magnetic Silica to the 50 µL DNA in water
6. Three 200 µL washes with 70% ethanol
7. Elute DNA from Magnetic Silica with 100 µL water.

The revised protocol is as follows.
1. Twenty five microliters of PCR product are added to 1 unit of Shrimp Alkaline Phosphatase
2. Incubate 15 minutes at room temperature
3. Add 175 µL Magnetic Silica
4. Three 200 µL washes with 70% ethanol
5. Dry DNA bound to Magnetic Silica 10 minutes at room temperature
6. Elute DNA from Magnetic Silica with 100 µL water.

In this example, the standard protocol was compared to the revised protocol using Factor V Leiden and wild type PCR product and interrogation oligonucleotides as described in Example 32. The wild-type oligonucleotides used were FV1 (SEQ ID NO:25) and FV2 (SEQ ID NO:26). The mutant oligonucleotides used were FV3 (SEQ ID NO:27) and FV4 (SEQ ID NO:28). The probes used were FV7 (wild-type) (SEQ ID NO:110) and FV8 (mutant) (SEQ ID NO:111). The interrogation reaction was added to 100 µL of L/L reagent (Promega, F202A) and the relative light units determined on a Turner® TD20/20 luminometer. The values for each are shown below.

| Protocol | Wild Type Interro* | Mutant Interro | No Interro | Discrim* |
|---|---|---|---|---|
| Standard (2 washes) | 1867 | 289.7 | 165.0 | 13.7 |
| Standard (1 wash) | 2144 | 775.6 | 623.6 | 10.0 |
| Revised | 1475 | 393.4 | 190.7 | 6.3 |

*Interro = interrogation; Discrim = discrimination

The Standard Protocol with two sets of washes worked best based on absolute background and fold discrimination over background. Pre-treating with Shrimp Alkaline Phosphatase before a single round of DNA capture and washes as in the revised protocol gave relatively low backgrounds, but the discrimination ratio was lower.

FV1
5'CTAATCTGTAAGAGCACATCCCTGGACAGGCGAGGAATACAGAGGGCAGCA   SEQ ID NO:25
GACATCGAAGAGCT 3'

FV2
5'AGCTCTTCGATGTCTGCTGCCCTCTGTATTCCTCGCCTGTCCAGGGATCTG   SEQ ID NO:26
CTCTTACAGATTAGAGCT 3'

FV3
5'CTAATCTGTAAGAGCAGATCCCTGGACAGGCAAGCAATACAGAGGGCAGCA   SEQ ID NO:27
GACATCGAAGAGCT 3'

FV4
5'AGCTCTTCGATGTCTGCTGCCCTCTGTATTCCTTGCCTGTCCAGGGATCTG   SEQ ID NO:28
CTCTTACAGATTAGAGCT 3'

FV7   5' GACAAAATACCTGTATTCCTCG 3'                      SEQ ID NO:110

FV8   5' GACAAAATACCTGTATTCCTTG 3'                      SEQ ID NO:111

EXAMPLE 73
Analysis of SNP Heterozygosity Level in DNA Isolated from Plant Materials Eight different rice DNA samples, with varying amounts of two alleles differing at an SNP site, were analyzed to determine the ability of pyrophosphorylation to detect the degree of heterozygosity in a plant sample. The DNA genotypes (G and T) are described in Example 39.

Eight coded heterozygous rice DNA samples and two homozygous rice DNA samples were obtained (Texas A&M, Crop Biotechnology Center) and PCR amplified with primers RS1 (SEQ ID NO:129) and RS2 (SEQ ID NO:130) as described in Example 39. The resulting PCR products were then treated with T7 Exonuclease 6 and purified as described in Example 39. The resulting DNA was interrogated by combining 4 µL of the PCR product with 150 pmoles of interrogation oligonucleotide and water to a final volume of 20 µL. This solution was incubated at 95° C. for 2 minutes, then at 37° C. for 10 minutes. Interrogation oligonucleotides used were RS3 (SEQ ID NO:131), RS4 (SEQ ID NO:132), and none. Twenty microliters of master mix were then added and the solution further incubated at 37° C. for 15 minutes. These solutions were then combined with 100 µL of L/L reagent (Promega, F202A) and light output measured in a Berthold Eg&G microlumat plus luminometer. The relative light units (rlu) were corrected for no oligonucleotide background and are listed below:

| Sample | G (RS3) Allele | T(RS4) Allele | % G | % T |
|---|---|---|---|---|
| 1 | 100,366 | 119,046 | 45.7 | 54.3 |
| 2 | 83,428 | 163,241 | 33.8 | 66.2 |
| 3 | 90,309 | 90,628 | 49.9 | 50.1 |
| 4 | 168,074 | 35,835 | 82.4 | 17.6 |
| 5 | 173,422 | 31,403 | 84.7 | 15.3 |
| 6 | 166,516 | 13,692 | 92.4 | 7.6 |
| 7 | 171,933 | 17,384 | 90.8 | 9.2 |
| 8 | 103,047 | 1,724 | 98.4 | 1.6 |

These G:T ratios were further confirmed by the following study. The eight heterozygote samples and the two homozygote samples were re-amplified as previously described, but the PCR reaction also included 1 µL of $^{32}$PdATP and $^{32}$PdCTP. Ten microliters of the resulting PCR product were then digested with 1 µL restriction endonuclease AccI in 2.5 mM MgCl$_2$ in the PCR buffer for one hour at 37° C. AccI cuts the G allele PCR product into a 120 bp doublet, but will not cut the 240 bp fragment from the T allele PCR product. The digest was run on a 10% acrylamide TBE gel, dried for one hour at 65° C. and resulting bands quantified for one hour on a Molecular Dynamics Fluoroimager screen. The following values were obtained.

| Sample | % G | % T |
|---|---|---|
| 1 | 47.6 | 52.4 |
| 2 | 35.8 | 64.2 |
| 3 | 57.2 | 42.8 |
| 4 | 77.6 | 22.3 |
| 5 | 81.1 | 18.9 |
| 6 | 89.2 | 10.8 |
| 7 | 85.4 | 14.6 |
| 8 | nd | nd |

No values were generated for sample 8 because the PCR reaction was not successful. The correlation coefficient between the two data sets was 0.992036.

| RS1 | 5' CCCAACACCTTACAGAAATTAGC 3' | SEQ ID NO:129 |
|---|---|---|
| RS2 | 5' TCTCAAGACACAAATAACTGCAG 3' | SEQ ID NO:130 |
| RS3 | 5' AGAACATCTGCAAGG 3' | SEQ ID NO:131 |
| RS4 | 5' AGAACATCTGCAAGT 3' | SEQ ID NO:132 |

EXAMPLE 74
Deoxyadenosine Triphosphate as a Luciferase Substrate

In the usual interrogation assay, the pyrophosphorylation activity of a polymerase is used to break down nucleotides at the 3' end of a hybridized probe into its dNTP subunits. The terminal phosphate group is then transferred from the released dNTPs to ADP by NDPK activity, thereby forming ATP. The ATP in turn is used as a substrate by luciferase resulting in light production. In this Example the pyrophosphorylation reaction is performed to determine if the dATP released by the pyrophosphorylation of a hybridized interrogation probe can be detected sufficiently to permit for discrimination from a mismatched interrogation probe in the absence of NDPK and ADP.

It has been previously shown that dATP is an inefficient substrate for light production by luciferase relative to ATP. The use of dATP by luciferase produces about 2% of the light output as the use of ATP. However, dATP is used by luciferase much more efficiently than any of the other nucleoside triphosphates or deoxynucleoside triphosphates (*Analytical Biochemistry* 134:187–189, 1983).

The targets in this Example are 10800 (SEQ ID NO:171) and 10801 (SEQ ID NQ:172) and represent wild-type cytomegalovirus. The probes in this example are wild-type 10337 (SEQ ID NO:284) and mutant 10338 (SEQ ID NQ:285). Six replicates of the following solutions were assembled.

|  | μL<br>Water | μL<br>CMV Target | μL<br>CMV Probe |
|---|---|---|---|
| Match | 18 | 1, WT* | 1, WT |
| Mismatch | 18 | 1, Mut 2* | 1, Mut 2 |
| Probe only | 19 | none | 1, WT |
| Target only | 19 | 1, WT | none |
| No DNA control | 20 | none | none |

*WT = wild type; MUT = mutant

These solutions were incubated at 86° C. for 5 minutes, then cooled at room temperature for 45 minutes. Two different master mix solutions were assembled.

|  | Master Mix 1 | Master Mix 2 |
|---|---|---|
| Water | 288 μL | 300 μL |
| 10X DNA Pol buffer | 80 μL | 80 μL |
| 40 mM NaPPi | 10 μL | 10 μL |
| Klenow exo- (1 U/μL) | 10 μL | 10 μL |
| NDPK (1 U/μL) | 4 μL | none |
| ADP 10 μM | 8 μL | none |

Twenty microliters of each type of master mix were added to three of the six replicates of the sample type: match, mismatch, probe only, target only and no DNA control. The resulting solutions were incubated at 37° C. for 15 minutes, then added to 100 μL of L/L reagent (Promega, F202A) and the light output determined on a Turner™ TD20/20 luminometer. The results of the study are shown below.

| Solution | Master Mix 1 | | | Master Mix 2 | | |
|---|---|---|---|---|---|---|
| Match | 1469 | 1522 | 1536 | 1.702 | 2.081 | 1.723 |
| Mismatch | 126.6 | 127.2 | 126.4 | 1.081 | 1.090 | 0.988 |
| Probe only | 23.7 | 23.9 | 27.6 | 0.681 | 10.93 | 3.068 |
| Target only | 20.3 | 20.8 | 21.1 | 0.564 | 0.640 | 1.315 |
| No DNA | 18.2 | 23.2 | 16.5 | 0.863 | 0.365 | 0.378 |

This Example demonstrates that discrimination can be achieved in the usual interrogation assay that is lacking in NDPK and ADP. The degree of discrimination is much lower than it would be in the presence of NDPK and ADP. Two of the values using probe only solution with master mix two are artificially high, presumably due to contamination. These measurements were repeated and the following values obtained when 35 μL of the interrogation reaction were combined with 100 μL of L/L reagent and the light output determined on a Turner™ TD20/20 luminometer.

| Solution | Master Mix 2 | | | | | |
|---|---|---|---|---|---|---|
| Match | 2.381 | 2.347 | 2.402 | 2.235 | 3.150 | 2.800 |
| Mismatch | 1.331 | 1.312 | 1.290 | 1.308 | 1.260 | 1.261 |
| Probe only | 1.308 | 1.289 | 1.334 | 1.313 | 1.311 | 1.315 |
| Target only | 1.142 | 1.233 | 1.229 | 1.297 | 1.190 | 2.353 |
| No DNA | 1.050 | 1.025 | 1.036 | 0.977 | 1.104 | 0.898 |

EXAMPLE 75

Detection of Human Immunodeficiency Virus (HIV) Drug-Resistant Mutants

Chemotherapeutic selection pressure in vivo often results in mutations within the genome of the infectious agent that the drug is intended to destroy. This demonstration of evolutionary adaptation is widely reported for human immunodeficiency virus (HIV) under the selective pressure of protease inhibitors or reverse transcriptase inhibitors (Martinez-Picado, *J. Virology*, 73:3744–3752, 1999; Back, *EMBO J.*, 15:4040–4049, 1996).

The first viral mutants to be selected during therapy are typically those with single-amino-acid substitutions. Some of the nucleotides of the HIV reverse transcriptase (RT) and protease genes are known in the art to be "hotspots" for developing such point mutations. Additional mutations accumulate with ongoing therapy. After about 6 months to 1 year of treatment with AZT, HIV typically mutates the RT gene and so becomes resistant to treatment.

The ability to detect and identify such viral mutant genomes in a reliable and sensitive assay would assist with understanding the progression of the infection and with developing the best treatment regimens for infected individuals. Switching to a different treatment course before or as soon as a resistant mutant virus takes hold is important in prolonging patient life.

This Example demonstrates that drug resistant mutations that occur within the HIV-1 reverse transcriptase gene, when under the selective pressure of reverse transcriptase inhibitors, such as the nucleoside analog drugs AZT and ddI, can be detected using the process of the invention. Three specific "hotspot" sites of RT mutation were chosen for study. These three mutations all exist within a short region of the RT gene, spanning about 10 amino acids, from codon 65 to 75 of the protein.

Codon 67 (Site 1) of RT changes from GAC to AAC in the presence of the drug AZT, codon 70 (Site 2) changes from AAA to AGA in the presence of AZT, and codon 75 (Site 3) changes from GTA to ATA in the presence of the combination of drugs AZT and ddI. Target oligonucleotides were synthesized to span codons 65 through 81 of the RT genome of HIV-1 strain HXB2 wild type genome as well as oligonucleotides that vary only at one position as defined above for Site 1, Site 2, and Site 3 point mutations. Probe oligonucleotides exactly complementary to the wild type target and to the mutant targets at these three sites were also synthesized. The sequence and names of these oligonucleotides are listed below.

```
10800  5' CGTGTATGCCACTTTGATATTACACCCATGAACGTG  SEQ ID NO:171
       CTCATCGACGTGAACCCGCACAACGAGCT 3'

10801  5' CGTTGTGCGGGTTCACGTCGATGAGCACGTTCATGG  SEQ ID NO:172
       GTGTAATATCAAAGTGGCATACACGAGCT 3'

10337  5' CACTTTGATATTACACCCATG 3'                SEQ ID NO:284

10338  5' CACTTTGATATTACACCCGTG 3'                SEQ ID NO:285
```

The probe oligonucleotides were dissolved in TE Buffer to a final concentration of 0.5 μg/μL. The target oligonucleotides were dissolved in TE Buffer to a final concentration of 5 μg/mL. One microliter of target was combined with 1 μL of probe and 18 μL of water; and for the controls, 1 μL of each oligonucleotide was combined with 19 μL of water. These solutions were then heated at 95° C. for 3 minutes and cooled at room temperature for 10 minutes. Twenty microliters of master mix were then added to each tube. The master mix is described below.

| Master Mix: | |
|---|---|
| 10X DNA Polymerase buffer (Promega, M195A) | 120 μL |
| 40 mM Sodium pyrophosphate | 15 μL |
| Klenow exo- enzyme (1 U/μL; Promega, M218A) | 15 μL |
| NDPK (1 U/μL) | 6 μL |
| ADP (10 μM) | 12 μL |
| Nanopure water | 432 μL |

The tubes with the master mix added were then incubated for 15 minutes at 37° C. Five microliters of the solutions were then combined with L/L reagent (Promega, F202A) and the light output was measured on a Turner® TD20/20 luminometer. The relative light unit (rlu) data obtained are listed below.

| Solution | Target | Probe | Reading 1 | Reading 2 | Reading 3 |
|---|---|---|---|---|---|
| 1) | 11814 (wt*) | — | 2.55 | 3.82 | 10.78 |
| 2) | 11815 (mut 1*) | — | 2.54 | 2.57 | 2.99 |
| 3) | — | 11808 (wt 1) | 162.8 | 207.2 | 165.5 |
| 4) | — | 11809 (mut 1) | 2.81 | 2.17 | 2.20 |
| 5) | 11816 (mut 2) | — | 3.84 | 3.98 | 3.81 |
| 6) | — | 11810 (wt 2) | 4.57 | 4.77 | 5.29 |
| 7) | — | 11811 | 3.84 | 3.98 | 3.81 |
| 8) | 11817 (mut 3) | — | 2.04 | 1.64 | 1.44 |
| 9) | — | 11812 (wt 3) | 2.36 | 2.57 | 2.41 |
| 10) | — | 11813 (mut 3) | 4.05 | 2.06 | 1.77 |
| 11) | 11814 (wt) | 11808 (wt 1) | 418.7 | 711.6 | 682.1 |
| 12) | 11814 (wt) | 11809 (mut 1) | 20.69 | 29.05 | 21.25 |
| 13) | 11815 (mut 1) | 11808 (wt 1) | 218.4 | 185.6 | 118.1 |
| 14) | 11815 (mut 1) | 11809 (mut 1) | 682.6 | 737.8 | 599.7 |
| 15) | 11814 (wt) | 11810 (wt 2) | 1055.0 | 920.2 | 744.7 |
| 16) | 11814 (wt) | 11811 (mut 2) | 175.3 | 188.1 | 171.1 |
| 17) | 11815 (mut 2) | 11810 (wt 2) | 136.9 | 121.0 | 114.4 |
| 18) | 11815 (mut 2) | 11811 (mut 2) | 822.3 | 865.9 | 729.0 |
| 19) | 11814 (wt) | 11812 (wt 3) | 31.49 | 33.22 | 43.83 |
| 20) | 11814 (wt) | 11813 (mut 3) | 2.55 | 3.79 | 2.49 |
| 21) | 11815 (mut 2) | 11812 (wt 3) | 5.26 | 6.00 | 6.33 |
| 22) | 11815 (mut 2) | 11813 (mut 3) | 77.58 | 78.46 | 82.85 |
| 23) | no DNA | | 2.18 | 2.48 | 1.37 |

*wt = wild type; mut = mutant. wt and mut a, 2, and 3 are defined hereinafter.

All three HIV RT drug-resistance mutations were detectable with discrimination of mutant:wild type rlu ratios ranging from about 3 to about 7. Probe 11808, which is directed to site one and is completely complementary to wild type target, had high background values when tested alone. The other oligonucleotides all had acceptably low levels of background.

```
Target and Probe Sequences
11808 5' CCATTTAGTACTGTCT 3'          SEQ ID NO:271
HIV WT Probe Site 1

11809 5' CCATTTAGTACTGTTT 3'          SEQ ID NO:272
HIV Mutant Probe Site 1

11810 5'CTAGTTTTCTCCATTT 3'           SEQ ID NO:273
HIV WT Probe Site 2

11811 5' CTAGTTTTCTCCATCT 3'          SEQ ID NO:274
HIV Mutant Probe Site 2

11812 5' TTCTCTGAAATCTACT 3'          SEQ ID NO:275
HIV WT Probe Site 3

11813 5' TTCTCTGAAATCTATT 3'          SEQ ID NO:276
HIV Mutant Probe Site 3

11814 5' AAAAAAGACAGTACTAAATGGAGAAAACTAGTA
```

-continued

```
GATTTCAGAGAACTTAA 3'                               SEQ ID NO:
                                                   277
HIV WT Target 11815 5' AAAAAAAACAGTACTAAATGGAGAAAACTAGTAGA
TTTCAGAGAACTTAA 3'                                 SEQ ID NO:278
HIV Mutant Target Site 1

11816 AAAAAAGACAGTACTAGATGGAGAAAAC-
TAGTAGATTTCAG
AGAACTTAA 3'                                       SEQ ID NO:279
HIV Mutant Target Site 25'

11817 5' AAAAAAGACAGTACTAAATGGAGAAAACTAA
TAGATTTCAGAGAACTTAA 3'                             SEQ ID NO:280
HIV Mutant Target Site 3
```

EXAMPLE 76

Interrogation Assay at 70° C. Using Pfu NDPK and Tvu DNA Polymerase

In this Example, a mutation that exists in the prohibitin gene in the population was interrogated using synthetic templates and the one-step interrogation assay. The assay was performed with two thermostable enzymes: NDPK of *Pyrococcus furiosis* (Pfu) and the DNA Polymerase of *Thermoactinomyces vulgaris* (Tvu).

One microliter of each wild type target oligonucleotide 9354 (SEQ ID NO:4) and 9355 (SEQ ID NO:5), at a concentration of 2.5 µg/mL in water, were combined with 1 µL of either 9695 wild type probe (SEQ ID NO:281) or 9498 mutant probe (SEQ ID NO:282)(1 mg/ml) and 18 µL water. Similarly, one microliter of mutant target oligonucleotides 9356 (SEQ ID NO:6) and 9357 (SEQ ID NO:7) were combined with 1 µL of either probe 9695 or probe 9498 oligonucleotides and 18 µL water. For the control solutions, 1 µL of each oligonucleotide was combined with 19 µL of water in separate tubes. These solutions were then heated to 95° C. for 5 minutes and cooled for 10 minutes at room temperature.

The following master mix was assembled.

| | |
|---|---|
| 10X DNA Polymerase Buffer (Promega, M195A) | 100 µL |
| 25 mM MgCl$_2$ | 100 µL |
| 40 mM Sodium Pyrophosphate | 25 µL |
| 1 µM ADP | 10 µL |
| Tvu DNA Polymerase (5 U/µL) | 5 µL |

-continued

| | |
|---|---|
| Pfu NDPK (0.5 U/µL) | 5 µL |
| Nanopure water | 255 µL |

Twenty microliters of master mix were added to each solution and they were then incubated at 70° C. for 10 minutes. Four microliters of each reaction were then combined with 100 µL of L/L reagent (Promega, F202A) and the luminescence (rlu) was measured on a TMDE#14728 luminometer. The results are listed below.

| Solution | Target | Probe | rlu | net rlu |
|---|---|---|---|---|
| 1. | — | — | 9.939 | |
| 2. | wild type | — | 18.88 | |
| 3. | mutant | — | 28.57 | |
| 4. | — | wild type | 10.10 | |
| 5. | — | mutant | 9.67 | |
| 6. | wild type | wild type | 583.9* | 564.8 |
| 7. | wild type | mutant | 24.1* | 5.4 |
| 8. | mutant | wild type | 40.7* | 11.9 |
| 9. | mutant | mutant | 840.6* | 812.2 |

*Average of duplicate measurements

This combination of enzymes provides excellent discrimination between wild type and mutant prohibitin sites.

```
Probe and Target Sequences
9354 5' CTGCTGGGGCTOAACATGCCTGCCAAAGACGTGTCC
GACCTACOTTCCTGGCCCCCTCGAGCT 3'                    SEQ ID NO:4
Prohibitin wild type strand - target 9355 5' CGAGGGGGCCAGGAACGTAGGTCGGACACGTCTTTG
GCAGGCATGTTCAGCCCCAGCAGAGCT 3'                    SEQ ID NO:5
Prohibitin wild type strand - target 9356 5' CTGCTGGGGCTGAACATGCCTGCCAAAGATGTOTCC
GACCTACOTTCCTOGCCCCCTCGAGCT 3'                    SEQ ID NO:6
Prohibitin mutant strand - probe 9357 5' CGAGGGGGCCAGGAACGTAGGTCGGACACATCTTTG
GCAGGCATGTTCAOCCCCAGCAGAOCT 3'                    SEQ ID NO:7
Prohibitin mutant strand - probe 9695 5' CTGAACATGCCTGCCAPAGACG 3'                  SEQ ID NO:281
Prohibitin wild type probe
```

```
                                    -continued
9498  ' CTGAACATGCCTGCCAAAGATG 3'              SEQ ID NO:232
Prohibitin mutant probe
```

EXAMPLE 77

Interrogation for Factor V Leiden Mutation: Mass Spectroscopy Analysis

This Example demonstrates that nucleotides released from the 3'-terminus of a hybridized probe by a process of the invention can be detected by mass spectroscopy. Probes PT5 (SEQ ID NO:104) and PT6 (SEQ ID NO:105) are used to PCR-amplify a region of human genomic DNA spanning about 500 base pairs encoding the prothrombin gene. Probe PT5 has phosphorothioate linkages between the first five bases at the 5' end. The PCR reaction conditions are detailed in Example 71. The PCR product is treated with T7 gene 6 Exonuclease (USB Amersham) and separated from free nucleotides as described in Example 71.

The prothrombin interrogation probes are 11265 (SEQ ID NO:268), that is totally complementary to a segment of the mutant prothrombin sequence, and 11266 (SEQ ID NO:269), that is totally complementary to a segment of the wild-type prothrombin sequence. Each of these probes has a destabilizing mutation eight bases from the 3'-end as discussed in Example 30.

The purified PCR product is interrogated with each interrogation probe. Two separate interrogation reactions for each of the interrogation probes are assembled as follows.

| | |
|---|---|
| 40 μL | PCR product |
| 1.5 nmol | Interrogation oligo |
| Water is added to a final volume of 50 μL. | |

The reactions are incubated at 95° C. for 3 minutes and then at 37° C. for 15 minutes for Klenow exo- reactions.

A replicate set of solutions is incubated at 95° C. for 3 minutes and then 55° C. for 15 minutes for the Tne triple mutant reactions.

Fifty microliters of the appropriate master mix are then added. One master mix contains Klenow exo- polymerase and yeast NDPK. The other master mix contains Tne triple mutant polymerase and Pfu NDPK. The compositions of the master mixes are as described in Example 57. The reaction containing Klenow exo- proceeds at 37° C. for 15 minutes. The reaction containing Tne triple mutant polymerase proceeds at 55° C. for 15 minutes.

The presence or absence of released nucleotides, converted to ATP, is analyzed for by silicon desorption ionization mass spectroscopy (Wei, J. et al. *Nature*. 399:243–246, 1999). This method is sensitive to femtomole and attomole levels of analyte. The samples are prepared as described in that paper. An observance of released nucleotide from either of the reactions containing the mutant probe, 11265, at levels greater than background, indicates the presence of a mutant prothrombin gene in the genomic DNA sample assayed. An observance of released nucleotide from the either reaction containing the wild-type probe, 11266, at levels greater than background, indicates the presence of a wild-type prothrombin gene in the genomic DNA sample assayed.

```
PT5    5' ATAGCACTGGGAGCATTGAGGC 3'    SEQ ID NO:104

PT6    5' GCACAGACGGCTGTTCTCTT 3'      SEQ ID NO:105
```

```
                    -continued
11265  5' GTGATTCTCAGCA 3'             SEQ ID NO:268

11266  5' GTGATTCTCAGCG 3'             SEQ ID NO:269
```

EXAMPLE 78

Multiplex Interrogation for Factor V Leiden and Prothrombin Mutation: Mass Spectroscopy Analysis This Example demonstrates that nucleotides released from the 3'-terminus of a hybridized probe in a multiplex reaction by a process of the invention can be detected by mass spectroscopy and thereby determine whether a mutant allele exists at one of the loci being studied.

Probes PT5 (SEQ ID NO:104) and PT6 (SEQ ID NO:105) are used to PCR-amplify a region of human genomic DNA spanning about 500 base pairs encoding the prothrombin gene. Probes 10861 (SEQ ID NO:264) and 9828 (SEQ ID NO:265) are used to PCR amplify a region of human genomic DNA spanning about 300 base pairs encoding the Factor V gene. These probes and the PCR reaction conditions are detailed in Example 71. Probes PT5 and 10861 have phosphorothioate linkages between the first five bases at the 5' end. The PCR product is treated with T7 gene 6 Exonuclease (USB Amersham) and separated from free nucleotides as described in Example 71.

The prothrombin interrogation probe, 11265 (SEQ ID NO:268), is totally complementary to a segment of the mutant prothrombin sequence. The Factor V interrogation probe, 11432 (SEQ ID NO:267), is totally complementary to a segment of the mutant Factor V Leiden mutation sequence. Each of these probes has a destabilizing mutation eight bases from the 3'-end as discussed in Example 30.

The PCR products are synthesized, Exo 6 treated, and purified as described in Example 71. The interrogation reactions are assembled with 40 μL of each PCR product and 1.5 nmol of each interrogation probe. Water is added to a final volume of 100 μL. These reactions are assembled in duplicate so that one can be assayed with Klenow exo- polymerase and yeast NDPK at 37° C., while the other is assayed with Tne triple mutant polymerase and Pfu NDPK at 70° C.

These assembled reactions are incubated at 95° C. for 3 minutes and then at 37° C. for 10 minutes. The assembled reactions may be lyophilized to decrease the volume. The two different master mixes are assembled as described in Example 77. An equal volume of each master mix is separately added to the reaction solutions described above. Then the solution containing Klenow exo- as the polymerase is incubated at 37° C. for 15 minutes, while the solution containing Tne triple mutant polymerase is incubated at between 55° C. and 70° C.

The presence or absence of released nucleotides, converted to ATP, is analyzed for by silicon desorption ionization mass spectroscopy (Wei, J. et al. *Nature*. 399:243–246, 1999). This method is sensitive to femtomole and attomole levels of analyte. The samples are prepared as described in that paper. Essentially, analytes are dissolved in a deionized water/methanol mixture (1:1) at concentrations typically ranging from 0.001 to 10.0 μM. Aliquots (at least 0.5 to 1.0 μL, corresponding to at least 0.5 femtomol to 100 picomol analyte) of solution are deposited onto the porous surfaces and allowed to dry before mass spectrometry analysis. These experiments are performed on a Voyager DE-STR, time-of-flight mass spectrometer (PerSeptive Biosystems) using a pulsed nitrogen laser (Laser Science) operated at 337 nm.

Once formed, ions are accelerated into the time-of-flight mass analyzer with a voltage of 20 kV. Other liquid chromatography-mass spectrometry (LC-MS) instrumentation may also be used for analysis (Niessen W. *J. Chromatogra A* 794: (407–435, 1998).

An observance of released nucleotide from either of the reactions containing the two mutant probe, at levels greater than background, indicates the presence of a at least one mutant prothrombin or Factor V Leiden allele in the genomic DNA sample assayed.

| 10861 | 5' TGCCCAGTGCTTAACAAGACCA 3' | SEQ ID NO:264 |
|---|---|---|
| 9828 | 5' TGTTATCACACTGGTGCTAA 3' | SEQ ID NO:265 |
| PT5 | 5' ATAGCACTGGGAGCATTGAGGC 3' | SEQ ID NO:104 |
| PT6 | 5' GCACAGACGGCTGTTCTCTT 3' | SEQ ID NO:105 |
| 11265 | 5' GTGATTCTCAGCA 3' | SEQ ID NO:268 |
| 11432 | 5' GACAAAATACCTGTATTCCTTG 3' | SEQ ID NO:267 |

EXAMPLE 79

Interrogation Using Fluorescence

This Example demonstrates that nucleotides released from the 3'-terminus of a probe hybridized to a target nucleic acid of interest by a process of the invention can be detected by mass spectrometry or by fluorimetric HPLC and thereby provide evidence of the presence or absence of the target nucleic acid in a nucleic acid sample or of a specific base at an interrogation position of the target.

The interrogation probe is designed to have a fluorescent label attached to the 3'-terminal nucleotide in a manner such that the label does not interfere with the ability of the depolymerizing enzyme to remove the nucleotide from the probe. Such fluorescent tags, such as fluorescein or rhodamine, can be incorporated into the probe during synthesis with a fluorescent molecule attached to the phosphoramadite nucleotide with a linker of at least 6 carbons (Glen Research). Additionally, in this Example an identical, but unlabeled, probe is used and released nucleotides are fluorescently labeled only after the nucleotide is released from the probe by a process of the invention.

Probes PT5 (SEQ ID NO:104) and PT6 (SEQ ID NO:105) are used to PCR-amplify a region of human genomic DNA spanning about 500 base pairs encoding the prothrombin gene. Probe PT5 has phosphorothioate linkages between the first five bases at the 5' end. The PCR reaction conditions are detailed in Example 71. The PCR product is treated with T7 gene 6 Exonuclease (USB Amersham) and separated from free nucleotides as described in Example 71.

The prothrombin interrogation probes are 11265 (SEQ ID NO:268), that is totally complementary to a segment of the mutant prothrombin sequence, and 11266 (SEQ ID NO:269), that is totally complementary to a segment of the wild-type prothrombin sequence. Each of these probes has a destabilizing mutation eight bases from the 3' end as discussed in Example 30. Also, each of these probes is synthesized in two forms: with and without a fluorescent nucleotide analog (fluorescein-derivative) at the 3'-terminal nucleotide position. When the probe has the fluorescent tag, it is incorporated during synthesis of the probe as described above.

The purified PCR product is interrogated in separate reactions with each of the four interrogation probes (wild-type and mutant, with and without fluorescent tag). Interrogation reactions for each of the interrogation probes are assembled as follows.

| 40 μL | PCR product |
|---|---|
| 1.5 nmol | Interrogation oligo |
| Water is added to a final volume of 50 μL. | |

The reactions are incubated at 95° C. for 3 minutes and then at 37° C. for 15 minutes.

Fifty microliters of master mix are then added. The composition of the master mix containing Klenow exo- is described in Example 57 with the exception that there is no ADP and no NDPK. The reaction then proceeds at 37° C. for 15 minutes. The two reactions that do not contain fluorescent-labeled nucleotides are further treated to label the released nucleotides with a fluorescein tag (Jain, R. et al. *Biochem Biophys Res Commun.* 200:1239–1244, 1994; Shuker, D. et al. *IARC Sci Publ* 124:227–232, 1993).

The solutions are then split in half and analyzed using two different methods. In one method, the presence or absence of released nucleotides in the solutions is analyzed by silicon desorption ionization mass spectroscopy (Wei, J. et al. *Nature.* 399:243–246, 1999). This method is sensitive to femtomole and attomole levels of analyte. The samples are prepared for spectrometry as described in that paper. Essentially, analytes are dissolved in a deionized water/methanol mixture (1:1) at concentrations typically ranging from 0.001 to 10.0 μM. Aliquots (at least 0.5 to 1.0 μL, corresponding to at least 0.5 femtomol to 100 picomol analyte) of solution are deposited onto the porous surfaces and allowed to dry before mass spectrometry analysis. These experiments are performed on a Voyager DE-STR, time-of-flight mass spectrometer (PerSeptive Biosystems) using a pulsed nitrogen laser (Laser Science) operated at 337 nm. Once formed, ions are accelerated into the time-of-flight mass analyzer with a voltage of 20 kV. Other liquid chromatography-mass spectrometry (LC-MS) instrumentation may also be used for analysis (Niessen W. *J. Chromatogra A* 794: (407–435, 1998).

In a second method, the presence or absence of released nucleotides in the solutions is analyzed by HPLC using a fluorescence detector as described in Jain, et al. *Biochem Biophys Res Commun* 200:1239–1244, 1994 or Levitt, B. et al. *Anal Biochem* 137:93–100, 1984.

An observance of released nucleotide from either of the reactions containing the mutant probe, 11265, at levels greater than background (control reactions that contain no enzyme), indicates the presence of at least one mutant prothrombin allele in the genomic DNA sample assayed. An observance of released nucleotide from either reaction containing the wild-type probe, 11266, at levels greater than background, indicates the presence of at least one wild-type prothrombin allele in the genomic DNA sample assayed.

| PT5 | 5' ATAGCACTGGGAGCATTGAGGC 3' | SEQ ID NO:104 |
|---|---|---|
| PT6 | 5' GCACAGACGCCTGTTCTCTT 3' | SEQ ID NO:105 |
| 11265 | 5' GTGATTCTCAGCA 3' | SEQ ID NO:268 |
| 11266 | 5' GTGATTCTCAGCG 3' | SEQ ID NO:269 |

EXAMPLE 80

Multiplex Interrogation Using Fluorescent Labels

This example demonstrates that nucleotides released from the 3'-terminus of multiple probes, each hybridized to a target nucleic acid of interest, by a process of the invention can be detected by mass spectrometry or by fluorimetric HPLC and thereby provide evidence of the presence or absence of the target nucleic acid in a nucleic acid sample or of a specific base at an interrogation position of the target.

Each interrogation probe is designed to have a different fluorescent label attached to the 3'-terminal nucleotide in a manner such that the label does not interfere with the ability of the depolymerizing enzyme to remove the nucleotide from the probe. Such fluorescent tags, such as fluorescein or rhodamine, can be incorporated into the probe during synthesis with a fluorescent molecule attached to the phosphoramadite nucleotide with a linker of at least 6 carbons (Glen Research).

Probes PT5 (SEQ ID NO:104) and PT6 (SEQ ID NO:105) are used to PCR-amplify a region of human genomic DNA spanning about 500 base pairs encoding the prothrombin gene. Probes 10861 (SEQ ID NQ:264) and 9828 (SEQ ID NO:265) are used to PCR amplify a region of human genomic DNA spanning about 300 base pairs encoding the Factor V gene. These probes and the PCR reaction conditions are detailed in Example 71. The PCR products are treated with T7 gene 6 Exonuclease (USB Amersham) and separated from free nucleotides as described in Example 71.

The prothrombin interrogation probes are 11265 (SEQ ID NO:268), that is totally complementary to a segment of the mutant prothrombin sequence, and 11266 (SEQ ID NO:269), that is totally complementary to a segment of the wild-type prothrombin sequence. Each of these probes has a destabilizing mutation eight bases from the 3'-end as discussed in Example 30. Also, each of these probes is synthesized with a fluorescent nucleotide analog at the 3'-terminal nucleotide position. The prothrombin probes are tagged with fluorescein; the factor V probes are tagged with rhodamine.

The purified PCR products are interrogated in separate reactions with either both wild-type probes or both mutant probes. Interrogation reactions are assembled as follows: 40 µL each of the two PCR products 1.5 nmol each of the wild type or each of the mutant labeled interrogation oligos water is added to a final volume of 100 µL.

The reactions are incubated at 95° C. for 3 minutes and then at 37° C. for 15 minutes. The reactions are then lyophilized to a final volume of 20 µL.

Twenty microliters of master mix are then added. The composition of the master mix containing Klenow exo- is described in Example 57 with the exception that there is no ADP and no NDPK. The reaction then proceeds at 37° C. for 15 minutes.

The solutions are then split in half and analyzed using two different methods. In one method, the presence or absence of released nucleotides in the solutions is analyzed by silicon desorption ionization mass spectroscopy (Wei, J. et al. *Nature*. 399:243–246, 1999). This method is sensitive to femtomole and attomole levels of analyte. The samples are prepared for spectrometry as described in that paper. Essentially, analytes are dissolved in a deionized water/methanol mixture (1:1) at concentrations typically ranging from 0.001 to 10.0 µM. Aliquots (at least 0.5 to 1.0 µL, corresponding to at least 0.5 femtomol to 100 picomol analyte) of solution are deposited onto the porous surfaces and permitted to dry before mass spectrometry analysis.

These studies are performed on a Voyager DE-STR, time-of-flight mass spectrometer (PerSeptive Biosystems) using a pulsed nitrogen laser (Laser Science) operated at 337 nm. Once formed, ions are accelerated into the time-of-flight mass analyser with a voltage of 20 kV. Other liquid chromatography-mass spectrometry (LC-MS) instrumentation may be used for analysis (Niessen W. *J. Chromatogra A* 794:407–435, 1998)

In a second method, the presence or absence of released nucleotides in the solutions is analyzed by HPLC using a fluorescence detector as described in Jain, et al. *Biochem Biophys Res Commun* 200:1239–1244, 1994 or Levitt, B. et al. Anal Biochem 137:93–100, 1984.

An observance of released nucleotide from the reactions containing the mutant probes, at levels greater than background (control reactions that contain no enzyme), is indicative of the presence of at least one mutant prothrombin or Factor V Leiden allele in the genomic DNA sample assayed. An observance of released nucleotide from the reaction containing the wild-type probes, at levels greater than background, is indicative of the presence of at least one wild-type prothrombin or Factor V allele in the genomic DNA sample assayed.

| PT5 | 5' ATAGCACTGGGAGCATTGAGGC 3' | SEQ ID NO:104 |
|---|---|---|
| PT6 | 5' GCACAGACGGCTGTTCTCTT 3' | SEQ ID NO:105 |
| 10861 | 5' TGCCCAGTGCTTAACAAGACCA 3' | SEQ ID NO:264 |
| 9828 | 5' TGTTATCACACTGGTGCTAA 3' | SEQ ID NO:265 |

EXAMPLE 81

Exonuclease

In this Example, an interrogation for the presence or absence of a Factor V Leiden mutant allele in a genomic DNA sample is demonstrated with the use of *E. coli* Exonuclease III and, in a separate reaction, with the use of *E. coli* Klenow Fragment.

Probes PT5 (SEQ ID NO:104) and PT6 (SEQ ID NO:105) are used to PCR-amplify a region of human genomic DNA spanning about 500 base pairs encoding the prothrombin gene. Probe PT5 has phosphorothioate linkages between the first five bases at the 5'-end. The PCR reaction conditions are detailed in Example 71. The PCR product is treated with T7 gene 6 Exonuclease (USB Amersham) and separated from free nucleotides as described in Example 71.

The prothrombin interrogation probes are 11265 (SEQ ID NO:268), that is totally complementary to a segment of the mutant prothrombin sequence, and 11266 (SEQ ID NO:269), that is totally complementary to a segment of the wild-type prothrombin sequence. Each of these probes has a destabilizing mutation eight bases from the 3'-end as discussed in Example 30.

The purified PCR product is interrogated with each interrogation probe, 11265 and 11266. Two separate interrogation reactions are assembled as follows:

| 40 µL | PCR product |
|---|---|
| 150 nmol | interrogation oligo |
| water is added to a final volume of 20 µL. | |

The reactions are incubated at 95° C. for 3 minutes and then at 37° C. for 45 minutes. Twenty microliters of each of the two master mixes below are then added to a tube containing the mutant interrogation oligonucleotide and to a tube containing the wild type interrogation oligonucleotide. The reaction proceeds at 37° C. for 15 minutes. The composition of each master mix is:

| Master mix 1 | | Master mix 2 | |
|---|---|---|---|
| 10 U Klenow (Promega, M220A) | 1 µL | 10 U Exonuclease III (Promega, M181A) | 1 µL |
| 10X enzyme buffer | 10 µL | 10X enzyme buffer | 10 µL |
| 40 mM NaPPi | 5 µL | 40 mM NaPPi | 5 µL |
| water | 84 µl | water | 84 µl |

The released NMPs (reaction 3) are converted to the corresponding NTP by the enzyme PRPP synthetase as described in Example 86, hereinafter.

One hundred microliters of the L/L Reagent (Promega, F202A) are added, and the light output measured in a luminometer. The presence or absence of released nucleotides can also be assayed for by silicon desorption ionization mass spectroscopy (Wei, J. et al. *Nature*. 399:243–246, 1999) as described in Example 80.

An observance of released nucleotide resulting from the Klenow reaction containing the mutant probe, indicates the presence of at least one mutant prothrombin allele in the genomic DNA sample assayed. An observance of released nucleotide resulting from the Exo III reaction containing the mutant probe indicates the presence of at least one wild type prothrombin allele in the genomic DNA sample assayed. Conversely, an observance of released nucleotide resulting from the Klenow reaction containing the wild-type probe, indicates the presence of at least one wild-type prothrombin allele in the genomic DNA sample assayed. An observance of released nucleotide resulting from the Exo III reaction containing the mutant probe indicates the presence of at least one mutant prothrombin allele.

| | | |
|---|---|---|
| PT5 | 5' ATAGCACTGGGAGCATTGAGGC 3' | SEQ ID NO:104 |
| PT6 | 5' GCACAGACGGCTGTTCTCTT 3' | SEQ ID NO:105 |
| 11265 | 5' GTGATTCTCAGCA 3' | SEQ ID NO:268 |
| 11266 | 5' GTGATTCTCAGCG 3' | SEQ ID NO:269 |

EXAMPLE 82

Interrogation Using Fluorescence-II

This example demonstrates that nucleotides released from the 3'-terminus of a probe hybridized to a target nucleic acid of interest by a process of the invention can be detected by mass spectrometry or by fluorimetric HPLC and thereby provide evidence of the presence or absence of the target nucleic acid in a nucleic acid sample or of a specific base at an interrogation position of the target.

The interrogation probe is designed to have a fluorescent label attached to the 5'-terminal nucleotide. Fluorescent tags, such as fluorescein or rhodamine, can be incorporated into the probe during synthesis with a fluorescent molecule attached to the phosphoramadite nucleotide present at the 5'-end of the oligonucleotide that will be used as a probe (Glen Research).

Probes PT5 (SEQ ID NO:104) and PT6 (SEQ ID NO:105) are used to PCR-amplify a region of human genomic DNA spanning about 500 base pairs encoding the prothrombin gene. Probe PT5 has phosphorothioate linkages between the first five bases at the 5' end The PCR reaction conditions are detailed in Example 71. The PCR product is treated with T7 gene 6 Exonuclease (USB Amersham) and purified from free nucleotides as described in Example 71.

The prothrombin interrogation probes are 11265 (SEQ ID NO:268), that is totally complementary to a segment of the mutant prothrombin sequence, and 11266 (SEQ ID NO:269), that is totally complementary to a segment of the wild-type prothrombin sequence. Each of these probes has a destabilizing mutation eight bases from the 3' end as discussed in Example 30. And each of these probes has a label at its 5'-end, incorporated during synthesis of the probe as described above.

The purified PCR product is interrogated in separate reactions with each of the two interrogation probes (wild-type and mutant). Interrogation reactions, with the target molecule in molar excess over the probe molecule, for each of the interrogation probes are assembled as follows:

| | |
|---|---|
| 40 µL | PCR product |
| 15 pmol | Interrogation oligo |
| water is added to a final volume of 50 µL. | |

The reactions are incubated at 95° C. for 3 minutes and then at 37° C. for 15 minutes.

Fifty microliters of master mix are then added. The composition of the master mix containing Klenow exo- is described in Example 57 with the exception that there is no ADP and no NDPK. The reaction then proceeds at 37° C. for 15 minutes. The hybrid is then denatured by incubating the reaction at 95° C. for 3 minutes, adding 100 µL water to dilute the separated strands and placing the resulting denatured solution tube on ice.

The solutions are then split in half and analyzed using two different methods. In one method, the size of the labeled probe in the solutions is analyzed by silicon desorption ionization mass spectroscopy (Wei, J. et al. *Nature*. 399:243–246, 1999). This method is sensitive to femtomole and attomole levels of analyte. The samples are prepared for spectrometry as described in that paper. Essentially, analytes are dissolved in a deionized water/methanol mixture (1:1) at concentrations typically ranging from 0.001 to 10.0 µM. Aliquots (at least 0.5 to 1.0 µL, corresponding to at least 0.5 femtomol to 100 picomol analyte) of solution are deposited onto the porous surfaces and allowed to dry before mass spectrometry analysis.

These studies are performed on a Voyager DE-STR, time-of-flight mass spectrometer (PerSeptive Biosystems) using a pulsed nitrogen laser (Laser Science) operated at 337 nm. Once formed, ions are accelerated into the time-of-flight mass analyzer with a voltage of 20 kV. Other liquid chromatography-mass spectrometry (LC-MS) instrumentation may also be used for analysis (Niessen W. *J. Chromatog. A* 794:407–435 (1998)

In a second method, the size of the denatured labeled probe strand in the solution is analyzed by HPLC using a fluorescence detector as described in Jain, et al. *Biochem. Biophys. Res. Commun.* 200:1239–1244 (1994) or Levitt, B. et al. *Anal. Biochem.* 137:93–100 (1984). The size of the denatured labeled probe strand is confirmed on an ABI 377.

The size of the labeled probe strand present in the denatured solution indicates whether or not a nucleotide was released from the 3'-terminus of the probe, and therefore whether a match or mismatch base pair existed at the 3' terminus of the probe/template hybrid. For the denatured solution containing wild-type probe, the observance of a labeled probe that is shorter than the length of the original probe indicates that there is a matched base at the 3'-terminus of at least one allele in the original sample and therefore, that at least one allele in the original sample is wild-type. For the denatured solution containing mutant probe, the observance of a labeled probe that is shorter than the length of the original probe indicates that there is a matched base at the 3'-terminus of at least one allele in the original sample and therefore, that at least one allele in the original sample is wild-type. In both cases, the analytical output can be quantified to determine whether the genotype is homozygous or heterozygous at that locus.

| | | |
|---|---|---|
| PT5 | 5' ATAGCACTGGGAGCATTGAGGC 3' | SEQ ID NO:104 |
| PT6 | 5' GCACAGACGGCTGTTCTCTT 3' | SEQ ID NO:105 |
| 11265 | 5' GTGATTCTCAGCA 3' | SEQ ID NO:258 |

-continued 11266  5' GTGATTCTCAGCG 3'    SEQ ID NO:269

EXAMPLE 83

Detection of E. coli Repetitive Sequence without Nucleic Acid Amplification

In this Example repetitive sequence in E. coli is detected without the need for amplification of the target sequence prior to pyrophosphorylation. This target sequence is denoted as 'colirep'.

Oligonucleotide 11707 (SEQ ID NO:283) is totally complementary to a segment of colirep DNA sequence. Twelve microliters of oligonucleotide 11707 solution (1 mg/mL) were combined with 204 µL of water to make solution A. Another solution was prepared by combining 4 µL of 11707 (1 mg/mL) with 204 µL water and 8 µL 10 mM Tris, pH 8.0 to make solution B. The E. coli is Sigma cat#D4889, E. coli Strain B ultra pure.

Four nanograms (2 µL) E. coli DNA were combined with 18 µL solution A and with 18 µL solution B in separate tubes. Similarly, 40 ng E. coli DNA was combined with 18 µL solution A and with 18 µL solution B in separate tubes. These solutions were then incubated at 92° C. for 3 minutes and cooled at room temperature for 15 minutes. The following master mix was assembled:

| | |
|---|---|
| 10X DNA Polymerase buffer | 240 µL |
| 40 mM NaPPi | 30 µL |
| Klenow exo- (10 U/µL) | 30 µL |
| NDPK (1 U/µL) | 12 µL |
| 10 µM ADP (Sigma) | 24 µL |
| water | 864 µL |

Twenty microliters of master mix were added to each reaction and they were then incubated at 37° C. for 15 minutes. One hundred microliters of L/L Reagent were then added and the relative light output (rlu) immediately measured with a Turner® TD 20/20 luminometer. The rlu were:

| Solution | rlu-1 | rlu-2 | rlu-3 | Average |
|---|---|---|---|---|
| Tris | 2.85 | 3.562 | 3.059 | 3.157 |
| 11707 (A) | 13.69 | 12.13 | 13.67 | 13.16 |
| 11707 (B) | 7.473 | 7.234 | 6.981 | 7.259 |
| 40 ng DNA + Tris | 75.62 | 75.52 | 73.24 | 74.79 |
| 40 ng DNA + 11707 (A) | 97.71 | 134.2 | 105.1 | 112.3 |
| 40 ng DNA + 11707 (B) | 81.46 | 87.56 | 76.28 | 81.77 |
| 4 ng DNA + Tris | 6.719 | 8.084 | 5.882 | 6.895 |
| 4 ng DNA + 11707 (A) | 24.50 | 25.97 | 25.17 | 25.21 |
| 4 ng DNA + 11707 (B) | 15.69 | 17.22 | 16.99 | 16.63 |

The data reflect that oligonucleotide probe 11707 can detect E. coli DNA without amplification by a process of the invention.

Interrogation oligonucleotide:

11707  5' AGTGACTGGGG 3'   SEQ ID NO:283

EXAMPLE 84

PRPP Synthetase, Reactions with Deoxyadenosine Monophosphate

Some schemes for the detection of DNA require the conversion of dAMP, generated by nuclease digestion of DNA, to dATP. This example demonstrates that the enzyme PRPP synthetase can perform the transformation of dAMP to dATP using PRPP as a co-substrate. In addition, this transformation can be monitored by luciferase detection at much higher sensitivities if the dATP formed is used to transform ADP to ATP through the action of NDPK added to the reaction.

The reactions were assembled in duplicate. The concentrations of the reaction components were as follows: $2.9 \times 10^{-4}$ M dAMP in 10 mM Tris pH 7.3; $2.9 \times 10^{-4}$ M AMP in 10 mM Tris pH 7.3; $2.6 \times 10^{-4}$ M PRPP in 10 mM Tris pH 7.3; 100× dilution of PRPP Syn (PRPP synthetase) (Sigma #P0287) stock enzyme which is at 0.03 U/µL. The components were added to twenty microliters of PRPP Synthetase Buffer (50 mM triethanolamine, 50 mM potassium phosphate, pH 7, 0.37 mM EDTA, 10 mM $MgCl_2$, 1 mg/mL BSA). After incubating for 47 minutes at 37° C., 100 µL LAR Buffer were added to all reactions along with 10 ng luciferase and the light output of the reactions was immediately measured. The data are presented in Relative Light Unit table below. PRPP was able to utilize DAMP as a substrate (comparing reaction 1 to 2, 3, 4 and 5). However, the amount of light produced by reaction was low, probably due to the fact that luciferase uses dATP at a much lower efficiency than ATP.

| Reaction | dAMP | PRPP | PRPP Syn |
|---|---|---|---|
| 1 | 2 µL | 2 µL | 2 µL |
| 2 | 2 µL | — | 2 µL |
| 3 | 2 µL | 2 µL | — |
| 4 | 2 µL | — | — |
| 5 | — | 2 µL | 2 µL |

| | Relative Light Unit | | |
|---|---|---|---|
| Reaction | Tube A | Tube B | Avg. Light |
| 1 | 18.2 | 22.1 | 20.15 |
| 2 | 1.4 | 1.4 | 1.4 |
| 3 | 4.2 | 3.8 | 4 |
| 4 | 2.1 | 1.8 | 1.95 |
| 5 | 13.1 | 15.8 | 14.45 |

In order to demonstrate the transfer of phosphate from dATP to ADP to form ATP, the reactions, as shown below, were assembled in duplicate in twenty microliters of PRPP Synthetase Buffer (above). They were then incubated at 37° C. for 34 minutes. The added components had the following formulations: $2.3 \times 10^{-2}$ M ADP in 10 mM Tris-Cl pH 7.3; 1000× dilution of NDPK (Sigma #N0379) at 10 U/µL (final concentration 0.01 U/µL). The tubes were then incubated for an additional 60 minutes at 37° C., 10 ng luciferase added, and the light output measured using a Turner® TD-20e Luminometer. The data are presented in the table below. These data indicate that the dATP produced by the PRPP Synthetase reaction can be transferred to ADP by the action of NDPK to produce ATP.

| Reactions Assembled | | | | | |
|---|---|---|---|---|---|
| Reaction | dAMP | PRPP | PRPP Syn | ADP | NDPK |
| 1 | 2 μL | 2 μL | 2 μL | 2 μL | 2 μL |
| 2 | 2 μL | 2 μL | 2 μL | — | — |
| 3 | 2 μL | 2 μL | 2 μL | 2 μL | — |
| 4 | 2 μL | 2 μL | 2 μL | — | 2 μL |
| 5 | — | 2 μL | 2 μL | 2 μL | 2 μL |

| Light Units | | |
|---|---|---|
| Reaction | Tube A | Tube B |
| 1 | 812.1 | 839.3 |
| 2 | 19.2 | 37.5 |
| 3 | 53.6 | 52.6 |
| 4 | 168.4 | 173.1 |
| 5 | 43.6 | 38.9 |

EXAMPLE 85
Digestion of PhiX 174 HinF1 Fragments

Polynucleotides encountered in nature are often double stranded. The DNA fragments generated by digestion of PhiX 174 DNA using endonuclease HinFI are double-stranded DNA fragments of various sizes. In order to test whether double stranded DNA could be detected, PhiX 174 DNA was directly used as a target nucleic acid substrate or digested with nucleases to produce nucleotides that could be converted to nucleoside triphosphates as in previous Examples.

The following conditions were used to digest DNA fragments from bacteriophage PhiX 174.

The following materials were placed in three 1.5 mL polypropylene tubes: 50 μL of PhiX 174 HinFI fragments (Promega G175A, Lot #773603); 40 μL 5 mM MgSO$_4$; 5 μL Exo III buffer (10x) (Promega E577B, 4853216), and 5 μL Nanopure water. Fifty microliters TE buffer and 40 μL 5 mM MgSO$_4$; 5 μL ExoIII buffer (10x) and 5 μL Nanopure water were added to one sample. Two of the samples containing PhiX 174 DNA were further treated with 2 μL Exo III (Promega M181A, 5512708) and the tubes placed in a 37° C. water bath for 60 minutes. ExoIII was also added to the sample without DNA and the sample incubated at 37° C. 60 minutes.

At this time, 800 μL Nanopure water and 100 μL (10x) S1 Nuclease Buffer (Promega, M577A, Lot #6748605) were added to all samples. Three microliters S1 nuclease (Promega, E576B, Lot #789881) were then added to all samples. All samples were incubated at 37° C. for 30 minutes.

Two hundred microliters from each of the three tubes containing DNA were diluted with 300 μL 1x TE Buffer and the absorbance read at 260 nm using a Beckman DU 650 spectrophotometer. The readings recorded were: tube one (no nuclease addition), 0.3073; tube two (treatment with Exo III), 0.5495; tube three (treatment with Exo III and S1), 0.5190. The increased absorbance values of the tubes treated with nuclease indicate that the polymer was digested. These digests were subsequently used in other studies (see Example 86, below).

EXAMPLE 86
Detection of PhiX 174 HinF1 Fragments Using Nucleases, PRPP Synthetase, NDPK This example demonstrates the detection of DNA by digestion of the polymer to nucleoside monophosphates using nucleases, transformation of the nucleoside monophosphates to nucleoside triphosphates using PRPP Synthetase and PRPP along with transformation of ADP to ATP using the nucleoside triphosphates generated by the action of PRPP Synthetase, and detection of the ATP using luciferase. A sample of deoxynucleotide (Poly (dA)) was prepared as described in Example 85. Different amounts of deoxynucleotide were used in the reactions as presented in Table 30.

The following additions were made to each reaction: 2 μL PRPP, 2 μL PRPP Synthetase, and 20 μL PRPP Synthetase buffer. The reactions proceeded at 37° C. for 28 minutes, at which time the reactions were transferred to 100 μl LAR Buffer containing 2 μL ADP and 2 μL NDPK. This second reaction was permitted to proceed at room temperature for 20 minutes. The amount of ATP produced was measured by the addition of 10 ng of luciferase followed by measuring light output with a luminometer. The data are presented in table below. These data show that this combination of enzymes permitted detection of DNA.

| Reaction | Nucleotide | Amount In Reaction | Light Units |
|---|---|---|---|
| 1 | dAMP | 200 ng, 600 pmoles | 1018 |
| 2 | dAMP | 20 ng, 60 pmoles | 636 |
| 3 | dAMP | 2 ng, 6 pmoles | 178 |
| 4 | dAMP | 200 pg, 600 fmoles | 83 |
| 5 | none | zero ng | 69 |
| 6 | PhiX 174 only | 100 ng (= 300 pmoles dNMP; about 75 pmoles dAMP) | 46 |
| 7 | PhiX 174 + ExoIII | 100 ng | 472 |
| 8 | PhiX 174 + Exo + S1 | 100 ng | 448 |
| 9 | No DNA + Exo + S1 | zero ng | 55 |

EXAMPLE 87
NDPK Transformation of ADP to ATP Using Deoxynucleotides

Luciferase can detect ATP at much lower concentrations than dATP or other nucleotides. By using dNTPs to generate ATP, an increase in sensitivity results. In this experiment, the ability of enzymes to transfer the terminal phosphate of dNTPs to ADP, forming ATP and dNDPs, was analyzed.

Reactions were assembled which contained 100 μL LAR Buffer, long luciferase in the presence or absence of dNTPs (1 μM final concentration when added), and 10 units NDPK (Sigma #N0379, Lot #127F81802). The reactions were assembled with the exception of luciferase and incubated for 15 minutes at room temperature. Luciferase was added and light output of the reactions was measured immediately using a Turner TD-20e Luminometer. The light output values measured are provided in the data table below. These data confirm that NDPK is capable of transferring the phosphate from nucleoside triphosphates to ADP to form ATP, which can be detected using luciferase.

| Data Table | | | | | |
|---|---|---|---|---|---|
| Tube # | dNTP | ADP | NDPK | ATP | Light Units |
| 1 | – | + | + | | 883 |
| 2 | – | – | + | + | 15361 |
| 3 | – | + | – | | 543 |
| 4 | – | – | – | + | 21970 |
| 5 | dATP | + | + | | 13356 |
| 6 | dATP | – | + | | 151 |

-continued

Data Table

| Tube # | dNTP | ADP | NDPK | ATP | Light Units |
|---|---|---|---|---|---|
| 7 | dCTP | + | + | | 13007 |
| 8 | dCTP | − | + | | 6.9 |
| 9 | dGTP | + | + | | 13190 |
| 10 | dGTP | − | + | | 7.3 |
| 11 | TTP | + | + | | 19230 |
| 12 | TTP | − | + | | 9.0 |

EXAMPLE 88
NDPK Transformation of ADP to ATP Using NDPK and ATP Analogs

Some enzymes that may be used to transform nucleotides show specificity for adenosine nucleotides as phosphate donors. Adenosine nucleotides are not used as high energy phosphate donors for these converting enzymes if a luciferase detection system is to be utilized. This is because light is generated by luciferase from the added adenosine nucleotide. However, the converting enzymes can be utilized if an analog of adenosine is identified that can be used by the converting enzymes but not by luciferase. This example indicates how such analogs can be analyzed for their ability to be used by converting enzymes but not by luciferase.

Approximately 5 mg ATP (Sigma A9187, Lot #36H7808), α,β methyleneadenosine 5'-Triphosphate (AMP-CPP) (Sigma M6517, Lot #96H7813) and β,γ methylene adenosine 5'-triphosphate (AMP-PCP) (Sigma M7510, Lot #34H7840) were diluted in Tris-Cl, 10 mM, pH 7.5. The absorbance of a 1:100 dilution of these solutions into 50 mM Tris-Cl, pH 7.5 was read at 259 nm using a Beckman DU650 Spectrophotometer. The absorbances were used to determine the concentration of these solutions using a molar extinction coefficient of $15.4 \times 10^3$ Molar. Recombinant luciferase was diluted into CCLR containing 1 mg/mL BSA to a concentration of 2.5 ng/μL. When the reactions were assembled, 2 μL of luciferase were added from the 2.5 ng/μL stock solution and the light emission of the solutions were immediately read using a Turner TD-20e Luminometer. The data are provided in Table below.

| Reaction | LAR | ATP | AMP-CPP* | AMP-PCP* | # rxns | Avg. |
|---|---|---|---|---|---|---|
| 1 | 50 μL | — | — | — | 3 | 426.4 |
| 2 | 50 μL | 4 μM | — | — | 7 | 5762 |
| 3 | 50 μL | — | 552 μM | — | 2 | 349.2 |
| 4 | 50 μL | 4 μM | 552 μM | — | 2 | 5072.5 |
| 5 | 50 μL | — | 5.52 μM | — | 2 | 465.8 |
| 6 | 50 μL | 4 μM | 5.52 μM | — | 2 | 5843.5 |
| 7 | 50 μL | — | 55.2 nM | — | 2 | 429.8 |
| 8 | 50 μL | 4 μM | 55.2 nM | — | 2 | 4152 |
| 9 | 50 μL | — | — | 1.14 mM | 2 | 260.35 |
| 10 | 50 μL | 4 μM | — | 1.14 mM | 2 | 3735.5 |
| 11 | 50 μL | — | — | 11.4 μM | 2 | 431.25 |
| 12 | 50 μL | 4 μM | — | 11.4 μM | 2 | 5930 |
| 13 | 50 μL | — | — | 114 nM | 2 | 389.35 |
| 14 | 50 μL | 4 μM | — | 114 nM | 2 | 6093.5 |

*Final concentration in the reaction, solution produced by addition of 5 μL of a more concentrated stock solution.

Micromolar solutions of these ATP analogs do not produce light above that of reactions containing no added nucleotide and do not greatly lower the light output of reactions containing low levels of ATP from the values seen in the absence of these analogs. These analogs do not inhibit luciferase and are not utilized by luciferase. Thus, these data indicate that these analogs can be analyzed for their ability to be used with enzymes for the transformation of nucleotides.

The following reactions were performed to determine if either AMP-CPP or AMP-PCP could be used by NDPK. All reactions were assembled in duplicate and incubated at room temperature for 20 minutes. Ten nanograms of luciferase were added and the light output of the reactions immediately measured using a Turner TD-20e luminometer. The data are provided in Table below. These data demonstrate that the analog AMP-CPP is utilized by the enzyme NDPK as a substrate to generate ATP from ADP. The values seen with AMP-CPP, ADP and NDPK present are substantially higher than those seen for ADP alone, ADP and NDPK without AMP-CPP and NDPK alone. Analogous experiments can be performed to test other enzymes for their ability to use nucleotide substrates in a similar fashion.

| Reaction | LAR-CoA | ADP ($2 \times 10^{-4}$M) | NDPK | AMP-CPP ($2 \times 10^{-5}$M) | AMP-PCP ($2 \times 10^{-5}$M) | Avg. |
|---|---|---|---|---|---|---|
| 1 | 100 μL | — | — | — | — | 0.21 |
| 2 | 100 μL | 0.5 μL | — | — | — | 60.23 |
| 3 | 100 μL | 0.5 μL | 1 μL | — | — | 59.77 |
| 4 | 100 μL | 0.5 μL | 1 μL | 5 μL | — | 617.95 |
| 5 | 100 μL | — | 1 μL | 5 μL | — | 1.81 |
| 6 | 100 μL | 0.5 μL | 1 μL | — | 5 μL | 69.35 |
| 7 | 100 μL | — | 1 μL | — | 5 μL | 0.03 |
| 8 | 100 μL | — | 1 μL | — | — | 0.05 |

EXAMPLE 89
Interrogation with a Self-Annealing Primer II

This example and FIG. 2 illustrate use of a different type of oligonucleotide probe, a "REAPER™", probe in a process of this invention. This example demonstrates a method for eliminating the need for adding a probe specific to the interrogation site to the interrogation reaction.

Here, the oligonucleotide first probe (SEQ ID NO:287), at its 3'-end, anneals to the target strand (SEQ ID NO:286) at a position downstream of (3' to) the interrogation position in the target strand (FIG. 2A). The probe has at its 5'-end an unannealed region of nucleotides including about 5 to about 20 nucleotides that are identical to a region on the target strand including the interrogation position. This region of identity is present in the same orientation on both the target and the probe strands.

The annealed 3'-end of the probe is then extended through the interrogation position of the target strand forming what is referred to as a first extended probe and an extended first hybrid as is illustrated in FIG. 2B (SEQ ID NO:288). The extended first hybrid is denatured and a second probe (SEQ ID NO:289) is annealed to the first extended probe to form a second hybrid. This second probe is complementary to the first extended probe strand at a region downstream of the interrogation position on the first extended probe strand (FIG. 2C).

The second probe is then extended and a second extended hybrid is formed as illustrated in FIG. 2D. The second extended hybrid is comprised of the first extended probe and second extended probe (SEQ ID NO:290).

The strands of the second extended hybrid are denatured and permitted to renature to form a hairpin structure. Upon hairpin formation, the first extended probe forms a hairpin structure that has a 3'-overhang, whereas the second extended probe forms a hairpin structure that contains a 5'-overhang that provides a substrate for depolymerization. The second extended probe strand is then depolymerized and the analytical output obtained as described elsewhere herein. The analytical output determines the presence or absence of the original target strand or of a particular base in the original target strand as is also discussed elsewhere herein.

SEQ ID NO:286 oligonucleotide is diluted to 1 mg/mL in water. This solution is labeled 286. SEQ ID NO:287 oligonucleotide is diluted to 1 mg/mL in water and this solution is labeled 287. One microliter of each solution 286 and 287 is combined with 18 µL water. The solution is heated to 95° C. for 5 minutes then is cooled at room temperature for 10 minutes to permit oligonucleotides of SEQ ID NOs:286 and 287 to anneal.

To this solution are added dNTP mixture to a final concentration of 0.25 mM for each dNTP, 10× Klenow buffer to a final concentration of 1×, and 5 U of Klenow enzyme. The tube with these components is incubated at 37° C. for 30 minutes. The extended first hybrid DNA so formed (containing SEQ ID NO: 288) is purified (Qiagen, Mermaid system) and eluted into 50 µl of water.

To this solution of the purified extended first hybrid is added 1 µl SEQ ID NO: 289 oligonucleotide (1 mg/mL) as second probe. The solution is then heated to 95° C. for 5 minutes and is cooled at room temperature to permit 289 and 288 to anneal as illustrated in FIG. 2C to form the second hybrid. To this solution are added a dNTP mixture to a final concentration of 0.25 mM for each dNTP, 10× Klenow buffer to a final concentration of 1×, and 5 U of Klenow enzyme. The tube with these components is incubated at 37° C. for 30 minutes to form a second extended hybrid that contains a second extended probe (oligonucleotide SEQ ID NO: 290).

The SEQ ID NO: 290/288 second extended hybrid DNA (FIG. 2D) formed is purified (Qiagen, Mermaid system) to separate the extended hybrid from the unreacted dNTPs and eluted into 50 µl water. (Alternatively, the original 287 oligo is biotinylated at it's 5'-end and this biotin is then also present in strand of SEQ ID NO: 288. This biotinylated strand 288 is then denatured from strand 290 and removed from the solution with streptavidin coated paramagnetic particles according to the manufacturer's instructions (Promega, Z5481) and the 290 hairpin structure is allowed to form as below).

This hybrid solution is then heated to 95° C. for 5 minutes diluted to 100 µl with water and is cooled on ice for 10 minutes to permit hairpin structure formation.

The following master mix is assembled and mixed.

| Component | Amount |
| --- | --- |
| 10X DNA Pol Buffer (Promega, M195A) | 200 µL |
| Klenow exo- (1 U/µL) (Promega M218B) | 12.5 µL |
| 40 mM Sodium Pyrophosphate (Promega C350B) | 25 µL |
| NDPK (1 U/µL) | 10 µL |
| 10 uM ADP (Sigma A5285) | 20 µL |
| Water | 732.5 µL |

Twenty microliters of this master mix are added to 20 µL of the above hairpin-containing solutions after cooling, and the resulting mixtures are heated at 37° C. for 15 minutes. After this incubation, duplicate 4 µL samples of the solution are removed, added to 100 µL of L/L Reagent (Promega, F202A) and the light produced by the reaction is measured immediately using a Turner® TD20/20 luminometer. A positive analytical output at levels over background (no enzyme) indicates that a matched base was present at the 3'-terminus of the hairpin structure and this further indicates the presence of the target strand, and for this particular example, it also indicates the presence of a G base at the interrogation position of the target.

5' CCCGGAGAGACCTCCTTAAGGGGCCATATTATTTCGTCGATTCCAGTGTT GGCCAAACGGAT 3'   SEQ ID NO: 286

5' GGGGCCATATTATTTCGCCGTTTGGCCAACACTGGAATCGA 3'   SEQ ID NO: 287

5' GGGGCCATATTATTTCGCCGTTTGGCCAACACTGGAATCGACGAAATAAT ATGGCCCCTTAAGGAGGTCTCTCCGGG 3'   SEQ ID NO: 288

5' CCCGGAGAGACCTCCT 3'   SEQ ID NO: 289

5' CCCGGAGAGACCTCCTTAAGGGGCCATATTATTTCGTCGATTCCAGTGTT GGCCAAACGGCGAAATAATATGGCCCC 3'   SEQ ID NO: 290

EXAMPLE 90
Detection of Specific Endonuclease Activity

In this example, a different endonuclease, Rsa I, is incubated with closed circular plasmid DNA. Closed circular DNA is not normally a substrate for pyrophosphorylation. However, if the endonuclease creates double-strand DNA breaks in the plasmid, the resulting linear DNA will be a substrate for the reaction using T4 DNA polymerase. Samples of plasmid DNA incubated with Rsa I are taken and subjected to the pyrophosphorylation reaction. The resulting solutions are then added to solutions of luciferase and luciferin and the ATP formed detected by light production. The resulting data indicate that the activity of endonucleases can be detected at very low levels using such methods.

A 1× Buffer C stock was made by diluting 20 μl of 10× Buffer C (Promega R003, lot 7544205) with 180 μl nanopure water (Promega AA399, lot LSS652). This was used to produce an Rsa I dilution buffer by adding 20 μl 10 mg/ml BSA (Promega R396, lot 8560803) to 180 μl 1× Buffer C. The Rsa I dilution buffer was used to dilute a solution of Rsa I (Promega R937 lot 7980003) to concentrations 0.1×, 0.01×, 0.001×, 0.00033×, 0.0001×, 0.000033× and 0.00001× the starting enzyme concentration (3 u/ul).

A solution of plasmid substrate was made by dilution of 1 μl of plasmid (pGEM 3ZF, Promega P227, 814180) to 100 μl with 10 mM Tris-Cl pH 7.3 (made by dilution of a 2M stock with nanopure water) to yield a 10 ng/μl plasmid DNA solution.

Six reaction tubes were assembled that contained: 13 μl nanopure water, 2 μl 10× Buffer C, 10 mg/ml BSA, 2 μl 10 ng/μl DNA. One of these tubes received 1 μl RSA I dilution buffer. The remaining 5 tubes received 1 μl of the Rsa I dilutions from 0.001 to 0.00001×. The tubes were incubated overnight at 37° C.

The next day, 2 μl samples of the incubated tubes were added to pyrophosphorylation reaction mixes as described in the previous example and incubated 18 min at 37° C. After that time, the content of the tubes was added to 100 μl of L/L and the light produced by this reaction was measured using a Turner 20/20 Luminometer. The data shown in the following table illustrate that very low levels of Rsa I as a model endonuclease can be detected using this assay.

| Rsa I Dilution | Light Units | | | Average |
|---|---|---|---|---|
| 0.001X | 555.9 | 584.3 | 535.5 | 558.6 |
| 0.00033X | 302.9 | 298.4 | 296.4 | 299.2 |
| 0.0001X | 299.5 | 310.9 | 325.4 | 311.9 |
| 0.000033X | 176.0 | 181.3 | 182.8 | 180.0 |
| 0.00001X | 96.7 | 104.4 | 106.4 | 102.5 |
| No Rsa 1 | 136.3 | 150.8 | 146.6 | 144.6 |

EXAMPLE 91
Detection of Low Levels of Exonuclease

In this example, exonuclease will be detected by: using the exonuclease to produce 5' nucleotide monophosphates; transforming the dAMPs to the triphosphate form using PRPP Synthetase and PRPP; using the dATP to transform ADP to ATP using NDPK and measuring the ATP using luciferase.

An Exonuclease III dilution buffer was made by first diluting 20 μl 10× Exonuclease III reaction buffer (Promega E577, lot 4853218) with 180 μl nanopure water (Promega AA399, LSS9652) to form a 1× Exonuclease III solution then diluting 20 μl 10 mg/ml BSA (Promega R396, lot 8569803) with 180 μl 1× Exonuclease III buffer.

Exonuclease III (Promega M181, lot 5512708) was serially diluted with the exonuclease III dilution buffer to obtain enzyme concentrations 0.1×, 0.01×, 0.001×, 0.00033×, 0.0001×, 0.000033× and 0.09001× the stock enzyme concentration (175 u/ul).

Seven microliters of DNA (Phix 174 HinF I DNA, Promega G175, lot 7733604) was diluted with 14 μl 10 mM Tris-Cl buffer made as in the previous example to obtain a solution containing 115 ng/μl DNA.

Six reaction tubes were assembled that contained: 13 μl nanopure water, 2 μl 10× Exonuclease III reaction buffer, 2 μl 10 mg/ml BSA, and 1 μl of the 115 ng/μl DNA stock. One tube received an additional microliter of nanopure water to act as a negative control reaction. The other five tubes received 1 μl of the diluted Exonuclease III samples at the concentrations ranging from 0.001× to 0.09001× concentration. The reactions were incubated at 37° C. for 1 hr.

Eighteen 0.5 ml microfuge tubes received 5 μl of one of the digests made as described in the paragraph above, 2 μl ADP, 2 μl NDPK (both made as in the previous example), 2 μl PRPP (100 ug/ml made by diluting PRPP from the solid, Sigma Chemical Co.), 17 μl PRPP Synthase Reaction Buffer and 2 μl 0.01× PRPP Synthase in PRPP Synthase reaction Buffer. The tubes were incubated at 37° C. for 30 min and then the reactions added to L/L and measured the light produced by the reaction. The data listed in the following table show that Exonuclease III can be detected at dilutions at least as low as 0.0001× of 175 u/μl under these conditions.

| Exonuclease III Dilution | Light Values | | | Average Light Values |
|---|---|---|---|---|
| 0.001X | 106.3 | 96.2 | 110.0 | 104.2 |
| 0.00033X | 64.5 | 63.9 | 57.2 | 61.9 |
| 0.0001X | 58.6 | 48.4 | 51.3 | 52.8 |
| 0.000033X | 44.1 | 41.5 | 41.8 | 42.5 |
| 0.00001X | 38.9 | 38.3 | 42.6 | 39.9 |
| no enzyme | 49.9 | 40.7 | 40.4 | 43.6 |

EXAMPLE 92

Detection of Exonuclease Activity by Substrate Digestion

In this example, an exonuclease is used to digest a linear double-stranded DNA. The remaining DNA is measured using pyrophosphorylation, phosphate transfer and luciferase-based light production. Since the exonuclease does not produce deoxynucleotide triphosphates from the DNA, any DNA digested by the exonuclease is expected to result in a loss of substrate for the latter reaction. Thus, by measuring the drop in substrate concentration left after incubation with the exonuclease, one can detect the exonuclease activity.

Exonuclease III was diluted as described in the previous example. A 1 μl simple of a 500 bp linear DNA segment (Promega G370, lot 79280), 1.46 mg/ml was diluted to 146 μl with nanopure water to form a solution of 10 ug/ml.

Six 0.5 ml tubes were assembled containing 12 μl nanopure water, 2 μl Exonuclease III 10× reaction buffer, 2 μl 10 mg/ml BSA, 1 μl diluted 500 bp DNA fragment. One of the tubes received an additional microliter nanopure water and was used as a no enzyme control. The other tubes received 1 μl concentrated Exonuclease III or diluted Exonuclease III at concentrations ranging from 0.1 to 0.0001× (stock 175 μ/μl). The tubes were incubated at 37° C. for 1 hr.

A master reaction mix was made that contained 275 μl nanopure water, 44 μl 10× Buffer A (Promega R001, lot 7651103), 22 μl NDPK (0.1 μ/μl), 22 μl ADP(2 μM), 11 μl sodium pyrophosphate (Promega C113, lot 6675705) and 22 μl T4 DNA polymerase (Promega M241, lot 6175711). Eighteen 0.5 ml microfuge tubes received 18 μl master reaction mix and 2 μl of each of the six tubes incubated at 37° C. with various concentrations of Exonuclease III were added to the tubes in triplicate. These new tubes were incubated for 1 hr at 37° C. and the contents of the tubes were added to 100 µl L/L and light output of the reaction measured using a Turner luminometer. The results shown in the following table were obtained and show that low levels of a double-stranded DNA exonuclease can be measured using this method.

| Exonuclease III Dilution | Light Values | | | Average Light Values |
|---|---|---|---|---|
| 1X (no dilution) | 21.6 | 23.5 | 19.3 | 21.5 |
| 0.1X | 32.0 | 44.9 | 32.8 | 36.6 |
| 0.01X | 72.0 | 69.9 | 75.3 | 72.4 |
| 0.001X | 554.3 | 539.2 | 542.6 | 545.4 |
| 0.0001X | 1028 | 1041 | 1025 | 1031 |
| no enzyme | 1170 | 1172 | 1114 | 1152 |

These data show that low levels of a double-stranded DNA exonuclease can be measured using this method.

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

What is claimed is:

1. A method of detecting the presence of nuclease activity in a sample comprising:
   a) providing a mixture comprising
      i) a solution suspected of containing nuclease activity; and
      ii) a deoxyribonucleic acid substrate, wherein said nucleic acid substrate is selected from the group consisting of linear deoxyribonucleic acid and closed circular deoxyribonucleic acid;
   b) incubating said mixture for a period of time sufficient for said nuclease to act on said nucleic acid;
   c) reacting said mixture under conditions such that free nucleotides are produced; wherein said reacting step further comprises:
      i) providing a second solution comprising said nucleic acid substrate, adenosine 5' diphosphate, and pyrophosphate, said nucleic acid substrate having a terminal nucleotide and terminal internucleotide phosphodiester bond, said terminal nucleotide covalently joined to said nucleic acid by said terminal internucleotide phosphodiester bond;
      ii) depolymerizing said nucleic acid at a terminal nucleotide by enzymatically cleaving said terminal internucleotide phosphodiester bond to form a free nucleoside triphosphate molecule with a pyrophosphate molecule according to the reaction:

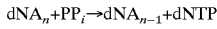

iii) enzymatically transferring terminal 5' phosphate groups from the nucleoside triphosphate molecules to adenosine 5'-diphosphate molecules to form adenosine 5'-triphosphate according to the following general reaction:

dNTP*+ADP→dNTP+ATP* wherein P* is the terminal 5' phosphate so transferred; and
   d) detecting said nucleotides using an ATP detection method, wherein the presence of nucleotides suggests the presence of nuclease activity.

2. The method of claim 1 wherein said detecting step further comprises quantitating said adenosine 5' triphosphate.

3. The method of claim 1 wherein the detecting step is selected from the group consisting of luciferase and NADH detection systems.

4. The method of claim 1, wherein said depolymerization is catalyzed by E. coli polymerase 1.

5. The method of claim 1, wherein said depolymerization is catalyzed by T4 DNA polymerase.

6. A method of detecting the presence of exonuclease activity comprising:
   a) providing a mixture comprising
      i) a solution suspected of containing exonuclease activity; and
      ii) a deoxyribonucleic acid substrate;

b) incubating said mixture to allow degradation of said deoxyribonucleic acid substrate by said exonuclease activity, thereby forming nucleoside monophosphates;

c) converting said nucleoside monophosphates into nucleoside triphosphates i) providing a second solution comprising phosphoribosylpyrophosphate, adenosine 5' diphosphate, and phosphoribosyl transferase;

ii) enzymatically transferring pyrophosphate from phosphoribosylpyrophosphate molecules to deoxyadenosine monophosphate molecules to form deoxyadenosine triphosphate molecules according to the following reaction catalyzed by phosphoribosyl pyrophosphate transferase:

dAMP+PRPP→dATP+ribose-5-PO$_4$; and iii) enzymatically transferring terminal 5' phosphate groups from said deoxyribonucleoside triphosphate molecules to said adenosine 5'-diphosphate molecules according to the following reaction:

dATP*+ADP→dADP+ATP*, wherein P* is the terminal 5' phosphate so transferred; and d) detecting said nucleoside triphosphates wherein the presence of nucleoside triphosphates suggests the presence of exonuclease activity.

7. The method of claim 6 wherein said detecting step further comprises quantitating said adenosine 5' triphosphate.

8. The method of claim 6 wherein the detecting step is selected from the group consisting of luciferase and NADH detection systems.

* * * * *